(12) United States Patent
Hoffmann

(10) Patent No.: US 12,000,002 B2
(45) Date of Patent: Jun. 4, 2024

(54) PRE-SURGICAL RISK STRATIFICATION BASED ON PDE4D7 EXPRESSION AND PRE-SURGICAL CLINICAL VARIABLES

(71) Applicant: KONINKLIJKE PHILIPS N.V., Eindhoven (NL)

(72) Inventor: Ralf Dieter Hoffmann, Brueggen (DE)

(73) Assignee: KONINKLIJKE PHILIPS N.V., Eindhoven (NL)

(*) Notice: Subject to any disclaimer, the term of this patent is extended or adjusted under 35 U.S.C. 154(b) by 1018 days.

(21) Appl. No.: 16/771,558

(22) PCT Filed: Dec. 19, 2018

(86) PCT No.: PCT/EP2018/086015
§ 371 (c)(1),
(2) Date: Jun. 10, 2020

(87) PCT Pub. No.: WO2019/122037
PCT Pub. Date: Jun. 27, 2019

(65) Prior Publication Data
US 2020/0308654 A1 Oct. 1, 2020

(30) Foreign Application Priority Data
Dec. 21, 2017 (EP) .................... 17209506

(51) Int. Cl.
*G01N 33/48* (2006.01)
*C12Q 1/6886* (2018.01)
*G16B 25/10* (2019.01)
*G16B 40/00* (2019.01)
*G16H 50/30* (2018.01)

(52) U.S. Cl.
CPC .......... *C12Q 1/6886* (2013.01); *G16B 25/10* (2019.02); *G16B 40/00* (2019.02); *G16H 50/30* (2018.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2012/0129788 A1 | 5/2012 | Hoffmann |
| 2013/0196321 A1 | 8/2013 | Shak |
| 2017/0073778 A1 | 3/2017 | Hoffmann |
| 2018/0148794 A1 | 5/2018 | Hoffmann |
| 2021/0277479 A1 | 9/2021 | Hoffman |

OTHER PUBLICATIONS

Böttcher, René, et al. "Human phosphodiesterase 4D7 (PDE4D7) expression is increased in TMPRSS2-ERG-positive primary prostate cancer and independently adds to a reduced risk of post-surgical disease progression." British Journal of Cancer 113.10 (2015): 1502-1511.*
Henderson, D. J. P., et al. "The cAMP phosphodiesterase-4D7 (PDE4D7) is downregulated in androgen-independent prostate cancer cells and mediates proliferation by compartmentalising cAMP at the plasma membrane of VCaP prostate cancer cells." British journal of cancer 110.5 (2014): 1278-1287.*
International Search Report and Written Opinion of PCT/EP2018/086015, dated Mar. 28, 2019.
Bottcher, R. et al "Human Phosphodiesterase 4D7 (PDE4D7) Expression is increased in TMPRSS2-ERG-Positive Primary Prostate Cancer and Independently adds to a reduced Risk of Post-Surgical Disease Progression", Bristish Journal of Cancer, vol. 113, No. 10, 2015.
Brajtbord, Jonathan S. et al "The CAPRA Score at 10 years: Contemporary Perspectives and Analysis of Supporting Studies", European Association of Urology, vol. 71, No. 5, 2017, pp. 705-709.
Bottcher, R. et al "Human PDE4D Isoform Composition is Deregulated in Primary Prostate Cancer and Indicative for Disease Progression and Development of Distant Metastases", Oncotarget, vol. 7, No. 43, 2016.
Van Strijp, Dianne et al "The Prognostic PDE4D7 Score in a Diagnostic Biopsy Prostate Cancer Patient Cohort with Longitudinal Biological Outcomes", Prostate Cancer, 2018, 11 pages.
Wang, Siao-Yi et al "miR-19, miR-345, miR-519c-5p Serum Levels Predict Adverse Pathology in Prostate Cancer Patients Eligible for Active Surveillance", PLOS One, vol. 9, Issue 6, 2014.
Alves De Inda, Marcia et al "Validation of Cyclic Adenosine Monophosphate Phosphodiesterase-4D7 for its Independent Contribution to risk Stratification in a Prostate cancer Patient Cohort with Longitudinal biological Outcomes", European Association of Urology, 2017.
Alves De Inda, Marcia et al "Supplementary Material: Validation of Cyclic Adenosine Monophosphate Phosphodiesterase-4D7 for its Independent Contribution to risk Stratification in a Prostate cancer Patient Cohort with Longitudinal biological Outcomes", European Urology Focus, 2017.
Ferlay, J. et al Globalcon 2012, Cancer Incidence and Mortality Worldwide: IARC Cancerbase No. 11 (Internet). Lyon. Fr. Int. Agency Res. Cancer 11: http://globocan.iarc.fr.

(Continued)

*Primary Examiner* — Anna Skibinsky

(57) ABSTRACT

The invention relates to a method of pre-surgical risk stratification of a prostate cancer subject, comprising determining a gene expression profile for phosphodiesterase 4D variant 7 (PDE4D7) in a biological sample obtained from the subject, determining gene expression profile, and determining a pre-surgical prognostic risk score for the subject based on the expression based risk score and pre-surgical clinical variables of the subject. This may allow for an improved stratification of the subject in a pre-surgical setting that may result in better primary treatment decisions. For instance, the pre-surgical prognostic risk score may allow to make better recommendation on whether to select active surveillance vs. active intervention, e.g., radical prostatectomy, for certain sub-populations of prostate cancer patients.

13 Claims, 24 Drawing Sheets
Specification includes a Sequence Listing.

(56) References Cited

OTHER PUBLICATIONS

Rodrigues, G. et al "Pretreatment risk stratification of prostate cancer patients: A Critical review", Canadian Urological Association Journal, vol. 6, No. 2, pp. 121-127, 2012.

Mohler, J. et al NCCN Clinical Practice Guidelines in Onocolgy: Prostate Cancer, Version 1, 2016, Journal of the National Comprehensive Cancer Network, vol. 14, No. 1, pp. 19-30-, 2016.

Hernandez, D.J. et al "Contemporary Evaluation of the D'amico Risk Classification of Prostate Cancer", Journal of Urology, vol. 70, No. 5, pp. 931-935. 2007.

Jung, J.W. et al "Stratification of Patients with Intermediate-risk Prostate Cancer", BJU International, vol. 115, No. 6, pp. 907-912, 2015.

Abern, M.R. et al "Delayed Radical Prostatectomy for Intermediate-Risk Prostate Cancer is Associated with biochemical recurrence: Possible Implications for Active Suveillance from the Search database", The Prostate, vol. 73, No. 4, pp. 409-417, 2013.

Merkle, D. et al "Roles of cAMP and cAMP-dependent Protein Kinase in the Progression of Prostate Cancer: Cross-Talk with the Androgen Receptor", Cellular Signalling, vol. 23, No. 3, pp. 507-515, 2011.

Conti, M. et al "Biochemistry and Physiology of Cyclic Nucleotide Phosphodiestreases: Essential components in cyclic nucleotide Signaling", Annual Review of Biochemistry, vol. 76, pp. 481-511, 2007.

Lughezzani, G. et al "Predictive and Prognostic Models in radical Prostatectomy candidates: A Critical analysis of the literature", European Urology, vol. 58, No. 5, pp. 687-700, 2010.

Cooperberg, M.R. "The UCSF Cancer of the prostate Risk Assessment (CAPRA) Score: A Straighforward and reliable pre-operative predictor of disease recurrence after radical prostatectomy", Journal of Urology, vol. 173 No. 6, pp. 1938-1942, 2005.

Vickers, A.J. et al "Decision curve analysis: A novel method for evaluating prediction models", Medical Decision Making, vol. 26, No. 6, pp. 565-574, 2006.

Godtman, R.A. et al "Long-term Results of Active Surveillance in the Goteborg Randomized, Population-based Prostate Cancer Screening Trial", European Urology, vol. 70, No. 5, pp. 760-766, 2016.

Hamdy, F.C. et al "10-Year Outcomes after Monitoring, Surgery, or radiotherapy for Localized Prostate cancer", New England Journal of Medicine, vol. 375, pp. 1415-1424, 2016.

Van Den Bergh, R.C.N. et al "Expectant Management for Prostate Cancer: Lessions from the past, Challenges for the Future", European Urology, vol. 70, pp. 767-770, 2016.

Garisto, J.D. et al "Active Surveillance for Prostate cancer: How to do it right", Oncology, vol. 31, No. 5, pp. 333-340, 2017.

Bokhorst, L.P. et al "Compliance Rates with the Prostate Cancer Research International Active Surveillance (PRIAS) Protocol and Disease Reclassification in Noncompliers", European Urology, vol. 68, No. 5, 2015.

Li, B. et al "RNA-Seq gene Expression Estimation with read mapping uncertainty", Bioinformatics, vol. 26, No. 4, pp. 493-500, 2010.

Taylor, B.S. et al "Integrative Genomic Profiling of human prostate cancer", Cancer Cell, vol. 18, No. 1, pp. 11-22, 2010.

Vickers, A.J. et al "Extension to decision curve analysis, a novel method for evaluating diagnostic tests, prediction models and molecular markers", BMC Medical Informatics and Decision Making, vol. 8, pp. 1-17, 2008.

Vickers, A.J. et al Net Benefit Approaches to the Evaluation of Prediction Models, Molecular Markers, and diagnostic tests, BMJ, vol. 25, 2016.

Briganti, A. et al "Active Surveillance for Low-Risk Prostate Cancer: The European Association of urology Position in 2018" European Urology, vol. 74, No. 3, pp. 357-368, 2017.

Eineluoto, J.T. "Repeat Multiparametic MRI in Prostate Cancer Patients on Active Surveillance", PLOS One, vol. 12, No. 12, 2017.

Canfield, S. et al "Active Surveillance Use among a Low-Risk Prostate cancer Population in a Large US Payer System: 17 Gene Genomic Prostate Score Versue other risk Stratification methods", Reviews in Urology, vol. 19, No. 4, pp. 203-212, 2017.

Keegan, K.A. et al "Active Surveillance for Prostate Cancer Compared with Immediate Treatment an economic Analysis", Cancer, vol. 118, No. 14, pp. 3512-3518, 2012.

Dall'era, M.A. "The Economics of Active Surveillance for Prostate Cancer", Current Opinion in Urology, vol. 23, No. 3, pp. 278-282, 2013. Abstract Only.

Boorjian, Stephen et al "Mayo Clinic validation of the D'Amico Risk Group Classification for Predicting Survival Following Radical Prostatectomy", Journal of Urology, vol. 179, No. 4, pp. 1354-1360, 2008.

Reese, Adam C. et al "Contemporary evaluation of the National Comprehensive Cancer Network prostate cancer risk classification system", Urology, vol. 80, No. 5, pp. 1075-1079, 2012.

Gandaglia, Giorgio et al "Identification of Pathologically Favorable Disease in Intermediate-Risk Prostate Cancer Patients: Implications for Active Surveillance Candidates Selection", The Prostate, vol. 75, pp. 1484-1491, 2015.

Hong, Sung Kyu et al "Insignificant Disease among men with Intermediate-risk prostate cancer", World Journal of Urology, vol. 32, No. 6, pp. 1417-1421, 2014.

Lugnier, Claire "Cyclic Nucleotide Phosphodiesterase ((PDE) Superfamily: A New Target for the Development of Specific Therapeutic Agent", Pharmacology & Therapeutics, vol. 109, pp. 366-398, 2006.

Houslay, Miles D. "Underpinning compartmentalised cAMP signalling through targeted cAMP breakdown", Trends in Biochemical Sciences, pp. 91-100, 2010.

Gretarsdottir, Solveig et al "The gene encoding phosphodiesterase 4D confers risk of ischemic stroke", Nature Genetics, vol. 35, No. 2, pp. 131-138. 2003.

Michot, Caroline et al "Exome sequencing identifies PDE4D mutations as another cause of acrodysostosis", American Society of Human Genetics, vol. 90, No. 4, pp. 740-745, 2012.

Lee, H. et al "Exome Sequencing Identifies PDE4D Mutations in Acrodysostosis", The American Society of Human Genetics, vol. 90, No. 4, pp. 746-751, 2012.

Tomppo, Liisa et al "Association Between Genes of Disrupted in Schizophrenia 1 (DISC1) Interactors anSchizophrenia Supports the Role of the DISC1 Pathway in the Etiology of Major Mental Illnesses", Biology Psychiatry, vol. 65, No. 12, pp. 1055-1062, 2009.

Yoon, H-K et al "Polymorphisms in PDE4D are associated with a risk of COPD in non-emphysematous Koreans", COPD: Journal of Chronic Obstructive Pulmonary Disease, vol. 11, No. 6, pp. 652-658, 2014.

Henderson, D.J.P. et al "The cAMP phosphodiesterase-4D7 (PDE4D7) is downregulated in androgen-independent prostate cancer cells and mediates proliferation by compartmentalising cAMP at the plasma membrane of VCaP prostate cancer cells", British Journal of Cancer, vol. 110, pp. 1278-1287, 2014.

Hoffmann, Ralf et al "cAMP-specific phosphodiesterase HSPDE4D3 mutants which mimic activation and changes in rolipram inhibition triggered by protein kinase A phosphorylation of Ser-54: generation of a molecular model", Biochem J. vol. 333, pp. 139-140, 1998.

Hoffmann, Ralf et al "The MAP kinase ERK2 inhibits the cyclic AMP-specific phosphodiesterase HSPDE4D3 by phosphorylating it at Ser579", The EMBO Journal, vol. 18, No. 4, pp. 893-903, 1999.

Byrne. Ashleigh M. et al "The activity of cAMP-phosphodiesterase 4D7 (PDE4D7) is regulated by protein kinase A-dependent phosphorylation within its unique N-terminus", FEBS Letters, vol. 589, pp. 750-755, 2015.

Baillie, George S. et al "Beta-Arrestin-Medicated PDE4 cAMP phosphodiesterase recruitment regulates beta-adrenoceptor switching from Gs to Gi", Proceeding of the National Academy of Science, vol. 100, No. 3, pp. 940-945, 2003.

Rubin, Mark A. et al "Genomic Correlates to the Newly Proposed Grading Prognostic Groups for Prostate Cancer", European Urology, vol. 69, pp. 557-560, 2016.

\* cited by examiner

PRE-SURGICAL RISK STRATIFICATION BASED ON PDE4D7 EXPRESSION AND PRE-SURGICAL CLINICAL VARIABLES

FIELD OF THE INVENTION

The invention relates to a method of pre-surgical risk stratification of a prostate cancer subject. Moreover, the invention relates to a diagnostic kit, to a use of the kit in a method of pre-surgical risk stratification of a prostate cancer subject, to a use of a gene expression profile for phosphodiesterase 4D variant 7 (PDE4D7) in pre-surgical risk stratification of a prostate cancer subject, and to a corresponding computer program product.

BACKGROUND OF THE INVENTION

Cancer is a class of diseases in which a group of cells displays uncontrolled growth, invasion and sometimes metastasis. These three malignant properties of cancers differentiate them from benign tumors, which are self-limited and do not invade or metastasize. Prostate Cancer (PCa) is the most commonly-occurring non-skin malignancy in men. It displays as a heterogeneous disease with varying potential to develop progressively to deadly forms of the disease. Of the estimated 417,000 annual new cases in Europe, around 92,000 will die from their disease (see Ferlay J. et al., GLOBOCAN 2012 v1.0, Cancer Incidence and Mortality Worldwide: IARC CancerBase No. 11 [Internet], Lyon, France, International Agency for Research on Cancer, 2013).

Clinically, various schemes for pre-surgical risk classification have been developed based upon longitudinal biological patient outcomes (see Rodrigues G. et al., "Pre-treatment risk stratification of prostate cancer patients: A critical review", Canadian Urological Association Journal, Vol. 6, No. 2, pages 121-127, 2012). While active surveillance (AS) is recommended by the various national and international guidelines for men with very low and low risk prostate cancer (see Mohler J. et al., "NCCN clinical practice guidelines in oncology: Prostate cancer, Version 1.2016", Journal of the National Comprehensive Cancer Network, Vol. 14, No. 1, pages 19-30, 2016), there is a significant sub-group in this patient population with a risk of 10 to 25% cancer recurrence after primary treatment (see, for example, Hernandez D. J. et al., "Contemporary evaluation of the D'amico risk classification of prostate cancer", Journal of Urology, Vol. 70, No. 5, pages 931-935, 2007). These patients suffer from the burden of follow-up treatments that are typically triggered by biochemical relapse. Likewise, in the intermediate risk group there is a sub-population with low risk of biochemical progression (see, for example, Jung J. W. et al., "Stratification of patients with intermediate-risk prostate cancer", BJU International, Vol. 115, No. 6, pages 907-912, 2015). Nevertheless, this group is heterogeneous, comprising patients with varied outcomes, including those with aggressive pathological characteristics (see Abern M. R. et al., "Delayed radical prostatectomy for intermediate-risk prostate cancer is associated with biochemical recurrence: Possible implications for active surveillance from the SEARCH database", The Prostate, Vol. 73, No. 4, pages 409-417, 2013).

Clinical risk descriptors do not delineate effectively either the extent of the disease or its aggressiveness for all patients. Thus, there is a need for better patient stratification in order to optimize primary treatment decisions.

SUMMARY OF THE INVENTION

It is an object of the invention to provide a method of pre-surgical risk stratification of a prostate cancer subject, which may allow making better primary treatment decisions. It is a further object of the invention to provide a diagnostic kit, a use of the kit in a method of pre-surgical risk stratification of a prostate cancer subject, a use of a gene expression profile for phosphodiesterase 4D variant 7 (PDE4D7) in pre-surgical risk stratification of a prostate cancer subject, and a corresponding computer program product.

In a first aspect of the present invention, a method of pre-surgical risk stratification of a prostate cancer subject is presented, comprising:
- determining a gene expression profile for phosphodiesterase 4D variant 7 (PDE4D7) in a biological sample obtained from the subject,
- determining an expression based risk score for the subject based on the gene expression profile, and
- determining a pre-surgical prognostic risk score for the subject based on the expression based risk score and pre-surgical clinical variables of the subject.

The cAMP signaling pathway is known to play an important role in both the development and progression of prostate cancer (see Merkle D. and Hoffmann R., "Roles of cAMP and cAMP-dependent protein kinase in the progression of prostate cancer: Cross-talk with the androgen receptor", Cellular Signalling, Vol. 23, No. 3, pages 507-515, 2011). While a family of adenylate cyclases is responsible for the synthesis of cAMP, cyclic nucleotide phosphodiesterases (PDEs) appear to represent the only cellular mechanism for its destruction. PDEs provide both signal termination and, importantly, the compartmentalization of cAMP signaling within the 3D matrix of cells. This is achieved through the spatially discrete destruction of cAMP via sub-populations of distinct PDE isoforms sequestered by localized anchor proteins/signalosomes (see, for example, Conti M. and Beavo J., "Biochemistry and physiology of cyclic nucleotide phosphodiesterases: essential components in cyclic nucleotide signaling", Annual Review of Biochemistry, Vol. 76, pages 481-511, 2007). Thus changes in the expression and/or activity of distinct PDE iso forms can alter downstream signaling pathways during disease development and progression, providing potential targets for novel biomarkers and for targeted therapeutic intervention. Indeed, alterations in the expression of members of the cAMP-degrading PDE4 family appear to be associated with a number of different diseases, including stroke, acrodysostosis, schizophrenia, and COPD. Recently, it was shown that down-regulation of a particular PDE4 isoform (PDE4D7) may have an impact on prostate cancer (see, for example, Böttcher R. et al., "Human phosphodiesterase 4D7 (PDE4D7) expression is increased in TMPRSS2-ERG positive primary prostate cancer and independently adds to a reduced risk of post-surgical disease progression", Britisch Journal of Cancer, Vol. 113, No. 10, pages 1502-1511, 2015). PDE4D7 isoform is a so-called long isoform as it contains both the UCR1 and UCR2 regulatory domains. UCR1 is found in long, but not short, PDE4 isoforms and allows for regulation by various protein kinases, including PKA and MK2 and also determines the functional outcome of catalytic unit phosphorylation by ERK. Functionally, it provides part of the cellular desensitization system to cAMP and enables cross-talk between signaling pathways that lead to the activation of ERK and AMPK, for example.

By determining an expression based risk score for a prostate cancer subject based on the gene expression profile of PDE4D7, additional molecular information representing the biology of the disease is obtained. The prognostic power of PDE4D7 is utilized in pre-surgical patient risk assessment by determining a pre-surgical prognostic risk score that is not only based on pre-surgical clinical variables of the subject but that is further based on the expression based risk score. This may allow for an improved stratification of the subject in a pre-surgical setting that may result in better primary treatment decisions. For instance, the pre-surgical prognostic risk score may allow to make better recommendations on whether to select active surveillance vs. active intervention, e.g., radical prostatectomy, for certain subpopulations of prostate cancer patients.

The term "phosphodiesterase 4D7" or "PDE4D7" refers to the splice variant 7 of the human phosphodiesterase PDE4D, i.e., the human phosphodiesterase PDE4D7 gene, for example, to the sequence as defined in NCBI Reference Sequence: NM_001165899.1, specifically, to the nucleotide sequence as set forth in SEQ ID NO:19, which corresponds to the sequence of the above indicated NCBI Reference Sequence of the PDE4D7 transcript, and also relates to the corresponding amino acid sequence for example as set forth in SEQ ID NO:20, which corresponds to the protein sequence defined in NCBI Protein Accession Reference Sequence NP_001159371.1 encoding the PDE4D7 polypeptide. The term "phosphodiesterase 4D7" or "PDE4D7" also relates to the amplicon that can be generated by the primer pair PDE4D7_forward (SEQ ID NO:21) and the PDE4D7_reverse (SEQ ID NO:22) and can be detected by probe SEQ ID NO:23.

The PDE4D7 polypeptide can also be detected with primer pair PDE4D7-2 forward (SEQ ID NO:24) and the PDE4D7_reverse (SEQ ID NO:25) and can be detected by probe SEQ ID NO:26.

The term "PDE4D7" also comprises nucleotide sequences showing a high degree of homology to PDE4D7, e.g., nucleic acid sequences being at least 75%, 80%, 85%, 90%, 91%, 92%, 93%, 94%, 95%, 96%, 97%, 98% or 99% identical to the sequence as set forth in SEQ ID NO:19 or amino acid sequences being at least 75%, 80%, 85%, 90%, 91%, 92%, 93%, 94%, 95%, 96%, 97%, 98% or 99% identical to the sequence as set forth in SEQ ID NO:20 or nucleic acid sequences encoding amino acid sequences being at least 75%, 80%, 85%, 90%, 91%, 92%, 93%, 94%, 95%, 96%, 97%, 98% or 99% identical to the sequence as set forth in SEQ ID NO:20 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:19.

The term "biological sample" or "sample obtained from a subject" refers to any biological material obtained via suitable methods known to the person skilled in the art from a subject, e.g., a prostate cancer patient. The biological sample used may be collected in a clinically acceptable manner, e.g., in a way that nucleic acids (in particular RNA) or proteins are preserved.

The biological sample(s) may include body tissue and/or a fluid, such as, but not limited to, blood, sweat, and urine. Furthermore, the biological sample may contain a cell extract derived from or a cell population including an epithelial cell, such as a cancerous epithelial cell or an epithelial cell derived from tissue suspected to be cancerous. The biological sample may contain a cell population derived from a glandular tissue, e.g., the sample may be derived from the prostate of a male subject. Additionally, cells may be purified from obtained body tissues and fluids if necessary, and then used as the biological sample. In some realizations, the sample may be a tissue sample, a urine sample, a urine sediment sample, a blood sample, a saliva sample, a semen sample, a sample including circulating tumor cells, extracellular vesicles, a sample containing prostate secreted exosomes, or cell lines or cancer cell line.

In one particular realization, biopsy or resections samples may be obtained and/or used. Such samples may include cells or cell lysates.

It is also conceivable that the content of a biological sample is submitted to an enrichment step. For instance, a sample may be contacted with ligands specific for the cell membrane or organelles of certain cell types, e.g., prostate cells, functionalized for example with magnetic particles. The material concentrated by the magnetic particles may subsequently be used for detection and analysis steps as described herein above or below.

Furthermore, cells, e.g., tumor cells, may be enriched via filtration processes of fluid or liquid samples, e.g., blood, urine, etc. Such filtration processes may also be combined with enrichment steps based on ligand specific interactions as described herein above.

The term "prostate cancer" refers to a cancer of the prostate gland in the male reproductive system, which occurs when cells of the prostate mutate and begin to multiply out of control. Typically, prostate cancer is linked to an elevated level of prostate-specific antigen (PSA). In one embodiment of the present invention the term "prostate cancer" relates to a cancer showing PSA levels above 4.0. In another embodiment the term relates to cancer showing PSA levels above 2.0. The term "PSA level" refers to the concentration of PSA in the blood in ng/ml.

The term "non-progressive prostate cancer state" means that a sample of an individual does not show parameter values indicating "biochemical recurrence" and/or "clinical recurrence".

The term "progressive prostate cancer state" means that a sample of an individual shows parameter values indicating "biochemical recurrence" and/or "clinical recurrence".

The term "biochemical recurrence" generally refers to recurrent biological values of increased PSA indicating the presence of prostate cancer cells in a sample. However, it is also possible to use other markers that can be used in the detection of the presence or that rise suspicion of such presence.

The term "clinical recurrence" refers to the presence of clinical signs indicating the presence of tumor cells as measured, for example using in vivo imaging.

The term "prognosticating prostate cancer" as used herein refers to the prediction of the course or outcome of a diagnosed or detected prostate cancer, e.g., during a certain period of time, during a treatment or after a treatment. The term also refers to a determination of chance of survival or recovery from the disease, as well as to a prediction of the expected survival time of a subject. A prognosis may, specifically, involve establishing the likelihood for survival of a subject during a period of time into the future, such as 6 months, 1 year, 2 years, 3 years, 5 years, 10 years or any other period of time.

It is preferred that the pre-surgical clinical variables comprise one or more of: (i) an age of the subject; (ii) a prostate-specific antigen (PSA) level; (iii) a primary and secondary biopsy Gleason score; (iv) a clinical stage; and (v) a percentage of tumor positive biopsies.

Treatment decisions in primary, localized prostate cancer are largely subject to a combination of the risk of future disease progression and life expectancy. The National Comprehensive Cancer Network (NCCN) has defined five risk categories based on pre-surgical clinical variables (see Mohler J. et al.). For each risk group, ranging from very low, low, intermediate (dichotomized into favorable vs. unfavorable intermediate), high and very high risk, several options of interventions are presented in current practice prostate cancer guidelines. More advanced tools of clinical risk prediction have been presented in the past in the form of mathematical models, which combine the value of clinical variables into a single score (see Lughezani G. et al., "Predictive and prognostic models in radical prostatectomy candidates: A critical analysis of the literature". European Urology, Vol. 58, No. 5, pages 687-700, 2010). One of the most extensively validated clinical risk algorithms for pre-surgical decision support is the pre-surgical CAPRA score (see Cooperberg M. R., "The UCSF Cancer of the Prostate Risk Assessment (CAPRA) Score: A straightforward and reliable pre-operative predictor of disease recurrence after radical prostatectomy", Journal of Urology, Vol. 173, No. 6, pages 1938-1942, 2005). The score is a combination of clinically available information, i.e., patient age, pre-operative PSA, biopsy Gleason, percentage of tumor positive biopsies, and clinical stage. Initially published in 2005, this score has been validated in several studies since then (see Brajtbord J. S. et al., "The CAPRA score at 10 years: Contemporary perspectives and analysis of supporting studies", European Urology, Vol. 71, No. 5, pages 705-709, 2017). By combining the molecular information provided by the expression based risk score with the information from such extensively validated pre-surgical clinical variables, a pre-surgical prognostic risk score with an improved prognostic power may be obtained.

It is also preferred that the method further comprises:
determining a pre-surgical Cancer of the Prostate Risk Assessment (CAPRA) score for the subject,
wherein the pre-surgical prognostic risk score is determined by combining the expression based risk score and the pre-surgical CAPRA score.

As mentioned above, the pre-surgical CAPRA score is one of the most extensively validated clinical risk algorithm for pre-surgical decision support in prostate cancer. It provides a categorical score between 1 and 10 with three categories of low risk (pre-surgical CAPRA scores 0 to 2), intermediate risk (pre-surgical CAPRA scores 3 to 5), and high risk (pre-surgical CAPRA scores 6 to 10). In view of its current level of validation as a prognostic algorithm in prostate cancer as well as its easy-to-interpret single score output, the pre-surgical CAPRA score can advantageously be combined with the expression based risk score into a pre-surgical prognostic risk score that may easily be determined in clinical practice and that may allow for a further improvement in pre-surgical prognosis compared to the use of the pre-surgical CAPRA algorithm alone.

It is further preferred that the expression based risk score and the pre-surgical CAPRA score are combined with a regression function derived from a population of prostate cancer subjects.

Regression analysis helps one understand how the typical value of the dependent variable (or "criterion variable") changes when any one of the independent variables is varied, while the other independent variables are held fixed. This relationship between the dependent variable and the independent variables is captured in the regression function, which can be used to predict the dependent variable given the values of the independent variables. The dependent variable can be, for example, a binary variable, such as biochemical relapse within 5 years after surgery. In this case, the regression is a logistic regression that is based on a logit function of the independent variables, which, here, comprise or consist of the expression based risk score and the pre-surgical CAPRA score. By means of the regression function, an improved prediction of e.g. the 5-year risk of biochemical recurrence after surgery may be possible.

In an alternative, it is preferred that the pre-surgical prognostic risk score is determined as a modified pre-surgical Cancer of the Prostate Risk Assessment (CAPRA) score for the subject, in which a primary and secondary biopsy Gleason score is replaced by the expression based risk score.

The biopsy Gleason score has, on one hand, a significant impact to the pre-surgical CAPRA score. At the same time, however, it was found by the present inventor that Gleason scoring is subject to substantial variability amongst pathologists. By replacing the information of the biopsy Gleason score within the pre-surgical CAPRA score with the molecular information provided by the expression based risk score, a modified pre-surgical CAPRA score may be obtained that can be more reliable and less susceptible to variations in the assessment provided by different pathologists.

It is further preferred that the expression based risk score is a value in a predefined range, wherein depending on the value a number of points in the range from 0 to 3 are added in the modified pre-surgical CAPRA score.

The primary and secondary biopsy Gleason score is considered in the pre-surgical CAPRA score as follows: If both the primary and secondary biopsy Gleason score are in the range of 1 to 3, no point is added in the modified pre-surgical CAPRA score. Alternatively, if the primary biopsy Gleason score is in the range of 1 to 3 and the secondary biopsy Gleason score is in the range of 4 to 5, one point is added in the modified pre-surgical CAPRA score. Finally, if the primary biopsy Gleason score is in the range of 4 to 5 and the secondary biopsy Gleason score is in the range of 1 to 5, three points are added in the modified pre-surgical CAPRA score. By adding, depending on the value of the expression based risk score, a number of points in the range from 0 to 3 in the modified pre-surgical CAPRA score, the overall structure of the resulting modified pre-surgical CAPRA score can be kept the same with a minimum total score of 0 and a maximum total score of 10.

In one preferred example, the expression based risk score is a value in the range of 1 to 5 and three points are added in the modified pre-surgical CAPRA score if the value is in the range of 1 to <2, whereas two points are added if the value is in the range of 2 to <3, one point is added if the value is in the range of 3 to <4, and no point is added if the value is in the range of 4 to <5.

It is preferred that the method further comprises:
proposing a primary treatment for the subject based on the pre-surgical prognostic risk score,
wherein the primary treatment is selected from the group consisting of: (i) at least a partial prostatectomy; (ii) an active therapy selected from radiation treatment, hormone therapy, chemotherapy, and a combination thereof; and (iii) active surveillance.

As mentioned above, the various national and international guidelines recommend different treatments for a prostate cancer subject depending on the risk of future disease progression and life expectancy. For example, for men with very low and low risk prostate cancer active surveillance (AS) is generally recommended, whereas for high risk cancer a radical prostatectomy could be indicated. However, as also mentioned before, the known clinical risk descriptors do not delineate effectively either the extent of the disease or its aggressiveness for all patients. For instance, it has been found that in the NCCN very low and low risk groups, there is a significant sub-group of patients population with a risk of 10 to 25% cancer recurrence after primary treatment. Likewise, it is known that in the intermediate risk group there is a sub-population with low risk of biochemical progression. By basing the proposing of a primary treatment for the subject on the pre-surgical prognostic risk score, better recommendations on e.g. whether to select active surveillance vs. active intervention, e.g., radical prostatectomy, may be made for certain sub-populations of prostate cancer patients.

It is further preferred that the method comprises:
normalizing the gene expression profile with respect to one or more reference genes selected from the group consisting of: Homo sapiens hypoxanthine phosphoribosyltransferase 1 (HPRT1), Tubulin-Alpha-1b (TUBA1B), Homo sapiens pumilio RNA-Binding Family Member (PUM1), and Homo sapiens TATA box binding protein (TBP),
wherein the expression based risk score is determined based on the normalized gene expression profile.

By normalizing the gene expression profile with respect to one or more reference genes and by determining the expression based risk score is determined based on the normalized gene expression profile, variability in the determination of the expression based risk score can be reduced. This enables differentiation between real variations in gene expression profiles and variations due to the measurement processes. In this respect, it has been found that HPRT1, TUBA1B, PUM1, and TBP are particularly well suited as reference genes for normalizing the PDE4D7 gene expression profile.

The gene expression profile may be determined by detecting mRNA expression using one or more primers and/or probes and/or one or more sets thereof. Moreover, the gene expression profile may be determined by an amplification based method and/or microarray analysis and/or RNA sequencing. The determining of the gene expression profile may include performing Real-Time Quantitative Polymerase Chain Reaction (RT-qPCR) on RNA extracted from the biological sample. In other embodiments, the gene expression profile is determined by RNA sequencing, conventional PCR (using, e.g., end point analysis by gel electrophoresis), or multiplex-PCR. In the case of RT-qPCR, the determining of the gene expression profile may include determining a threshold cycle (Ct) value for PDE4D7 and each of the one or more reference genes. The PCR may be performed with at least one primer and/or probe for measuring a reference gene selected from HPRT1, TUBA1B, PUM1, and TBP.

It is preferred that the one or more reference genes comprise at least two, or at least three of HPRT1, TUBA1B, PUM1, and TBP. In a particularly preferred realization, the one or more reference genes comprise all of HPRT1, TUBA1B, PUM1, and TBP.

Other reference genes which may be additionally or alternatively used for normalizing the PDE4D7 gene expression profile include: Homo sapiens actin, beta, mRNA (ACTB); Homo sapiens 60S acidic ribosomal phosphoprotein P0 mRNA (RPLP0); Polymerase (RNA) II (DNA Directed) Polypeptide A, 220 kDa (POLR2A); Beta-2-Microglobulin (B2M); and Aminolevulinate-Delta-Synthase (ALAS-1).

It is further preferred that the expression based risk score is determined with a scoring function, based on the gene expression profile, the scoring function having been derived from gene expression profiles for biological samples of prostate cancer subjects.

Herein, it is particularly preferred that the scoring function is based on the normalized gene expression profile, e.g., the gene expression profile normalized with respect to all of HPRT1, TUBA1B, PUM1, and TBP, and that the scoring function is derived from correspondingly normalized gene expression profiles for biological samples of prostate cancer subjects. In one preferred realization, the scoring function is a linear transformation that transforms the normalized gene expression profile into a predefined range of values, such as the above-mentioned range of 1 to 5. Such a transformation can be determined by considering the frequency distribution of the normalized gene expression profile values for PDE4D7 for biological samples of a population of prostate cancer subjects and by determining the transformation that transforms the frequency distribution into the desired range. By making use of such a scoring function, the expression based risk score can be expressed in a way that is intuitive to a user, such as in a small positive value range. This is similar to other categories used in the clinical routine, e.g., in histo-pathology grading (Gleason) or multi-parametric MRI radiology scoring (PIRADS).

In one particular realization, the expression based risk score is determined as follows:

$$EBRS=(((PDE4D7\_norm+A)*B)+1), \quad (1)$$

where "EBRS" is the expression based risk score, "PDE4D7 norm" is the normalized PDE4D7 gene expression profile value, and A and B are variables.

In one example, A may be about 6-8, such as 6.7167499999999, B may be 0.4-0.45, such as 0.420780231744713, and the expression based risk score may be a value in the range of 1 to 5 (as mentioned above). The expression based risk score can may also be classified or categorized into one of at least two risk groups, based on the value of the expression based risk score. For example, there may be two risk groups, or three risk groups, or four risk groups, or more than four predefined risk groups. Each risk group covers a respective range of (non-overlapping) expression based risk score. For example, a risk group may include all expression based risk scores from 1 to <2, another risk group from 2 to <3, another risk group from 3 to <4, and another risk group from 4 to <5.

It is particularly preferred that the determining of the gene expression profile comprises performing RT-qPCR on RNA extracted from the biological sample, wherein a Cq value is determined for PDE4D7 and for each of the one or more reference genes, and wherein the determining of the expression based risk score includes normalizing the Cq value for PDE4D7 using the Cq value for each of the one or more reference genes and computing the expression based risk score as a linear function of the normalized Cq value.

For example, the normalized Cq value for PDE4D7 may be generated by applying the following:

$$N(Cq_{PDE4D7})=\text{Mean}(Cq_{ref\_genes})-(Cq_{PDE4D7}), \quad (2)$$

where $N(Cq_{PDE4D7})$ is the normalized genes expression profile value (quantification cycle, Cq) of PDE4D7, $\text{Mean}(Cq_{ref\_genes})$ is the arithmetic mean of the PCR Cq values of the one or more reference gene, and $Cq_{PDE4D7}$ is the PCR Cq value of PDE4D7.

It is preferred that the gene expression profile further includes expression information from phosphodiesterase 4D variant 5 (PDE4D5) and/or from phosphodiesterase 4D variant 9 (PDE4D9), wherein an expression based risk score is determined for the subject for each of the phosphodiesterase 4D variants based on the gene expression profile, and wherein the pre-surgical prognostic risk score for the subject is determined based on the expression based risk scores and the pre-surgical clinical variables of the subject.

In a further aspect of the present invention, a diagnostic kit is presented, comprising:

at least one primer and/or probe for determining the gene expression profile for phosphodiesterase 4D variant 7 (PDE4D7) in a biological sample obtained from a prostate cancer subject; and optionally, at least one primer and/or probe for determining the gene expression profile for one or more reference genes selected from the group consisting of: *Homo sapiens* hypoxanthine phosphoribosyltransferase 1 (HPRT1), Tubulin-Alpha-1b (TUBA1B) *Homo sapiens* pumilio RNA-Binding Family Member (PUM1), and *Homo sapiens* TATA box binding protein (TBP); and optionally, at least one agent for determining a prostate-specific antigen (PSA) level in a biological sample obtained from the subject; and optionally, instructions for computing a pre-surgical prognostic risk score based on the gene expression profile for PDE4D7 and pre-surgical clinical variables of the subject, the instructions optionally being stored on a computer program product which, when executed by a computer, perform a method comprising:

determining an expression based risk score for the subject based on the gene expression profile for PDE4D7, and determining the pre-surgical prognostic risk score for the subject based on the expression based risk score and the pre-surgical clinical variables of the subject, optionally, wherein the method comprises:

normalizing the gene expression profile for PDE4D7 with respect to the one or more reference genes, wherein the expression based risk score is determined based on the normalized gene expression profile for PDE4D7, optionally, wherein the pre-surgical clinical variables comprise the prostate-specific antigen (PSA) level.

The at least one agent for determining the prostate-specific antigen (PSA) level can be, e.g., a PSA specific antibody or the like.

In a further aspect of the present invention, a use of the kit as defined in claim 13 in a method of pre-surgical risk stratification of a prostate cancer subject is presented.

In a further aspect of the present invention, a use of a gene expression profile for phosphodiesterase 4D variant 7 (PDE4D7) in pre-surgical risk stratification of a prostate cancer subject is presented, comprising:

determining the gene expression profile in a biological sample obtained from the subject, determining an expression based risk score for the subject based on the gene expression profile, and determining a pre-surgical prognostic risk score for the subject based on the expression based risk score and pre-surgical clinical variables of the subject.

In a further aspect of the present invention, a computer program product is presented comprising instructions which, when the program is executed by a computer, cause the computer to carry out a method comprising:

determining a gene expression profile for phosphodiesterase 4D variant 7 (PDE4D7) in a biological sample obtained from a prostate cancer subject, determining an expression based risk score for the subject based on the gene expression profile, and determining a pre-surgical prognostic risk score for the subject based on the expression based risk score and pre-surgical clinical variables of the subject.

It shall be understood that the method of claim 1, the diagnostic kit of claim 13, the use of the diagnostic kit of claim 14, the use of a gene expression profile of claim 15, and the computer program of claim 16 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Overview of pre-surgical risk stratification

Figure 1:
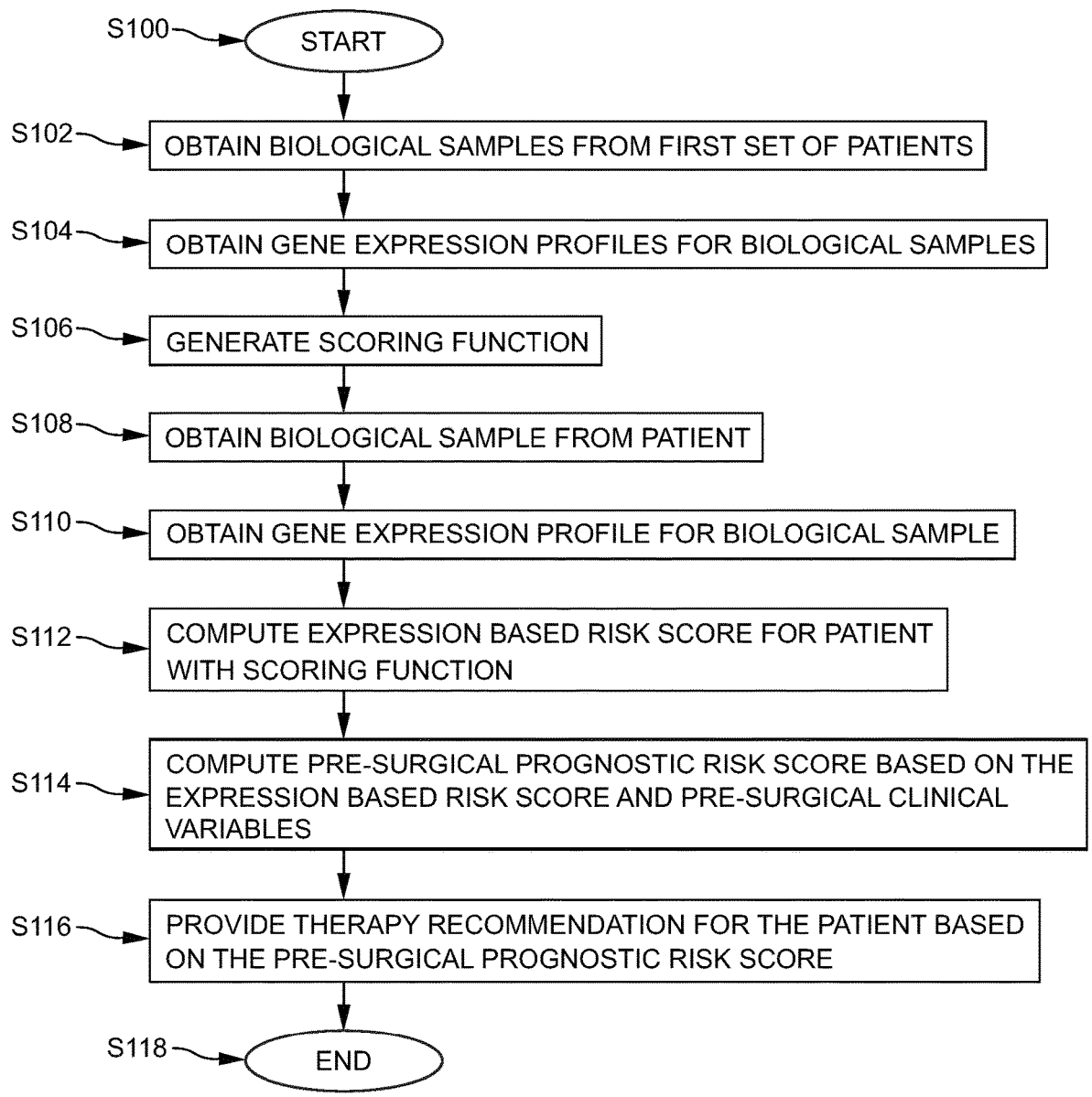
FIG. 1 shows schematically and exemplarily a flowchart of an embodiment of a method of pre-surgical risk stratification of a prostate cancer subject.

FIG. 1 shows schematically and exemplarily a flowchart of an embodiment of a method of pre-surgical risk stratification of a prostate cancer subject.

The method begins at step S100.

At step S102, a biological sample is obtained from each of a first set of patients (subjects) diagnosed with prostate cancer. Preferably, monitoring prostate cancer has been performed for these prostate cancer patients over a period of time, such as at least one year, or at least two years, or about five years, after obtaining the biological sample.

At step S104, a gene expression profile for PDE4D7 is obtained for each of the biological samples obtained from the first set of patients, e.g., by performing RT-qPCR (real-time quantitative PCR) on RNA extracted from each biological sample. The exemplary gene expression profile includes an expression level (e.g., value) for PDE4D7 which can be normalized using value(s) for each of a set of reference genes, such as HPRT1, TUBA1B, PUM1, and/or TBP. In one realization, the gene expression profile value of PDE4D7 is normalized to with respect to one or more reference genes selected from the group consisting of HPRT1, TUBA1B, PUM1, and TBP, e.g., at least one, or at least two, or at least three, or, preferably, all of these reference genes.

At step S106, a scoring function for assigning an expression based risk score is determined, based on the gene expression profile for PDE4D7 obtained for at least some of the biological samples obtained for the first set of patients and respective results obtained from the monitoring. In one preferred realization, the scoring function is a linear transformation that transforms the normalized gene expression profile into a predefined range of values, such as the above-mentioned range of 1 to 5. As mentioned above, such a transformation can be determined by considering the frequency distribution of the normalized gene expression profile values for PDE4D7 for biological samples of a population of prostate cancer subjects (here, the first set of patients) and by determining the transformation that transforms the frequency distribution into the desired range. In one particular realization, the expression based risk score is determined as specified in Eq. (1) above.

At step S108, a biological sample is obtained from a patient (subject or individual). The patient can be a new patient or one of the first set.

At step S110, a gene expression profile is obtained for PDE4D7, e.g., by performing PCR on the biological sample. In one realization, the gene expression profile value of PDE4D7 is normalized to with respect to one or more reference genes selected from the group consisting of HPRT1, TUBA1B, PUM1, and TBP, e.g., at least one, or at least two, or at least three, or, preferably, all of these reference genes. This is substantially the same as in step S104.

Other reference genes which may be additionally or alternatively used in steps S104 and S110 include: Homo sapiens actin, beta, mRNA (ACTB); Homo sapiens 60S acidic ribosomal phosphoprotein P0 mRNA (RPLP0); Polymerase (RNA) II (DNA Directed) Polypeptide A, 220 kDa (POLR2A); Beta-2-Microglobulin (B2M); and Aminolevulinate-Delta-Synthase (ALAS-1).

At step S112, an expression based risk score is determined for the patient, based on the gene expression profile, using the derived scoring function.

At step S114, a pre-surgical prognostic risk score is determined for the patient based on the expression based risk score and pre-surgical clinical variables of the patient. This will be described in more detail later in the description.

At S116, a therapy recommendation may be provided, e.g., to the patient or his or her guardian, to a doctor, or to another healthcare worker, based on the pre-surgical prognostic risk score. To this end, the pre-surgical prognostic risk score may be categorized into one of a predefined set of risk groups, based on the value of the pre-surgical prognostic risk score. Providing a therapy recommendation may include one or more of: a) proposing a therapy for the patient based on the assigned risk group, with at least two of the risk groups being associated with different therapies, b) computing a disease progression risk prediction of the patient before or after prostate surgery; and c) computing a therapy response prediction for the patient before or after prostate surgery. Example therapies include at least a partial prostatectomy, an active therapy selected from radiation treatment, chemotherapy, and a combination thereof, and observation alone, i.e., without performing prostatectomy or active therapy (i.e., active surveillance).

The method ends at S118.

Each of the risk groups may be associated with a respective proposed therapy, which differs in its aggressiveness. Each proposed therapy may be based on the results of the patients from the first set that were assigned to that risk group and is one which is predicted to provide the least aggressive therapy which does not exceed a threshold clinical risk for development of prostate cancer. In some cases, this enables a new patient to be assigned to a risk group associated with a less aggressive proposed therapy than would be the case for other risk profiling methods, such as that using the Gleason score, the NCCN risk categories, or the pre-surgical CAPRA score.

In one embodiment, the gene expression profiles at steps S104 and S110 are determined by detecting mRNA expression using one or more primers and/or probes and/or one or more sets thereof.

A detailed description of PDE4D7 and the one or more reference genes including their Transcript ID (NCBI RefSeq) and the corresponding amino acid sequences for the primer pair and probe are shown in TABLE 3. This table also shows, for each gene, a sense primer, and antisense primer, and a probe sequence that specifically binds to the amplicon.

TABLE 1

Exemplary primer and probe nucleic acid sequences

| Gene Name | Exemplary NCBI RefSeq | Exemplary Protein Accession | Sense Primer | Antisense primer | Probe Sequence |
|---|---|---|---|---|---|
| PDE4D7 | NM_001165 899.1 (SEQ ID NO: 19) | NP_001159 371.1 (SEQ ID NO: 20) | GAACATTCAA CGACCAACCA (SEQ ID | TGCCATTGT CCACATCA AAA (SEQ | CTGCCGCTGAT TGCTATCACTTC TGCA (SEQ ID |

TABLE 1-continued

Exemplary primer and probe nucleic acid sequences

| Gene Name | Exemplary NCBI RefSeq | Exemplary Protein Accession | Sense Primer | Antisense primer | Probe Sequence |
|---|---|---|---|---|---|
| | | | NO: 21) CGCTGATTGC TATCACTTCT GC (SEQ ID NO: 24) | ID NO: 22) GTCGTTGAC TGTGGACA AAATTTG (SEQ ID NO:25) | NO:23) TTCCCTTGGATC CCATGACCAGC CCATAAGGGAA (SEQ ID NO:26) |
| HPRT1 | NM_000194.2 (SEQ ID NO: 34) | NP_000185.1 (SEQ ID NO: 35) | GAGGATTTGG AAAGGGTGTT TATT (SEQ ID NO: 36) | ACAGAGGG CTACAATGT GATG (SEQ ID NO: 37) | ACGTCTTGCTC GAGATGTGATG AAGG (SEQ ID NO:38) |
| TUBA1B | NM_006082.2 (SEQ ID NO: 39) | NP_006073.2 (SEQ ID NO: 40) | TGACTCCTTC AACACCTTCT TC (SEQ ID NO: 41) | TGCCAGTGC GAACTTCAT (SEQ ID NO: 42) | CCGGGCTGTGT TTGTAGACTTG GA (SEQ ID NO:43) |
| PUM1 | NM_001020658.1 (SEQ ID NO: 44); NMJM4676.2 (SEQ ID NO:45) | NP_001018494.1 (SEQ ID NO: 46); NP_055491.1 (SEQ ID NO:47) | GCCAGCTTGT CTTCAATGAA AT (SEQ ID NO: 48) | CAAAGCCA GCTTCTGTT CAAG (SEQ ID NO: 49) | ATCCACCATGA GTTGGTAGGCA GC (SEQ ID NO:50) |
| TBP | NM_003194.4 (SEQ ID NO: 51) | NP_003185.1 (SEQ ID NO: 52) | GCCAAGAAG AAAGTGAAC ATCAT (SEQ ID NO: 53) | ATAGGGAT TCCGGGAG TCAT (SEQ ID NO: 54) | TCAGAACAACA GCCTGCCACCT TA (SEQ ID NO: 55) |
| ACTB | NM_001101.3 (SEQ ID NO: 56) | NP_001092.1 (SEQ ID NO: 57) | CCAACCGCGA GAAGATGA (SEQ ID NO: 58) | CCAGAGGC GTACAGGG ATAG (SEQ ID NO: 59) | CCATGT ACGTT GCTATCCAGGC T (SEQ ID NO: 60) |
| RPLP0 | NM_001002.3 (SEQ ID NO: 61) | NP_44450 5.1/NP_000993.1 (SEQ ID NO: 62/63) | TAAACCCTGC GTGGCAAT (SEQ ID NO: 64) | ACATTTCGG ATAATCATC CAATAGTTG (SEQ ID NO: 65) | AAGTAGTTGGA CTTCCAGGTCG CC (SEQ ID NO: 66) |
| ALAS-1 | NM_000688.5/NM_199166.2 (SEQ ID NO: 67/68) | NP_000679.1/NP_954635.1 (SEQ ID NO: 69/70) | AGCCACATCA TCCCTGT (SEQ ID NO: 71) | CGTAGATGT TATGTCTGC TCAT (SEQ ID NO: 72) | TTTAGCAGCAT CTGCAACCCGC (SEQ ID NO: 73) |

To explore the prognostic power of PDE4D7 in pre-surgical patient risk assessment, the correlation to disease recurrence in the context of pre-surgical risk variables and algorithms like the pre-surgical CAPRA score were investigated. Combination models of the expression based risk score together with pre-surgical variables were developed in a surgery cohort and the model was validated in independent patients on diagnostic biopsy tissue. The results show that PDE4D7 may add additional information to pre-surgical variables or prognostic scores that are based on such variables, such as the pre-surgical CAPRA score, that may allow for better patient stratification in order to optimize primary treatment decisions.

EXAMPLES

Patient Cohorts and Samples

Two patient cohorts, a radical prostatectomy (RP) patient cohort and a diagnostic biopsy (DB) patient cohort, with the demographics shown in TABLE 2, were employed. For the RP patient cohort, a small biopsy punch (approximately 1 millimeter by 2 millimeters) of tissue was collected of a representative tumor area from the resected prostate from 550 patients who had been consecutively operated on between 2000 and 2004 at a single high-volume clinical center in Germany. After quality control of the study data based on pre-defined criteria and removal of patients who underwent adjuvant hormone therapy 503 patient samples were found eligible for statistical analysis. For the DB patient cohort, a single biopsy punch (approximately 1 millimeter by 2 millimeters) was collected from the tumor positive diagnostic biopsy with the highest Gleason grade per patient. The 168 patients in this case were diagnosed with prostate cancer and operated on between 1995 and 2011 at the University Klinik Muenster, Germany. In total, diagnostic needle biopsy tissues of 151 patients were found eligible for statistical analysis.

TABLE 2

Demographics of the radical prostatectomy (RP) patient cohort and the diagnostic biopsy (DB) patient cohort

| Surgery: 2000-2004 | Parameter | RP cohort (#503) | DB cohort (#151) |
|---|---|---|---|
| Clinical Range (median; IQR) | Age (at RP) | 41.3-74.5 (62.6; 7.4) | 47.4-77.4 (64.9; 8.5) |
| | Preoperative PSA | 0.18-73.16 (6.7; 5.5) | 2.0-49.1 (8.1; 5.7) |
| | Percent tumor in biopsy | 0.2-79.7 (10.3; 16.0) | N/A |
| | Prostate Volume | 9-148 (42; 22.5) | 13.6-148.0 (38.5; 19.2) |
| | PSA density | 0.1-2.03 (0.16; 0.14) | 0.03-1.6 (0.2; 0.17) |
| CAPRA Risk Category No. of patients (percentage) | Low Risk (CAPRA 0-2) | 225 (44.7%) | 38 (25.2%) |
| | Intermediate Risk (CAPRA 3-5) | 263 (52.3%) | 82 (54.3%) |
| | High Risk (CAPRA > 5) | 15 (3.0%) | 31 (20.5%) |
| Pre-Surgery Pathology No. of patients (percentage) | Biopsy Gleason 3 + 3 (GG1) | 316 (62.8%) | 77 (51.0%) |
| | Biopsy Gleason 3 + 4 (GG2) | 149 (29.6%) | 38 (25.2%) |
| | Biopsy Gleason 4 + 3 (GG3) | 25 (5.0%) | 20 (13.2%) |
| | Biopsy Gleason ≥4 + 4 (≥GG4) | 13 (2.6%) | 16 (10.6%) |
| | cT1 | 342 (68%) | |
| | cT2 | 150 (29.8%) | 97 (64.2%) |
| | cT3 | 11 (2.2%) | 54 (35.8%) |
| Post-Surgery Pathology No. of patients (percentage) | Pathology Gleason 3 + 3 (GG1) | 201 (40%) | 46 (30.5%) |
| | Pathology Gleason 3 + 4 (GG2) | 257 (51.1%) | 52 (34.4%) |
| | Pathology Gleason 4 + 3 (GG3) | 41 (8.2%) | 31 (20.5%) |
| | Pathology Gleason >= 4 + 4 (≥GG4) | 4 (0.8%) | 22 (14.6%) |
| | pT2 | 331 (65.8%) | 88 (58.3%) |
| | pT3 | 172 (34.2%) | 63 (41.7%) |
| | pT4 | 0 (0%) | 0 (0%) |
| | Positive Surgical Margins | 120 (23.9%) | 33 (21.9%) |
| | Capsular Status | 113 (22.5) (=T3a) | 57 (39.3%) infiltrated |
| | | | 75 (51.7%) penetrated |
| | Positive Seminal Vesicle Invasion | 60 (11.9%) | N/A |
| | Positive Lymph Node Invasion | 5 (1%) | 10 (6.6%) |
| Follow-up Months | Mean IQR median | 123.6 | 73.7 |
| | | 141.8 | 73.6 |
| Outcome No. of events/ Surgery: 2000-2004 total no. of patients (percentage) | <5 y BCR | 92/446 (20.6%) | 45/151 (29.8%) |
| | <10 y BCR | 134/347 (38.6%) | N/A |
| | Parameter | RP cohort (#503) | DB cohort (#151) |
| | <5 y CR | 5/441 (1.1%) | N/A |
| | <10 y CR | 13/306 (4.2%) | N/A |
| Salvage Treatment No. of events/ total no. of patients (percentage) | <5 y SRT | 53/439 (12.1%) | 12/151 (7.9%) |
| | <10 y SRT | 83/320 (25.9%) | N/A |
| | <5 y SADT | 27/441 (6.1%) | 16/151 (10.6%) |
| | <10 y SADT | 54/312 (17.3%) | N/A |
| Mortality No. of events/ total no. of patients (percentage) | <5 y PCSS | 17/453 (1.1%) | 1/151 (0.7%) |
| | <10 y PCSS | 38/330 (2.6%) | 0/151 (0%) |
| | <5 y OS | 5/441 (3.7%) | 1/151 (0.7%) |
| | <10 y OS | 10/302 (11.2%) | 5/151 (3.3%) |

For patient age, preoperative PSA, percentage of tumor in biopsy, prostate volume, and PSA density, the minimum and maximum values in the each cohort are shown, while the median and IQR values are depicted in parentheses. For the CAPRA risk categories, the number of patients and percentage per risk group are shown. In case of pre-surgical pathology, the biopsy Gleason scores and the Gleason grade groups as well as clinical stages are indicated (by number and percentage of patients). Post-surgical pathology is represented by the pathology Gleason scores and Gleason grade groups, the pathology stages, the surgical margin status after prostatectomy, the tumor invasion status of the seminal vesicles and pelvic lymph nodes (by number and percentage of patients). In this respect, it is noted that the extracapsular extension was not provided as a primary parameter but was derived from pathology stage pT3a. The follow-up demonstrates the mean and median follow-up periods in months after surgery for all patients. The outcome category illustrates the cumulative 5- and 10-year biochemical recurrence (BCR) and clinical recurrence to metastases (CR) post-surgical primary treatment. The treatment category lists the cumulative 5- and 10-year start to salvage radiation therapy (SRT) or salvage androgen deprivation therapy (SADT) after surgery. Mortality is shown as prostate cancer specific survival (PCSS) as well as overall survival (OS). For all outcomes, the number of men experiencing the outcome per total number of men with the respective 5- or 10-year follow are shown, wherein the percentage of events is given in parentheses. (B) Demographics of the diagnostic biopsy patient cohort. (N/A=not available).

Laboratory Methods

All used laboratory methods including oligonucleotide primers and probes for RT-qPCR (quantitative real-time PCR), RNA extraction, and quality control and procedures to include/discard samples from the statistical analysis were as described previously in Böttcher R. et al. The primers and probes used for the RT-qPCR to measure the genes of interest as well as the reference genes are also given in TABLE 1.

RESULTS

Correlation of the Expression Based Risk Score to Longitudinal Clinical Outcomes The continuous expression based risk score (i.e., the reference gene normalized and transformed expression of the PDE4D7 transcript) was correlated to pre-surgical clinical variables in the two patient cohorts: the RP patient cohort and the DB patient cohort.

TABLES 3 to 8 show the uni- and multivariate Cox regression analysis of the biochemical recurrence (BCR) free survival and overall survival (OS) of the continuous expression based risk scores. In the multivariate analysis, the expression based risk scores were adjusted by pre-surgical clinical variables, namely, by the age at surgery, the pre-operative PSA, the PSA density, the biopsy Gleason grade group, the percentage of tumor positive biopsy cores, the percentage of tumor in biopsy, and the clinical stage (see TABLES 3, 5, and 7) or by the pre-surgical Cancer of the Prostate Risk Assessment (CAPRA) score (see TABLES 4, 6, and 8). The biopsy Gleason grade group and the clinical stage were modeled as categories with the lowest category used as a reference. All other demographic and clinical variables as well as the expression based risk scores were modeled as continuous variables. All variables were entered into the multivariate model and the respective statistical measures are given in the tables.

Univariate Cox regression analysis demonstrated a very significant correlation of the continuous expression based risk score to time to BCR in the two investigated patient cohorts with HR=0.53; 95% CI=0.41–0.67; p<0.0001, and HR=0.43; 95% CI=0.33–0.65, p<0.0001, respectively (see TABLES 3 and 7). Adjusting the multivariate Cox regression analysis for the pre-surgical variables or the pre-surgical CAPRA score resulted in a significant independent contribution to the prediction of post-surgical BCR for the continuous expression based risk score (see TABLES 3, 4, 7, and 8). Moreover, when testing the endpoint overall survival (OS) in the RP patient cohort, we observed a similar independent predictive power of the continuous expression based risk score when adjusting to the relevant pre-surgical clinical variables or the pre-surgical CAPRA score (see TABLES 5 and 6). Interestingly though, only age (HR=1.1; 95% CI=1.03–1.2; p=0.007) and clinical stage cT2 and cT3 remained significant predictors in the multivariate model apart from the expression based risk score (HR=0.43; 95% CI=0.29–0.62; p<0.0001). The pre-surgical CAPRA score was a significant predictor of overall survival in the univariate analysis (HR=1.2; 95% CI=1.3–1.6; p=0.01), while it fell below statistical significance in the multivariate analysis (HR=1.2; 95% CI 0.99–1.4; p=0.06). The continuous expression based risk score remained very significant also in the multivariate modeling (HR=0.4; 95% CI=0.28–0.58; p<0.0001; TABLES 5 and 6).

TABLE 3

Uni- and multivariate Cox regression analysis of the biochemical recurrence (BCR) free survival of the expression based risk score in the RP patient cohort (#503), wherein the expression based risk score was adjusted for pre-surgical variables in the multivariate analysis.

| Pre-Surgical Clinical parameters | Univariate (enter) | | | Multivariate (enter) | | |
|---|---|---|---|---|---|---|
| Endpoint BCR (#148/#503; 29.4%) | p value | HR | 95% CI of HR | p value | HR | 95% CI of HR |
| Age at surgery | 0.88 | 1.0 | 0.97-1.03 | 0.77 | 1.00 | 0.96-1.02 |
| Pre-operative PSA | 0.0002 | 1.03 | 1.01-1.04 | 0.00 | 1.08 | 1.03-1.1 |
| PSA density | 0.0100 | 2.15 | 1.2 to 3.8 | 0.03 | 0.12 | 0.02-0.8 |
| Biopsy Gleason GG1 (#316), Reference | | | | | | |
| Biopsy Gleason GG2 (#149) | 0.0003 | 1.9 | 1.4-2.8 | 0.02 | 1.56 | 1.06-2.3 |
| Biopsy Gleason ≥GG3 (#38) | <0.0001 | 6.2 | 3.9-9.7 | <0.0001 | 4.82 | 2.9-7.9 |
| Percentage Tumor Positive Biopsy Cores | <0.0001 | 4.2 | 2.3-7.7 | 0.08 | 2.29 | 0.91-5.7 |
| Percentage Tumor in Biopsy | <0.0001 | 1.0 | 1.02-1.04 | 0.00 | 1.02 | 1.01-1.04 |
| Clinical Stage cT1c (#342); Reference | | | | | | |
| Clinical stage cT2&cT3 (#161) | <0.0001 | 2.1 | 1.5 to 2.9 | 0.20 | 1.27 | 0.88-1.8 |
| Expression based risk score (continuous) | <0.0001 | 0.53 | 0.41 to 0.67 | <0.0001 | 0.52 | 0.4-0.68 |

TABLE 4

Uni- and multivariate Cox regression analysis of the biochemical recurrence (BCR) free survival of the expression based risk score in the RP patient cohort (#503), wherein the expression based risk score was adjusted for the pre-surgical CAPRA score in the multivariate analysis.

| Pre-Surgical Clinical parameters | Univariate (enter) | | | Multivariate (enter) | | |
|---|---|---|---|---|---|---|
| Endpoint BCR (#148/#503; 29.4%) | p value | HR | 95% CI of HR | p value | HR | 95% CI of HR |
| CAPRA score | <0.0001 | 1.5 | 1.3 to 1.6 | <0.0001 | 1.7 | 1.5 to 1.9 |
| Expression based risk score (continuous) | <0.0001 | 0.53 | 0.41 to 0.67 | <0.0001 | 0.52 | 0.4-0.68 |

TABLE 5

Uni- and multivariate Cox regression analysis of the overall survival (OS) of the expression based risk score in the RP patient cohort (#503), wherein the expression based risk score was adjusted for pre-surgical variables in the multivariate analysis.

| Pre-Surgical Clinical parameters | Univariate (enter) | | | Multivariate (enter) | | |
| --- | --- | --- | --- | --- | --- | --- |
| Endpoint BCR (#52/#503; 10.3%) | p value | HR | 95% CI of HR | p value | HR | 95% CI of HR |
| Age at surgery | 0.001 | 1.1 | 1.03-1.2 | 0.007 | 1.1 | 1.01-1.1 |
| Pre-operative PSA | 0.93 | 1.0 | 0.96-1.03 | 0.74 | 0.99 | 0.96-1.03 |
| Biopsy Gleason GG1 (#316), Reference | | | | | | |
| Biopsy Gleason GG2 (#149) | 0.04 | 1.7 | 1.01-3.0 | 0.20 | 1.5 | 081-2.6 |
| Biopsy Gleason ≥GG3 (#38) | 0.001 | 3.3 | 1.6-6.8 | 0.14 | 1.8 | 0.82-3.9 |
| Percentage Tumor Positive Biopsy Cores | 0.86 | 1.1 | 0.39-3.0 | 0.75 | 1.3 | 0.3-5.4 |
| Percentage Tumor in Biopsy | 0.71 | 1.0 | 0.99-1.01 | 0.75 | 1.0 | 0.97-1.02 |
| Clinical Stage cT1c (#342); Reference | | | | | | |
| Clinical stage cT2&cT3 (#161) | 0.02 | 1.77 | 1.1-2.9 | 0.03 | 1.8 | 1.05-3.1 |
| Expression based risk score (continuous) | <0.0001 | 0.39 | 0.27-56 | <0.0001 | 0.43 | 0.29-0.62 |

TABLE 6

Uni- and multivariate Cox regression analysis of the overall survival (OS) of the expression based risk score in the RP patient cohort (#503), wherein the expression based risk score was adjusted for the pre-surgical CAPRA score in the multivariate analysis.

| Pre-Surgical Clinical parameters | Univariate (enter) | | | Multivariate (enter) | | |
| --- | --- | --- | --- | --- | --- | --- |
| Endpoint BCR (#64/#503; 12.7%) | p value | HR | 95% CI of HR | p value | HR | 95% CI of HR |
| CAPRA score | 0.01 | 1.2 | 1.3-1.6 | 0.06 | 1.2 | 0.99-1.4 |
| Expression based risk score (continuous) | <0.0001 | 0.39 | 0.33-0.65 | <0.0001 | 0.40 | 0.28-0.58 |

TABLE 7

Uni- and multivariate Cox regression analysis of the biochemical recurrence (BCR) free survival of the expression based risk score in the DB patient cohort (#151), wherein the expression based risk score was adjusted for pre-surgical variables in the multivariate analysis.

| Pre-Surgical Clinical parameters | Univariate (enter) | | | Multivariate (enter) | | |
| --- | --- | --- | --- | --- | --- | --- |
| Endpoint BCR (#55/#151; 36.4%) | p value | HR | 95% CI of HR | p value | HR | 95% CI of HR |
| Age at surgery | 0.81 | 0.99 | 0.95-1.04 | 0.006 | 0.94 | 0.89-0.98 |
| Pre-operative PSA | 0.0001 | 1.04 | 1.02-1.06 | 0.002 | 1.1 | 1.03-1.2 |
| PSA density | 0.003 | 2.7 | 1.4-5.3 | 0.18 | 0.26 | 0.04-1.9 |
| Biopsy Gleason GG1 (#85), Reference | | | | | | |
| Biopsy Gleason GG2 (#44) | 0.07 | 1.9 | 0.95-3.8 | 0.10 | 1.9 | 0.89-3.9 |
| Biopsy Gleason GG3 (#20) | 0.0001 | 4.3 | 2.04-9.2 | 0.02 | 2.6 | 1.2-5.7 |
| Biopsy Gleason GG4 (#7) | 0.0007 | 5.7 | 2.1-15.8 | 0.01 | 4.1 | 1.4-11.6 |

TABLE 7-continued

Uni- and multivariate Cox regression analysis of the biochemical recurrence (BCR) free survival of the expression based risk score in the DB patient cohort (#151), wherein the expression based risk score was adjusted for pre-surgical variables in the multivariate analysis.

| Pre-Surgical Clinical parameters | Univariate (enter) | | | Multivariate (enter) | | |
|---|---|---|---|---|---|---|
| Endpoint BCR (#55/#151; 36.4%) | p value | HR | 95% CI of HR | p value | HR | 95% CI of HR |
| Biopsy Gleason GG5 (#11) | <0.0001 | 8.0 | 3.5-18.4 | 0.03 | 2.9 | 1.1-7.6 |
| Percentage Tumor Positive Biopsy Cores | 0.013 | 4.6 | 1.4-15.2 | 0.19 | 2.4 | 0.63-9.4 |
| Clinical Stage cT2 (#108); Reference | | | | | | |
| Clinical stage cT3 (#60) | 0.007 | 2.0 | 1.2-3.4 | 0.05 | 1.7 | 0.99-3.1 |
| Expression based risk score (continuous) | <0.0001 | 0.47 | 0.33-0.65 | <0.0001 | 0.43 | 0.29-0.63 |

TABLE 8

Uni- and multivariate Cox regression analysis of the biochemical recurrence (BCR) free survival of the expression based risk score in the DB patient cohort (#151), wherein the expression based risk score was adjusted for the pre-surgical CAPRA score in the multivariate analysis.

| Pre-Surgical Clinical parameters | Univariate (enter) | | | Multivariate (enter) | | |
|---|---|---|---|---|---|---|
| Endpoint BCR (#55/#151; 36.4%) | p value | HR | 95% CI of HR | p value | HR | 95% CI of HR |
| CAPRA score | <0.0001 | 1.5 | 1.3-1.6 | <0.0001 | 1.4 | 1.2-1.6 |
| expression based risk score (continuous) | <0.0001 | 0.47 | 0.33-0.65 | 0.0001 | 0.53 | 0.38-0.74 |

Pre-surgical Prognostic Risk Score Based on the Expression Based Risk Score and Pre-Surgical Clinical Variables To further explore the prognostic power of PDE4D7, the benefit of a combination of the expression based risk score with pre-surgical clinical variables used to prognosticate prostate cancer patients for various treatment regimens was tested. Based on the multivariate Cox regression data, it was hypothesized that a combination of the pre-surgical CAPRA score together with the expression based risk score will provide a significant improvement in prognostic power over pre-surgical clinical variables alone. To evaluate this hypothesis, a sub-cohort of 449 patients (92 events; 20.5%) of the RP patient cohort with complete 5-year outcome histories was selected and a logistic regression model to combine the expression based risk score with the pre-surgical CAPRA score to predict the 5-year risk of biochemical recurrence after surgery was generated. The logit (p) regression function was transformed to $p=1/(1+\hat{\ }(-logit(p))$ in order to calculate the probability p for an individual patient to experience a biochemical relapse within 5 years after surgery.

The modeling proved the independent predictive value of the expression based risk score to the pre-surgical CAPRA metric (Odds ratio 0.46; 95% CI 0.3-0.69; p=0.0002; data not shown). Next, this pre-surgical CAPRA score and expression based risk score logistic regression model was tested independently on 151 patients who were eligible for statistical data analysis. All patients had a minimum of 60 months of follow-up after operation. The methods used to investigate the power of the pre-surgical CAPRA score and expression based risk score logistic regression model were (i) Kaplan-Meier survival analysis, (i) ROC curve analysis, as well as (iii) re-classification and decision curve analysis.

Figure 2:
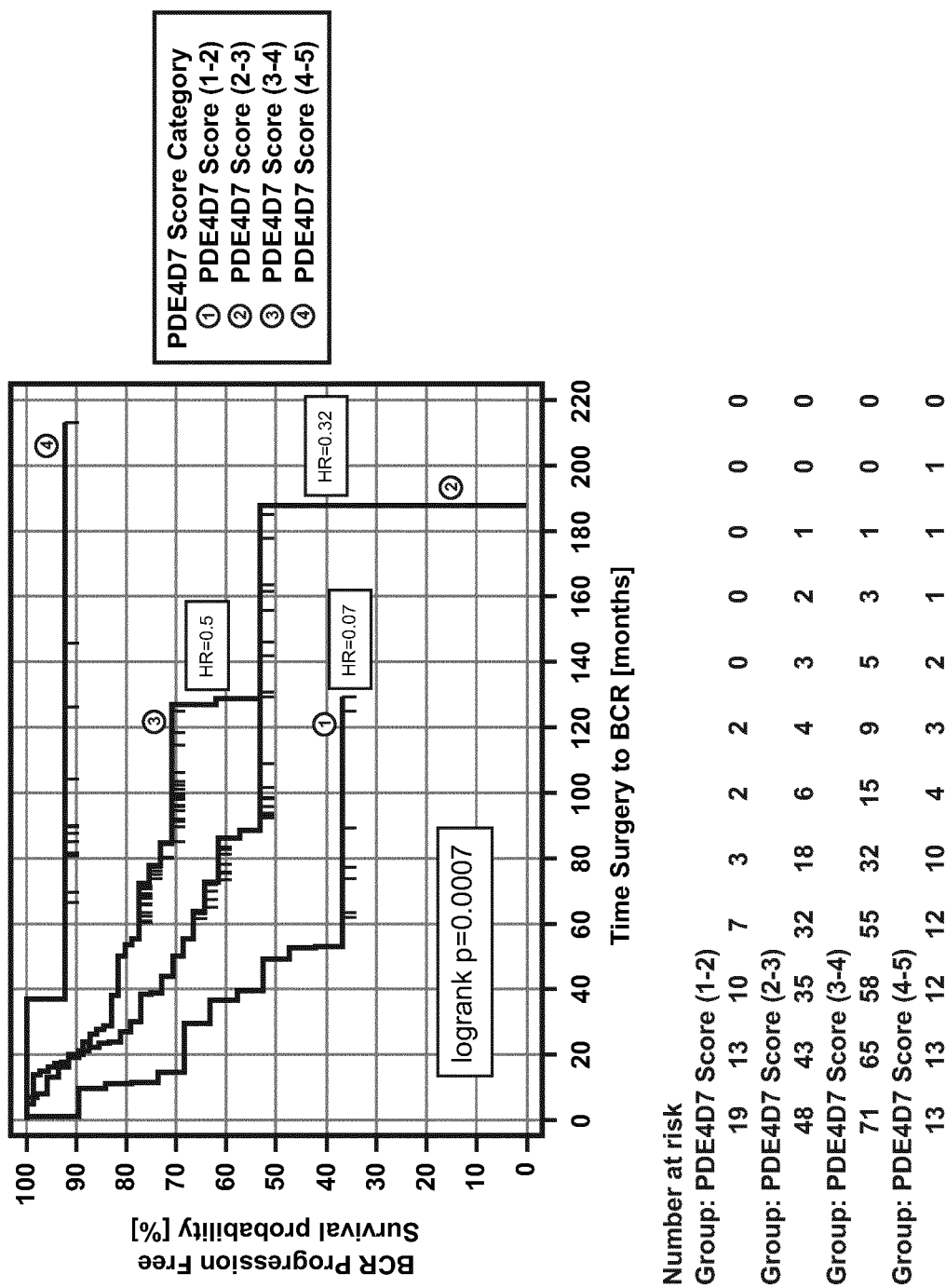
FIGS. 2 to 7 show results of Kaplan-Meier survival analysis of the time to PSA relapse or start of any salvage therapy after radical prostatectomy in the DB patient cohort (#151)
Figure 3:
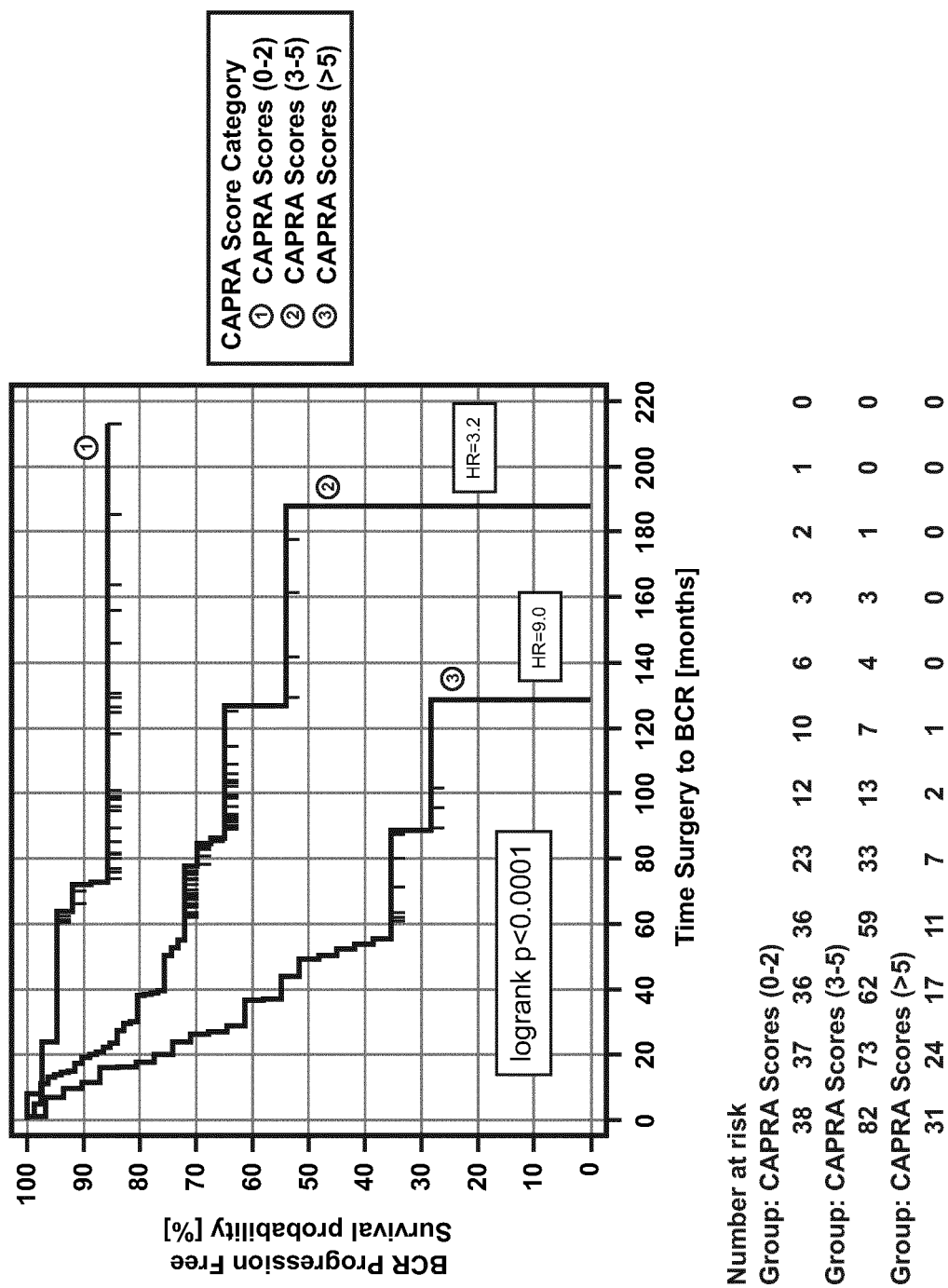
Figure 4:
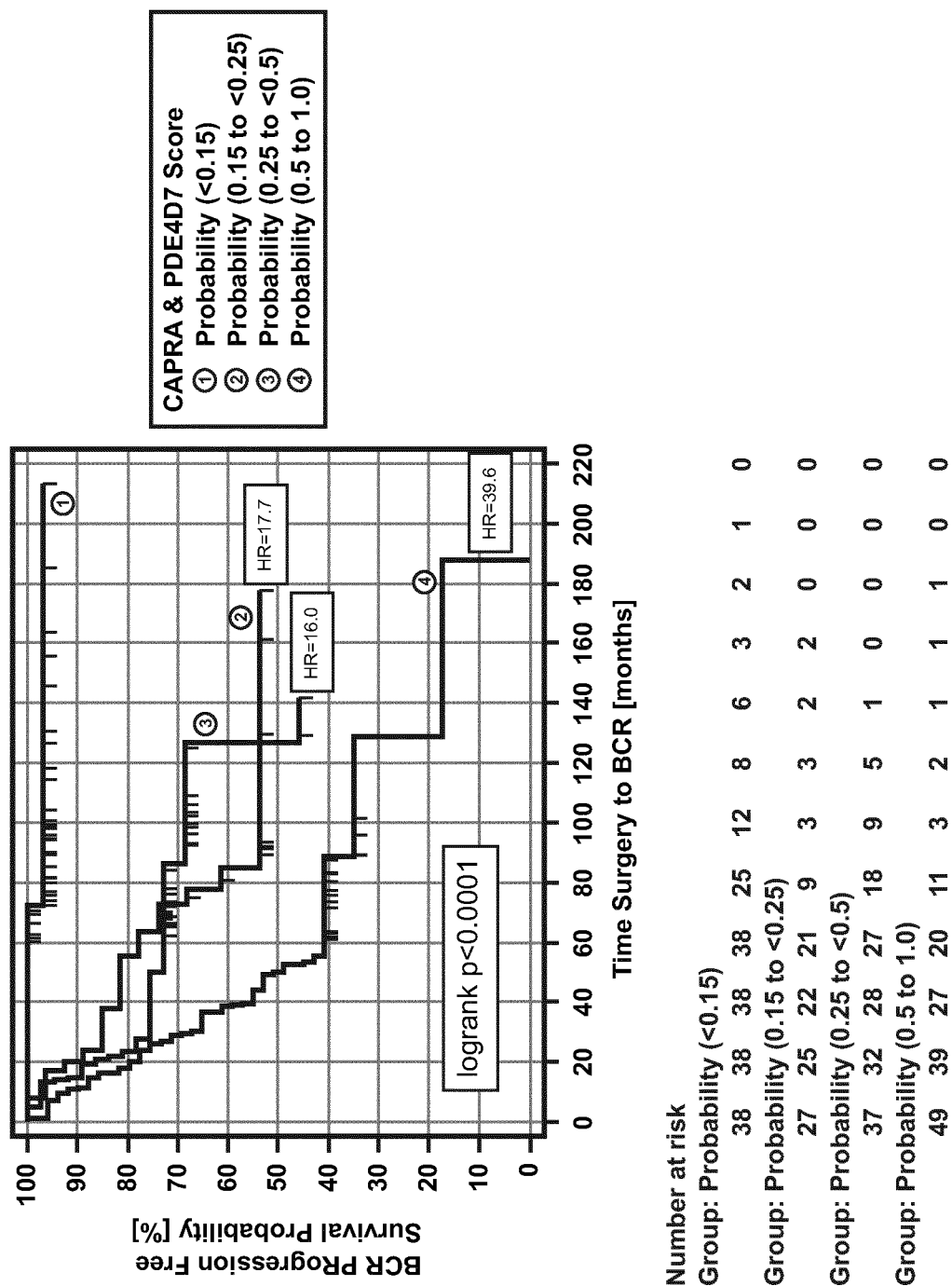
Figure 5:
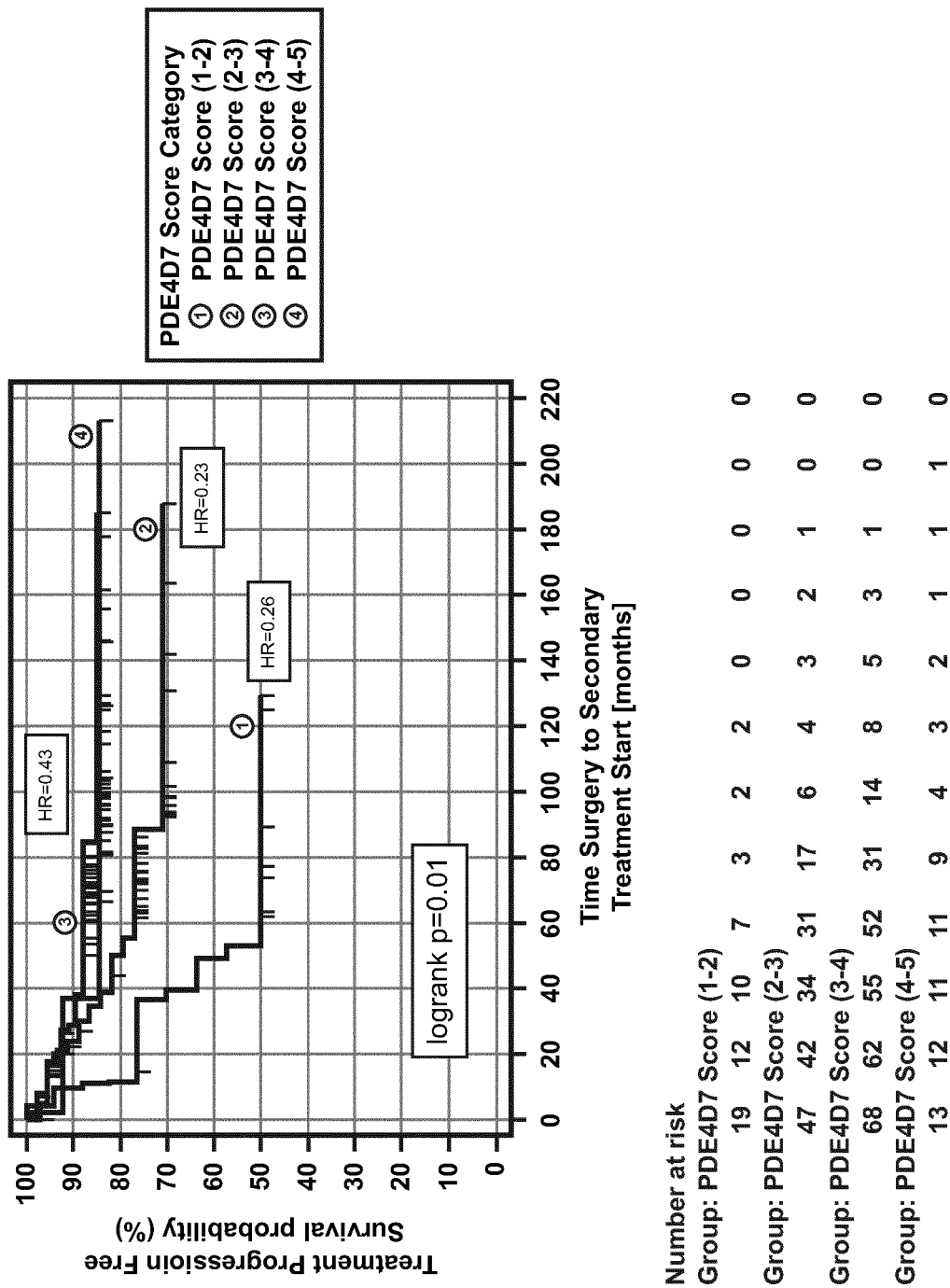
Figure 6:
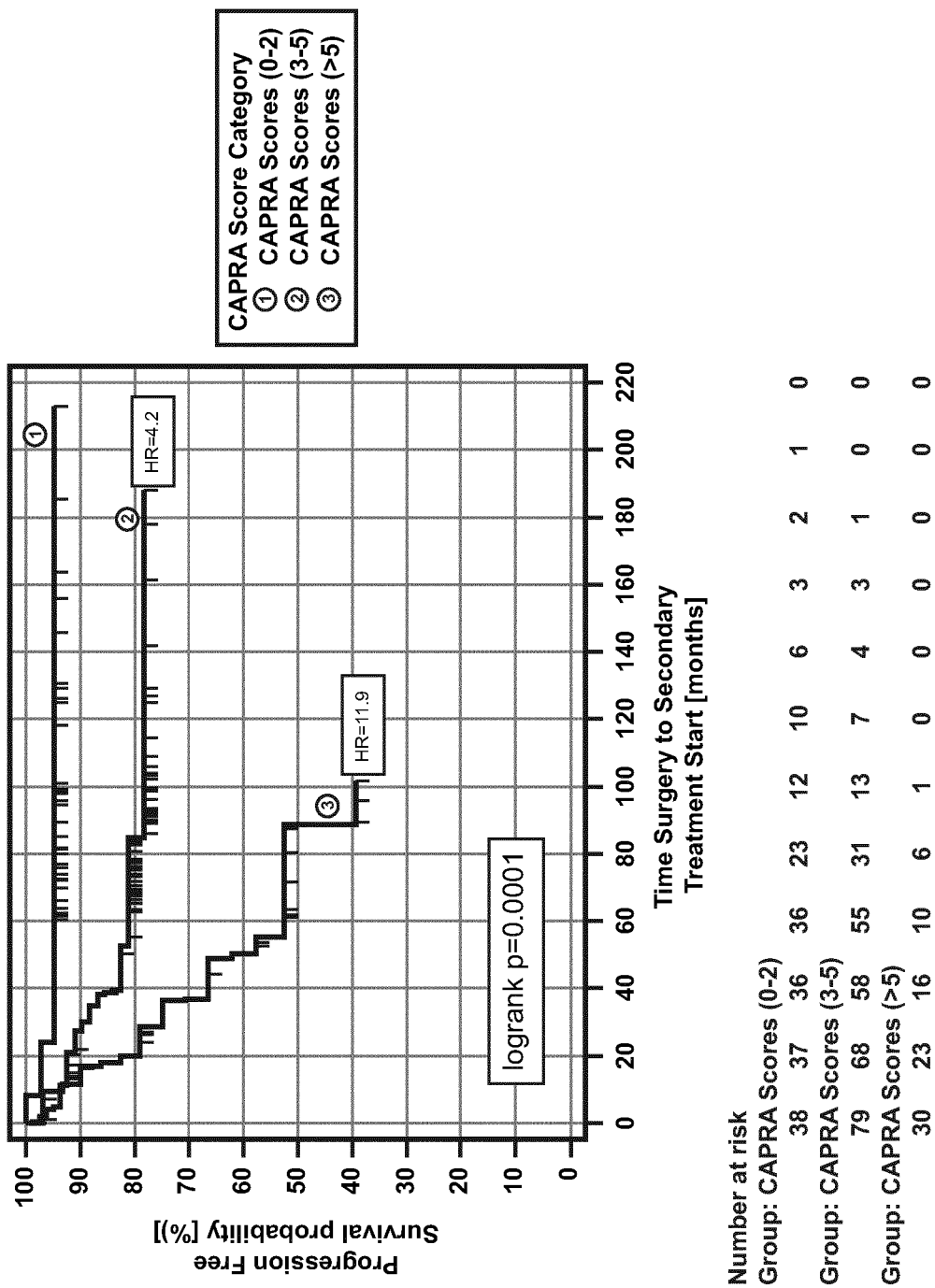
Figure 7:
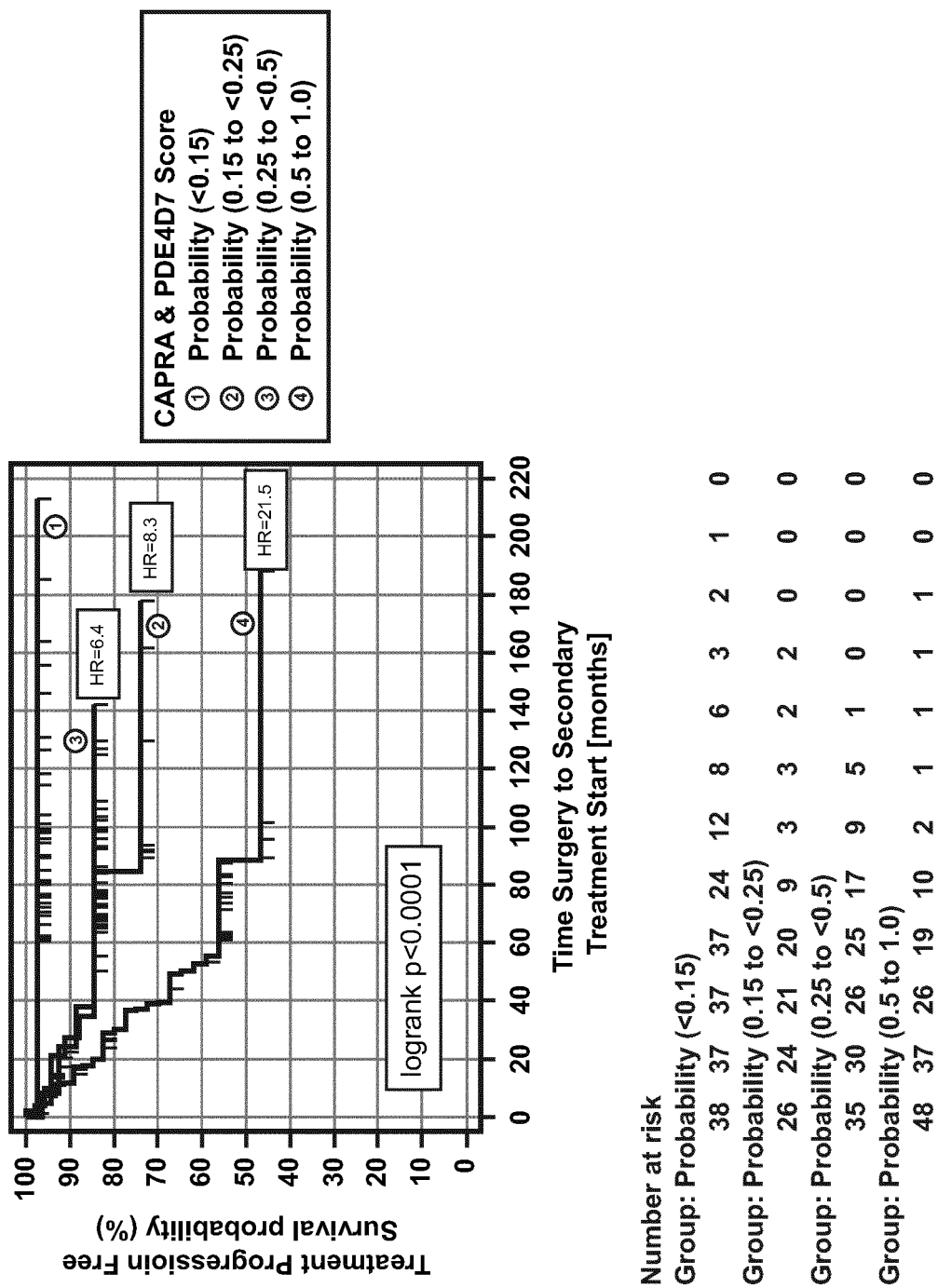

FIGS. 2 to 7 show results of Kaplan-Meier survival analysis of the time to PSA relapse or start of any salvage therapy after radical prostatectomy in the DB patient cohort (#151). FIGS. 2 to 4: Kaplan-Meier analysis of the biochemical recurrence (BCR) free survival in the DB patient cohort of the categorized expression based risk score (indicated as "PDE4D7 Score" in FIG. 2), the pre-surgical CAPRA score categories (indicated as "CAPRA Score" in FIG. 3), and the pre-surgical CAPRA score and expression based risk score combination model (indicated as "CAPRA & PDE4D7 Score" in FIG. 4). FIGS. 5 to 7: Kaplan-Meier analysis of post-surgical time to start of any salvage therapy free survival in the DP patient cohort of the categorized expression based risk score (indicated as "PDE4D7 Score" in FIG. 5), the pre-surgical CAPRA score categories (indicated as "CAPRA Score" in FIG. 6), and the pre-surgical CAPRA score expression based risk score combination model (indicated as "CAPRA & PDE4D7 Score" in FIG. 7). In all figures, censored patients are indicated by vertical bars. The Hazard Ratio's (HR) compared to the reference group and the logrank p-values are provided. The number of men at risk are given in the tables below the Kaplan-Meier survival graphs. The expression based risk score categories were defined as: "PDE4D7 Score (1-2)": expression based risk score in the range of 1 to <2; "PDE4D7 Score (2-3)": expression based risk score in the range of 2 to <3; "PDE4D7 Score (3-4)": expression based risk score in the range of 3 to <4; and "PDE4D7 Score (4-5)": expression based risk score in the range of 4 to ≤5. The highest expression based risk score category "PDE4D7 Score (4-5)" was used as the reference category. The pre-surgical CAPRA score categories were defined as: "CAPRA scores (0-2)": pre-surgical CAPRA scores in the range of 0 to 2; "CAPRA scores (3-5)": pre-surgical CAPRA scores in the range of 3 to 5; and "CAPRA scores (>5)": pre-surgical CAPRA scores in the range of 6 to 10. The lowest pre-surgical CAPRA score category "CAPRA scores (0-2)" was used as the reference category. The categories of the pre-surgical CAPRA score and expression based risk score combination model were defined according to the probability to experience PSA failure after surgery based on the logit(p) function of the logistic regression model as: "Probability (<0.15)"; "Probability (0.15 to <0.25)"; "Probability (0.25 to <0.5)"; and "Probability (0.5 to 1.0)".

The Kaplan-Meier survival studies on the DB patient cohort showed a significant separation of patients into different risks to experience post-operative PSA relapse or start of any salvage therapy after radical prostatectomy based on the pre-surgical measurement of the expression based risk score in a tissue punch of a diagnostic biopsy (see FIG. 2). Concerning the logistic regression model, which combines the pre-surgical CAPRA score and the expression based risk score in a regression function, the model-calculated probability to experience the endpoint was classified or categorized into four groups (as described above) and the hazard ratios between the lowest vs. highest recurrence risk groups were compared with the patient groups stratified by the pre-surgical CAPRA score categories alone. The addition of the expression based risk score to the pre-surgical CAPRA categories proved to significantly increase in the hazard ratio from the lowest to the highest risk group (9.0 vs. 39.6, respectively) while the patient numbers in these risk categories remained virtually the same (see FIGS. 3 and 4).

When testing the clinically relevant endpoint of start of any salvage therapy (radiation, hormone ablation) after PSA failure, it was found that, as before, the results show an improved risk separation between patients with lowest vs. highest risk to receive post-surgical secondary treatment when combining the pre-surgical CAPRA score with the expression based risk score (see FIGS. 5 to 7).

Figure 8:
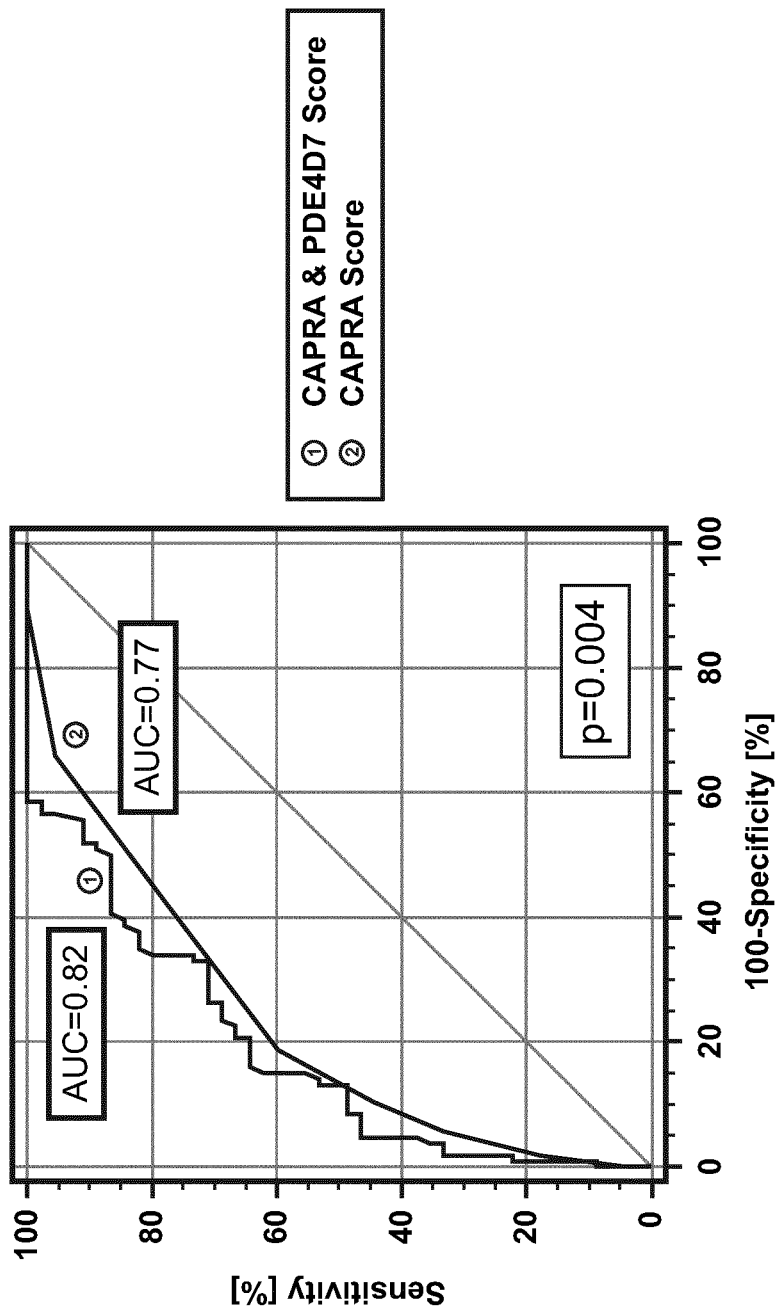
FIGS. 8 to 10 show results of ROC curve analysis of 5-year biochemical recurrence (BCR) after surgery in the DB patient cohort.

Furthermore, the prediction of 5-years PSA relapse after primary treatment of the pre-surgical CAPRA score vs. the logistic regression model, which combines the pre-surgical CAPRA score and the expression based risk score in a regression function and which was previously developed using the RP cohort with complete 5-year follow-up (#449), was tested. Using a ROC analysis, the 5-year AUCs (area under the curve) were calculated as 0.77 for the pre-surgical CAPRA score alone and as 0.82 for the logistic regression model (see FIG. 8). The AUCs of the two models were tested to be significantly different (p=0.004).

In another test, the benefit of adding the expression based risk score to the pre-surgical CAPRA score was explored. The pre-surgical CAPRA metric categorizes its individual components and gives weighted points to these categories. The pre-surgical CAPRA score is the sum of these weighted points (see Cooperberg M. R.). As mentioned above, the biopsy Gleason score has, on one hand, a significant impact to the CAPRA score. At the same time, however, it was found by the present inventor that Gleason scoring is subject to substantial variability amongst pathologists. Therefore, the information of the biopsy Gleason score within the pre-surgical CAPRA score was replaced with the molecular information provided by the expression based risk score. In particular, depending on the value of the expression based risk score, a number of points in the range from 0 to 3 were in a modified pre-surgical CAPRA score. By doing so, the overall structure of the resulting modified pre-surgical CAPRA score could be kept the same with a minimum total score of 0 and a maximum total score of 10 (see TABLE 9).

TABLE 9

Replacement of the biopsy Gleason score by the expression based risk score in the pre-surgical CAPRA model.

| CAPRA Score | | |
| --- | --- | --- |
| Variable | Range | Points |
| PSA [ng/ml] | 2.0-6.0 | 0 |
|  | >6.0-10.0 | 1 |
|  | >10.0-20.0 | 2 |
|  | >20.0-30.0 | 3 |
|  | >30.0 | 4 |
| Biopsy Gleason [primary/ secondary] | 1-3/1-3 | 0 |
|  | 1-3/4-5 | 1 |
|  | 4-5/1-5 | 3 |
| Clinical stage [cT] | cT1/cT2 | 0 |
|  | cT3a | 1 |
| [%]Tumor positive biopsies | <34% | 0 |
|  | ≥34% | 1 |
| Patient age [yrs] | <50 | 0 |
|  | ≥50 | 1 |
| Min total CAPRA Score |  | 0 |
| Max total CAPRA Score |  | 10 |

| CAPRA (-BxGl/+PDE4D7) Score | | |
| --- | --- | --- |
| Variable | Range | Points |
| PSA [ng/ml] | 2.0-6.0 | 0 |
|  | >6.0-10.0 | 1 |
|  | >10.0-20.0 | 2 |
|  | >20.0-30.0 | 3 |
|  | >30.0 | 4 |
| Expression based risk score | 4-5 | 0 |
|  | 3-4 | 1 |
|  | 2-3 | 2 |
|  | 1-2 | 3 |
| Clinical stage [cT] | cT1 /cT2 | 0 |
|  | cT3a | 1 |
| [%]Tumor positive biopsies | <34% | 0 |
|  | ≥34% | 1 |
| Patient age [yrs] | <50 | 0 |
|  | ≥50 | 1 |
| Min total CAPRA (-BxGl/+PDE4D7) Score |  | 0 |
| Max total CAPRA (-BxGl/+PDE4D7) Score |  | 10 |

Figure 9:
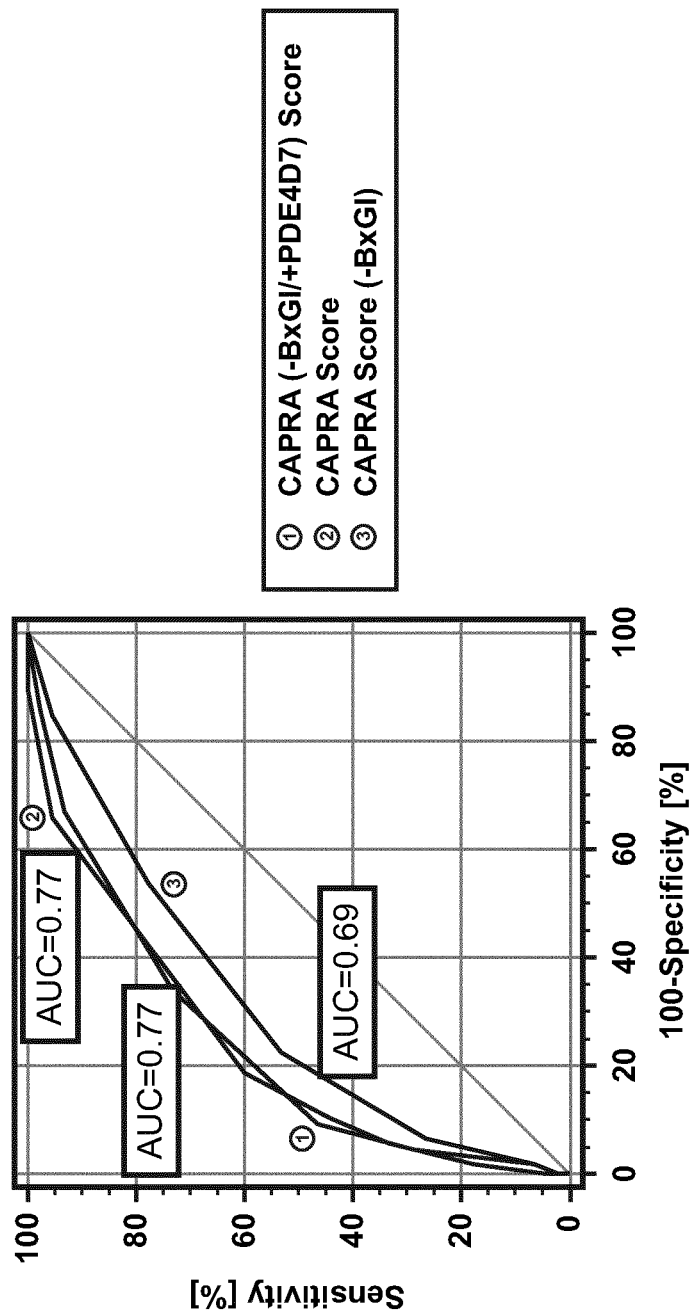

When testing this model for 5-year BCR outcome prediction in ROC analysis, the resulting AUC of the "CAPRA (-BxGl/+PDE4D7) Score" remained the same as compared to the pre-surgical CAPRA score which includes the information of the biopsy Gleason score (AUC=0.77; see FIG. 9). While replacing the biopsy Gleason score with the expression based risk score does not impact the model performance, the 5-year prediction of PSA failure of the pre-surgical CAPRA model drops significantly in case the biopsy Gleason information is removed from the clinical model (AUC=0.77 vs. AUC=0.69 with and without the biopsy Gleason score; p=0.008; see FIG. 9, where the pre-surgical CAPRA score without the biopsy Gleason information is indicated as "CAPRA Score (-BxGl)").

Figure 10:
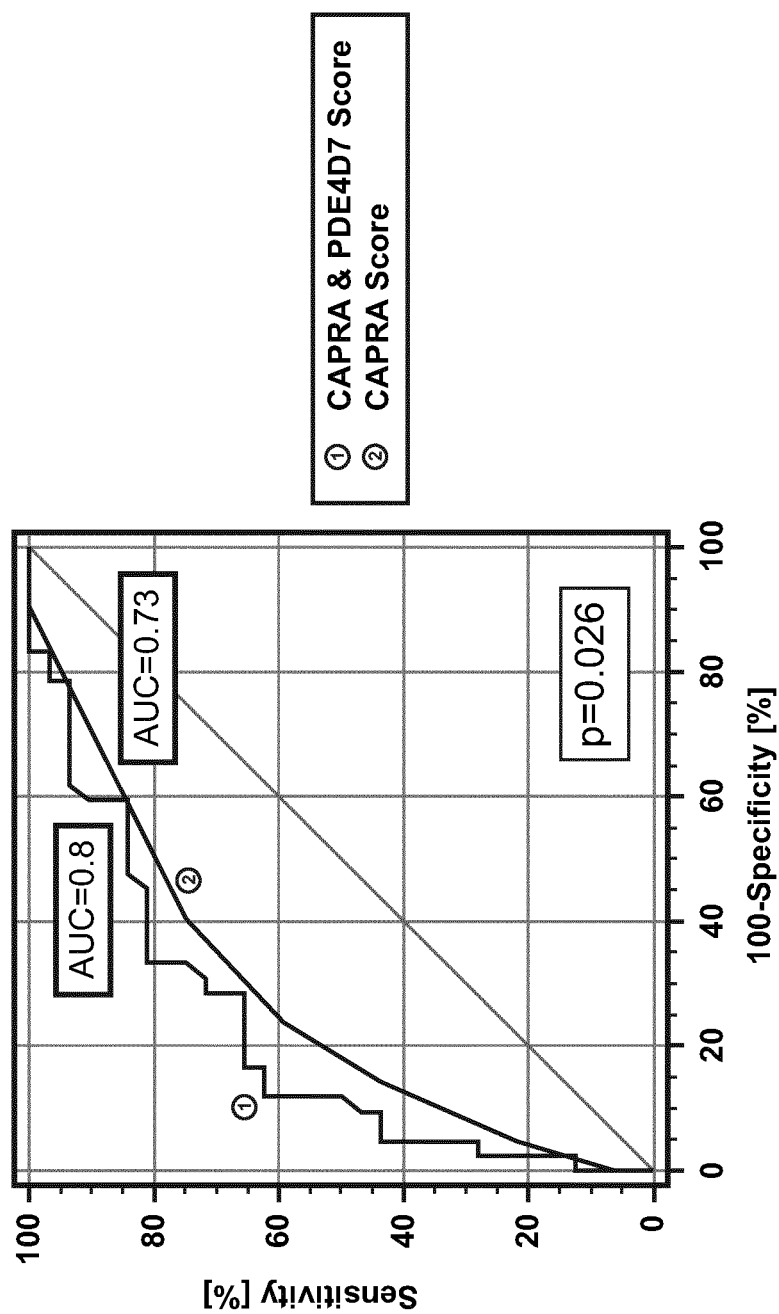

In the patient cohort with biopsy Gleason ≤6, only a limited number of men experience PSA relapse after surgery (21.2% in the RP cohort and in the DB cohort, respectively) or, even more relevant, progress to metastases (1.9% in the RP cohort), or suffer from disease specific death (1.3% in the RP cohort). Therefore, a sub-cohort analysis (#74) of the pre-surgical CAPRA score vs. the pre-surgical CAPRA score and expression based risk score combination model was performed in the DP patient cohort including only patients with a biopsy Gleason score ≥7. The combination model showed equivalent performance compared to testing the complete cohort (AUC=0.8 vs. 0.82, respectively), while there was more performance drop in the pre-surgical CAPRA model alone in the sub-cohort analysis (AUC=0.73 vs. 0.77, respectively; see FIG. 10). This may indicate an improved discrimination performance of the combination model in patients with higher risk characteristics.

Figure 11:
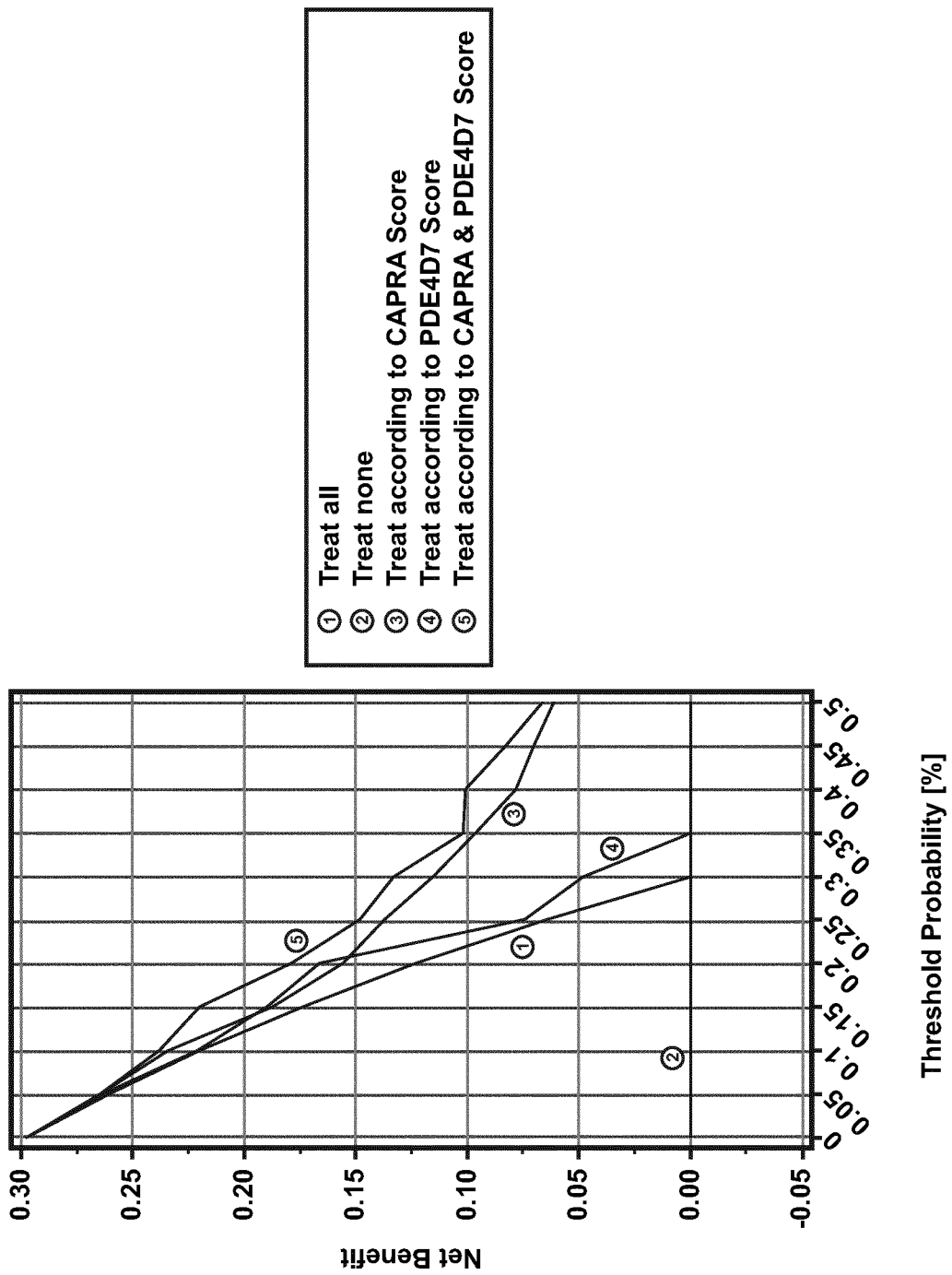
FIG. 11 shows results of decision curve analysis of the net benefit of five different treatment strategies for men who experience disease recurrence within 5 years after surgery (in total 45 of the 151 investigated patients failed the initial primary treatment of surgery by PSA recurrence (29.8%))

Recently, the concept of decision curve analysis (DCA) was introduced into the field of testing the value of a biomarker or prediction model in clinical practice (see Vickers A. J. and Elkin E. B., "Decision curve analysis: A novel method for evaluating prediction models", Medical Decision Making, Vol. 26, No. 6, pages 565 to 574, 2006). DCA is a net benefit analysis, which compares the true-positive to the weighted false-positive rates across different risk thresholds to decide on the start of secondary treatment after surgery due to risk of future PSA failure. Here, the net benefit of secondary treatment triggered by PSA relapse after surgery was explored for the three models (i.e., the expression based risk score, the pre-surgical CAPRA score, and the pre-surgical CAPRA score and expression based risk score regression model) in decision curve analysis (DCA). Five different treatment strategies were compared: (1, 2) treat all or none patients; (3 to 5) treat according to the expression based risk score, the pre-surgical CAPRA score, or the combined regression model of the pre-surgical CAPRA score and the expression based risk score. For this, the true (TPR) and the false positive rate (FPR) was determined for all strategies between varying decision thresholds ranging from 0% to 50% in 5% steps (see FIG. 11). The analysis demonstrated that all used models show better net benefit compared to the "treat all" strategy while the pre-surgical CAPRA score and expression based risk score regression model revealed the best net benefit across all modeled decision thresholds.

The provided results show that a predictive model of the pre-surgical clinical risk algorithm CAPRA with quantitative measurements of the prostate cancer biomarker PDE4D7 in a biological sample of a prostate cancer subject may provide an improved risk stratification. It was demonstrated in multiple analyses that this risk prediction model performs better in stratifying prostate cancer patients to treatment relevant risk categories compared to using risk schemas based solely on pre-surgical clinical parameters, as recommended by the various currently employed national prostate cancer guidelines.

Discussion

Treatment decisions in primary, localized prostate cancer are largely subject to a combination of the risk of future disease progression and life expectancy. The provided data illustrate that the expression based risk score adds independent information to the pre-surgical CAPRA metric to predict disease recurrence, while in prediction of overall survival (of which ~80% of the events is due to non-disease specific death) the expression based risk score remains the only variable that significantly contributes to survival prediction. Thus, PDE4D7 may be adding prognostic value to clinical prediction models based on pre-surgical variables, like the pre-surgical CAPRA score, for disease specific outcomes as well as to the prediction of survival to support treatment decision making.

Recently, the long-term results of the active surveillance cohort within the Göteborg randomized prostate cancer screening trial were published. This indicated that men with clinically low risk disease may have a considerable risk to experience progressive disease under a deferred treatment regime (see Godtman R. A. et al., "Long-term Results of Active Surveillance in the Göteborg Randomized, Population-based Prostate Cancer Screening Trial", European Urology, Vol. 70, No. 5, pages 760-766, 2016). Therefore, the present inventor questioned whether men other than those with very low risk disease would be eligible for expectant management strategies. The recent publication of the 10-year outcomes of the ProtecT study indicates similar conclusions in the active monitoring arm of the trial (see Hamdy F. C. et al., "10-Year Outcomes after Monitoring, Surgery, or Radiotherapy for Localized Prostate Cancer", New England Journal of Medicine Vol. 375, pages 1415-1424, 2016). Although there is some debate about the validity of these results to contemporary practice (see Bergh R. C. N. van den, Murphy D. G., Poel H. G. van der, "Expectant Management for Prostate Cancer: Lessions from the past, Challenges for the Future", European Urology, Vol. 70, pages 767-770, 2016), they may suggest that only patients with the very lowest risk are safe of any progression during deferred treatment management. While the use of clinical criteria like the pre-surgical CAPRA model allow the selection of such a low risk patient cohort of (45% of the RP cohort with a 9.3% risk of 5-year post-surgical BCR; 27.7% of the DP cohort with a 4.8% risk of 5-year post-surgical BCR), the addition of molecular markers may allow to enlarge this very low risk patient group. In fact, the developed pre-surgical CAPRA score and expression based risk score regression model defines a very low risk cohort of 38 out of 151 patients (25.2%) in the DB patient cohort with a NPV (negative predictive value) of 100% for a 5-year risk of post-treatment PSA recurrence.

Active surveillance (AS) has been established as a suitable and safe treatment alternative for men with low risk prostate cancer over the last years (see Garisto J. D. and Klotz L., "Active surveillance for prostate cancer: How to do it right", Oncology (Williston Park), Vol. 31, No. 5, pages 333 to 340 2017). A big challenge though associated with AS are the strict monitoring schedules that men are advised to follow in order to not miss signs of progressive disease like raise in PSA or up-grading in biopsy Gleason which are typically protocol triggers to switch from AS to active treatment. Longitudinal AS studies have published decreasing patient compliance to the monitoring protocols in AS over time in particular when it comes to additional biopsy procedures (see Bokhorst L. P. et al., "Compliance Rates with the Prostate Cancer Research International Active Surveillance (PRIAS) Protocol and Disease Reclassification in Noncompliers", European Urology, Vol. 68, No. 5, 2015). This issue can be addressed with a selection algorithm as proposed here, i.e., the combination of a clinical model like the pre-surgical CAPRA score with the prognostic genomic biomarker PDE4D7 to define a patient cohort with virtually no risk to progress over a period of 5 years. This provides a way forward to include men into active surveillance on the basis of very limited (or no) follow-up for a given time period after AS start.

Other variations to the disclosed realizations can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

One or more steps of the method illustrated in FIG. 1 may be implemented in a computer program product that may be executed on a computer. The computer program product may comprise a non-transitory computer-readable recording medium on which a control program is recorded (stored), such as a disk, hard drive, or the like. Common forms of non-transitory computer-readable media include, for example, floppy disks, flexible disks, hard disks, magnetic tape, or any other magnetic storage medium, CD-ROM, DVD, or any other optical medium, a RAM, a PROM, an EPROM, a FLASH-EPROM, or other memory chip or cartridge, or any other non-transitory medium from which a computer can read and use.

Alternatively, the one or more steps of the method may be implemented in transitory media, such as a transmittable carrier wave in which the control program is embodied as a data signal using transmission media, such as acoustic or light waves, such as those generated during radio wave and infrared data communications, and the like.

The exemplary method may be implemented on one or more general purpose computers, special purpose computer(s), a programmed microprocessor or microcontroller and peripheral integrated circuit elements, an ASIC or other integrated circuit, a digital signal processor, a hard-wired electronic or logic circuit such as a discrete element circuit, a programmable logic device such as a PLD, PLA, FPGA, Graphical card CPU (GPU), or PAL, or the like. In general, any device, capable of implementing a finite state machine that is in turn capable of implementing the flowchart shown in FIG. 1, can be used to implement one or more steps of the method of risk stratification for therapy selection in a patient with prostate cancer is illustrated. As will be appreciated, while the steps of the method may all be computer implemented, in some embodiments one or more of the steps may be at least partially performed manually.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

While the invention has described so far based on the gene expression profile for PDE4D7, which can include an expression level (e.g., value) for PDE4D7 which can be normalized using value(s) for each of a set of reference genes, the gene expression profile may further include expression information from other PDE4D variants. For example, the other PDE4D variant(s) may include one or more of PDE4D1, PDE4D2, PDE4D3, PDE4D4, PDE4D5, PDE4D6, PDE4D8 and PDE4D9. The diagnostic kit may then additionally comprise at least one primer and/or probe for determining the gene expression profile for each of the other PDE4D variant(s) in the biological sample obtained from the prostate cancer subject. Preferably, however, only the gene expression profile for PDE4D7, in particular, an expression level (e.g., value) for PDE4D7 which can be normalized using value(s) for each of a set of reference genes, is employed.

The term "phosphodiesterase 4D1" or "PDE4D1" relates to the splice variant 1 of the human phosphodiesterase PDE4D, i.e., the human phosphodiesterase PDE4D1 gene, for example, to the sequence as defined in NCBI Reference Sequence: NM_001197222.1, specifically, to the nucleotide sequence as set forth in SEQ ID NO:1, which corresponds to the sequence of the above indicated NCBI Reference Sequence of the PDE4D1 transcript, and also relates to the corresponding amino acid sequence for example as set forth in SEQ ID NO:2, which corresponds to the protein sequence defined in NCBI Protein Accession Reference Sequence NP_001184151.1 encoding the PDE4D1 polypeptide. The term "phosphodiesterase 4D1" or "PDE4D1" also relates to the amplicon that can be generated by the primer pair PDE1D1D2_forward (SEQ ID NO:3) and the PDE1D1D2_reverse (SEQ ID NO:4) and can be detected by probe SEQ ID NO:5.

The term "phosphodiesterase 4D2" or "PDE4D2" refers to the splice variant 2 of the human phosphodiesterase PDE4D, i.e., the human phosphodiesterase PDE4D2 gene, for example, to the sequence as defined in NCBI Reference Sequence: NM_001197221.1, specifically, to the nucleotide sequence as set forth in SEQ ID NO:6, which corresponds to the sequence of the above indicated NCBI Reference Sequence of the PDE4D2 transcript, and also relates to the corresponding amino acid sequence for example as set forth in SEQ ID NO:7, which corresponds to the protein sequence defined in NCBI Protein Accession Reference Sequence NP_001184150.1 encoding the PDE4D2 polypeptide.

The term "phosphodiesterase 4D3" or "PDE4D3" refers to the splice variant 3 of the human phosphodiesterase PDE4D, i.e., the human phosphodiesterase PDE4D3 gene, for example, to the sequence as defined in NCBI Reference Sequence: NM_006203.4, specifically, to the nucleotide sequence as set forth in SEQ ID NO:8, which corresponds to the sequence of the above indicated NCBI Reference Sequence of the PDE4D3 transcript, and also relates to the corresponding amino acid sequence for example as set forth in SEQ ID NO:9, which corresponds to the protein sequence defined in NCBI Protein Accession Reference Sequence NP_006194.2 encoding the PDE4D3 polypeptide.

The term "phosphodiesterase 4D4" or "PDE4D4" refers to the splice variant 4 of the human phosphodiesterase PDE4D, i.e., the human phosphodiesterase PDE4D4 gene, for example, to the sequence as defined in NCBI Reference Sequence: NM_001104631.1, specifically, to the nucleotide sequence as set forth in SEQ ID NO:10, which corresponds to the sequence of the above indicated NCBI Reference Sequence of the PDE4D4 transcript, and also relates to the corresponding amino acid sequence for example as set forth in SEQ ID NO:11, which corresponds to the protein sequence defined in NCBI Protein Accession Reference Sequence NP_001098101.1 encoding the PDE4D4 polypeptide.

The term "phosphodiesterase 4D5" or "PDE4D5" refers to the splice variant 5 of the human phosphodiesterase PDE4D, i.e., the human phosphodiesterase PDE4D5 gene, for example, to the sequence as defined in NCBI Reference Sequence: NM_001197218.1, specifically, to the nucleotide sequence as set forth in SEQ ID NO:12, which corresponds to the sequence of the above indicated NCBI Reference Sequence of the PDE4D5 transcript, and also relates to the corresponding amino acid sequence for example as set forth in SEQ ID NO:13, which corresponds to the protein sequence defined in NCBI Protein Accession Reference Sequence NP_001184147.1 encoding the PDE4D5 polypeptide. The term "phosphodiesterase 4D5" or "PDE4D5" also relates to the amplicon that can be generated by the primer pair PDE4D5_forward (SEQ ID NO:14) and the PDE4D5_reverse (SEQ ID NO:15) and can be detected by probe SEQ ID NO:16.

The term "phosphodiesterase 4D6" or "PDE4D6" refers to the splice variant 6 of the human phosphodiesterase PDE4D, i.e., the human phosphodiesterase PDE4D6 gene, for example, to the sequence as defined in NCBI Reference Sequence: NM_001197223.1, specifically, to the nucleotide sequence as set forth in SEQ ID NO:17, which corresponds to the sequence of the above indicated NCBI Reference Sequence of the PDE4D6 transcript, and also relates to the corresponding amino acid sequence for example as set forth in SEQ ID NO:18, which corresponds to the protein sequence defined in NCBI Protein Accession Reference Sequence NP_001184152.1 encoding the PDE4D6 polypeptide.

The term "phosphodiesterase 4D8" or "PDE4D8" relates to the splice variant 8 of the human phosphodiesterase PDE4D, i.e., the human phosphodiesterase PDE4D8 gene, for example, to the sequence as defined in NCBI Reference Sequence: NM_001197219.1, specifically, to the nucleotide sequence as set forth in SEQ ID NO:27, which corresponds to the sequence of the above indicated NCBI Reference Sequence of the PDE4D8 transcript, and also relates to the corresponding amino acid sequence for example as set forth in SEQ ID NO:28, which corresponds to the protein sequence defined in NCBI Protein Accession Reference Sequence NP_001184148.1 encoding the PDE4D8 polypeptide.

The term "phosphodiesterase 4D9" or "PDE4D9" relates to the splice variant 9 of the human phosphodiesterase PDE4D, i.e., the human phosphodiesterase PDE4D9 gene, for example, to the sequence as defined in NCBI Reference Sequence: NM_001197220.1, specifically, to the nucleotide sequence as set forth in SEQ ID NO:29, which corresponds to the sequence of the above indicated NCBI Reference Sequence of the PDE4D9 transcript, and also relates to the corresponding amino acid sequence for example as set forth in SEQ ID NO:30 which corresponds to the protein sequence defined in NCBI Protein Accession Reference Sequence NP_001184149.1 encoding the PDE4D9 polypeptide. The term "phosphodiesterase 4D9" or "PDE4D9" also relates to the amplicon that can be generated by the primer pair PDE4D9_forward (SEQ ID NO:31) and the PDE4D9_reverse (SEQ ID NO:32) and can be detected by probe SEQ ID NO:33.

The terms "PDE4D1," "PDE4D2," "PDE4D3," "PDE4D4," "PDE4D5," "PDE4D6," "PDE4D8," and "PDE4D9" also comprises nucleotide sequences showing a high degree of homology to PDE4D1, PDE4D2, PDE4D3, PDE4D4, PDE4D5, PDE4D6, PDE4D8 and PDE4D9 respectively, e.g., nucleic acid sequences being at least 75%, 80%, 85%, 90%, 91%, 92%, 93%, 94%, 95%, 96%, 97%, 98% or 99% identical to the sequence as set forth in SEQ ID NOs: 1, 6, 8, 10, 12, 17, 27 or 29 respectively or amino acid sequences being at least 75%, 80%, 85%, 90%, 91%, 92%, 93%, 94%, 95%, 96%, 97%, 98% or 99% identical to the sequence as set forth in SEQ ID NO:2, 7, 9, 11, 13, 18, 28 or 30 respectively or nucleic acid sequences encoding amino acid sequences being at least 75%, 80%, 85%, 90%, 91%, 92%, 93%, 94%, 95%, 96%, 97%, 98% or 99% identical to the sequence as set forth in SEQ ID NO:2, 7, 9, 11, 13, 18, 28 or 30 or amino acid sequences being encoded by nucleic acid sequences being at least 75%, 80%, 85%, 90%, 91%, 92%, 93%, 94%, 95%, 96%, 97%, 98% or 99% identical to the sequence as set forth in SEQ ID NO:1, 6, 8, 10, 12, 17, 27 or 29.

Adding Information from PDE4D5 and PDE4D9 to the Pre-Surgical Prognostic Risk Score Like the PDE4D7 iso form, the PDE4D5 and PDE4D7 iso forms are long iso forms that each contain both the UCR1 and UCR2 regulatory domains. Here, we investigated the added value of including information from the gene expression profiles for PDE4D5 and PDE4D9 in the CAPRA & PDE4D7 score combination model to predict longitudinal clinical outcomes.

EXAMPLES

Patient Cohorts and Samples

Two patient cohorts, a radical prostatectomy (RP) patient cohort and a diagnostic biopsy (DB) patient cohort, with the demographics shown in TABLE 10, were employed. For the RP patient cohort, two small biopsy punches (approximately 1 millimeter by 2 millimeters) of tissue were collected of a representative tumor area (index lesion of the tumor) from the resected prostate from 606 patients who had been consecutively operated on between 2000 and 2004 at a single high-volume clinical center in Germany. For the DB patient cohort, a single biopsy punch (approximately 1 millimeter by 2 millimeters) was collected from the tumor positive diagnostic biopsy with the highest Gleason grade per patient. The 168 patients in this case were diagnosed with prostate cancer and operated on between 1995 and 2011 at the University Klinik Muenster, Germany. After quality control of the RNAseq and the RT-qPCR data 536 and 151 patient samples were found eligible for statistical analysis in the RP cohort and the DB cohort, respectively.

TABLE 10

Demographics of the radical prostatectomy (RP) patient cohort and the diagnostic biopsy (DB) patient cohort.

| | Parameter | RP cohort (#536) | DB cohort (#151) |
|---|---|---|---|
| Clinical Range (median; IQR)) | Age (at RP) | 41.3-74.5 (62.5; 7.5) | 47.4-77.4 (64.9; 8.5) |
| | Preoperative PSA | 0.18-120.0 (7.1; 6.2) | 2.0-49.1 (8.1; 5.7) |
| | Percent tumor in biopsy | 0.2-80.0 (10.6; 20.2) | N/A |
| | Prostate Volume | 9-244 (41.0; 21.0) | 13.6-148.0 (38.5; 19.2) |
| | PSA density | 0.01-4.0 (0.17; 0.16) | 0.03-1.6 (0.2; 0.17) |
| CAPRA Risk Category No. of patients (percentage) | Low Risk (CAPRA 0-2) | 199 (37.1%) | 38 (25.2%) |
| | Intermediate Risk (CAPRA 3-5) | 273 (50.9%) | 82 (54.3%) |
| | High Risk (CAPRA > 5) | 44 (8.2%) | 31 (20.5%) |
| | N/A | 20 (3.7%) | — |
| Pre-Surgery Pathology | Biopsy Gleason 3 + 3 (GG1) | 282 (52.6%) | 77 (51.0%) |
| | Biopsy Gleason 3 + 4 (GG2) | 172 (32.1%) | 38 (25.2%) |

TABLE 10-continued

Demographics of the radical prostatectomy (RP) patient cohort and the diagnostic biopsy (DB) patient cohort.

|  | Parameter | RP cohort (#536) | DB cohort (#151) |
|---|---|---|---|
| No. of patients (percentage) | Biopsy Gleason 4 + 3 (GG3) | 46 (8.6%) | 20 (13.2%) |
|  | Biopsy Gleason ≥4 + 4 (≥GG4) | 36 (6.7%) | 16 (10.6%) |
|  | cT1 | 348 (64.9%) | 97 (64.2%) |
|  | cT2 | 175 (32.6%) |  |
|  | cT3 | 13 (2.3%) | 54 (35.8%) |
|  | N/A | 1 (0.2%) | — |
| Post-Surgery Pathology No. of patients (percentage) | Pathology Gleason 3 + 3 (GG1) | 176 (32.8%) | 46 (30.5%) |
|  | Pathology Gleason 3 + 4 (GG2) | 268 (50.0%) | 52 (34.4%) |
|  | Pathology Gleason 4 + 3 (GG3) | 69 (12.9%) | 31 (20.5%) |
|  | Pathology Gleason >= 4 + 4 (≥GG4) | 23 (4.3%) | 22 (14.6%) |
|  | pT2 | 312 (58.2%) | 88 (58.3%) |
|  | pT3 | 224 (41.8%) | 63 (41.7%) |
|  | pT4 | 0 (0%) | 0 (0%) |
|  | Positive Surgical Margins | 197 (36.8%) | 33 (21.9%) |
|  | Capsular Status | 139 (25.9%) | 37/151 (24.5%) |
|  | Positive Seminal Vesicle Invasion | 87 (16.2%) | N/A |
|  | Positive Lymph Node Invasion | 17 (3.2%) | 10 (6.6%) |
| Follow-up Months | Mean | 105.1 | 73.7 |
|  | IQR median | 120.2 | 73.6 |
| Outcome No. of events/ total no. of patients (percentage) | <5 y BCR | 169/480 (35.2%) | 45/151 (29.8%) |
|  | <10 y BCR | 210/402 (52.2%) | — |
|  | <5 y CR | 46/472 (9.7%) | 4/151 (2.6%) |
|  | <10 y CR | 61/337 (18.1%) | — |
| Salvage Treatment No. of events/ total no. of patients (percentage) | <5 y SRT | 130/475 (27.4%) | 12/151 (7.9%) |
|  | <10 y SRT | 164/381 (43.0%) | — |
|  | <5 y SADT | 75/467 (16.1%) | 16/151 (10.6%) |
|  | <10 y SADT | 110/350 (31.4%) | — |
| Mortality No. of events/ total no. of patients (percentage) | <5 y PCSS | 13/453 (2.9%) | 1/151 (0.7%) |
|  | <10 y PCSS | 25/304 (8.2%) | — |
|  | <5 y OS | 25/465 (5.4%) | 1/151 (0.7%) |
|  | <10 y OS | 51/331 (15.4%) | — |

For patient age, preoperative PSA, percentage of tumor in biopsy, prostate volume, and PSA density, the minimum and maximum values in the each cohort are shown, while the median and IQR values are depicted in parentheses. For the CAPRA risk categories, the number of patients and percentage per risk group are shown. In case of pre-surgical pathology, the biopsy Gleason scores and the Gleason grade groups as well as clinical stages are indicated (by number and percentage of patients). Post-surgical pathology is represented by the pathology Gleason scores and Gleason grade groups, the pathology stages, the surgical margin status after prostatectomy, the tumor invasion status of the seminal vesicles and pelvic lymph nodes (by number and percentage of patients). In this respect, it is noted that the extracapsular extension was not provided as a primary parameter but was derived from pathology stage pT3a. The follow-up demonstrates the mean and median follow-up periods in months after surgery for all patients. The outcome category illustrates the cumulative 5- and 10-year biochemical recurrence (BCR) and clinical recurrence to metastases (CR) post-surgical primary treatment. The treatment category lists the cumulative 5- and 10-year start to salvage radiation therapy (SRT) or salvage androgen deprivation therapy (SADT) after surgery. Mortality is shown as prostate cancer specific survival (PCSS) as well as overall survival (OS). For all outcomes, the number of men experiencing the outcome per total number of men with the respective 5- or 10-year follow are shown, wherein the percentage of events is given in parentheses. (B) Demographics of the diagnostic biopsy patient cohort. (N/A=not available).

Laboratory Methods

To account for potential tumor heterogeneity the two tissue punches of the RP cohort were combined before nucleic acid extraction. A potential difference in tumor cellularity of the tissue punches was addressed by normalization of the RT-qPCR results of the PDE4D transcripts to the four reference genes HPRT1, TUBA1B, PUM1, and TBP. All used molecular laboratory methods including oligonucleotide primers and probes for RT-qPCR (quantitative real-time PCR), RNA extraction, and quality control and procedures to include/discard samples from the statistical analysis were described before (see Alves de Inda M. et al., "Validation of Cyclic Adenosine Monophosphate Phosphodiesterase-4D7 for its Independent Contribution to Risk Stratification in a Prostate Cancer Patient Cohort with Longitudinal Biological Outcomes", European Urology Focus, 2017).

RNA Sequencing

RNA Sample Processing: 100 ng of total RNA was used as input to remove ribosomal RNA using Ribo-Zero Gold (Human/Mouse/Rat) rRNA Removal Kit (Illumina Inc.) according to the instructions of the manufacturer. For library construction, we used the total of the depleted RNA as input into the Scriptseq V2 RNA-Seq Library Preparation Kit (Epicentre/Illumina Inc.). Prepared RNAseq libraries were sequenced using a NextSeq 500 sequencing system (paired-end; 2×75 bp read length; approx. 80 million total reads per sample).

RNAseq Data Processing: The RNAseq raw data were pre-processed using Illumina's bcl2fastq software incorporating a filtering by phred scores, thereby reducing low quality reads. Since FFPE may degenerate the bases the sequencing results have been filtered using a scoring algorithm to select reads representing the high-quality fraction. The score was calculated for a set of reads in a sample as follows: The set of reads was aligned against a reference genome. The alignment result for each read (i.e. the number of bases mapping correctly to the reference genome) was counted per read. The total number of successfully mapped bases was summed over all reads of the set. This sum was divided by the total number of bases of the set. The resulting relative number was called the score:

Score=sum over all reads in sample ($N\_BAS$-$ES\_ALIGNED$ per read)/$N\_BASES\_SAMPLE$;  (2)

A score filter was used to select the subset of reads which contribute to the EQ Score by their good alignment result (all or most of the bases map correctly to the genome). The derived subset of high-quality reads was selected for further processing. If reads were mapped by fragmenting them (which may be required when aligning RNA) the measure was calculated based on the fragments alignment quality and the fragments were selected accordingly.

Read quality filtering: To retain only high quality reads the following filtering steps were applied. Reads were discarded when >50% of the bases had a phred score <11; bases at the read ends cut read if phred score <11; reads <63 bases discarded; reads with unknown (N) base calls were deleted; only read were kept pairs where each read passed the quality filter.

Gene expression calculation: To ensure comparability of expression values between samples all read counts were normalized by the transcripts per million method (TPM) as implemented in the RSEM algorithm (see Li B. et al., "RNA-Seq gene expression estimation with read mapping uncertainty", Bioinformatics, Vol. 26, No. 4, pages 493-500, 2010).

Data Analysis and Statistics

Generation of normalized PDE4D transcript expression was performed by subtracting the RT-qPCR Cq of the respective PDE4D transcript from the averaged RT-qPCR Cq of the reference genes. Normalized PDE4D5, PDE4D7, and PDE4D9 expression profiles were transformed to PDE4D5, PDE4D7, and PDE4D9 scores, as outlined for PDE4D7 in detail above. In correlation analysis for various available biological and treatment related outcomes (see TABLE 10), the PDE4D transcript scores were either used as a continuous or as a categorical variable defined as: a) PDE4D5/7/9 score (1≤2); b) PDE4D5/7/9 score (>2 and ≤3); c) PDE4D5/7/9 score (>3 and ≤4); and d) PDE4D5/7/9 score (>4 and ≤5). The CAPRA risk score and corresponding low (1), intermediate (2), high-risk (3) categories were calculated as described in Cooperberg M. R. Uni- and multivariate Cox regression and Kaplan Meier analyses were applied to correlate biochemical recurrence (BCR) progression free survival, or secondary treatment (salvage radiation and or androgen deprivation) free survival (STFS) to the PDE4D7 score in the RP cohort (n=536) and the RP* cohort from Taylor B. S. et al., "Integrative genomic profiling of human prostate cancer", Cancer Cell, Vol. 18, No. 1, pages 11-22, 2010 (178 patients of which 130 were included in our study) and the DB cohort (n=151). To determine the TMPRSS2-ERG status of patient samples in Exon Array cohorts, we used relative ERG expression values and applied Partitioning Around Medoids (PAM, R-package 'cluster', k=2) to assign the patient samples to the ERG positive or negative group based on expression. Decision curve analyses was performed as described in Vickers A. J. et al., "Extension to decision curve analysis, a novel method for evaluating diagnostic tests, prediction models and molecular markers", BMC Medical Informatics and Decision Making, Vol. 8, pages 1-17, 2008. For statistical analysis the software package MedCalc (MedCalc Software BVBA, Ostend, Belgium) was used.

RESULTS

Association of PDE4D Transcript Scores to Longitudinal Clinical Outcomes Depends on the TMPRSS2-ERG Fusion Status Firstly, we set out to do Kaplan-Meier survival analysis of the PDE4D7 score categories in TMPRSS2-ERG rearrangement positive vs. gene fusion negative patient samples. In total 536 patient samples with data on TMPRSS2-ERG status were included of which 280 (52.2%) were defined as fusion positive while 256 samples (47.8%) were defined to be absent of this prostate specific fusion event. Biochemical recurrence (BCR) was selected as a surrogate endpoint for post-surgical disease progression due to the significant number of events for this outcome in the studied patient cohorts (see TABLE 10).

Figure 12:
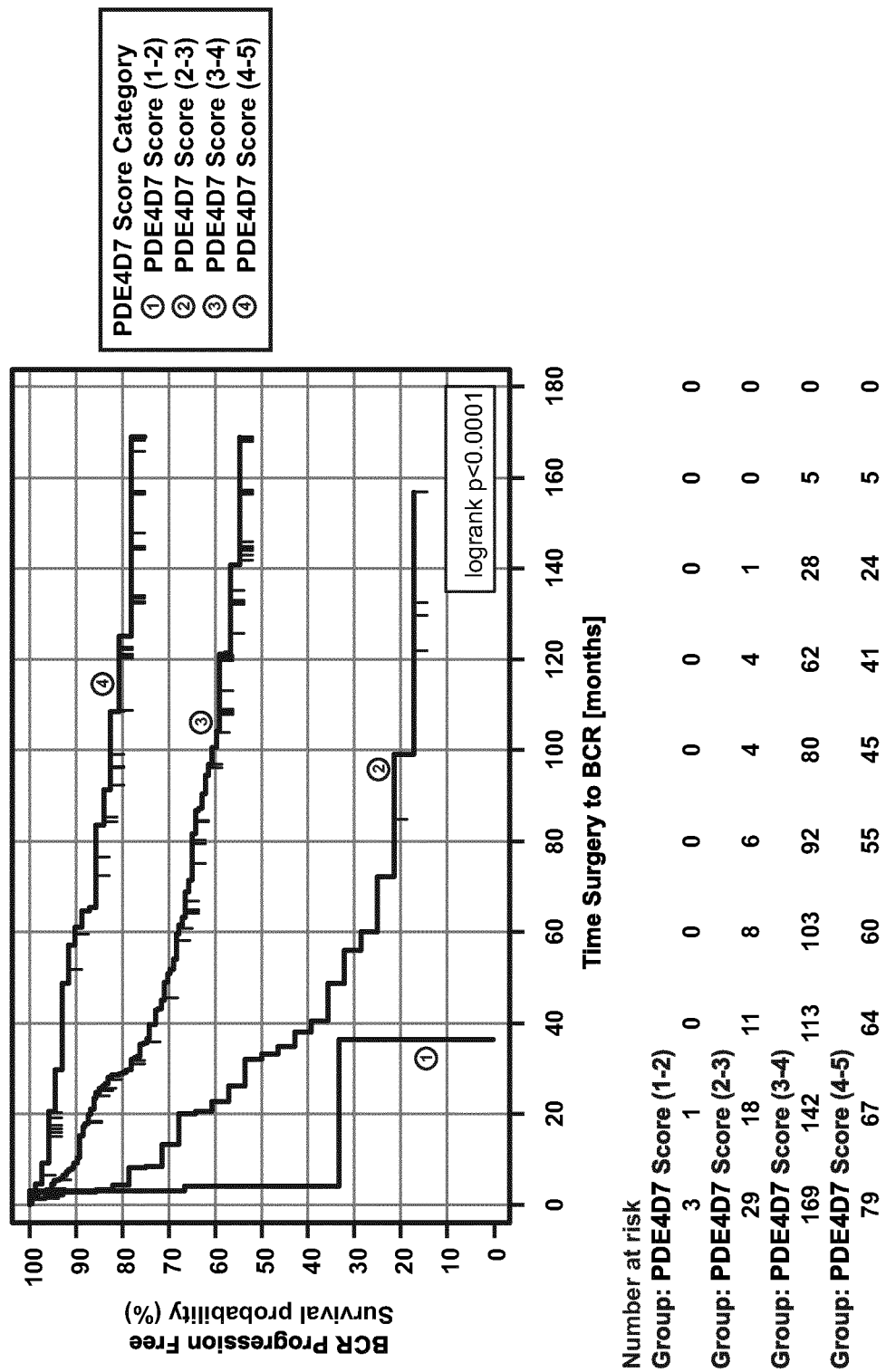
FIGS. 12 to 17 show results of Kaplan Meier survival analysis of the time to PSA relapse (endpoint: BCR) in the RP patient cohort (n=536) for the PDE4D5, PDE4D7, and PDE4D9 scores.
Figure 13:
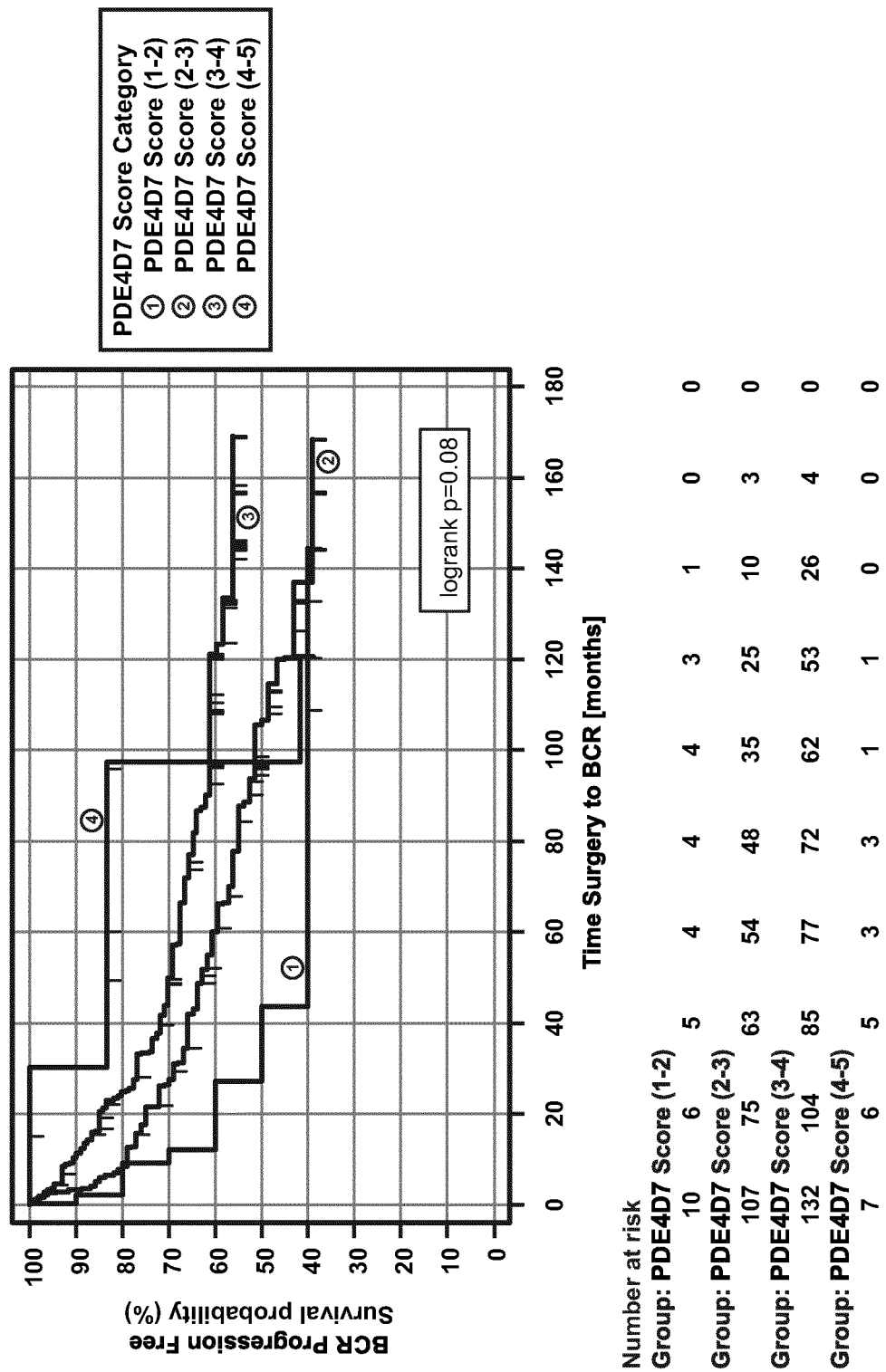
Figure 14:
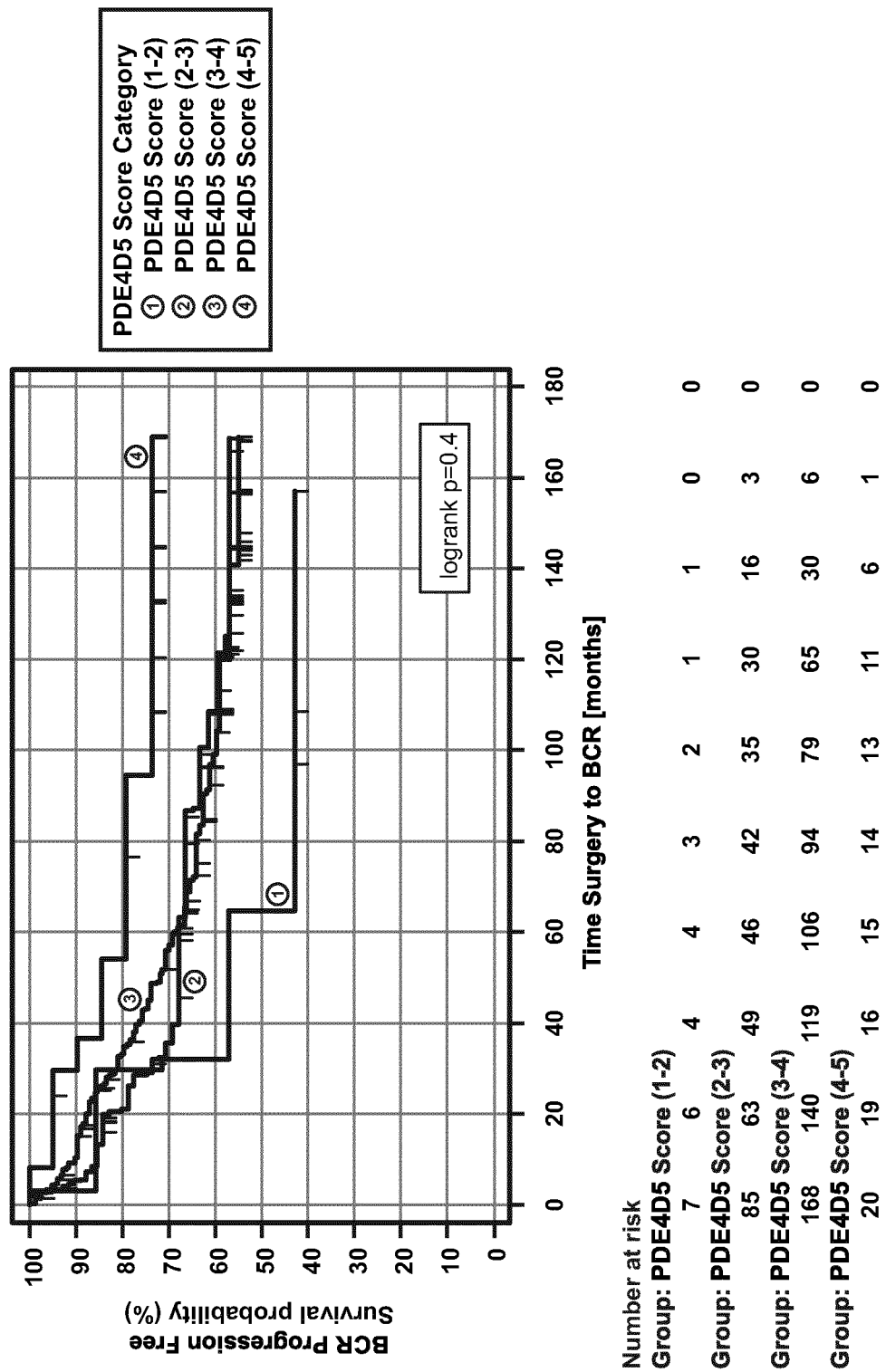
Figure 15:
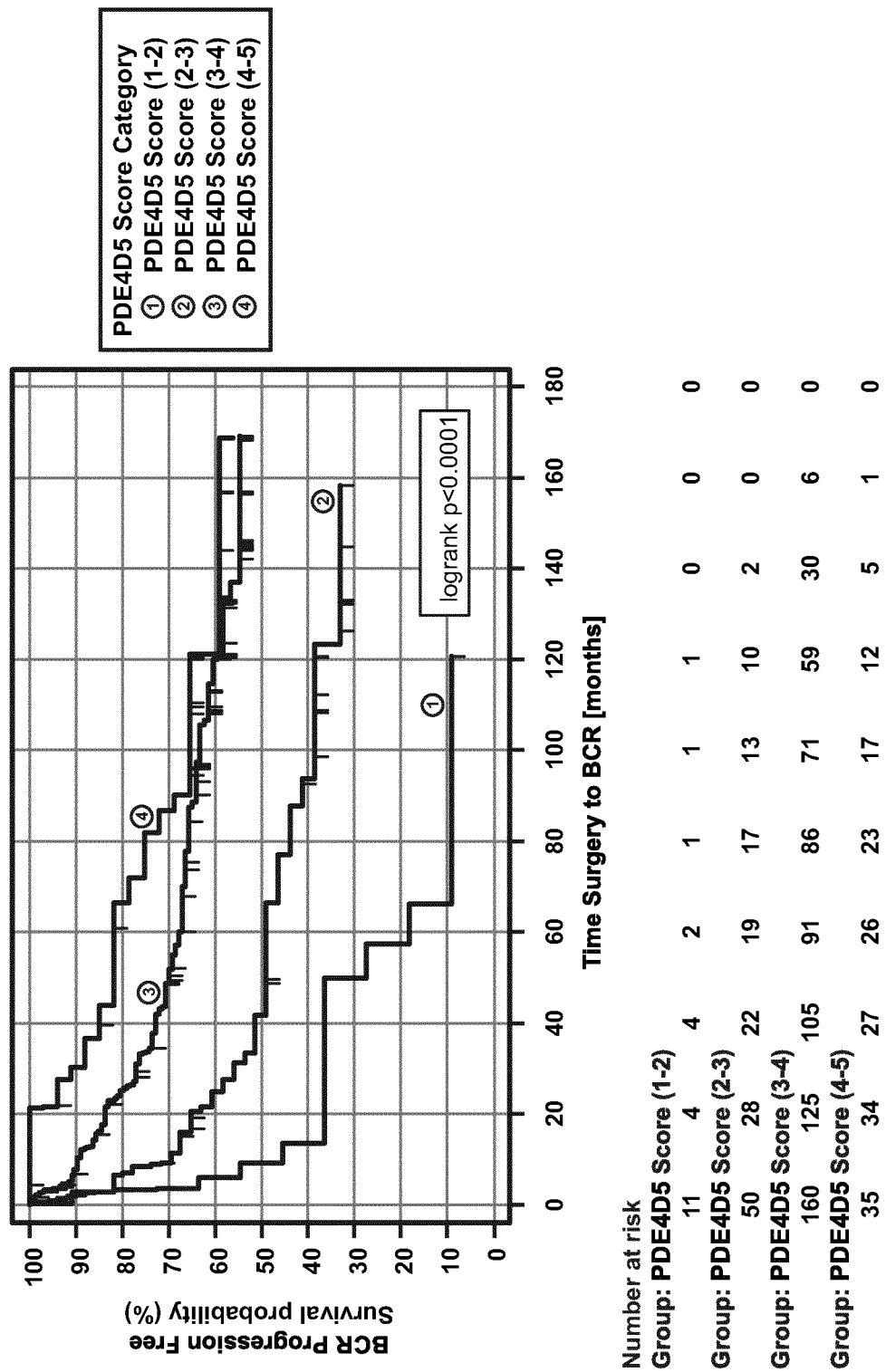
Figure 16:
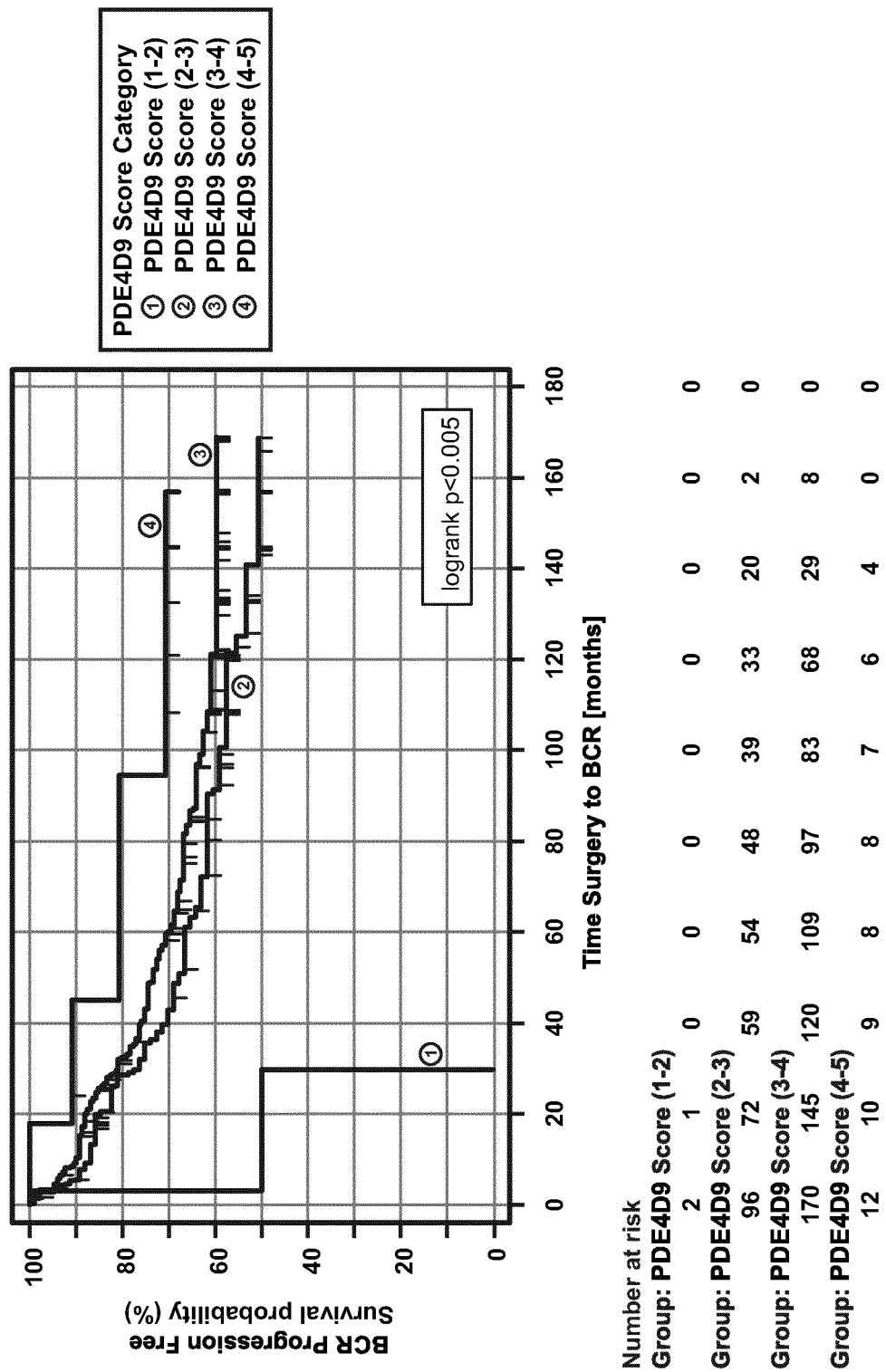
Figure 17:
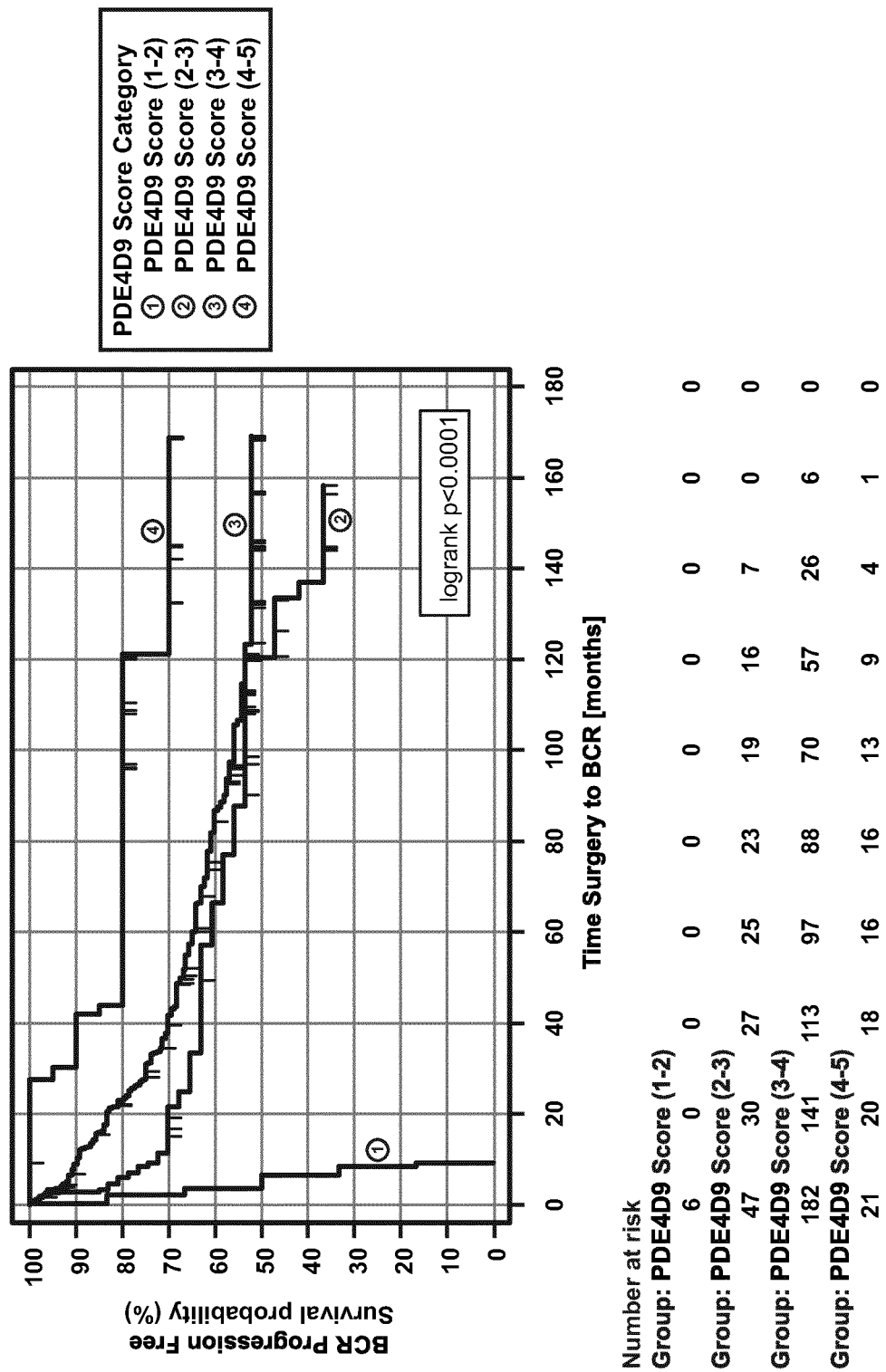

A clear difference in BCR progression free survival analysis was observed between the fusion positive vs. negative tumors with a highly significant logrank p-value (<0.0001) for the PDE4D7 categories in the presence of the rearranged TMPRSS2-ERG gene fusion (see FIG. 12). The patient group with the highest level of PDE4D7 expression (i.e., PDE4D7 scores 4-5) showed the lowest risk of disease progression after surgery in the TMPRSS2-ERG fusion positive cancers. In contrast, in prostate tumors without an ERG gene fusion event the discrimination in Kaplan-Meier survival between the defined four different PDE4D7 categories was non-significant (logrank p-value=0.08; see FIG. 13). Interestingly, when looking at BCR progression free survival analysis of the PDE4D5 score we found the opposite situation compared to what was observed for the PDE4D7 scores. Only in gene fusion free tumors the PDE4D5 score categories significantly (logrank p-value<0.0001) predicted biochemical relapse (see FIGS. 14 and 15). We observed a similar result as for the PDE4D5 scores also for the PDE4D9 score categories with a logrank p-value<0.0001 in survival analysis in TMPRSS2-ERG negative tumors. However, in contrast to the analysis of PDE4D5 scores, the survival analysis of PDE4D9 score categories in gene fusion positive cancers also resulted in a significant association to biochemical recurrence although with a somewhat weaker p-value compared to the TMPRSS2-ERG negative tumors (logrank p-value=0.005 vs. logrank p<0.0001, respectively; see FIGS. 16 and 17).

Figure 18:
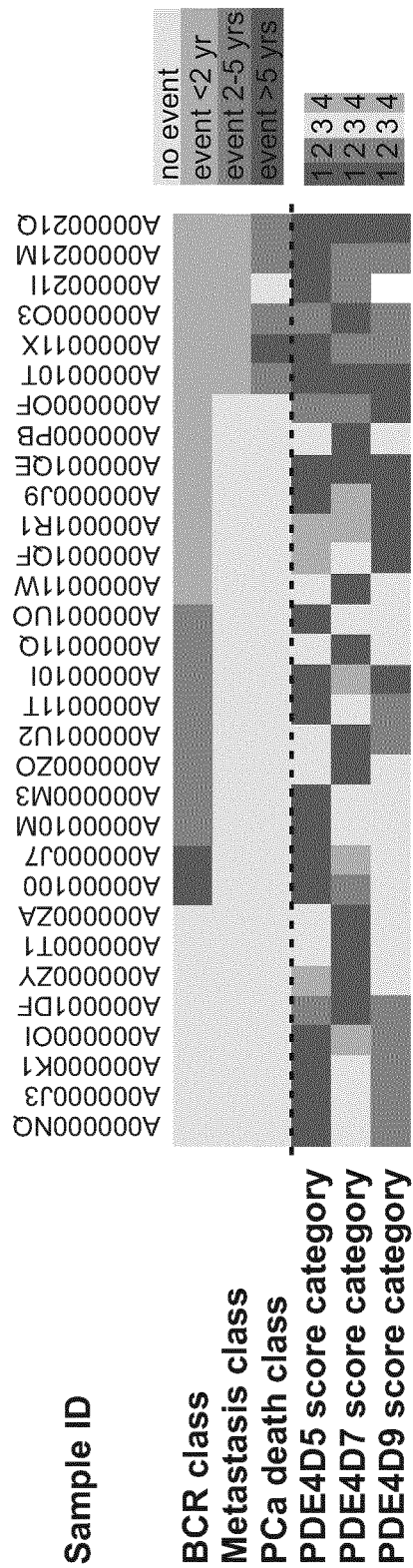
FIG. 18 shows a heatmap of TMPRSS2-ERG negative tumor samples of the RP patient cohort (n=256)

Next, it was investigated to what extent the score categories for the three different prostate cancer expressed PDE4D transcripts were determined to be mutually exclusive in individual patient samples or whether the same score category (e.g., [1-2] or [4-5]) was seen across the same samples for the three studied PDE4D splice variants. For this, we plotted a heatmap (not shown in the figures) including all 536 patient samples with an initial split of between TMPRSS2-ERG gene fusion positive vs. fusion negative samples. While the samples within the TMPRSS2-ERG negative samples were ordered according to their PDE4D5 or PDE4D9 score category the samples with positive for the gene fusion were ordered according to their PDE4D7 score category from low to high. The heatmaps replicated the results of the Kaplan-Meier survival analysis with more events in the lower PDE4D iso form score categories. However, the PDE4D transcript score categories were to some extent non-overlapping within a patient sample. When focusing on the lowest score category (i.e., all scores for PDE4D5/PDE4D7/PDE4D9 between [1-2]) we identified 31 samples with at least one of the three PDE4D transcripts with a score category [1-2] (see FIG. 18). For three samples (marked in bold) we measured the lowest score category for all three PDE4D transcripts while for two samples (marked in bold italic) at least two PDE4D transcripts belonged to the lowest score category. For the other 26 samples only one PDE4D splice variant was measured as expressed very low while the two respectively other isoforms showed higher expression levels in these samples. The risk to develop metastases or to die from prostate cancer (6 and 5 out of the 31 patients, respectively) increases strongly with reduced expression levels of multiple long prostate expressed PDE4D isoforms (see FIG. 18). Also, the time scale after surgery to an event like BCR was generally shorter (<2 years) in those patients with at least two PDE4D transcript scores [1-2] and/or [2-3]. Vice versa, the higher the expression level of at least one of the three PDE4D splice variants the less likely was the chance to experience BCR after surgery. Or, in case the event happened, it was typically on a longer time scale (2-5 years, in some cases >5 years after primary treatment). Taken together, these data indicate that, next to PDE4D7, other long transcripts of PDE4D, namely PDE4D5 and PDE4D9, may also have significant prognostic value in prostate cancer. Therefore, we hypothesized that the addition of the PDE4D5 and PDE4D9 score, to that of PDE4D7, might increase the power to predict post-surgical risk of disease progression either over the clinical variables or over the above-described PDE4D7 based model (see also Alves de Inda M. et al. and van Strijp D. et al., "The Prognostic PDE4D7 Score in a Diagnostic Biopsy Prostate Cancer Patient Cohort with Longitudinal Biological Outcomes", Prostate Cancer, 2018).

Logistic Regression Model of Clinical Variables and Prostate Cancer Expressed Long PDE4D Transcripts To test this concept, we developed a prognostic model to include the clinical CAPRA score (see Cooperberg M. R.) together with the gene expression profile scores of PDE4D5, PDE4D7 and PDE4D9. For model development the RP (n=536) and RP* cohorts (n=130) were used. Logistic regression analysis was performed to predict post-surgical biochemical relapse in the RP and RP* cohorts to estimate the weights for the CAPRA score as well as for the PDE4D transcripts. The coefficients were calculated by logistic regression. Next, we adjusted the initial coefficients after logistic regression analysis of the four model inputs on the RP* cohort by calculating an average of the coefficients for the RP and RP* cohorts, thus taking the heterogeneity of different patient groups into account. The final CAPRA & PDE4D5/7/9 model ($co_1 \cdot$PDE4D5 score+$co_2 \cdot$PDE4D7 score+$co_3 \cdot$PDE4D9 score+$co_4 \cdot$CAPRA score, where $co_1$, $co_2$, $co_3$ and $co_4$ are the regression coefficients) was tested for its prognostic power to predict BCR as well as start of secondary treatment of after surgery (i.e., radiation, or hormone deprivation) in the independent DB patient cohort. For any other outcome, like metastases or death, we used the RP and RP* cohorts (note: these clinical endpoints were not used during model development). An overview of the logistic regression modelling is provided in the following TABLE 11.

TABLE 11

The CAPRA & PDE4D5/7/9 score combination model was developed by logistic regression of the CAPRA score and the normalized PD4D5, PDE4D7, and PDE4D9 expression values in the RP patient cohort (n = 480 with completed 5-years follow-up after surgery) and in the RP* cohort (n = 130; Taylor et al, 2010). The logistic regression coefficients for the two cohorts were averaged to generate a mean coefficient for PD4D5, PDE4D7, and PDE4D9 and the CAPRA score based on the data of two independent patients cohorts in order to take the variation of different patient groups into account. These coefficients were used as weights in the final CAPRA & PDE4D5/7/9 regression model. Note: The CAPRA score is calculated based on Cooperberg M. R.; however, as the information on the number of positive biopsy cores was missing for the RP* cohort, the CAPRA score for this cohort was calculated using only patient age, pre-operative PSA, biopsy Gleason score, and clinical stage. The influence of the missing information on the biopsy cores was very limited as tested on the RP cohort as well as the DB cohort (data not shown).

| Logistic Regression RP Cohort (PDE4D5, PDE4D7, PDE4D9, CAPRA) | | | | |
|---|---|---|---|---|
| DependentY | | | BCR | |
| Method | | | Enter | |
| Sample size | | | 480 | |
| Positive cases | | | 169 (35.21%) | |
| Negative cases | | | 311 (64.79%) | |
| Variable | Coefficient | Std. Error | Wald | P |
| PDE4D5 | −0.60657 | 0.16298 | 13.8512 | 0.0002 |
| Constant | 1.371151 | 0.53891 | 6.5336 | 0.0106 |
| PDE4D7 | −0.95369 | 0.16742 | 32.4485 | <0.0001 |
| Constant | 2.51574 | 0.5518 | 20.7859 | <0.0001 |
| PDE4D9 | −0.68031 | 0.189 | 12.9565 | 0.0003 |
| Constant | 1.60341 | 0.61852 | 6.7201 | 0.0095 |
| CAPRA Score | 0.81575 | 0.086203 | 89.5511 | <0.0001 |
| Constant | −3.53088 | 0.33073 | 113.9781 | <0.0001 |

| Logistic Regression RP* Cohort (PDE4D5, PDE4D7, PDE4D9, CAPRA) | | | | |
|---|---|---|---|---|
| DependentY | | | BCR | |
| Method | | | Enter | |
| Sample size | | | 130 | |
| Positive cases | | | 26 (20.00%) | |
| Negative cases | | | 104 (80.00%) | |
| Variable | Coefficient | Std. Error | Wald | P |
| PDE4D5 | −0.91989 | 0.41366 | 4.9451 | 0.0262 |
| Constant | 6.8611 | 3.68577 | 3.4652 | 0.0627 |
| PDE4D7 | −0.47163 | 0.23486 | 4.0326 | 0.0446 |
| Constant | 2.4353 | 1.88706 | 1.6655 | 0.1969 |
| PDE4D9 | −0.77544 | 0.32339 | 5.7495 | 0.0165 |
| Constant | 5.30545 | 2.77079 | 3.6664 | 0.0555 |
| CAPRA Score | 0.48565 | 0.13132 | 13.6763 | 0.0002 |
| Constant | −2.32506 | 0.37523 | 38.394 | <0.0001 |

| Average Model | | |
|---|---|---|
| Coefficients | | |
| $co_1$ | PDE4D5 | −0.76 |
| $co_2$ | PDE4D7 | −0.71 |
| $co_3$ | PDE4D9 | −0.73 |
| $co_4$ | CAPRA Score | 0.65 |

[a] 459 samples for CAPRA analysis

In a particularly preferred realization, the coefficient $co_1$ for PDE4D5 is in the range from −1.26 to −0.26, preferably, in the range from −1.16 to −0.36, more preferably, in the range from −1.06 to −0.46, more preferably, in the range from −0.96 to −0.56, more preferably, in the range from −0.86 to −0.66, most preferably, −0.76, and/or the coefficient $co_1$ for PDE4D7 is in the range from −1.21 to −0.21, preferably, in the range from −1.11 to −0.31, more preferably, in the range from −1.01 to −0.41, more preferably, in the range from −0.91 to −0.51, more preferably, in the range from −0.81 to −0.61, most preferably, −0.71, and/or the coefficient $co_3$ for PDE4D9 is in the range from −1.23 to −0.23, preferably, in the range from −1.13 to −0.33, more preferably, in the range from −1.03 to −0.43, more preferably, in the range from −0.93 to −0.53, more preferably, in the range from −0.83 to −0.63, most preferably, −0.73, and/or the coefficient $co_4$ for the pre-surgical CAPRA score is in the range from 0.15 to 1.15, preferably, in the range from 0.25 to 1.05, more preferably, in the range from 0.35 to 0.95, more preferably, in the range from 0.45 to 0.85, more preferably, in the range from 0.55 to 0.75, most preferably, 0.65.

Kaplan-Meier Survival Analysis of the CAPRA & PDE4D5/7/9 Model

Figure 19:
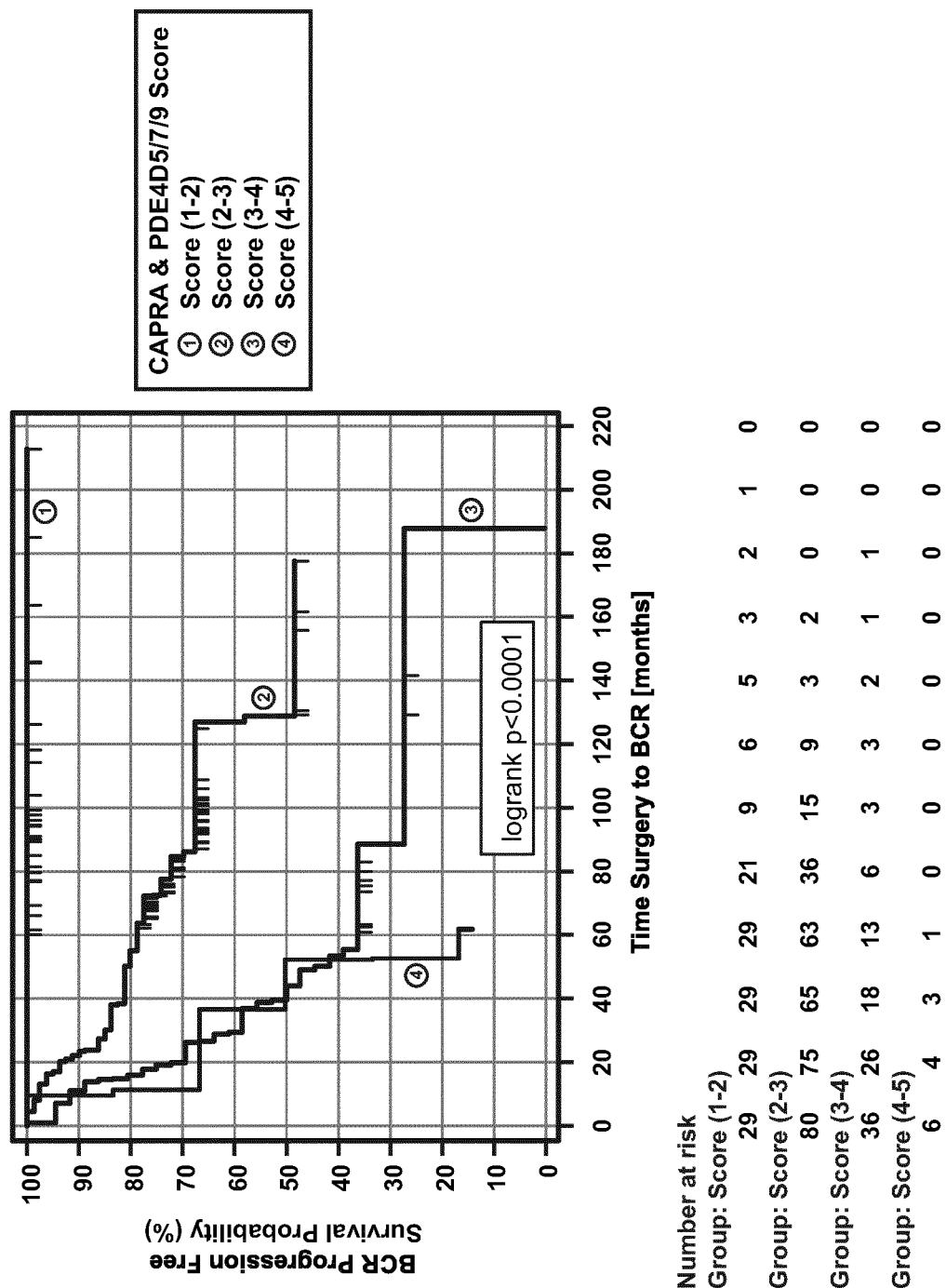
FIGS. 19 and 20 show results of Kapaln Meier survival analysis of biochemical recurrence (BCR) progression free survival amd secondary treatment (salvage radiation and or androgen deprivation) free survival (STFS) in the DB patient cohort for the categorized CAPRA & PDE4D5/7/9 combination score.
Figure 20:
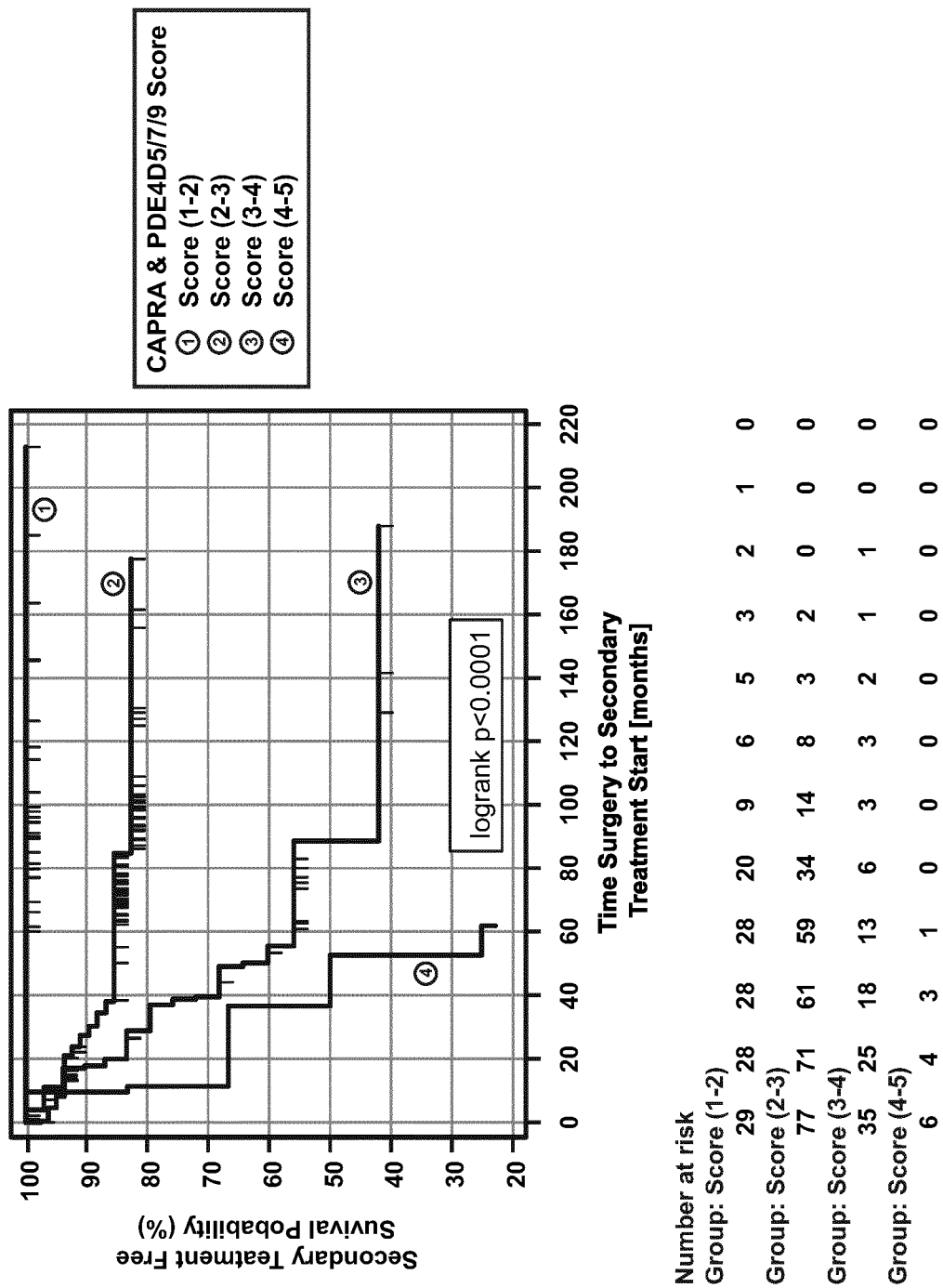

In Kaplan-Meier survival analysis the CAPRA & PDE4D5/7/9 model stratified 29 men (19.2%) of the total DB cohort (n=151) within the lowest score class [1-2] into a patient group with no risk over the follow-up period of 60 to 200 months of PSA relapse nor any risk of starting secondary treatments (see FIGS. 19 and 20). By slightly increasing the cut-off of this model score category from [1-2] to [1-2.1] the number of men in this group with no risk of post-surgical disease progression will increase from 29 to 36 subjects (23.8%; data not shown). In contrast, the patient with the highest categories of CAPRA & PDE4D5/7/9 scores of [3-4] and [4-5] experience a risk of biochemical progression within 5 years after surgery of 63.9% and 83.3%, respectively. Similarly, the risk to undergo secondary treatment estimated from the survival analysis within a period of 5 years post-surgery was 44.1% and 75% for these patient groups, respectively (see FIGS. 19 and 20).

ROC Curve Analysis of the CAPRA & PDE4D5/7/9 Model

Figure 21:
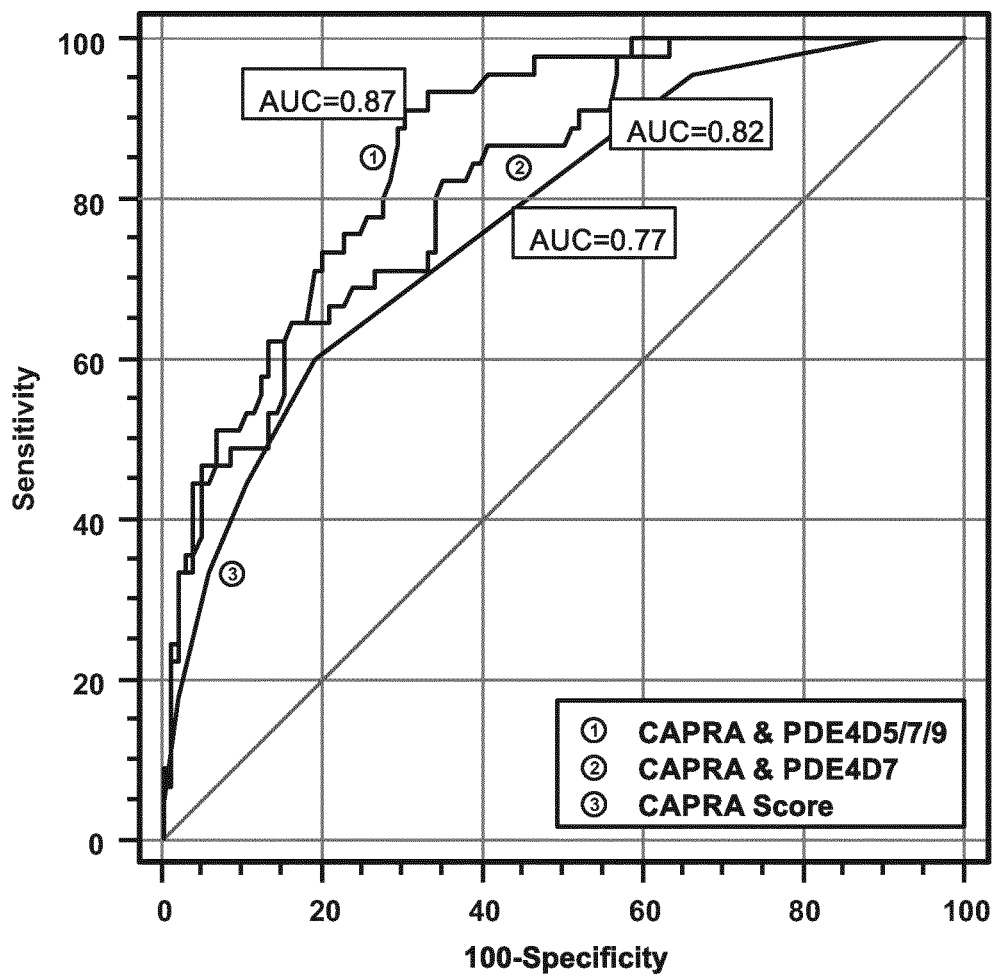
FIGS. 21 and 22 show results of ROC curve analysis of 5-year biochemical recurrence (BCR) after surgery and 5-year secondary treatment free survival (STFS) after surgery in the DB patient cohort for the CAPRA model vs. the CAPRA & PDE4D7 model vs. the CAPRA & PDE4D5/7/9 combination model.
Figure 22:
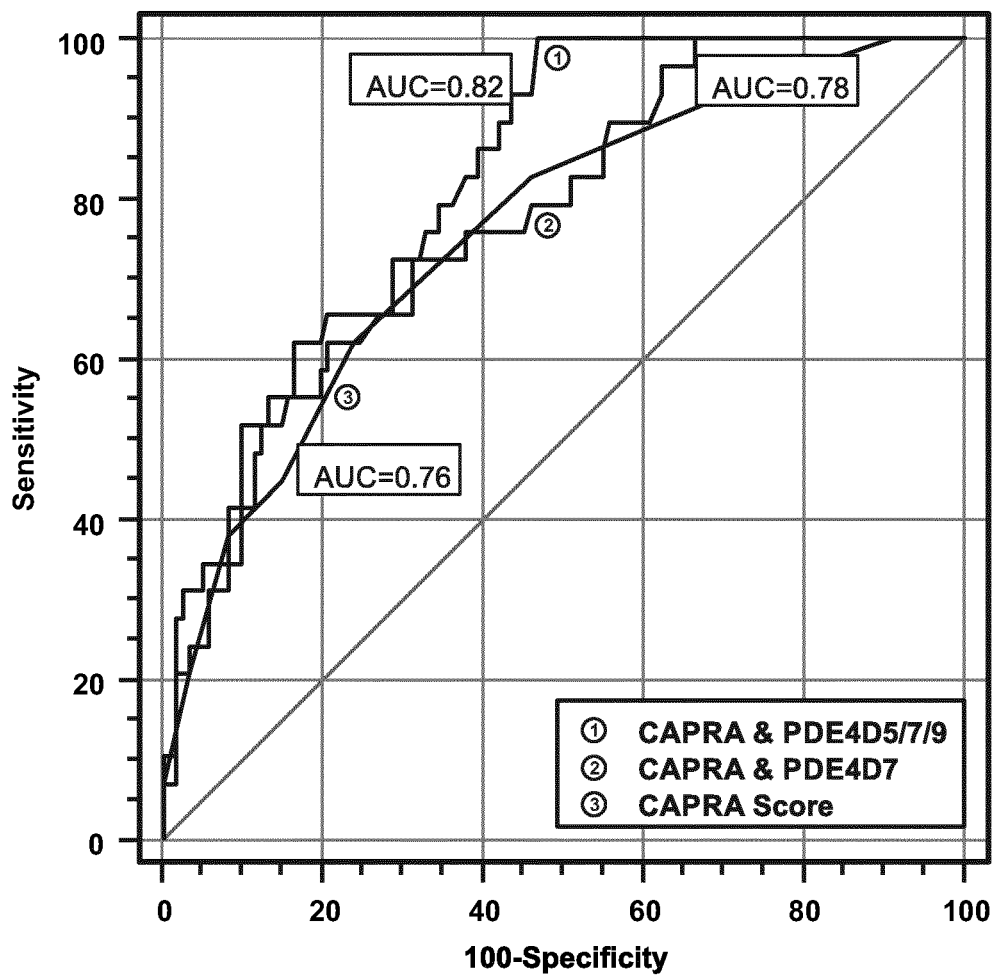

For the DB cohort (as above) BCR and start of secondary therapy were tested as outcomes. We compared the CAPRA & PDE4D5/7/9 model with the above-described CAPRA & PDE4D7 model (see also van Strijp D. et al.). For both tested clinical endpoints we identified an increase in the AUC (Area Under the Curve) of 10% and 6%, respectively, compared to the CAPRA score alone and 5% and 4%, respectively compared the CAPRA & PDE4D7 model (see FIGS. 21 and 22).

To further explore this effect we tested outcomes other than biochemical relapse. As we developed the combination model of the CAPRA and the PDE4D transcript scores using BCR as an endpoint in the two radical prostatectomy cohorts (RP and RP*) we did not test the model on that endpoints in these cohorts. Instead we used other outcomes for testing like the progression to metastases after surgery or death from prostate cancer after primary (i.e., RP) or secondary treatments (i.e., SRT—salvage radiation therapy; SADT—salvage androgen deprivation therapy) to investigate the potentially added value of PDE4D5 and PDE4D9 to the earlier described CAPRA & PDE4D7 model. TABLE 12 provides an overview of the increase in AUCs (areas under the curves) of up to 5% and up to 12% compared to the CAPRA score or the CAPRA & PDE4D7 score model, respectively when using the additional prognostic value of PDE4D5 and PDE4D9 in addition to the CAPRA & PDE4D7 score model. This data indicate that the use of additional prostate relevant PDE4D transcripts may increase the prognostic power of our previously published combination model of the CAPRA and PDE4D7 score.

TABLE 12

Overview of the AUCs for the CAPRA score, the CAPRA & PDE4D7, and the CAPRA & PDE4D5/7/9 regression models to predict multiple endpoints in various patient cohorts.

| Patient Cohort | Tested Clinical Endpoint (post treatment) | # events | CAPRA&PDE 4D5/7/9 Score | CAPRA&PDE 4D7 Score AUC | CAPRA Score |
|---|---|---|---|---|---|
| RP* (n = 130) | metastases (post-surgery) | 8 (6.2%) | 0.86 | 0.82 | 0.74 |
| DB (n = 151) | 5-yr PSA recurrence (post-surgery) | 45 (19.8%) | 0.87 | 0.82 | 0.77 |
| DB (n = 151) | 5-yr start of secondary treatment (post-surgery) | 27 (17.9%) | 0.82 | 0.78 | 0.76 |
| RP (n = 220) | 10-yr prostate cancer death (post-surgery) (pGleason >6) | 21 (11.1%) | 0.78 | 0.78 | 0.74 |
| RP (n = 86) | 10-yr prostate cancer death (post-SRT) | 18 (20.9%) | 0.78 | 0.76 | 0.7 |
| RP (n = 61) | 10-yr prostate cancer death (post-SADT) | 17 (27.9%) | 0.74 | 0.72 | 0.67 |

The patient cohort that was used for the respective endpoint is indicated including the number of patients with respective follow-up periods. The tested clinical endpoints are given including the number and percentage of the respectively tested events. Note: The CAPRA score is calculated based on Cooperberg M. R.; however, as the information on the number of positive biopsy cores was missing for the RP* cohort the CAPRA score for this cohort was calculated using patient age, pre-operative PSA, biopsy Gleason score, and clinical stage only. The influence of the missing information on the biopsy cores was very limited as tested on the RP as well as the DB cohort.

Decision Curve Analysis of the CAPRA & PDE4D5/7/9 Model

Figure 23:
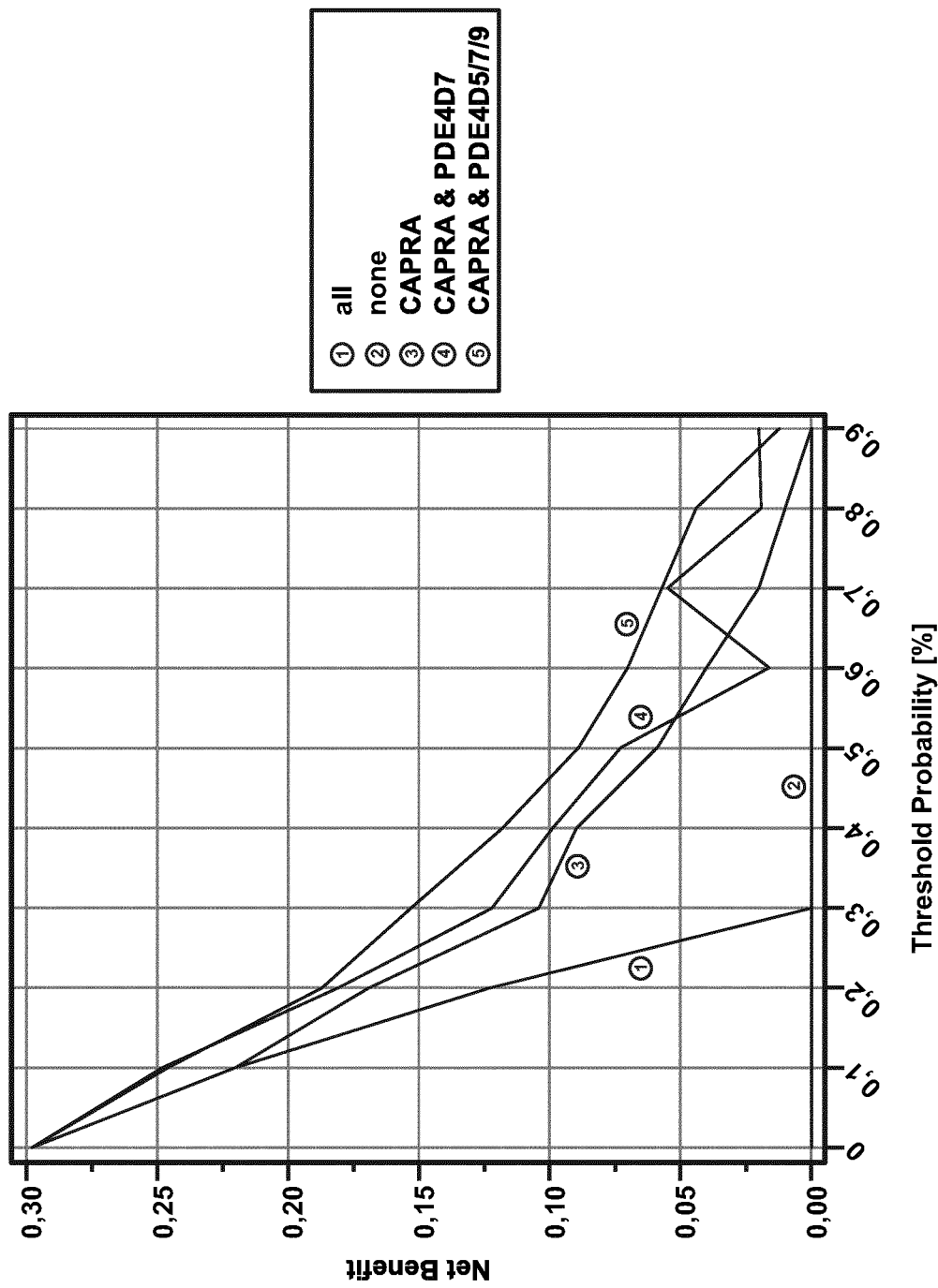
FIG. 23 shows results of decision curve analysis in the DB patient cohort of the net benefit of four different treatment decision strategies for men at risk to experience disease recurrence within 5 years after surgery.
Figure 24:
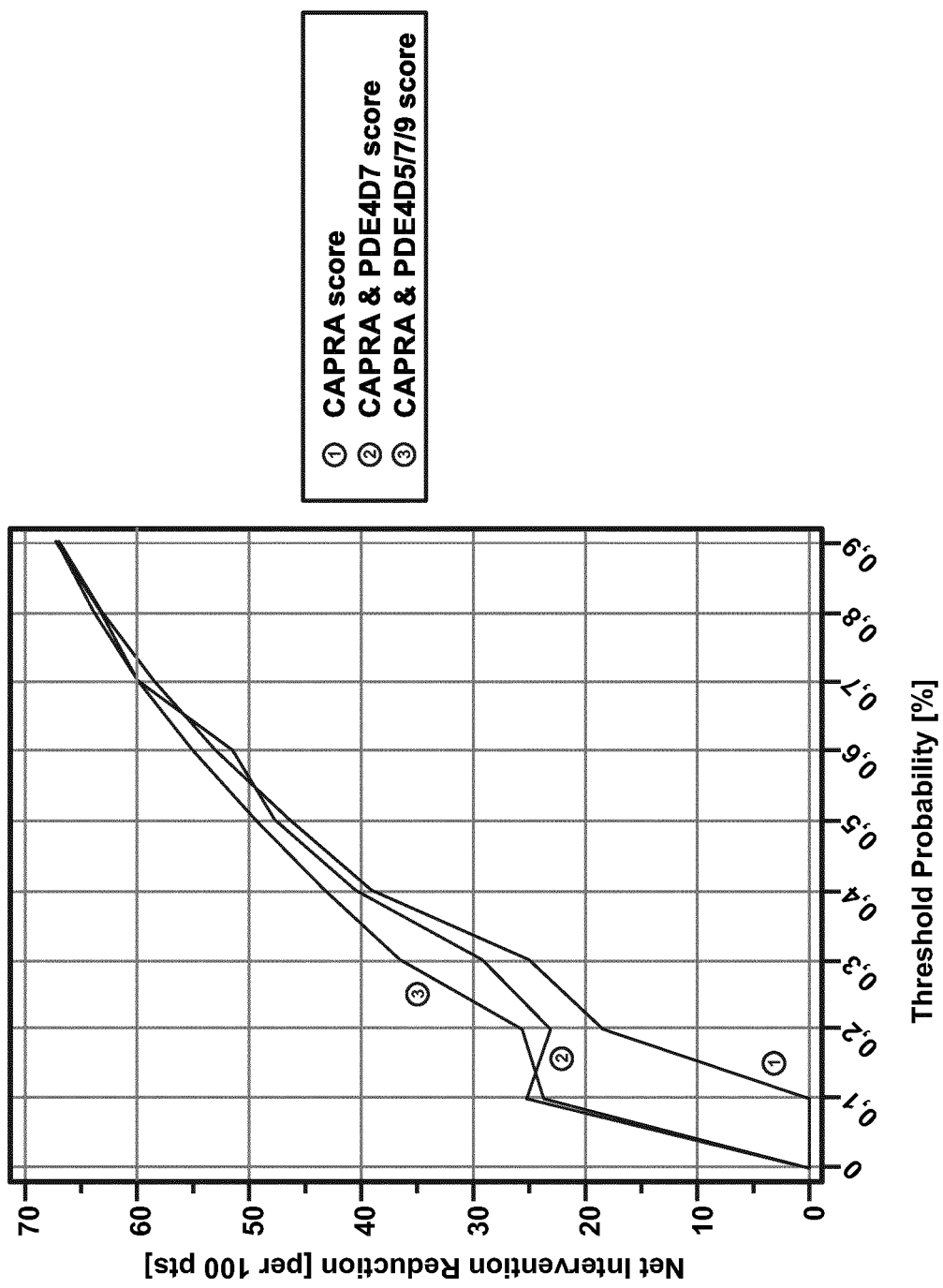
FIG. 24 shows results of decision curve analysis in the DB patient cohort of the net reduction of two different treatment decision strategies for men at risk to experience disease recurrence within 5 years after surgery.

Decision curve analysis is a net benefit analysis, which compares the true-positive to the weighted false-positive rates across different risk thresholds which a clinician/patient might want to accept (see Vickers A. J. et al., "Net benefit approaches to the evaluation of prediction models, molecular markers, and diagnostic tests", BMJ, Vol. 25, 2016). We explored the net benefit of avoiding primary treatment based on the predicted risk of a PSA relapse after surgery for the CAPRA score and the CAPRA & PDE4D7 score vs. the here presented CAPRA & PDE4D5/7/9 combination model. The analysis demonstrated that all models showed better net benefit compared to the "treat all" strategy while the combination model of CAPRA with the three PDE4D transcripts revealed the best net benefit across all modeled decision thresholds (see FIG. 23). Similarly, the net reduction analysis in primary treatment revealed a substantial difference in treatment reduction between the CARPA score and the CARPA & PDE4D5/7/9 combination model across all decision thresholds (see FIG. 24). Furthermore, the addition of PDE4D5 and PDE4D9 to the CAPRA & PDE4D7 model clearly improves the net benefit in decision curve analysis as well as would more effectively reduce the number of interventions per 100 patients compared to the CAPRA combination model with PDE4D7 alone.

We illustrated that the earlier presented CAPRA & PDE4D7 risk model can be further improved by adding other long PDE4D transcripts into the model. The rational for this added prognostic benefit of PDE4D5 and PDE4D9 is supported by the differences in prediction power between TMPRSS2-ERG positive vs. gene fusion negative patient tumors. By complementing PDE4D7 with the two other prostate cancer relevant PDE4D transcripts PDE4D5 and PDE4D9 we built a more comprehensive prognostic model to assess the risk of disease progression before primary intervention.

Discussion

It has been shown that a predictive model of the clinical risk algorithm CAPRA in combination with the prostate cancer biomarker PDE4D7 provides value to prostate cancer risk stratification (see also Alves de Inda M. et al. and van Strijp D. et al.). The provided experimental results demonstrate that PDE4D7 adds independent value to the clinical CAPRA model and significantly improves the prognostic power to predict post-surgical disease progression. In order to further increase the value of this CAPRA & PDE4D7 combination mode we identified expression differences of various long PDE4D iso forms in primary tumor material which were different for the prostate cancer specific TMRPSS2-ERG gene rearrangement (see Böttcher R. et al., "Human PDE4D isoform composition is deregulated in primary prostate cancer and indicative for disease progression and development of distant metastases", Oncotarget, Vol. 7, No. 43, pages 70669-70684, 2016).

The study data presented here enabled us to dissect the impact of three different PDE4D transcripts PDE4D5, PDE4D7 and PDE4D9 on the risk of post-surgical disease progression depending on the genomic background of the patient's tumor. Interestingly, PDE4D7 was found to be associated significantly with post-treatment disease recurrence in a TMRPSS2-ERG fusion positive background while less prognostic in patients without this particular gene fusion event. In contrast, PDE4D5 and PDE4D9 were highly prognostic in a non-fusion genomic background while PDE4D5 was not and PDE4D9 was less significantly associated with disease progression when the genomic fusion was present.

Active surveillance (AS) has become an accepted treatment alternative and is recommended by the national guidelines for men with low- and very-low risk prostate cancer (see Briganti A. et al., "Active Surveillance for Low-risk Prostate Cancer: The European Association of Urology Position in 2018", European Urology, Vol. 74, No. 3, pages 357-368, 2018). The guiding principle of AS is to delay, not to avoid the primary treatment. The switch from AS to active intervention should be taken while the treatment intent is still curative. Consequently, men in AS have to follow strict monitoring schedules as discontinuation and switch to active treatment takes place at the earliest sign of disease progression like a raise in PSA, a biopsy Gleason score or clinical stage migration. However, taken the low mortality risk of men in the active monitoring arm of the ProtecT trial into consideration it is questionable to what extent these observed changes in clinical presentation of the disease correlate with true biological disease progression (see Hamdy C. F. et al., "10-Year Outcomes after Monitoring, Surgery, or Radiotherapy for Localized Prostate Cancer", The New England Journal of Medicine, Vol. 375, pages 1415-1424, 2016).

Currently, new technology like multi-parametric MRI, or genomics is considered for stratification of men to active surveillance or for monitoring of men in AS (see Eineluoto J. T., "Repeat multiparametric MRI in prostate cancer patients on active surveillance", PLoS ONE, Vol. 12, No. 12, 2017, and Canfield S. et al., "Active Surveillance Use Among a Low-risk Prostate Cancer Population in a Large US Payer System: 17-Gene Genomic Prostate Score Versus Other Risk Stratification Methods", Reviews in Urology, Vol. 19, No. 4, pages 203-212, 2017). While the longitudinal cost of AS has been estimated to reach the same order of magnitude as primary interventions (see Keegan K. A. et al., "Active surveillance for prostate cancer compared with immediate treatment: an economic analysis", Cancer, Vol. 118, No. 14, pages 3512-3518, 2012) driven by the cost of repeated biopsies in particular (see Dall'Era M. A., "The economics of active surveillance for prostate cancer", Current Opinion in Urology, Vol. 23, No. 3, pages 278-282, 2013), any newly implemented technical tool might only be cost-effective if its use will lead to less men discontinuing AS with a switch to definitive treatment and/or if surveillance schedules will be minimized (or even avoided in some patients).

We believe that the combination of a clinical metric like the CAPRA score with genomic biomarkers like those presented here, namely evaluation of long form PDE4D(5/7/9) transcripts to predict the future risk of a patient to experience disease progression, may provide future support for selecting patients to be included into active surveillance that require very limited (little or no) follow-up for a defined time period after start of (active) surveillance.

Any reference signs in the claims should not be construed as limiting the scope.

The invention relates to a method of pre-surgical risk stratification of a prostate cancer subject, comprising determining a gene expression profile for phosphodiesterase 4D variant 7 (PDE4D7) in a biological sample obtained from the subject, determining an expression based risk score for the subject based on the gene expression profile, and determining a pre-surgical prognostic risk score for the subject based on the expression based risk score and pre-surgical clinical variables of the subject. This may allow for an improved stratification of the subject in a pre-surgical setting that may result in better primary treatment decisions. For instance, the pre-surgical prognostic risk score may allow to make better recommendations on whether to select active surveillance vs. active intervention, e.g., radical prostatectomy, for certain sub-populations of prostate cancer patients.

The attached Sequence Listing, entitled 2017PF02734_Sequence Listing_ST25 is incorporated herein by reference, in its entirety.

The invention claimed is:

1. A method of risk stratification of a prostate cancer subject, comprising:
   obtaining a biological sample from the prostate cancer subject, wherein the prostate cancer subject has not undergone prostate cancer surgery;
   determining a gene expression profile for phosphodiesterase 4D variant 7 (PDE4D7) in the biological sample obtained from the subject;
   determining an expression based risk score for the subject based on the gene expression profile;
   determining a prognostic risk score for the subject based on the expression based risk score and clinical variables of the subject; and
   administering a primary treatment for the subject based on the prognostic risk score, wherein the primary treatment is selected from the group consisting of: (i) at least a partial prostatectomy; and (ii) an active therapy selected from radiation treatment, hormone therapy, chemotherapy, and a combination thereof.

2. The method as defined in claim 1, wherein the clinical variables comprise one or more of: (i) an age of the subject; (ii) a prostate-specific antigen (PSA) level; (iii) a primary and secondary biopsy Gleason score; (iv) a clinical stage; and (v) a percentage of tumor positive biopsies.

3. The method as defined in claim 1, further comprising:
   determining a Cancer of the Prostate Risk Assessment (CAPRA) score for the subject;
   wherein the prognostic risk score is determined by combining the expression based risk score and the CAPRA score.

4. The method as defined in claim 3, wherein the expression based risk score and the CAPRA score are combined with a regression function derived from a population of prostate cancer subjects.

5. The method as defined in claim 1, wherein the prognostic risk score is determined as a modified Cancer of the Prostate Risk Assessment (CAPRA) score for the subject, in which a primary and secondary biopsy Gleason score is replaced by the expression based risk score.

6. The method as defined in claim 5, wherein the expression based risk score is a value in a predefined range, wherein depending on the value a number of points in the range from 0 to 3 are added in the modified CAPRA score.

7. The method as defined in claim 1, further comprising:
proposing a primary treatment for the subject based on the prognostic risk score;
wherein the primary treatment is selected from the group consisting of: (i) at least a partial prostatectomy; (ii) an active therapy selected from radiation treatment, hormone therapy, chemotherapy, and a combination thereof; and (iii) active surveillance.

8. The method as defined in claim 1, further comprising:
normalizing the gene expression profile with respect to one or more reference genes selected from the group consisting of: *Homo sapiens* hypoxanthine phosphoribosyltransferase 1 (HPRT1), Tubulin-Alpha-1b (TUBA1B), *Homo sapiens pumilio* RNA-Binding Family Member (PUM1), and *Homo sapiens* TATA box binding protein (TBP),
wherein the expression based risk score is determined based on the normalized gene expression profile.

9. The method as defined in claim 8, wherein the one or more reference genes comprise at least two, or at least three, or all of HPRT1, TUBAIB, PUM1, and TBP.

10. The method as defined in claim 1, wherein the expression based risk score is determined with a scoring function, based on the gene expression profile, the scoring function having been derived from gene expression profiles for biological samples of prostate cancer subjects.

11. The method as defined in claim 8, wherein the determining of the gene expression profile comprises performing RT-qPCR on RNA extracted from the biological sample, wherein a Cq value is determined for PDE4D7 and for each of the one or more reference genes, and wherein the determining of the expression based risk score includes normalizing the Cq value for PDE4D7 using the Cq value for each of the one or more reference genes and computing the expression based risk score as a linear function of the normalized Cq value.

12. The method as defined in claim 1, wherein the gene expression profile further includes expression information from phosphodiesterase 4D variant 5 (PDE4D5) and/or from phosphodiesterase 4D variant 9 (PDE4D9), wherein an expression based risk score is determined for the subject for each of the phosphodiesterase 4D variants based on the gene expression profile, and wherein the prognostic risk score for the subject is determined based on the expression based risk scores and the clinical variables of the subject.

13. Use of a gene expression profile for phosphodiesterase 4D variant 7 (PDE4D7) in risk stratification of a prostate cancer subject, comprising:
obtaining a biological sample from the prostate cancer subject, wherein the prostate cancer subject has not undergone prostate cancer surgery;
determining the gene expression profile in the biological sample obtained from the subject;
determining an expression based risk score for the subject based on the gene expression profile
determining a prognostic risk score for the subject based on the expression based risk score and clinical variables of the subject;
administering a primary treatment for the subject based on the prognostic risk score, wherein the primary treatment is selected from the group consisting of: (i) at least a partial prostatectomy; and (ii) an active therapy selected from radiation treatment, hormone therapy, chemotherapy, and a combination thereof.

* * * * *

SEQUENCE LISTING

<160> NUMBER OF SEQ ID NOS: 73

<210> SEQ ID NO 1
<211> LENGTH: 7801
<212> TYPE: DNA
<213> ORGANISM: Homo sapiens

<400> SEQUENCE: 1

| | | | | | |
|---|---|---|---|---|---|
| gtggtggccg | cgcacccggc | cgcggctgat | tcattcactt | caagtgccgt | gcagaaggct | 60 |
| cggcaggcgg | ggcgggcgtg | gggccgcggc | tccgggttgg | ggaccgagga | gatccggctg | 120 |
| tggaccagac | gctcctctgc | ggggcgggca | cccaagcgcg | ctcgccaccc | cctcgccatc | 180 |
| cgctagagcc | gggctcctgg | actgggactc | gggcccgccg | cacagttgaa | aagtcgcata | 240 |
| gtggtttttc | cgctcgcgtc | gctgtgtgaa | agttggctcg | ccgctctttg | cacgccctcc | 300 |
| ctggaggccg | acccgagacg | ccaagctgga | gagaccgtgc | ctccccgagg | ccggccgccc | 360 |
| cgcgagcaca | gcctccgccc | ccgttgcact | gccgggctgg | gcaatatgaa | ggagcagccc | 420 |
| tcatgtgccg | gcaccgggca | tccgagcatg | gcggggtatg | gcaggatggc | cccctttgaa | 480 |
| ctcgctagcg | gacccgtgaa | gcgcttgaga | actgagtccc | cctttccctg | tctcttcgca | 540 |
| gaggaggcct | accagaaact | ggccagcgag | accctggagg | agctggactg | gtgtctggac | 600 |
| cagctagaga | ccctacagac | caggcactcc | gtcagtgaga | tggcctccaa | caagtttaaa | 660 |
| aggatgctta | atcgggagct | cacccatctc | tctgaaatga | gtcggtctgg | aaatcaagtg | 720 |
| tcagagttta | tatcaaacac | attcttagat | aagcaacatg | aagtggaaat | tccttctcca | 780 |
| actcagaagg | aaaaggagaa | aagaaaaga | ccaatgtctc | agatcagtgg | agtcaagaaa | 840 |
| ttgatgcaca | gctctagtct | gactaattca | agtatcccaa | ggtttggagt | taaaactgaa | 900 |
| caagaagatg | tccttgccaa | ggaactagaa | gatgtgaaca | aatggggtct | tcatgttttc | 960 |
| agaatagcag | agttgtctgg | taaccggccc | ttgactgtta | tcatgcacac | catttttcag | 1020 |
| gaacgggatt | tattaaaaac | atttaaaatt | ccagtagata | ctttaattac | atatcttatg | 1080 |
| actctcgaag | accattacca | tgctgatgtg | gcctatcaca | acaatatcca | tgctgcagat | 1140 |
| gttgtccagt | ctactcatgt | gctattatct | acacctgctt | tggaggctgt | gtttacagat | 1200 |
| ttggagattc | ttgcagcaat | ttttgccagt | gcaatacatg | atgtagatca | tcctggtgtg | 1260 |
| tccaatcaat | ttctgatcaa | tacaaactct | gaacttgcct | tgatgtacaa | tgattcctca | 1320 |
| gtcttagaga | accatcattt | ggctgtgggc | tttaaattgc | ttcaggaaga | aaactgtgac | 1380 |
| attttccaga | atttgaccaa | aaaacaaaga | caatctttaa | ggaaaatggt | cattgacatc | 1440 |
| gtacttgcaa | cagatatgtc | aaaacacatg | aatctactgg | ctgatttgaa | gactatggtt | 1500 |
| gaaactaaga | aagtgacaag | ctctggagtt | cttcttcttg | ataattattc | cgataggatt | 1560 |
| caggttcttc | agaatatggt | gcactgtgca | gatctgagca | acccaacaaa | gcctctccag | 1620 |
| ctgtaccgcc | agtggacgga | ccggataatg | gaggagttct | tccgccaagg | agaccgagag | 1680 |
| agggaacgtg | gcatggagat | aagccccatg | tgtgacaagc | acaatgcttc | cgtggaaaaa | 1740 |
| tcacaggtgg | gcttcataga | ctatattgtt | catccctct | gggagacatg | gcagacctc | 1800 |
| gtccaccctg | acgccagga | tattttggac | actttggagg | acaatcgtga | atggtaccag | 1860 |
| agcacaatcc | ctcagagccc | ctctcctgca | cctgatgacc | cagaggaggg | ccggcagggt | 1920 |
| caaactgaga | aattccagtt | tgaactaact | ttagaggaag | atggtgagtc | agacacggaa | 1980 |
| aaggacagtg | gcagtcaagt | ggaagaagac | actagctgca | gtgactccaa | gactctttgt | 2040 |
| actcaagact | cagagtctac | tgaaattccc | cttgatgaac | aggttgaaga | ggaggcagta | 2100 |

-continued

```
gggaagaag aggaaagcca gcctgaagcc tgtgtcatag atgatcgttc tcctgacacg    2160
taacagtgca aaaactttca tgccttttt ttttttaagt agaaaaattg tttccaaagt     2220
gcatgtcaca tgccacaacc acggtcacac ctcactgtca tctgccagga cgtttgttga   2280
acaaaactga ccttgactac tcagtccagc gctcaggaat atcgtaacca gttttttcac   2340
ctccatgtca tccgagcaag gtggacatct tcacgaacag cgttttaac aagatttcag    2400 cttggtagag ctgacaaagc agataaaatc tactccaaat tattttcaag agagtgtgac   2460
tcatcaggca gcccaaaagt ttattggact tggggtttct attcctttt atttgtttgc    2520 aatatttca gaagaaaggc attgcacaga gtgaacttaa tggacgaagc aacaaatatg    2580
tcaagaacag gacatagcac gaatctgtta ccagtaggag gaggatgagc cacagaaatt   2640
gcataatttt ctaatttcaa gtcttcctga tacatgactg aatagtgtgg ttcagtgagc   2700
tgcactgacc tctacattt gtatgatatg taaaacagat tttttgtaga gcttactttt    2760
attattaaat gtattgaggt attatatta aaaaaaacta tgttcagaac ttcatctgcc    2820
actggttatt tttttctaag gagtaacttg caagttttca gtacaaatct gtgctacact   2880
ggataaaaat ctaatttatg aattttactt gcaccttata gttcatagca attaactgat   2940
ttgtagtgat tcattgtttg ttttatatac caatgacttc catattttaa aagagaaaaa   3000
caactttatg ttgcaggaaa cccttttgt aagtctttat tatttacttt gcattttgtt    3060
tcactctttc cagataagca gagttgctct tcaccagtgt ttttcttcat gtgcaaagtg   3120
actatttgtt ctataatact tttatgtgtg ttatatcaaa tgtgtcttaa gcttcatgca   3180
aactcagtca tcagttcgtg ttgtctgaag caagtgggag atatataaat acccagtagc   3240
taaaatggtc agtctttttt agatgtttc ctacttagta tctcctaata cgttttgct     3300 gtgtcactag atgttcattt cacaagtgca tgtctttcta ataatccaca catttcatgc   3360
tctaataatc cacacatttc atgctcattt ttattgtttt tacagccagt tatagtaaga   3420
aaaaggtttt tccccttgtg ctgctttata atttagcgtg tgtctgaacc ttatccatgt   3480
ttgctagatg aggtcttgtc aaatatatca ctaccattgt caccggtgaa aagaaacagg   3540
tagttaagtt agggttaaca ttcatttcaa ccacgaggtt gtatatcatg actagctttt   3600
actcttggtt tacagagaaa agttaaacag ccaactaggc agttttaag aatattaaca    3660 atatattaac aaacaccaat acaactaatc ctatttggtt ttaatgattt caccatggga   3720
ttaagaacta tatcaggaac atccctgaga aacggtttta agtgtagcaa ctactcttcc   3780
ttaatggaca gccacataac gtgtaggaag tccttatca cttatcctcg atccataagc    3840
atatcttgca gagggaact acttctttaa acacatggag ggaagaaga tgatgccact     3900 ggcaccagag ggtagtact gtgatgcatc ctaaaatatt tattatattg gtaaaaattc    3960
tggttaaata aaaaattaga gatcactctt ggctgatttc agcaccagga actgtattac   4020
agttttagag attaattcct agtgtttacc tgattatagc agttggcatc atggggcatt   4080
taattctgac tttatcccca cgtcagcctt aataaagtct tctttacctt ctctatgaag   4140
actttaaagc ccaaataatc attttcaca ttgatattca agaattgaga tagatagaag    4200
ccaaagtggg tatctgacaa gtggaaaatc aaacgtttaa gaagaattac aactctgaaa   4260
agcatttata tgtggaactt ctcaaggagc ctcctgggga ctggaaagta agtcatcagc   4320
caggcaaatg actcatgctg aagagagtcc ccatttcagt ccctgagat ctagctgatg    4380 cttagatcct ttgaaataaa aattatgtct ttataactct gatcttttac ataaagcaga   4440
```

```
agaggaatca actagttaat tgcaaggttt ctactctgtt tcctctgtaa agatcagatg    4500
gtaatctttc aaataagaaa aaaataaaga cgtatgtttg accaagtagt ttcacaagaa    4560
tatttgggaa cttgtttctt ttaattttat ttgtccctga gtgaagtcta gaaagaaagg    4620
taaagagtct agagtttatt cctctttcca aaacattctc attcctctcc tccctacact    4680
tagtatttcc cccacagagt gcctagaatc ttaataatga ataaaataaa aagcagcaat    4740
atgtcattaa caaatccaga cctgaaaggg taaagggttt ataactgcac taataaagag    4800
aggctctttt tttttcttcc agtttgttgg tttttaatgg taccgtgttg taaagatacc    4860
cactaatgga caatcaaatt gcagaaaagg ctcaatatcc aagagacagg gactaatgca    4920
ctgtacaatc tgcttatcct tgcccttctc tcttgccaaa gtgtgcttca gaaatatata    4980
ctgctttaaa aaagaataaa agaatatcct tttacaagtg gctttacatt tcctaaaatg    5040
ccataagaaa atgcaatatc tgggtactgt atggggaaaa aaatgtccaa gtttgtgtaa    5100
aaccagtgca tttcagcttg caagttactg aacacaataa tgctgtttta atttttgtttt   5160 atatcagtta aaattcacaa taatgtagat agaacaaatt acagacaagg aaagaaaaaa    5220
cttgaatgaa atggatttta cagaaagctt tatgataatt tttgaatgca ttatttattt    5280
tttgtgccat gcatttttt tctcaccaaa tgaccttacc tgtaatacag tcttgtttgt     5340
ctgtttacaa ccatgtattt attgcaatgt acatactgta atgttaattg taaattatct    5400
gttcttatta aaacatcatc ccatgatggg atggtgttga tatatttgga aactcttggt    5460
gagagaatga atggtgtgta tacatactct gtacattttt cttttctcct gtaatatagt    5520
cttgtcacct tagagcttgt ttatggaaga ttcaagaaaa ctataaaata cttaaagata    5580
tataaattta aaaaaacata gctgcaggtc tttggtccca gggctgtgcc ttaactttaa    5640
ccaatatttt cttctgtttt gctgcatttg aaaggtaaca gtggagctag gctgggcat     5700 tttacatcca ggcttttaat tgattagaat ctgccaata ggtggatttt acaaaaccac      5760
agacaacctc tgaaagattc tgagacccct ttgagacaga agctcttaag tacttcttgc    5820
cagggagcag cactgcatgt gtgatggttg tttgccatct gttgatcagg aactacttca    5880
gctacttgca tttgattatt ccttttttt ttttttttaa ctcggaaaca caactgggga     5940
aatatattct ttcccagtga ttataaacaa tctttttctt ttttttaagt ccttttggct    6000
tctagagctc ataggaaaat ggacttgatt tgaaattgga gccagagttt actcgtgttg    6060
gttatctatt catcagcttc ctgacatgtt aagagaatac attaaagaga aaatactgtt    6120
ttttaatcct aaaattttc ttccactaag ataaaccaaa tgtccttaca tatatgtaaa     6180
cccatctatt taaacgcaaa ggtgggttga tgtcagttta catagcagaa agcattcact    6240
atcctctaag atttgtttct gcaaaacttt cattgcttta gaattttaaa atttcacctt    6300
gtacaatggc cagcccctaa agcaggaaac atttataatg gattatatgg aaacatcctc    6360
ccagtacttg cccagccctt gaatcatgtg gcttttcagt gaaaggaaag attcttttc     6420 taggaaaaat gagcctattt tattttattt tatttattt tttgacacaa actgtagatt     6480
ttagcagccc tggcccaaag gaatttgatt acttttgttt taaacagtac aaggggaca    6540 ctataattac aaaaacatcc ttaactgatt tgagttgttt ttatttcttt ggatatattt    6600
tcagagtggt aaattgtgtg tgagaattac aaatgattat tcttttagtg gtttcttagc    6660
ctctcttaca gcccacgggg atagtactgt acatcaatac cttcatatga aattttttata   6720 tgcaatgaaa ataaaagcat gggttgattc tgcctattta tgactcaatc ttttacaaat    6780
aaaagattat tcatttaaa ttatagttca atcagcatgt ctcttaggat actgaacgtg    6840
```

-continued

```
gttgaaatga aaggatagtg acatcataag ttagtactga tattcataac caaataaagc   6900
caacttgagt aattttgcta cattaaaaat taccaaaatt acttagatgg cctataagat   6960
taagcatggt gttttctaag caagctttga aaggggcctt ccatacttac ttaattgaat   7020
attctgggat attgaaaatt attcagatac ttgacaatta ttttttggtta cctactccgc   7080 aaactacaaa gttttaagga ctcaacaata agttaatgag acacagtgtt tgctttcatg   7140
gagcttacag tctggagggg acaaaggctt aaacaatact catataatta tatatgtgat   7200
cagtacaatg aaggagctca gtggggtaaa taagcaggaa cctgaacttg atctgttccg   7260
gagggccaca gaaggcttcc ttgaggcctt gagaaagtga tttgcatctg agttctgaag   7320
gattgtaaga ggtaactagg gaaaaagttg acaggaagag gaaggggatc cagacaagaa   7380
acatttgcaa agatcttgag gcataaatga gcttgagaca tctggagaaa ctgaggaaaa   7440
gtgagagagt aggcagggcc tggagccgca gagccattgc taaccatcct gtgtgagata   7500 tccccccattc tgtagcttta ttctcataac cctgctcaat tttctttata acacttctca   7560
cagatttata tacgtgtttg ttttttgttat ctgtctctcc caccagacca cagctccatg   7620
agagcaaggt ctttgcttac caatatatca ctagcactta aaactatgcc tggtacacag   7680
taggttctta atatgtgttg aatatagcca tcaaattgat attggatata attcaatctg   7740
ataagatatt ttgagatatt aaagagtttt taacttgata ccataaaaaa aaaaaaaaa   7800 a                                                                  7801
```

<210> SEQ ID NO 2
<211> LENGTH: 585
<212> TYPE: PRT
<213> ORGANISM: Homo sapiens

<400> SEQUENCE: 2

```
Met Lys Glu Gln Pro Ser Cys Ala Gly Thr Gly His Pro Ser Met Ala
1               5                   10                  15

Gly Tyr Gly Arg Met Ala Pro Phe Glu Leu Ala Ser Gly Pro Val Lys
            20                  25                  30

Arg Leu Arg Thr Glu Ser Pro Phe Pro Cys Leu Phe Ala Glu Glu Ala
        35                  40                  45

Tyr Gln Lys Leu Ala Ser Glu Thr Leu Glu Glu Leu Asp Trp Cys Leu
    50                  55                  60

Asp Gln Leu Glu Thr Leu Gln Thr Arg His Ser Val Ser Glu Met Ala
65                  70                  75                  80

Ser Asn Lys Phe Lys Arg Met Leu Asn Arg Glu Leu Thr His Leu Ser
                85                  90                  95

Glu Met Ser Arg Ser Gly Asn Gln Val Ser Glu Phe Ile Ser Asn Thr
            100                 105                 110

Phe Leu Asp Lys Gln His Glu Val Glu Ile Pro Ser Pro Thr Gln Lys
        115                 120                 125

Glu Lys Glu Lys Lys Lys Arg Pro Met Ser Gln Ile Ser Gly Val Lys
    130                 135                 140

Lys Leu Met His Ser Ser Ser Leu Thr Asn Ser Ser Ile Pro Arg Phe
145                 150                 155                 160

Gly Val Lys Thr Glu Gln Glu Asp Val Leu Ala Lys Glu Leu Glu Asp
                165                 170                 175

Val Asn Lys Trp Gly Leu His Val Phe Arg Ile Ala Glu Leu Ser Gly
            180                 185                 190
```

```
Asn Arg Pro Leu Thr Val Ile Met His Thr Ile Phe Gln Glu Arg Asp
            195                 200                 205

Leu Leu Lys Thr Phe Lys Ile Pro Val Asp Thr Leu Ile Thr Tyr Leu
    210                 215                 220

Met Thr Leu Glu Asp His Tyr His Ala Asp Val Ala Tyr His Asn Asn
225                 230                 235                 240

Ile His Ala Ala Asp Val Val Gln Ser Thr His Val Leu Leu Ser Thr
                245                 250                 255

Pro Ala Leu Glu Ala Val Phe Thr Asp Leu Glu Ile Leu Ala Ala Ile
            260                 265                 270

Phe Ala Ser Ala Ile His Asp Val Asp His Pro Gly Val Ser Asn Gln
    275                 280                 285

Phe Leu Ile Asn Thr Asn Ser Glu Leu Ala Leu Met Tyr Asn Asp Ser
    290                 295                 300

Ser Val Leu Glu Asn His His Leu Ala Val Gly Phe Lys Leu Leu Gln
305                 310                 315                 320

Glu Glu Asn Cys Asp Ile Phe Gln Asn Leu Thr Lys Lys Gln Arg Gln
                325                 330                 335

Ser Leu Arg Lys Met Val Ile Asp Ile Val Leu Ala Thr Asp Met Ser
            340                 345                 350

Lys His Met Asn Leu Leu Ala Asp Leu Lys Thr Met Val Glu Thr Lys
    355                 360                 365

Lys Val Thr Ser Ser Gly Val Leu Leu Leu Asp Asn Tyr Ser Asp Arg
    370                 375                 380

Ile Gln Val Leu Gln Asn Met Val His Cys Ala Asp Leu Ser Asn Pro
385                 390                 395                 400

Thr Lys Pro Leu Gln Leu Tyr Arg Gln Trp Thr Asp Arg Ile Met Glu
                405                 410                 415

Glu Phe Phe Arg Gln Gly Asp Arg Glu Arg Glu Arg Gly Met Glu Ile
            420                 425                 430

Ser Pro Met Cys Asp Lys His Asn Ala Ser Val Glu Lys Ser Gln Val
    435                 440                 445

Gly Phe Ile Asp Tyr Ile Val His Pro Leu Trp Glu Thr Trp Ala Asp
    450                 455                 460

Leu Val His Pro Asp Ala Gln Asp Ile Leu Asp Thr Leu Glu Asp Asn
465                 470                 475                 480

Arg Glu Trp Tyr Gln Ser Thr Ile Pro Gln Ser Pro Ser Pro Ala Pro
                485                 490                 495

Asp Asp Pro Glu Glu Gly Arg Gln Gly Gln Thr Glu Lys Phe Gln Phe
            500                 505                 510

Glu Leu Thr Leu Glu Glu Asp Gly Glu Ser Asp Thr Glu Lys Asp Ser
    515                 520                 525

Gly Ser Gln Val Glu Glu Asp Thr Ser Cys Ser Asp Ser Lys Thr Leu
    530                 535                 540

Cys Thr Gln Asp Ser Glu Ser Thr Glu Ile Pro Leu Asp Glu Gln Val
545                 550                 555                 560

Glu Glu Glu Ala Val Gly Glu Glu Glu Ser Gln Pro Glu Ala Cys
                565                 570                 575

Val Ile Asp Asp Arg Ser Pro Asp Thr
            580                 585

<210> SEQ ID NO 3
<211> LENGTH: 21
<212> TYPE: DNA
```

```
<213> ORGANISM: Artificial Sequence
<220> FEATURE:
<223> OTHER INFORMATION: PDE4D1D2_forward primer

<400> SEQUENCE: 3
aatatgaagg agcagccctc a                                              21

<210> SEQ ID NO 4
<211> LENGTH: 18
<212> TYPE: DNA
<213> ORGANISM: Artificial Sequence
<220> FEATURE:
<223> OTHER INFORMATION: PDE4D1D2_reverse primer

<400> SEQUENCE: 4
gtctcgctgg ccagtttc                                                  18

<210> SEQ ID NO 5
<211> LENGTH: 18
<212> TYPE: DNA
<213> ORGANISM: Artificial Sequence
<220> FEATURE:
<223> OTHER INFORMATION: PDE4D1D2 probe

<400> SEQUENCE: 5
catccgagca tggcggga                                                  18

<210> SEQ ID NO 6
<211> LENGTH: 7715
<212> TYPE: DNA
<213> ORGANISM: Homo sapiens

<400> SEQUENCE: 6
gtggtggccg cgcacccggc cgcggctgat tcattcactt caagtgccgt gcagaaggct      60
cggcaggcgg ggcgggcgtg gggccgcggc tccgggttgg ggaccgagga gatccggctg     120
tggaccagac gctcctctgc ggggcgggca cccaagcgcg ctcgccaccc cctcgccatc     180
cgctagagcc gggctcctgg actgggactc gggcccgccg cacagttgaa aagtcgcata     240 gtggttttc cgctcgcgtc gctgtgtgaa agttggctcg ccgctctttg cacgccctcc     300
ctggaggccg acccgagacg ccaagctgga gagaccgtgc ctccccgagg ccggccgccc     360
cgcgagcaca gcctccgccc ccgttgcact gccgggctgg gcaatatgaa ggagcagccc     420
tcatgtgccg gcaccgggca tccgagcatg gcgggaggag gcctaccaga aactggccag     480
cgagaccctg gaggagctgg actggtgtct ggaccagcta gagaccctac agaccaggca     540
ctccgtcagt gagatggcct ccaacaagtt taaaaggatg cttaatcggg agctcaccca     600
tctctctgaa atgagtcggt ctggaaatca agtgtcagag tttatatcaa acacattctt     660
agataagcaa catgaagtgg aaattccttc tccaactcag aaggaaaagg agaaaaagaa     720
aagaccaatg tctcagatca gtggagtcaa gaaattgatg cacagctcta gtctgactaa     780
ttcaagtatc ccaaggtttg gagttaaaac tgaacaagaa gatgtccttg ccaaggaact     840
agaagatgtg aacaaatggg gtcttcatgt tttcagaata gcagagttgt ctggtaaccg     900
gcccttgact gttatcatgc acaccatttt tcaggaacgg gatttattaa aaacatttaa     960
aattccagta gatactttaa ttacatatct tatgactctc gaagaccatt accatgctga    1020
tgtggcctat cacaacaata tccatgctgc agatgttgtc cagtctactc atgtgctatt    1080
atctacacct gctttggagg ctgtgtttac agatttggag attcttgcag caattttgc    1140 cagtgcaata catgatgtag atcatcctgg tgtgtccaat caatttctga tcaatacaaa    1200
```

```
ctctgaactt gccttgatgt acaatgattc ctcagtctta gagaaccatc atttggctgt   1260
gggctttaaa ttgcttcagg aagaaaactg tgacatttc cagaatttga ccaaaaaaca    1320
aagacaatct ttaaggaaaa tggtcattga catcgtactt gcaacagata tgtcaaaaca   1380
catgaatcta ctggctgatt tgaagactat ggttgaaact aagaaagtga caagctctgg   1440
agttcttctt cttgataatt attccgatag gattcaggtt cttcagaata tggtgcactg   1500
tgcagatctg agcaacccaa caaagcctct ccagctgtac cgccagtgga cggaccggat   1560
aatggaggag ttcttccgcc aaggagaccg agagagggaa cgtggcatgg agataagccc   1620
catgtgtgac aagcacaatg cttccgtgga aaaatcacag gtgggcttca tagactatat   1680
tgttcatccc ctctgggaga catgggcaga cctcgtccac cctgacgccc aggatatttt   1740
ggacactttg gaggacaatc gtgaatggta ccagagcaca atccctcaga gcccctctcc   1800
tgcacctgat gacccagagg agggccggca gggtcaaact gagaaattcc agtttgaact   1860
aactttagag gaagatggtg agtcagacac ggaaaaggac agtggcagtc aagtggaaga   1920
agacactagc tgcagtgact ccaagactct ttgtactcaa gactcagagt ctactgaaat   1980
tccccttgat gaacaggttg aagaggaggc agtaggggaa gaagaggaaa gccagcctga   2040
agcctgtgtc atagatgatc gttctcctga cacgtaacag tgcaaaaact ttcatgcctt   2100
tttttttttt aagtagaaaa attgtttcca aagtgcatgt cacatgccac aaccacggtc   2160
acacctcact gtcatctgcc aggacgtttg ttgaacaaaa ctgaccttga ctactcagtc   2220
cagcgctcag gaatatcgta accagttttt tcacctccat gtcatccgag caaggtggac   2280
atcttcacga acagcgtttt taacaagatt tcagcttggt agagctgaca aagcagataa   2340
aatctactcc aaattatttt caagagagtg tgactcatca ggcagcccaa agtttattg    2400 gacttggggt ttctattcct ttttatttgt ttgcaatatt tcagaagaa aggcattgca    2460 cagagtgaac ttaatggacg aagcaacaaa tatgtcaaga acaggacata gcacgaatct   2520
gttaccagta ggaggaggat gagccacaga aattgcataa ttttctaatt tcaagtcttc   2580
ctgatacatg actgaatagt gtggttcagt gagctgcact gacctctaca ttttgtatga   2640
tatgtaaaac agatttttg tagagcttac ttttattatt aaatgtattg aggtattata    2700
tttaaaaaaa actatgttca gaacttcatc tgccactggt tatttttttc taaggagtaa   2760
cttgcaagtt ttcagtacaa atctgtgcta cactggataa aaatctaatt tatgaatttt   2820
acttgcacct tatagttcat agcaattaac tgatttgtag tgattcattg tttgttttat   2880
ataccaatga cttccatatt ttaaaagaga aaacaactt tatgttgcag gaaacccttt    2940
ttgtaagtct ttattattta ctttgcattt tgtttcactc tttccagata agcagagttg   3000
ctcttcacca gtgttttct tcatgtgcaa agtgactatt tgttctataa acttttatg     3060 tgtgttatat caaatgtgtc ttaagcttca tgcaaactca gtcatcagtt cgtgttgtct   3120
gaagcaagtg ggagatatat aaatacccag tagctaaaat ggtcagtctt ttttagatgt   3180
tttcctactt agtatctcct aataacgttt tgctgtgtca ctagatgttc atttcacaag   3240
tgcatgtctt tctaataatc cacacatttc atgctctaat aatccacaca tttcatgctc   3300 attttattg ttttacagc cagttatagt aagaaaagg ttttttcccct tgtgctgctt     3360 tataatttag cgtgtgtctg aaccttatcc atgtttgcta gatgaggtct tgtcaaatat   3420
atcactacca ttgtcaccgg tgaaaagaaa caggtagtta agttagggtt aacattcatt   3480
tcaaccacga ggttgtatat catgactagc ttttactctt ggtttacaga gaaaagttaa   3540
```

```
acagccaact aggcagtttt taagaatatt aacaatatat taacaaacac caatacaact    3600
aatcctattt ggttttaatg atttcaccat gggattaaga actatatcag gaacatccct    3660
gagaaacggt tttaagtgta gcaactactc ttccttaatg gacagccaca taacgtgtag    3720
gaagtccttt atcacttatc ctcgatccat aagcatatct tgcagagggg aactacttct    3780
ttaaacacat ggagggaaag aagatgatgc cactggcacc agagggttag tactgtgatg    3840
catcctaaaa tatttattat attggtaaaa attctggtta aataaaaaat tagagatcac    3900
tcttggctga tttcagcacc aggaactgta ttacagtttt agagattaat tcctagtgtt    3960
tacctgatta tagcagttgg catcatgggg catttaattc tgactttatc cccacgtcag    4020
ccttaataaa gtcttcttta ccttctctat gaagacttta aagcccaaat aatcattttt    4080
cacattgata ttcaagaatt gagatagata aagccaaag tgggtatctg acaagtggaa    4140
aatcaaacgt ttaagaagaa ttacaactct gaaaagcatt tatatgtgga acttctcaag    4200
gagcctcctg gggactggaa agtaagtcat cagccaggca aatgactcat gctgaagaga    4260
gtccccattt cagtcccctg agatctagct gatgcttaga tcctttgaaa taaaaattat    4320
gtctttataa ctctgatctt ttacataaag cagaagagga atcaactagt taattgcaag    4380
gtttctactc tgtttcctct gtaaagatca gatggtaatc tttcaaataa gaaaaaaata    4440
aagacgtatg tttgaccaag tagtttcaca agaatatttg ggaacttgtt tcttttaatt    4500
ttatttgtcc ctgagtgaag tctagaaaga aaggtaaaga gtctagagtt tattcctctt    4560
tccaaaacat tctcattcct ctcctcccta cacttagtat ttcccccaca gagtgcctag    4620
aatcttaata atgaataaaa taaaaagcag caatatgtca ttaacaaatc cagacctgaa    4680
agggtaaagg gtttataact gcactaataa agagaggctc tttttttttc ttccagtttg    4740
ttggttttta atggtaccgt gttgtaaaga tacccactaa tggacaatca aattgcagaa    4800
aaggctcaat atccaagaga cagggactaa tgcactgtac aatctgctta tccttgccct    4860
tctctcttgc caaagtgtgc ttcagaaata tatactgctt taaaaagaa taaaagaata    4920 tccttttaca agtggcttta catttcctaa aatgccataa gaaaatgcaa tatctgggta    4980
ctgtatgggg aaaaaaatgt ccaagtttgt gtaaaaccag tgcatttcag cttgcaagtt    5040
actgaacaca ataatgctgt tttaattttg ttttatatca gttaaaattc acaataatgt    5100
agatagaaca aattacagac aaggaaagaa aaaacttgaa tgaaatggat tttacagaaa    5160
gctttatgat aattttttgaa tgcattattt attttttgtg ccatgcattt ttttctcac     5220 caaatgacct tacctgtaat acagtcttgt ttgtctgttt acaaccatgt atttattgca    5280
atgtacatac tgtaatgtta attgtaaatt atctgttctt attaaaacat catcccatga    5340
tgggatggtg ttgatatatt tggaaactct tggtgagaga atgaatggtg tgtatacata    5400
ctctgtacat ttttcttttc tcctgtaata tagtcttgtc accttagagc ttgtttatgg    5460
aagattcaag aaaactataa aatacttaaa gatatataaa tttaaaaaaa catagctgca    5520
ggtctttggt cccagggctg tgccttaact ttaaccaata ttttcttctg ttttgctgca    5580
tttgaaaggt aacagtggag ctagggctgg gcatttaca tccaggcttt taattgatta     5640
gaattctgcc aataggtgga ttttacaaaa ccacagacaa cctctgaaag attctgagac    5700
ccttttgaga cagaagctct taagtacttc ttgccaggga gcagcactgc atgtgtgatg    5760 gttgttttgcc atctgttgat caggaactac ttcagctact tgcatttgat tatttccttt    5820 ttttttttttt ttaactcgga aacacaactg gggaaatata ttcttcccca gtgattataa    5880
acaatctttt tcttttttttt aagtcctttt ggcttctaga gctcatagga aaatggactt    5940
```

-continued

```
gatttgaaat tggagccaga gtttactcgt gttggttatc tattcatcag cttcctgaca    6000
tgttaagaga atacattaaa gagaaaatac tgtttttta  tcctaaaatt tttcttccac    6060
taagataaac caaatgtcct tacatatatg taaacccatc tatttaaacg caaaggtggg    6120
ttgatgtcag tttacatagc agaaagcatt cactatcctc taagatttgt ttctgcaaaa    6180
ctttcattgc tttagaattt taaaatttca ccttgtacaa tggccagccc ctaaagcagg    6240
aaacatttat aatggattat atggaaacat cctcccagta cttgcccagc ccttgaatca    6300
tgtggctttt cagtgaaagg aaagattctt tttctaggaa aaatgagcct atttattttt    6360 atttatttt  atttttgac acaaactgta gatttttagca gccctggccc aaaggaattt    6420
gattactttt gttttaaaca gtacaagggg gacactataa ttacaaaaac atccttaact    6480
gatttgagtt gttttatttt ctttggatat attttcagag tggtaaattg tgtgtgagaa    6540
ttacaaatga ttattctttt agtggtttct tagcctctct tacagcccac ggggatagta    6600
ctgtacatca ataccttcat atgaaatttt tatatgcaat gaaataaaa  gcatgggttg    6660 attctgccta tttatgactc aatcttttac aaataaaaga ttattcattt taaattatag    6720
ttcaatcagc atgtctctta ggatactgaa cgtggttgaa atgaaaggat agtgacatca    6780
taagttagta ctgatattca taaccaaata aagccaactt gagtaatttt gctacattaa    6840
aaattaccaa aattacttag atggcctata agattaagca tggtgttttc taagcaagct    6900
ttgaaagggg ccttccatac ttacttaatt gaatattctg ggatattgaa aattattcag    6960
atacttgaca attattttg gttacctact ccgcaaacta caaagttta  aggactcaac    7020 aataagttaa tgagacacag tgtttgcttt catggagctt acagtctgga ggggacaaag    7080
gcttaaacaa tactcatata attatatatg tgatcagtac aatgaaggag ctcagtgggg    7140
taaataagca ggaacctgaa cttgatctgt tccggagggc cacagaaggc ttccttgagg    7200
ccttgagaaa gtgatttgca tctgagttct gaaggattgt aagaggtaac tagggaaaaa    7260
gttgacagga agaggaaggg gatccagaca agaaacattt gcaaagatct tgaggcataa    7320
atgagcttga gacatctgga gaaactgagg aaaagtgaga gagtaggcag ggcctggagc    7380
cgcagagcca ttgctaacca tcctgtgtga gatatccccc attctgtagc tttattctca    7440
taaccctgct caattttctt tataacactt ctcacagatt tatatacgtg tttgttttg     7500 ttatctgtct ctcccaccag accacagctc catgagagca aggtctttgc ttaccaatat    7560
atcactagca cttaaaacta tgcctggtac acagtaggtt cttaatatgt gttgaatata    7620
gccatcaaat tgatattgga tataattcaa tctgataaga tattttgaga tattaaagag    7680
tttttaactt gataccataa aaaaaaaaaa aaaaa                              7715
```

<210> SEQ ID NO 7
<211> LENGTH: 507
<212> TYPE: PRT
<213> ORGANISM: Homo sapiens

<400> SEQUENCE: 7

```
Met Ala Ser Asn Lys Phe Lys Arg Met Leu Asn Arg Glu Leu Thr His
1               5                   10                  15

Leu Ser Glu Met Ser Arg Ser Gly Asn Gln Val Ser Glu Phe Ile Ser
            20                  25                  30

Asn Thr Phe Leu Asp Lys Gln His Glu Val Glu Ile Pro Ser Pro Thr
        35                  40                  45

Gln Lys Glu Lys Glu Lys Lys Arg Pro Met Ser Gln Ile Ser Gly
```

```
            50                  55                  60
Val Lys Lys Leu Met His Ser Ser Leu Thr Asn Ser Ser Ile Pro
 65                  70                  75                  80

Arg Phe Gly Val Lys Thr Glu Gln Glu Asp Val Leu Ala Lys Glu Leu
                 85                  90                  95

Glu Asp Val Asn Lys Trp Gly Leu His Val Phe Arg Ile Ala Glu Leu
                100                 105                 110

Ser Gly Asn Arg Pro Leu Thr Val Ile Met His Thr Ile Phe Gln Glu
             115                 120                 125

Arg Asp Leu Leu Lys Thr Phe Lys Ile Pro Val Asp Thr Leu Ile Thr
         130                 135                 140

Tyr Leu Met Thr Leu Glu Asp His Tyr His Ala Asp Val Ala Tyr His
145                 150                 155                 160

Asn Asn Ile His Ala Ala Asp Val Val Gln Ser Thr His Val Leu Leu
                165                 170                 175

Ser Thr Pro Ala Leu Glu Ala Val Phe Thr Asp Leu Glu Ile Leu Ala
             180                 185                 190

Ala Ile Phe Ala Ser Ala Ile His Asp Val Asp His Pro Gly Val Ser
         195                 200                 205

Asn Gln Phe Leu Ile Asn Thr Asn Ser Glu Leu Ala Leu Met Tyr Asn
210                 215                 220

Asp Ser Ser Val Leu Glu Asn His His Leu Ala Val Gly Phe Lys Leu
225                 230                 235                 240

Leu Gln Glu Glu Asn Cys Asp Ile Phe Gln Asn Leu Thr Lys Lys Gln
                245                 250                 255

Arg Gln Ser Leu Arg Lys Met Val Ile Asp Ile Val Leu Ala Thr Asp
             260                 265                 270

Met Ser Lys His Met Asn Leu Leu Ala Asp Leu Lys Thr Met Val Glu
         275                 280                 285

Thr Lys Lys Val Thr Ser Ser Gly Val Leu Leu Leu Asp Asn Tyr Ser
290                 295                 300

Asp Arg Ile Gln Val Leu Gln Asn Met Val His Cys Ala Asp Leu Ser
305                 310                 315                 320

Asn Pro Thr Lys Pro Leu Gln Leu Tyr Arg Gln Trp Thr Asp Arg Ile
                325                 330                 335

Met Glu Glu Phe Phe Arg Gln Gly Asp Arg Glu Arg Glu Arg Gly Met
             340                 345                 350

Glu Ile Ser Pro Met Cys Asp Lys His Asn Ala Ser Val Glu Lys Ser
         355                 360                 365

Gln Val Gly Phe Ile Asp Tyr Ile Val His Pro Leu Trp Glu Thr Trp
370                 375                 380

Ala Asp Leu Val His Pro Asp Ala Gln Asp Ile Leu Asp Thr Leu Glu
385                 390                 395                 400

Asp Asn Arg Glu Trp Tyr Gln Ser Thr Ile Pro Gln Ser Pro Ser Pro
                405                 410                 415

Ala Pro Asp Asp Pro Glu Glu Gly Arg Gln Gly Gln Thr Glu Lys Phe
             420                 425                 430

Gln Phe Glu Leu Thr Leu Glu Glu Asp Gly Glu Ser Asp Thr Glu Lys
         435                 440                 445

Asp Ser Gly Ser Gln Val Glu Glu Asp Thr Ser Cys Ser Asp Ser Lys
450                 455                 460

Thr Leu Cys Thr Gln Asp Ser Glu Ser Thr Glu Ile Pro Leu Asp Glu
465                 470                 475                 480
```

Gln Val Glu Glu Glu Ala Val Gly Glu Glu Glu Ser Gln Pro Glu
            485                 490                 495

Ala Cys Val Ile Asp Asp Arg Ser Pro Asp Thr
            500                 505

<210> SEQ ID NO 8
<211> LENGTH: 7783
<212> TYPE: DNA
<213> ORGANISM: Homo sapiens

<400> SEQUENCE: 8

| | | | | | |
|---|---|---|---|---|---|
| aatacttgtt | gcaataattg | cccacgatag | ctgctcaaac | aagagagttg | gaattcatct | 60 |
| gtaaaaatca | ctacatgtaa | cgtaggagac | aagaaaaata | ttaatgacag | aagatctgcg | 120 |
| aacatgatgc | acgtgaataa | ttttcccttt | agaaggcatt | cctggatatg | ttttgatgtg | 180 |
| gacaatggca | catctgcggg | acggagtccc | ttggatccca | tgaccagccc | aggatccggg | 240 |
| ctaattctcc | aagcaaattt | tgtccacagt | caacgacggg | agtccttcct | gtatcgatcc | 300 |
| gacagcgatt | atgacctctc | tccaaagtct | atgtcccgga | actcctccat | gccagtgat | 360 |
| atacacggag | atgacttgat | tgtgactcca | tttgctcagg | tcttggccag | tctgcgaact | 420 |
| gtacgaaaca | actttgctgc | attaactaat | ttgcaagatc | gagcacctag | caaaagatca | 480 |
| cccatgtgca | accaaccatc | catcaacaaa | gccaccataa | cagaggaggc | ctaccagaaa | 540 |
| ctggccagcg | agaccctgga | ggagctggac | tggtgtctgg | accagctaga | gaccctacag | 600 |
| accaggcact | ccgtcagtga | gatggcctcc | aacaagttta | aaaggatgct | taatcgggag | 660 |
| ctcacccatc | tctctgaaat | gagtcggtct | ggaaatcaag | tgtcagagtt | tatatcaaac | 720 |
| acattcttag | ataagcaaca | tgaagtgaa | attccttctc | caactcagaa | ggaaaaggag | 780 |
| aaaaagaaaa | gaccaatgtc | tcagatcagt | ggagtcaaga | aattgatgca | cagctctagt | 840 |
| ctgactaatt | caagtatccc | aaggtttgga | gttaaaactg | aacaagaaga | tgtccttgcc | 900 |
| aaggaactag | aagatgtgaa | caaatggggt | cttcatgttt | tcagaatagc | agagttgtct | 960 |
| ggtaaccggc | ccttgactgt | tatcatgcac | accattttc | aggaacggga | tttattaaaa | 1020 |
| acatttaaaa | ttccagtaga | tactttaatt | acatatctta | tgactctcga | agaccattac | 1080 |
| catgctgatg | tggcctatca | caacaatatc | catgctgcag | atgttgtcca | gtctactcat | 1140 |
| gtgctattat | ctacacctgc | tttggaggct | gtgtttacag | atttggagat | tcttgcagca | 1200 |
| atttttgcca | gtgcaataca | tgatgtagat | catcctggtg | tgtccaatca | atttctgatc | 1260 |
| aatacaaact | ctgaacttgc | cttgatgtac | aatgattcct | cagtcttaga | gaaccatcat | 1320 |
| ttggctgtgg | gctttaaatt | gcttcaggaa | gaaaactgtg | acattttcca | gaatttgacc | 1380 |
| aaaaaacaaa | gacaatcttt | aaggaaaatg | gtcattgaca | tcgtacttgc | aacagatatg | 1440 |
| tcaaaacaca | tgaatctact | ggctgatttg | aagactatgg | ttgaaactaa | gaaagtgaca | 1500 |
| agctctggag | ttcttcttct | tgataattat | tccgatagga | ttcaggttct | tcagaatatg | 1560 |
| gtgcactgtg | cagatctgag | caacccaaca | aagcctctcc | agctgtaccg | ccagtggacg | 1620 |
| gaccggatca | tggaggagtt | cttccgccaa | ggagaccgag | agagggaacg | tggcatggag | 1680 |
| ataagcccca | tgtgtgacaa | gcacaatgct | tccgtggaaa | aatcacaggt | gggcttcata | 1740 |
| gactatattg | ttcatccct | ctgggagaca | tgggcagacc | tcgtccaccc | tgacgcccag | 1800 |
| gatattttgg | acactttgga | ggacaatcgt | gaatggtacc | agagcacaat | ccctcagagc | 1860 |
| ccctctcctg | cacctgatga | cccagaggag | ggccggcagg | gtcaaactga | gaaattccag | 1920 |

-continued

```
tttgaactaa ctttagagga agatggtgag tcagacacgg aaaaggacag tggcagtcaa    1980
gtggaagaag acactagctg cagtgactcc aagactcttt gtactcaaga ctcagagtct    2040
actgaaattc cccttgatga acaggttgaa gaggaggcag taggggaaga agaggaaagc    2100
cagcctgaag cctgtgtcat agatgatcgt tctcctgaca cgtaacagtg caaaaacttt    2160
catgcctttt ttttttttaa gtagaaaaat tgtttccaaa gtgcatgtca catgccacaa    2220
ccacggtcac acctcactgt catctgccag gacgtttgtt gaacaaaact gaccttgact    2280
actcagtcca gcgctcagga atatcgtaac cagttttttc acctccatgt catccgagca    2340
aggtggacat cttcacgaac agcgttttta acaagatttc agcttggtag agctgacaaa    2400
gcagataaaa tctactccaa attattttca agagagtgtg actcatcagg cagcccaaaa    2460
gtttattgga cttgggttt ctattccttt ttatttgttt gcaatatttt cagaagaaag    2520
gcattgcaca gagtgaactt aatggacgaa gcaacaaata tgtcaagaac aggacatagc    2580
acgaatctgt taccagtagg aggaggatga gccacagaaa ttgcataatt ttctaatttc    2640
aagtcttcct gatacatgac tgaatagtgt ggttcagtga gctgcactga cctctacatt    2700
ttgtatgata tgtaaaacag atttttttgta gagcttactt ttattattaa atgtattgag    2760
gtattatatt taaaaaaaac tatgttcaga acttcatctg ccactggtta tttttttcta    2820
aggagtaact tgcaagtttt cagtacaaat ctgtgctaca ctggataaaa atctaattta    2880
tgaattttac ttgcacctta tagttcatag caattaactg atttgtagtg attcattgtt    2940
tgttttatat accaatgact tccatatttt aaagagaaaa aacaacttta tgttgcagga    3000 aaccctttt gtaagtcttt attatttact ttgcattttg tttcactctt tccagataag    3060
cagagttgct cttcaccagt gttttttcttc atgtgcaaag tgactatttg ttctataata    3120
cttttatgtg tgttatatca aatgtgtctt aagcttcatg caaactcagt catcagttcg    3180
tgttgtctga agcaagtggg agatatataa atacccagta gctaaaatgg tcagtctttt    3240
ttagatgttt tcctacttag tatctcctaa taacgttttg ctgtgtcact agatgttcat    3300
ttcacaagtg catgtctttc taataatcca cacatttcat gctctaataa tccacacatt    3360
tcatgctcat ttttattgtt tttacagcca gttatagtaa gaaaaaggtt tttcccccttg    3420 tgctgcttta taatttagcg tgtgtctgaa ccttatccat gtttgctaga tgaggtcttg    3480
tcaaatatat cactaccatt gtcaccggtg aaaagaaaca ggtagttaag ttagggttaa    3540
cattcatttc aaccacgagg ttgtatatca tgactagctt ttactcttgg tttacagaga    3600
aaagttaaac agccaactag gcagttttta agaatattaa caatatatta acaaacacca    3660
atacaactaa tcctatttgg ttttaatgat ttcaccatgg gattaagaac tatatcagga    3720
acatccctga gaaacggttt taagtgtagc aactactctt ccttaatgga cagccacata    3780
acgtgtagga agtcctttat cacttatcct cgatccataa gcatatcttg cagaggggaa    3840
ctacttcttt aaacacatgg agggaaagaa gatgatgcca ctggcaccag agggttagta    3900
ctgtgatgca tcctaaaata tttattatat tggtaaaaat tctggttaaa taaaaaatta    3960
gagatcactc ttggctgatt tcagcaccag gaactgtatt acagttttag agattaattc    4020
ctagtgttta cctgattata gcagttggca tcatggggca tttaattctg actttatccc    4080
cacgtcagcc ttaataaagt cttctttacc ttctctatga agactttaaa gcccaaataa    4140 tcattttca cattgatatt caagaattga gatagataga agccaaagtg ggtatctgac    4200
aagtggaaaa tcaaacgttt aagaagaatt acaactctga aaagcattta tatgtggaac    4260
ttctcaagga gcctcctggg gactggaaag taagtcatca gccaggcaaa tgactcatgc    4320
```

```
tgaagagagt ccccatttca gtccctgag atctagctga tgcttagatc ctttgaaata    4380
aaaattatgt cttataact ctgatctttt acataaagca gaagaggaat caactagtta    4440
attgcaaggt ttctactctg tttcctctgt aaagatcaga tggtaatctt tcaaataaga    4500
aaaaaataaa gacgtatgtt tgaccaagta gtttcacaag aatatttggg aacttgtttc    4560
tttaatttt atttgtccct gagtgaagtc tagaaagaaa ggtaaagagt ctagagttta    4620
ttcctctttc caaaacattc tcattcctct cctccctaca cttagtattt ccccacaga    4680
gtgcctagaa tcttaataat gaataaaata aaagcagca atatgtcatt aacaaatcca    4740
gacctgaaag ggtaaagggt ttataactgc actaataaag agaggctctt ttttttttctt    4800
ccagtttgtt ggtttttaat ggtaccgtgt tgtaaagata cccactaatg acaatcaaa    4860
ttgcagaaaa ggctcaatat ccaagagaca gggactaatg cactgtacaa tctgcttatc    4920
cttgcccttc tctcttgcca aagtgtgctt cagaaatata tactgcttta aaaagaata    4980
aaagaatatc ctttacaag tggctttaca tttcctaaaa tgccataaga aaatgcaata    5040
tctgggtact gtatggggaa aaaaatgtcc aagtttgtgt aaaaccagtg catttcagct    5100
tgcaagttac tgaacacaat aatgctgttt taatttgtt ttatatcagt taaaattcac    5160
aataatgtag atagaacaaa ttacagacaa ggaaagaaaa aacttgaatg aaatggattt    5220
tacagaaagc tttatgataa ttttgaatg cattatttat tttttgtgcc atgcattttt    5280
tttctcacca aatgacctta cctgtaatac agtcttgttt gtctgtttac aaccatgtat    5340
ttattgcaat gtacatactg taatgttaat tgtaaattat ctgttcttat taaaacatca    5400
tcccatgatg ggatggtgtt gatatatttg gaaactcttg gtgagagaat gaatggtgtg    5460
tatacatact ctgtacattt ttcttttctc ctgtaatata gtcttgtcac cttagagctt    5520
gtttatggaa gattcaagaa aactataaaa tacttaaaga tatataaatt taaaaaaaca    5580
tagctgcagg tctttggtcc cagggctgtg ccttaacttt aaccaatatt ttcttctgtt    5640
ttgctgcatt tgaaaggtaa cagtggagct agggctgggc attttacatc caggcttta    5700
attgattaga attctgccaa taggtggatt ttacaaaacc acagacaacc tctgaaagat    5760
tctgagaccc ttttgagaca gaagctctta agtacttctt gccagggagc agcactgcat    5820
gtgtgatggt tgtttgccat ctgttgatca ggaactactt cagctacttg catttgatta    5880
tttccttttt tttttttttt aactcggaaa cacaactggg gaaatatatt ctttcccagt    5940
gattataaac aatctttttc ttttttttaa gtccttttgg cttctagagc tcataggaaa    6000
atggacttga tttgaaattg gagccagagt ttactcgtgt tggttatcta ttcatcagct    6060
tcctgacatg ttaagagaat acattaaaga gaaaatactg tttttaatc ctaaaatttt    6120
tcttccacta agataaacca aatgtcctta catatatgta aacccatcta tttaaacgca    6180
aaggtgggtt gatgtcagtt tacatagcag aaagcattca ctatcctcta agatttgttt    6240
ctgcaaaact ttcattgctt tagaattta aaatttcacc ttgtacaatg gccagccct    6300
aaagcaggaa acatttataa tggattatat ggaaacatcc tcccagtact tgcccagccc    6360
ttgaatcatg tggcttttca gtgaaaggaa agattctttt tctaggaaaa atgagcctat    6420
tttatttat tttattttat tttttgacac aaactgtaga tttagcagc cctggcccaa    6480
aggaatttga ttacttttgt tttaaacagt acaaggggga cactataatt acaaaaacat    6540
ccttaactga tttgagttgt ttttattttct ttggatatat tttcagagtg gtaaattgtg    6600
tgtgagaatt acaaatgatt attcttttag tggtttctta gcctctctta cagcccacgg    6660
```

-continued

```
ggatagtact gtacatcaat accttcatat gaaatttta tatgcaatga aaataaaagc    6720
atgggttgat tctgcctatt tatgactcaa tcttttacaa ataaaagatt attcatttta    6780
aattatagtt caatcagcat gtctcttagg atactgaacg tggttgaaat gaaaggatag    6840
tgacatcata agttagtact gatattcata accaaataaa gccaacttga gtaattttgc    6900
tacattaaaa attaccaaaa ttacttagat ggcctataag attaagcatg gtgttttcta    6960
agcaagcttt gaaagggggcc ttccatactt acttaattga atattctggg atattgaaaa    7020
ttattcagat acttgacaat tatttttggt tacctactcc gcaaactaca aagttttaag    7080
gactcaacaa taagttaatg agacacagtg tttgctttca tggagcttac agtctggagg    7140
ggacaaaggc ttaaacaata ctcatataat tatatatgtg atcagtacaa tgaaggagct    7200
cagtggggta aataagcagg aacctgaact tgatctgttc cggagggcca cagaaggctt    7260
ccttgaggcc ttgagaaagt gatttgcatc tgagttctga aggattgtaa gaggtaacta    7320
gggaaaaagt tgacaggaag aggaagggga tccagacaag aaacatttgc aaagatcttg    7380
aggcataaat gagcttgaga catctggaga aactgaggaa aagtgagaga gtaggcaggg    7440
cctggagccg cagagccatt gctaaccatc ctgtgtgaga tatcccccat tctgtagctt    7500
tattctcata accctgctca attttcttta taacacttct cacagattta tatacgtgtt    7560
tgttttgtt atctgtctct cccaccagac cacagctcca tgagagcaag gtctttgctt    7620
accaatatat cactagcact taaaactatg cctggtacac agtaggttct taatatgtgt    7680
tgaatatagc catcaaattg atattggata taattcaatc tgataagata ttttgagata    7740
ttaaagagtt tttaacttga taccataaaa aaaaaaaaaa aaa                      7783
```

<210> SEQ ID NO 9
<211> LENGTH: 673
<212> TYPE: PRT
<213> ORGANISM: Homo sapiens

<400> SEQUENCE: 9

```
Met Met His Val Asn Asn Phe Pro Phe Arg Arg His Ser Trp Ile Cys
1               5                   10                  15

Phe Asp Val Asp Asn Gly Thr Ser Ala Gly Arg Ser Pro Leu Asp Pro
            20                  25                  30

Met Thr Ser Pro Gly Ser Gly Leu Ile Leu Gln Ala Asn Phe Val His
        35                  40                  45

Ser Gln Arg Arg Glu Ser Phe Leu Tyr Arg Ser Asp Ser Asp Tyr Asp
    50                  55                  60

Leu Ser Pro Lys Ser Met Ser Arg Asn Ser Ser Ile Ala Ser Asp Ile
65                  70                  75                  80

His Gly Asp Asp Leu Ile Val Thr Pro Phe Ala Gln Val Leu Ala Ser
                85                  90                  95

Leu Arg Thr Val Arg Asn Asn Phe Ala Ala Leu Thr Asn Leu Gln Asp
            100                 105                 110

Arg Ala Pro Ser Lys Arg Ser Pro Met Cys Asn Gln Pro Ser Ile Asn
        115                 120                 125

Lys Ala Thr Ile Thr Glu Glu Ala Tyr Gln Lys Leu Ala Ser Glu Thr
    130                 135                 140

Leu Glu Glu Leu Asp Trp Cys Leu Asp Gln Leu Glu Thr Leu Gln Thr
145                 150                 155                 160

Arg His Ser Val Ser Glu Met Ala Ser Asn Lys Phe Lys Arg Met Leu
                165                 170                 175
```

```
Asn Arg Glu Leu Thr His Leu Ser Glu Met Ser Arg Ser Gly Asn Gln
            180                 185                 190

Val Ser Glu Phe Ile Ser Asn Thr Phe Leu Asp Lys Gln His Glu Val
        195                 200                 205

Glu Ile Pro Ser Pro Thr Gln Lys Glu Lys Glu Lys Lys Lys Arg Pro
    210                 215                 220

Met Ser Gln Ile Ser Gly Val Lys Lys Leu Met His Ser Ser Ser Leu
225                 230                 235                 240

Thr Asn Ser Ser Ile Pro Arg Phe Gly Val Lys Thr Glu Gln Glu Asp
                245                 250                 255

Val Leu Ala Lys Glu Leu Glu Asp Val Asn Lys Trp Gly Leu His Val
            260                 265                 270

Phe Arg Ile Ala Glu Leu Ser Gly Asn Arg Pro Leu Thr Val Ile Met
        275                 280                 285

His Thr Ile Phe Gln Glu Arg Asp Leu Leu Lys Thr Phe Lys Ile Pro
    290                 295                 300

Val Asp Thr Leu Ile Thr Tyr Leu Met Thr Leu Glu Asp His Tyr His
305                 310                 315                 320

Ala Asp Val Ala Tyr His Asn Asn Ile His Ala Ala Asp Val Val Gln
                325                 330                 335

Ser Thr His Val Leu Leu Ser Thr Pro Ala Leu Glu Ala Val Phe Thr
            340                 345                 350

Asp Leu Glu Ile Leu Ala Ala Ile Phe Ala Ser Ala Ile His Asp Val
        355                 360                 365

Asp His Pro Gly Val Ser Asn Gln Phe Leu Ile Asn Thr Asn Ser Glu
    370                 375                 380

Leu Ala Leu Met Tyr Asn Asp Ser Ser Val Leu Glu Asn His His Leu
385                 390                 395                 400

Ala Val Gly Phe Lys Leu Leu Gln Glu Glu Asn Cys Asp Ile Phe Gln
                405                 410                 415

Asn Leu Thr Lys Lys Gln Arg Gln Ser Leu Arg Lys Met Val Ile Asp
            420                 425                 430

Ile Val Leu Ala Thr Asp Met Ser Lys His Met Asn Leu Leu Ala Asp
        435                 440                 445

Leu Lys Thr Met Val Glu Thr Lys Lys Val Thr Ser Ser Gly Val Leu
    450                 455                 460

Leu Leu Asp Asn Tyr Ser Asp Arg Ile Gln Val Leu Gln Asn Met Val
465                 470                 475                 480

His Cys Ala Asp Leu Ser Asn Pro Thr Lys Pro Leu Gln Leu Tyr Arg
                485                 490                 495

Gln Trp Thr Asp Arg Ile Met Glu Glu Phe Phe Arg Gln Gly Asp Arg
            500                 505                 510

Glu Arg Glu Arg Gly Met Glu Ile Ser Pro Met Cys Asp Lys His Asn
        515                 520                 525

Ala Ser Val Glu Lys Ser Gln Val Gly Phe Ile Asp Tyr Ile Val His
    530                 535                 540

Pro Leu Trp Glu Thr Trp Ala Asp Leu Val His Pro Asp Ala Gln Asp
545                 550                 555                 560

Ile Leu Asp Thr Leu Glu Asp Asn Arg Glu Trp Tyr Gln Ser Thr Ile
                565                 570                 575

Pro Gln Ser Pro Ser Pro Ala Pro Asp Asp Pro Glu Glu Gly Arg Gln
            580                 585                 590

Gly Gln Thr Glu Lys Phe Gln Phe Glu Leu Thr Leu Glu Glu Asp Gly
```

|  | 595 |  |  | 600 |  |  |  | 605 |  |  |  |
|---|---|---|---|---|---|---|---|---|---|---|---|
| Glu | Ser | Asp | Thr | Glu | Lys | Asp | Ser | Gly | Ser | Gln | Val | Glu | Glu | Asp | Thr |
|  | 610 |  |  |  | 615 |  |  |  | 620 |  |  |

Ser Cys Ser Asp Ser Lys Thr Leu Cys Thr Gln Asp Ser Glu Ser Thr
625                 630                 635                 640

Glu Ile Pro Leu Asp Glu Gln Val Glu Glu Ala Val Gly Glu Glu
                645                 650                 655

Glu Glu Ser Gln Pro Glu Ala Cys Val Ile Asp Asp Arg Ser Pro Asp
        660                 665                 670

Thr

<210> SEQ ID NO 10
<211> LENGTH: 8240
<212> TYPE: DNA
<213> ORGANISM: Homo sapiens

<400> SEQUENCE: 10

```
cccctctcgg tagccctgag gctctggcgc cttcaagtga gaagctaagc accagcctct      60
gctgggctgc agaagcggcg gcggcggcag cagcagcagc agcatcagga aggcgctcgg     120
gccagcgcgt tgaacccggg ctgggcagca ggtcgcggag ccgcgagcca ggatggaggc     180
agagggcagc agcgcgccgg cccgggcggg cagcggagag ggcagcgaca gcgccggcgg     240
ggccacgctc aaagccccca gcatctcctg gaggcacgag cagcaccacc agtacccgct     300
ccggcagccc cagttccgcc tcctgcatcc ccatcaccac ctgccccgc cgccgccacc     360
ctcgccccag cccagcccc agtgtccgct acagccgccg ccgccgcccc cctgccgcc     420
gcccccgccg ccgcccgggg ctgcccgcgg ccgctacgcc tcgagcgggg ccaccggccg     480
cgtccggcat cgcggctact cggacaccga gcgctacctg tactgtcgcg ccatggaccg     540
cacctcctac gcggtggaga ccggccaccg gcccggcctg aagaaatcca ggatgtcctg     600
gccctcctcg ttccagggac tcaggcgttt tgatgtggac aatggcacat ctgcgggacg     660
gagtcccttg gatcccatga ccagcccagg atccggctca attctccaag caaatttgt     720
ccacagtcaa cgacgggagt ccttcctgta tcgatccgac agcgattatg acctctctcc     780
aaagtctatg tcccggaact cctccattgc cagtgatata cacggagatg acttgattgt     840
gactccattt gctcaggtct tggccagtct gcgaactgta cgaaacaact ttgctgcatt     900
aactaatttg caagatcgag cacctagcaa aagatcaccc atgtgcaacc aaccatccat     960
caacaaagcc accataacag aggaggccta ccagaaactg gccagcgaga ccctggagga    1020
gctggactgg tgtctggacc agctagagac cctacagacc aggcactccg tcagtgagat    1080
ggcctccaac aagtttaaaa ggatgcttaa tcgggagctc acccatctct ctgaaatgag    1140
tcggtctgga aatcaagtgt cagagtttat atcaaacaca ttcttagata gcaacatga    1200
agtggaaatt ccttctccaa ctcagaagga aaaggagaaa aagaaaagac caatgtctca    1260
gatcagtgga gtcaagaaat tgatgcacag ctctagtctg actaattcaa gtatcccaag    1320
gtttggagtt aaaactgaac aagaagatgt ccttgccaag gaactagaag atgtgaacaa    1380
atggggtctt catgttttca gaatagcaga gttgtctggt aaccggccct tgactgttat    1440
catgcacacc attttcagg aacgggattt attaaaaaca tttaaaattc cagtagatac    1500
tttaattaca tatcttatga ctctcgaaga ccattaccat gctgatgtgg cctatcacaa    1560
caatatccat gctgcagatg ttgtccagtc tactcatgtg ctattatcta cacctgcttt    1620
ggaggctgtg tttacagatt tggagattct tgcagcaatt tttgccagtg caatacatga    1680
```

```
tgtagatcat cctggtgtgt ccaatcaatt tctgatcaat acaaactctg aacttgcctt    1740
gatgtacaat gattcctcag tcttagagaa ccatcatttg gctgtgggct ttaaattgct    1800
tcaggaagaa aactgtgaca ttttccagaa tttgaccaaa aaacaaagac aatctttaag    1860
gaaaatggtc attgacatcg tacttgcaac agatatgtca aaacacatga atctactggc    1920
tgatttgaag actatggttg aaactaagaa agtgacaagc tctggagttc ttcttcttga    1980
taattattcc gataggattc aggttcttca gaatatggtg cactgtgcag atctgagcaa    2040
cccaacaaag cctctccagc tgtaccgcca gtggacggac cggataatgg aggagttctt    2100
ccgccaagga gaccgagaga gggaacgtgg catggagata agccccatgt gtgacaagca    2160
caatgcttcc gtggaaaaat cacaggtggg cttcatagac tatattgttc atcccctctg    2220
ggagacatgg gcagacctcg tccaccctga cgcccaggat attttggaca ctttggagga    2280
caatcgtgaa tggtaccaga gcacaatccc tcagagcccc tctcctgcac ctgatgaccc    2340
agaggagggc cggcagggtc aaactgagaa attccagttt gaactaactt tagaggaaga    2400
tggtgagtca gacacggaaa aggacagtgg cagtcaagtg aagaagaca ctagctgcag    2460 tgactccaag actctttgta ctcaagactc agagtctact gaaattcccc ttgatgaaca    2520
ggttgaagag gaggcagtag gggaagaaga ggaaagccag cctgaagcct gtgtcataga    2580
tgatcgttct cctgacacgt aacagtgcaa aaactttcat gccttttttt ttttaagta    2640 gaaaaattgt ttccaaagtg catgtcacat gccacaacca cggtcacacc tcactgtcat    2700
ctgccaggac gtttgttgaa caaaactgac cttgactact cagtccagcg ctcaggaata    2760
tcgtaaccag ttttttcacc tccatgtcat ccgagcaagg tggacatctt cacgaacagc    2820 gttttaaca agatttcagc ttggtagagc tgacaaagca gataaaatct actccaaatt    2880
attttcaaga gagtgtgact catcaggcag cccaaaagtt tattggactt ggggtttcta    2940
ttccttttta tttgtttgca atattttcag aagaaaggca ttgcacagag tgaacttaat    3000
ggacgaagca acaaatatgt caagaacagg acatagcacg aatctgttac cagtaggagg    3060
aggatgagcc acagaaattg cataatttc taatttcaag tcttcctgat acatgactga    3120
atagtgtggt tcagtgagct gcactgacct ctacattttg tatgatatgt aaaacagatt    3180
ttttgtagag cttactttta ttattaaatg tattgaggta ttatatttaa aaaaaactat    3240
gttcagaact tcatctgcca ctggttattt ttttctaagg agtaacttgc aagttttcag    3300
tacaaatctg tgctacactg gataaaaatc taatttatga attttacttg caccttatag    3360
ttcatagcaa ttaactgatt tgtagtgatt cattgtttgt tttatatacc aatgacttcc    3420
atattttaaa agagaaaaac aactttatgt tgcaggaaac ccttttttgta agtctttatt    3480 atttactttg cattttgttt cactctttcc agataagcag agttgctctt caccagtgtt    3540
tttcttcatg tgcaaagtga ctatttgttc tataatactt ttatgtgtgt tatatcaaat    3600
gtgtcttaag cttcatgcaa actcagtcat cagttcgtgt tgtctgaagc aagtgggaga    3660
tatataaata cccagtagct aaaatggtca gtcttttta gatgttttcc tacttagtat    3720
ctcctaataa cgttttgctg tgtcactaga tgttcatttc acaagtgcat gtctttctaa    3780
taatccacac atttcatgct ctaataatcc acacatttca tgctcatttt tattgttttt    3840
acagccagtt atagtaagaa aaaggttttt ccccttgtgc tgctttataa tttagcgtgt    3900
gtctgaacct tatccatgtt tgctagatga ggtcttgtca aatatatcac taccattgtc    3960
accggtgaaa agaaacaggt agttaagtta gggttaacat tcatttcaac cacgaggttg    4020
```

```
tatatcatga ctagctttta ctcttggttt acagagaaaa gttaaacagc caactaggca    4080 gttttttaaga atattaacaa tatattaaca aacaccaata caactaatcc tatttggttt    4140
taatgatttc accatgggat taagaactat atcaggaaca tccctgagaa acggttttaa    4200
gtgtagcaac tactcttcct taatggacag ccacataacg tgtaggaagt cctttatcac    4260
ttatcctcga tccataagca tatcttgcag aggggaacta cttctttaaa cacatggagg    4320
gaaagaagat gatgccactg gcaccagagg gttagtactg tgatgcatcc taaaatattt    4380
attatattgg taaaaattct ggttaaataa aaaattagag atcactcttg gctgatttca    4440
gcaccaggaa ctgtattaca gttttagaga ttaattccta gtgtttacct gattatagca    4500
gttggcatca tggggcattt aattctgact ttatccccac gtcagcctta ataaagtctt    4560
ctttaccttc tctatgaaga ctttaaagcc caaataatca ttttttcacat tgatattcaa    4620 gaattgagat agatagaagc caaagtgggt atctgacaag tggaaaatca aacgtttaag    4680
aagaattaca actctgaaaa gcatttatat gtggaacttc tcaaggagcc tcctggggac    4740
tggaaagtaa gtcatcagcc aggcaaatga ctcatgctga agagagtccc catttcagtc    4800
ccctgagatc tagctgatgc ttagatcctt tgaaataaaa attatgtctt tataactctg    4860
atcttttaca taaagcagaa gaggaatcaa ctagttaatt gcaaggtttc tactctgttt    4920
cctctgtaaa gatcagatgg taatctttca aataagaaaa aaataaagac gtatgtttga    4980
ccaagtagtt tcacaagaat atttgggaac ttgtttctttt taattttatt tgtccctgag    5040
tgaagtctag aaagaaaggt aaagagtcta gagtttattc ctctttccaa aacattctca    5100
ttcctctcct ccctacactt agtatttccc ccacagagtg cctagaatct taataatgaa    5160
taaaataaaa agcagcaata tgtcattaac aaatccagac ctgaaagggt aaagggttta    5220
taactgcact aataaagaga ggctcttttt ttttcttcca gtttgttggt ttttaatggt    5280
accgtgttgt aaagataccc actaatggac aatcaaattg cagaaaaggc tcaatatcca    5340
agagacaggg actaatgcac tgtacaatct gcttatcctt gcccttctct cttgccaaag    5400
tgtgcttcag aaatatatac tgctttaaaa aagaataaaa gaatatcctt ttacaagtgg    5460 ctttacatttt cctaaaatgc cataagaaaa tgcaatatct gggtactgta tggggaaaaa    5520
aatgtccaag tttgtgtaaa accagtgcat ttcagcttgc aagttactga acacaataat    5580
gctgttttaa ttttgtttta tatcagttaa aattcacaat aatgtagata gaacaaatta    5640
cagacaagga aagaaaaaac ttgaatgaaa tggattttac agaaagcttt atgataattt    5700
ttgaatgcat tatttatttt ttgtgccatg cattttttttt ctcaccaaat gaccttacct    5760
gtaatacagt cttgtttgtc tgtttacaac catgtattta ttgcaatgta catactgtaa    5820
tgttaattgt aaattatctg ttcttattaa aacatcatcc catgatggga tggtgttgat    5880
atatttggaa actcttggtg agagaatgaa tggtgtgtat acatactctg tacattttttc    5940 ttttctcctg taatatagtc ttgtcaccctt agagcttgtt tatggaagat tcaagaaaac    6000
tataaaatac ttaaagatat ataaatttaa aaaaacatag ctgcaggtct ttggtcccag    6060
ggctgtgcct taactttaac caatattttc ttctgttttg ctgcatttga aaggtaacag    6120
tggagctagg gctgggcatt ttacatccag gcttttaatt gattagaatt ctgccaatag    6180
gtggatttta caaaccaca gacaacctct gaaagattct gagacccttt tgagacagaa    6240
gctcttaagt acttcttgcc agggagcagc actgcatgtg tgatggttgt ttgccatctg    6300
ttgatcagga actactcag ctacttgcat ttgattattt cctttttttt tttttttaac    6360
tcggaaacac aactggggaa atatattctt tcccagtgat tataaacaat cttttctctt    6420
```

```
ttttaagtc cttttggctt ctagagctca taggaaaatg gacttgattt gaaattggag   6480
ccagagttta ctcgtgttgg ttatctattc atcagcttcc tgacatgtta agagaataca   6540
ttaaagagaa aatactgttt tttaatccta aaatttttct tccactaaga taaaccaaat   6600
gtccttacat atatgtaaac ccatctattt aaacgcaaag gtgggttgat gtcagtttac   6660
atagcagaaa gcattcacta tcctctaaga tttgtttctg caaaactttc attgctttag   6720
aattttaaaa tttcaccttg tacaatggcc agccctaaa gcaggaaaca tttataatgg   6780
attatatgga aacatcctcc cagtacttgc ccagcccttg aatcatgtgg cttttcagtg   6840
aaaggaaaga ttcttttctc aggaaaaatg agcctatttt attttatttt atttttatttt  6900 ttgacacaaa ctgtagattt tagcagccct ggcccaaagg aatttgatta cttttgtttt   6960
aaacagtaca aagggacac tataattaca aaaacatcct taactgattt gagttgtttt   7020
tatttctttg gatatatttt cagagtggta aattgtgtgt gagaattaca aatgattatt   7080
cttttagtgg tttcttagcc tctcttacag cccacgggga tagtactgta catcaatacc   7140
ttcatatgaa attttatat gcaatgaaaa taaaagcatg ggttgattct gcctatttat   7200
gactcaatct tttacaaata aaagattatt catttaaat tatagttcaa tcagcatgtc   7260
tcttaggata ctgaacgtgg ttgaaatgaa aggatagtga catcataagt tagtactgat   7320
attcataacc aaataaagcc aacttgagta attttgctac attaaaaatt accaaaatta   7380
cttagatggc ctataagatt aagcatggtg ttttctaagc aagctttgaa aggggccttc   7440
catacttact taattgaata ttctgggata ttgaaaatta ttcagatact tgacaattat   7500
ttttggttac ctactccgca aactacaaag ttttaaggac tcaacaataa gttaatgaga   7560
cacagtgttt gctttcatgg agcttacagt ctggagggga caaaggctta aacaatactc   7620
atataattat atatgtgatc agtacaatga aggagctcag tggggtaaat aagcaggaac   7680
ctgaacttga tctgttccgg agggccacag aaggcttcct tgaggccttg agaaagtgat   7740
ttgcatctga gttctgaagg attgtaagag gtaactaggg aaaaagttga caggaagagg   7800
aaggggatcc agacaagaaa catttgcaaa gatcttgagg cataaatgag cttgagacat   7860
ctggagaaac tgaggaaaag tgagagagta ggcagggcct ggagccgcag agccattgct   7920
aaccatcctg tgtgagatat cccccattct gtagctttat tctcataacc ctgctcaatt   7980
ttctttataa cacttctcac agatttatat acgtgtttgt ttttgttatc tgtctctccc   8040
accagaccac agctccatga gagcaaggtc tttgcttacc aatatatcac tagcacttaa   8100
aactatgcct ggtacacagt aggttcttaa tatgtgttga atatagccat caaattgata   8160
ttggatataa ttcaatctga taagatattt tgagatatta aagagttttt aacttgatac   8220
cataaaaaaa aaaaaaaaaa                                               8240
```

<210> SEQ ID NO 11
<211> LENGTH: 809
<212> TYPE: PRT
<213> ORGANISM: Homo sapiens

<400> SEQUENCE: 11

```
Met Glu Ala Glu Gly Ser Ser Ala Pro Ala Arg Ala Gly Ser Gly Glu
 1               5                  10                  15

Gly Ser Asp Ser Ala Gly Gly Ala Thr Leu Lys Ala Pro Lys His Leu
                20                  25                  30

Trp Arg His Glu Gln His His Gln Tyr Pro Leu Arg Gln Pro Gln Phe
            35                  40                  45
```

```
Arg Leu Leu His Pro His His His Leu Pro Pro Pro Pro Pro Ser
    50              55                  60

Pro Gln Pro Gln Pro Gln Cys Pro Leu Gln Pro Pro Pro Pro Pro
65              70                  75                  80

Leu Pro Pro Pro Pro Pro Pro Gly Ala Ala Arg Gly Arg Tyr Ala
                85                  90                  95

Ser Ser Gly Ala Thr Gly Arg Val Arg His Arg Gly Tyr Ser Asp Thr
            100                 105                 110

Glu Arg Tyr Leu Tyr Cys Arg Ala Met Asp Arg Thr Ser Tyr Ala Val
        115                 120                 125

Glu Thr Gly His Arg Pro Gly Leu Lys Lys Ser Arg Met Ser Trp Pro
    130                 135                 140

Ser Ser Phe Gln Gly Leu Arg Arg Phe Asp Val Asp Asn Gly Thr Ser
145                 150                 155                 160

Ala Gly Arg Ser Pro Leu Asp Pro Met Thr Ser Pro Gly Ser Gly Leu
                165                 170                 175

Ile Leu Gln Ala Asn Phe Val His Ser Gln Arg Arg Glu Ser Phe Leu
            180                 185                 190

Tyr Arg Ser Asp Ser Asp Tyr Asp Leu Ser Pro Lys Ser Met Ser Arg
        195                 200                 205

Asn Ser Ser Ile Ala Ser Asp Ile His Gly Asp Asp Leu Ile Val Thr
210                 215                 220

Pro Phe Ala Gln Val Leu Ala Ser Leu Arg Thr Val Arg Asn Asn Phe
225                 230                 235                 240

Ala Ala Leu Thr Asn Leu Gln Asp Arg Ala Pro Ser Lys Arg Ser Pro
                245                 250                 255

Met Cys Asn Gln Pro Ser Ile Asn Lys Ala Thr Ile Thr Glu Glu Ala
            260                 265                 270

Tyr Gln Lys Leu Ala Ser Glu Thr Leu Glu Glu Leu Asp Trp Cys Leu
        275                 280                 285

Asp Gln Leu Glu Thr Leu Gln Thr Arg His Ser Val Ser Glu Met Ala
    290                 295                 300

Ser Asn Lys Phe Lys Arg Met Leu Asn Arg Glu Leu Thr His Leu Ser
305                 310                 315                 320

Glu Met Ser Arg Ser Gly Asn Gln Val Ser Glu Phe Ile Ser Asn Thr
                325                 330                 335

Phe Leu Asp Lys Gln His Glu Val Glu Ile Pro Ser Pro Thr Gln Lys
            340                 345                 350

Glu Lys Glu Lys Lys Lys Arg Pro Met Ser Gln Ile Ser Gly Val Lys
        355                 360                 365

Lys Leu Met His Ser Ser Ser Leu Thr Asn Ser Ser Ile Pro Arg Phe
    370                 375                 380

Gly Val Lys Thr Glu Gln Glu Asp Val Leu Ala Lys Glu Leu Glu Asp
385                 390                 395                 400

Val Asn Lys Trp Gly Leu His Val Phe Arg Ile Ala Glu Leu Ser Gly
                405                 410                 415

Asn Arg Pro Leu Thr Val Ile Met His Thr Ile Phe Gln Glu Arg Asp
            420                 425                 430

Leu Leu Lys Thr Phe Lys Ile Pro Val Asp Thr Leu Ile Thr Tyr Leu
        435                 440                 445

Met Thr Leu Glu Asp His Tyr His Ala Asp Val Ala Tyr His Asn Asn
    450                 455                 460
```

| | | | | | | | | | | | |
|---|---|---|---|---|---|---|---|---|---|---|---|
| Ile | His | Ala | Ala | Asp | Val | Val | Gln | Ser | Thr | His | Val | Leu | Leu | Ser | Thr |
| 465 | | | | 470 | | | | | 475 | | | | | 480 | |

Ile His Ala Ala Asp Val Val Gln Ser Thr His Val Leu Leu Ser Thr
465                 470                 475                 480

Pro Ala Leu Glu Ala Val Phe Thr Asp Leu Glu Ile Leu Ala Ala Ile
                485                 490                 495

Phe Ala Ser Ala Ile His Asp Val Asp His Pro Gly Val Ser Asn Gln
            500                 505                 510

Phe Leu Ile Asn Thr Asn Ser Glu Leu Ala Leu Met Tyr Asn Asp Ser
        515                 520                 525

Ser Val Leu Glu Asn His His Leu Ala Val Gly Phe Lys Leu Leu Gln
    530                 535                 540

Glu Glu Asn Cys Asp Ile Phe Gln Asn Leu Thr Lys Lys Gln Arg Gln
545                 550                 555                 560

Ser Leu Arg Lys Met Val Ile Asp Ile Val Leu Ala Thr Asp Met Ser
                565                 570                 575

Lys His Met Asn Leu Leu Ala Asp Leu Lys Thr Met Val Glu Thr Lys
            580                 585                 590

Lys Val Thr Ser Ser Gly Val Leu Leu Leu Asp Asn Tyr Ser Asp Arg
        595                 600                 605

Ile Gln Val Leu Gln Asn Met Val His Cys Ala Asp Leu Ser Asn Pro
    610                 615                 620

Thr Lys Pro Leu Gln Leu Tyr Arg Gln Trp Thr Asp Arg Ile Met Glu
625                 630                 635                 640

Glu Phe Phe Arg Gln Gly Asp Arg Glu Arg Glu Arg Gly Met Glu Ile
                645                 650                 655

Ser Pro Met Cys Asp Lys His Asn Ala Ser Val Glu Lys Ser Gln Val
            660                 665                 670

Gly Phe Ile Asp Tyr Ile Val His Pro Leu Trp Glu Thr Trp Ala Asp
        675                 680                 685

Leu Val His Pro Asp Ala Gln Asp Ile Leu Asp Thr Leu Glu Asp Asn
    690                 695                 700

Arg Glu Trp Tyr Gln Ser Thr Ile Pro Gln Ser Pro Pro Ala Pro
705                 710                 715                 720

Asp Asp Pro Glu Glu Gly Arg Gln Gly Gln Thr Glu Lys Phe Gln Phe
                725                 730                 735

Glu Leu Thr Leu Glu Glu Asp Gly Glu Ser Asp Thr Glu Lys Asp Ser
            740                 745                 750

Gly Ser Gln Val Glu Glu Asp Thr Ser Cys Ser Asp Ser Lys Thr Leu
        755                 760                 765

Cys Thr Gln Asp Ser Glu Ser Thr Glu Ile Pro Leu Asp Glu Gln Val
    770                 775                 780

Glu Glu Glu Ala Val Gly Glu Glu Glu Ser Gln Pro Glu Ala Cys
785                 790                 795                 800

Val Ile Asp Asp Arg Ser Pro Asp Thr
                805

<210> SEQ ID NO 12
<211> LENGTH: 7979
<212> TYPE: DNA
<213> ORGANISM: Homo sapiens

<400> SEQUENCE: 12
cagcagcagg ctcagacctg cttccctgga catttccggg accgtgagcg agggaaccac        60
gttgccctgg attcttgcca gctgtacaaa gttgaccagg aaaatggctc agcagacaag       120
cccggacact ttaacagtac ctgaagtgga taatccgcat tgtccaaacc cgtggctgaa       180

```
cgaagacctt gtgaaatcct tgcgagaaaa cctgttgcag catgagaagt ccaagacagc      240
gaggaaatcg gtttctccca agctctctcc agtgatctct ccgagaaatt cccccaggct      300
tctgcgcaga atgcttctca gcagcaacat ccccaaacag cggcgtttca cggtggcaca      360
tacatgtttt gatgtggaca atggcacatc tgcgggacgg agtcccttgg atcccatgac      420
cagcccagga tccgggctaa ttctccaagc aaattttgtc cacagtcaac gacgggagtc      480
cttcctgtat cgatccgaca gcgattatga cctctctcca agtctatgt cccggaactc       540 ctccattgcc agtgatatac acggagatga cttgattgtg actccatttg ctcaggtctt      600
ggccagtctg cgaactgtac gaaacaactt tgctgcatta actaatttgc aagatcgagc      660
acctagcaaa agatcaccca tgtgcaacca accatccatc aacaaagcca cataacaga       720 ggaggcctac cagaaactgg ccagcgagac cctggaggag ctggactggt gtctggacca      780
gctagagacc ctacagacca ggcactccgt cagtgagatg gcctccaaca gtttaaaag      840 gatgcttaat cgggagctca cccatctctc tgaaatgagt cggtctggaa atcaagtgtc      900
agagtttata tcaaacacat tcttagataa gcaacatgaa gtggaaattc cttctccaac      960
tcagaaggaa aaggagaaaa agaaaagacc aatgtctcag atcagtggag tcaagaaatt     1020
gatgcacagc tctagtctga ctaattcaag tatcccaagg tttggagtta aaactgaaca     1080
agaagatgtc cttgccaagg aactagaaga tgtgaacaaa tggggtcttc atgttttcag     1140
aatagcagag ttgtctggta accggccctt gactgttatc atgcacacca tttttcagga    1200
acgggattta ttaaaaacat ttaaaattcc agtagatact ttaattacat atcttatgac     1260
tctcgaagac cattaccatg ctgatgtggc ctatcacaac aatatccatg ctgcagatgt     1320
tgtccagtct actcatgtgc tattatctac acctgctttg gaggctgtgt tacagatttt    1380
ggagattctt gcagcaattt ttgccagtgc aatacatgat gtagatcatc ctggtgtgtc    1440
caatcaattt ctgatcaata caaactctga acttgccttg atgtacaatg attcctcagt    1500
cttagagaac catcatttgg ctgtgggctt taaattgctt caggaagaaa actgtgacat    1560
tttccagaat ttgaccaaaa aacaaagaca atctttaagg aaaatggtca ttgacatcgt    1620
acttgcaaca gatatgtcaa aacacatgaa tctactggct gatttgaaga ctatggttga    1680
aactaagaaa gtgacaagct ctggagttct tcttcttgat aattattccg ataggattca    1740
ggttcttcag aatatggtgc actgtgcaga tctgagcaac ccaacaaagc ctctccagct    1800
gtaccgccag tggacggacc ggataatgga ggagttcttc cgccaaggag accgagagag    1860
ggaacgtggc atggagataa gccccatgtg tgacaagcac aatgcttccg tggaaaaatc    1920
acaggtgggc ttcatagact atattgttca tcccctctgg agacatggg cagacctcgt     1980 ccaccctgac gcccaggata ttttggacac tttggaggac aatcgtgaat ggtaccagag    2040
cacaatccct cagagcccct ctcctgcacc tgatgaccca gaggagggcc ggcagggtca    2100
aactgagaaa ttccagtttg aactaacttt agaggaagat ggtgagtcag acacggaaaa    2160
ggacagtggc agtcaagtgg aagaagacac tagctgcagt gactccaaga ctctttgtac    2220
tcaagactca gagtctactg aaattcccct tgatgaacag gttgaagagg aggcagtagg    2280
ggaagaagag gaaagccagc ctgaagcctg tgtcatagat gatcgttctc ctgacacgta    2340
acagtgcaaa aactttcatg cctttttttt ttttaagtag aaaaattgtt ccaaagtgc    2400 atgtcacatg ccacaaccac ggtcacacct cactgtcatc tgccaggacg tttgttgaac    2460
aaaactgacc ttgactactc agtccagcgc tcaggaatat cgtaaccagt tttttcacct    2520
```

```
ccatgtcatc cgagcaaggt ggacatcttc acgaacagcg tttttaacaa gatttcagct    2580
tggtagagct gacaaagcag ataaaatcta ctccaaatta ttttcaagag agtgtgactc    2640
atcaggcagc ccaaaagttt attggacttg gggtttctat tcctttttat ttgtttgcaa    2700
tattttcaga agaaaggcat tgcacagagt gaacttaatg gacgaagcaa caaatatgtc    2760
aagaacagga catagcacga atctgttacc agtaggagga ggatgagcca cagaaattgc    2820
ataattttct aatttcaagt cttcctgata catgactgaa tagtgtggtt cagtgagctg    2880
cactgacctc tacattttgt atgatatgta aaacagattt tttgtagagc ttactttat     2940 tattaaatgt attgaggtat tatatttaaa aaaaactatg ttcagaactt catctgccac    3000
tggttatttt tttctaagga gtaacttgca agttttcagt acaaatctgt gctacactgg    3060
ataaaaatct aatttatgaa ttttacttgc accttatagt tcatagcaat taactgattt    3120
gtagtgattc attgtttgtt ttatatacca atgacttcca tattttaaaa gagaaaaaca    3180
actttatgtt gcaggaaacc ttttttgtaa gtctttatta tttactttgc attttgtttc    3240 actcttttcca gataagcaga gttgctcttc accagtgttt ttcttcatgt gcaaagtgac    3300
tatttgttct ataatacttt tatgtgtgtt atatcaaatg tgtcttaagc ttcatgcaaa    3360
ctcagtcatc agttcgtgtt gtctgaagca agtgggagat atataaatac ccagtagcta    3420
aaatggtcag tctttttag atgttttcct acttagtatc tcctaataac gttttgctgt     3480
gtcactagat gttcatttca caagtgcatg tctttctaat aatccacaca tttcatgctc    3540
taataatcca cacatttcat gctcattttt attgttttta cagccagtta tagtaagaaa    3600 aaggttttc cccttgtgct gctttataat ttagcgtgtg tctgaacctt atccatgttt     3660
gctagatgag gtcttgtcaa atatatcact accattgtca ccggtgaaaa gaaacaggta    3720
gttaagttag ggttaacatt catttcaacc acgaggttgt atatcatgac tagcttttac    3780
tcttggttta cagagaaaag ttaaacagcc aactaggcag tttttaagaa tattaacaat    3840
atattaacaa acaccaatac aactaatcct atttggtttt aatgatttca ccatgggatt    3900
aagaactata tcaggaacat ccctgagaaa cggttttaag tgtagcaact actcttcctt    3960
aatggacagc cacataacgt gtaggaagtc ctttatcact tatcctcgat ccataagcat    4020
atcttgcaga ggggaactac ttctttaaac acatggaggg aaagaagatg atgccactgg    4080
caccagaggg ttagtactgt gatgcatcct aaaatattta ttatattggt aaaaattctg    4140
gttaaataaa aaattagaga tcactcttgg ctgatttcag caccaggaac tgtattacag    4200
ttttagagat taattcctag tgtttacctg attatagcag ttggcatcat ggggcattta    4260
attctgactt tatccccacg tcagccttaa taaagtcttc tttaccttct ctatgaagac    4320
tttaaagccc aaataatcat ttttcacatt gatattcaag aattgagata gatagaagcc    4380
aaagtgggta tctgacaagt ggaaaatcaa acgtttaaga agaattacaa ctctgaaaag    4440
catttatatg tggaacttct caaggagcct cctggggact ggaaagtaag tcatcagcca    4500
ggcaaatgac tcatgctgaa gagagtcccc atttcagtcc cctgagatct agctgatgct    4560
tagatccttt gaaataaaaa ttatgtcttt ataactctga tcttttacat aaagcagaag    4620
aggaatcaac tagttaattg caaggtttct actctgtttc ctctgtaaag atcagatggt    4680
aatctttcaa ataagaaaaa aataaagacg tatgtttgac caagtagttt cacaagaata    4740
tttgggaact tgtttctttt aattttattt gtccctgagt gaagtctaga agaaaggta     4800 aagagtctag agtttattcc tctttccaaa acattctcat tcctctcctc cctacactta    4860
gtatttcccc cacagagtgc ctagaatctt aataatgaat aaaataaaaa gcagcaatat    4920
```

```
gtcattaaca aatccagacc tgaaagggta aagggtttat aactgcacta ataaagagag      4980 gctcttttt  tttcttccag tttgttggtt tttaatggta ccgtgttgta aagataccca      5040
ctaatggaca atcaaattgc agaaaaggct caatatccaa gagacaggga ctaatgcact      5100
gtacaatctg cttatccttg cccttctctc ttgccaaagt gtgcttcaga aatatatact      5160
gctttaaaaa agaataaaag aatatccttt tacaagtggc tttacatttc ctaaaatgcc      5220
ataagaaaat gcaatatctg ggtactgtat ggggaaaaaa atgtccaagt tgtgtaaaa       5280 ccagtgcatt tcagcttgca agttactgaa cacaataatg ctgttttaat tttgttttat      5340
atcagttaaa attcacaata atgtagatag aacaaattac agacaaggaa agaaaaaact      5400
tgaatgaaat ggattttaca gaaagcttta tgataatttt tgaatgcatt atttattttt      5460
tgtgccatgc atttttttt  tcaccaaatg accttacctg taatacagtc ttgtttgtct      5520
gtttacaacc atgtatttat tgcaatgtac atactgtaat gttaattgta aattatctgt      5580
tcttattaaa acatcatccc atgatgggat ggtgttgata tatttggaaa ctcttggtga      5640
gagaatgaat ggtgtgtata catactctgt acattttct  tttctcctgt aatatagtct      5700 tgtcaccta  gagcttgttt atggaagatt caagaaaact ataaaatact taaagatata      5760
taaatttaaa aaaacatagc tgcaggtctt tggtcccagg gctgtgcctt aactttaacc      5820
aatattttct tctgttttgc tgcatttgaa aggtaacagt ggagctaggg ctggcatttt      5880
tacatccagg cttttaattg attagaattc tgccaatagg tggattttac aaaaccacag      5940
acaacctctg aaagattctg agacccttt  gagacagaag ctcttaagta cttcttgcca      6000
gggagcagca ctgcatgtgt gatggttgtt tgccatctgt tgatcaggaa ctacttcagc      6060
tacttgcatt tgattatttc ctttttttt  tttttaact  cggaaacaca actggggaaa      6120
tatattcttt cccagtgatt ataaacaatc ttttctttt  ttttaagtcc ttttggcttc      6180
tagagctcat aggaaaatgg acttgatttg aaattggagc cagagtttac tcgtgttggt      6240
tatctattca tcagcttcct gacatgttaa gagaatacat taaagagaaa atactgtttt      6300
ttaatcctaa aattttctt  ccactaagat aaaccaaatg tccttacata tatgtaaacc      6360
catctattta aacgcaaagg tgggttgatg tcagtttaca tagcagaaag cattcactat      6420
cctctaagat ttgtttctgc aaaactttca ttgctttaga attttaaaat ttcaccttgt      6480
acaatggcca gcccctaaag caggaaacat ttataatgga ttatatgaa  acatcctccc      6540 agtacttgcc cagcccttga atcatgtggc ttttcagtga aaggaaagat tctttttcta      6600
ggaaaaatga gcctatttta ttttatttta ttttattttt tgcacaaaac tgtagatttt      6660
agcagccctg gcccaaagga atttgattac ttttgtttta aacagtacaa aggggacact      6720
ataattacaa aaacatcctt aactgatttg agttgttttt atttctttgg atatatttc       6780 agagtggtaa attgtgtgtg agaattacaa atgattattc ttttagtggt tccttagcct      6840
ctcttacagc ccacgggat  agtactgtac atcaatacct tcatatgaaa ttttttatatg     6900 caatgaaaat aaaagcatgg gttgattctg cctatttatg actcaatctt ttacaaataa      6960
aagattattc atttttaaatt atagttcaat cagcatgtct cttaggatac tgaacgtggt      7020
tgaaatgaaa ggatagtgac atcataagtt agtactgata ttcataacca aataagccaa       7080
acttgagtaa ttttgctaca ttaaaaatta ccaaaattac ttagatggcc tataagatta      7140
agcatggtgt tttctaagca agctttgaaa ggggccttcc atacttactt aattgaatat      7200
tctgggatat tgaaaattat tcagatactt gacaattatt tttggttacc tactccgcaa      7260
```

-continued

```
actacaaagt tttaaggact caacaataag ttaatgagac acagtgtttg ctttcatgga    7320
gcttacagtc tggaggggac aaaggcttaa acaatactca tataattata tatgtgatca    7380
gtacaatgaa ggagctcagt ggggtaaata agcaggaacc tgaacttgat ctgttccgga    7440
gggccacaga aggcttcctt gaggccttga gaaagtgatt tgcatctgag ttctgaagga    7500
ttgtaagagg taactaggga aaaagttgac aggaagagga aggggatcca gacaagaaac    7560
atttgcaaag atcttgaggc ataaatgagc ttgagacatc tggagaaact gaggaaaagt    7620
gagagagtag gcagggcctg gagccgcaga gccattgcta accatcctgt gtgagatatc    7680
ccccattctg tagctttatt ctcataaccc tgctcaattt tctttataac acttctcaca    7740
gatttatata cgtgtttgtt tttgttatct gtctctccca ccagaccaca gctccatgag    7800
agcaaggtct ttgcttacca atatatcact agcacttaaa actatgcctg gtacacagta    7860
ggttcttaat atgtgttgaa tatagccatc aaattgatat tggatataat tcaatctgat    7920
aagatatttt gagatattaa agagttttta acttgatacc ataaaaaaaa aaaaaaaaa    7979
```

```
<210> SEQ ID NO 13
<211> LENGTH: 745
<212> TYPE: PRT
<213> ORGANISM: Homo sapiens

<400> SEQUENCE: 13
```

Met Ala Gln Gln Thr Ser Pro Asp Thr Leu Thr Val Pro Glu Val Asp
1               5                   10                  15

Asn Pro His Cys Pro Asn Pro Trp Leu Asn Glu Asp Leu Val Lys Ser
            20                  25                  30

Leu Arg Glu Asn Leu Leu Gln His Glu Lys Ser Lys Thr Ala Arg Lys
        35                  40                  45

Ser Val Ser Pro Lys Leu Ser Pro Val Ile Ser Pro Arg Asn Ser Pro
    50                  55                  60

Arg Leu Leu Arg Arg Met Leu Leu Ser Ser Asn Ile Pro Lys Gln Arg
65                  70                  75                  80

Arg Phe Thr Val Ala His Thr Cys Phe Asp Val Asp Asn Gly Thr Ser
                85                  90                  95

Ala Gly Arg Ser Pro Leu Asp Pro Met Thr Ser Pro Gly Ser Gly Leu
            100                 105                 110

Ile Leu Gln Ala Asn Phe Val His Ser Gln Arg Arg Glu Ser Phe Leu
        115                 120                 125

Tyr Arg Ser Asp Ser Asp Tyr Asp Leu Ser Pro Lys Ser Met Ser Arg
    130                 135                 140

Asn Ser Ser Ile Ala Ser Asp Ile His Gly Asp Asp Leu Ile Val Thr
145                 150                 155                 160

Pro Phe Ala Gln Val Leu Ala Ser Leu Arg Thr Val Arg Asn Asn Phe
                165                 170                 175

Ala Ala Leu Thr Asn Leu Gln Asp Arg Ala Pro Ser Lys Arg Ser Pro
            180                 185                 190

Met Cys Asn Gln Pro Ser Ile Asn Lys Ala Thr Ile Thr Glu Glu Ala
        195                 200                 205

Tyr Gln Lys Leu Ala Ser Glu Thr Leu Glu Glu Leu Asp Trp Cys Leu
    210                 215                 220

Asp Gln Leu Glu Thr Leu Gln Thr Arg His Ser Val Ser Glu Met Ala
225                 230                 235                 240

Ser Asn Lys Phe Lys Arg Met Leu Asn Arg Glu Leu Thr His Leu Ser
                245                 250                 255

```
Glu Met Ser Arg Ser Gly Asn Gln Val Ser Glu Phe Ile Ser Asn Thr
            260                 265                 270

Phe Leu Asp Lys Gln His Glu Val Glu Ile Pro Ser Pro Thr Gln Lys
            275                 280                 285

Glu Lys Glu Lys Lys Arg Pro Met Ser Gln Ile Ser Gly Val Lys
    290             295                 300

Lys Leu Met His Ser Ser Leu Thr Asn Ser Ser Ile Pro Arg Phe
305             310                 315                 320

Gly Val Lys Thr Glu Gln Glu Asp Val Leu Ala Lys Glu Leu Glu Asp
                325                 330                 335

Val Asn Lys Trp Gly Leu His Val Phe Arg Ile Ala Glu Leu Ser Gly
            340                 345                 350

Asn Arg Pro Leu Thr Val Ile Met His Thr Ile Phe Gln Glu Arg Asp
            355                 360                 365

Leu Leu Lys Thr Phe Lys Ile Pro Val Asp Thr Leu Ile Thr Tyr Leu
        370                 375                 380

Met Thr Leu Glu Asp His Tyr His Ala Asp Val Ala Tyr His Asn Asn
385                 390                 395                 400

Ile His Ala Ala Asp Val Val Gln Ser Thr His Val Leu Leu Ser Thr
                405                 410                 415

Pro Ala Leu Glu Ala Val Phe Thr Asp Leu Glu Ile Leu Ala Ala Ile
                420                 425                 430

Phe Ala Ser Ala Ile His Asp Val Asp His Pro Gly Val Ser Asn Gln
            435                 440                 445

Phe Leu Ile Asn Thr Asn Ser Glu Leu Ala Leu Met Tyr Asn Asp Ser
        450                 455                 460

Ser Val Leu Glu Asn His His Leu Ala Val Gly Phe Lys Leu Leu Gln
465                 470                 475                 480

Glu Glu Asn Cys Asp Ile Phe Gln Asn Leu Thr Lys Lys Gln Arg Gln
            485                 490                 495

Ser Leu Arg Lys Met Val Ile Asp Ile Val Leu Ala Thr Asp Met Ser
            500                 505                 510

Lys His Met Asn Leu Leu Ala Asp Leu Lys Thr Met Val Glu Thr Lys
            515                 520                 525

Lys Val Thr Ser Ser Gly Val Leu Leu Leu Asp Asn Tyr Ser Asp Arg
            530                 535                 540

Ile Gln Val Leu Gln Asn Met Val His Cys Ala Asp Leu Ser Asn Pro
545                 550                 555                 560

Thr Lys Pro Leu Gln Leu Tyr Arg Gln Trp Thr Asp Arg Ile Met Glu
                565                 570                 575

Glu Phe Phe Arg Gln Gly Asp Arg Glu Arg Glu Arg Gly Met Glu Ile
            580                 585                 590

Ser Pro Met Cys Asp Lys His Asn Ala Ser Val Glu Lys Ser Gln Val
        595                 600                 605

Gly Phe Ile Asp Tyr Ile Val His Pro Leu Trp Glu Thr Trp Ala Asp
            610                 615                 620

Leu Val His Pro Asp Ala Gln Asp Ile Leu Asp Thr Leu Glu Asp Asn
625                 630                 635                 640

Arg Glu Trp Tyr Gln Ser Thr Ile Pro Gln Ser Pro Ser Pro Ala Pro
                645                 650                 655

Asp Asp Pro Glu Glu Gly Arg Gln Gly Gln Thr Glu Lys Phe Gln Phe
            660                 665                 670
```

```
Glu Leu Thr Leu Glu Glu Asp Gly Glu Ser Asp Thr Glu Lys Asp Ser
            675                 680                 685

Gly Ser Gln Val Glu Asp Thr Ser Cys Ser Asp Ser Lys Thr Leu
    690                 695                 700

Cys Thr Gln Asp Ser Glu Ser Thr Glu Ile Pro Leu Asp Glu Gln Val
705                 710                 715                 720

Glu Glu Glu Ala Val Gly Glu Glu Glu Ser Gln Pro Glu Ala Cys
            725                 730                 735

Val Ile Asp Asp Arg Ser Pro Asp Thr
            740                 745

<210> SEQ ID NO 14
<211> LENGTH: 19
<212> TYPE: DNA
<213> ORGANISM: Artificial Sequence
<220> FEATURE:
<223> OTHER INFORMATION: PDE4D5_forward primer

<400> SEQUENCE: 14
gcttctcagc agcaacatc                                                    19

<210> SEQ ID NO 15
<211> LENGTH: 20
<212> TYPE: DNA
<213> ORGANISM: Artificial Sequence
<220> FEATURE:
<223> OTHER INFORMATION: PDE4D5_reverse primer

<400> SEQUENCE: 15
tgccattgtc cacatcaaaa                                                   20

<210> SEQ ID NO 16
<211> LENGTH: 24
<212> TYPE: DNA
<213> ORGANISM: Artificial Sequence
<220> FEATURE:
<223> OTHER INFORMATION: PDE4D5 probe

<400> SEQUENCE: 16
acagcggcgt ttcacggtgg caca                                              24

<210> SEQ ID NO 17
<211> LENGTH: 7591
<212> TYPE: DNA
<213> ORGANISM: Homo sapiens

<400> SEQUENCE: 17
agttccttat ttggtagctt ttgacaggac tagcctttct tgcaactaag catcttgaca      60
tacattattc attaagccct ggagctcggg agagaaagat gcagacccct agatctttag     120
atattccttt atcacgtgga ttttctttat tcagaatagt tgctgaattt tgtgccattc     180
tggagtctta caaatggcat gtattcgatg ggaagacggc tggatgggat ttaatgcgag     240
gctttcttat gtatacttaa ttaccaaaaa tctttaaaaa ctcatactct gcgtggcttg     300
tggaggttgt taaagtgtcg agattttgaa gctaaataca ttttagagct tactatatat     360
atacatatat atatatatac ataatcaa tcaaaaatgc tgaagcaaa ctatttactg        420 tcagtgtctt ggggctacat aaagtttaaa aggatgctta atcgggagct cacccatctc     480
tctgaaatga gtcggtctgg aaatcaagtg tcagagttta tatcaaacac attcttagat     540
aagcaacatg aagtggaaat tccttctcca actcagaagg aaaaggagaa aaagaaaga     600
```

```
ccaatgtctc agatcagtgg agtcaagaaa ttgatgcaca gctctagtct gactaattca    660
agtatcccaa ggtttggagt taaaactgaa caagaagatg tccttgccaa ggaactagaa    720
gatgtgaaca atgggggtct tcatgttttc agaatagcag agttgtctgg taaccggccc    780
ttgactgtta tcatgcacac catttttcag gaacgggatt tattaaaaac atttaaaatt    840
ccagtagata ctttaattac atatcttatg actctcgaag accattacca tgctgatgtg    900
gcctatcaca acaatatcca tgctgcagat gttgtccagt ctactcatgt gctattatct    960
acacctgctt tggaggctgt gtttacagat ttggagattc ttgcagcaat tttttgccagt   1020
gcaatacatg atgtagatca tcctggtgtg tccaatcaat ttctgatcaa tacaaactct   1080
gaacttgcct tgatgtacaa tgattcctca gtcttagaga accatcattt ggctgtgggc   1140
tttaaattgc ttcaggaaga aaactgtgac attttccaga atttgaccaa aaaacaaaga   1200
caatctttaa ggaaaatggt cattgacatc gtacttgcaa cagatatgtc aaaacacatg   1260
aatctactgg ctgatttgaa gactatggtt gaaactaaga aagtgacaag ctctggagtt   1320
cttcttcttg ataattattc cgataggatt caggttcttc agaatatggt gcactgtgca   1380
gatctgagca acccaacaaa gcctctccag ctgtaccgcc agtggacgga ccggataatg   1440
gaggagttct tccgccaagg agaccgagag agggaacgtg gcatggagat aagccccatg   1500
tgtgacaagc acaatgcttc cgtggaaaaa tcacaggtgg gcttcataga ctatattgtt   1560
catcccctct gggagacatg ggcagacctc gtccaccctg acgcccagga tattttggac   1620
actttggagg acaatcgtga atggtaccag agcacaatcc ctcagagccc ctctcctgca   1680
cctgatgacc cagaggaggg ccggcagggt caaactgaga aattccagtt tgaactaact   1740
ttagaggaag atggtgagtc agacacggaa aaggacagtg gcagtcaagt ggaagaagac   1800
actagctgca gtgactccaa gactctttgt actcaagact cagagtctac tgaaattccc   1860
cttgatgaac aggttgaaga ggaggcagta ggggaagaag aggaaagcca gcctgaagcc   1920
tgtgtcatag atgatcgttc tcctgacacg taacagtgca aaaactttca tgccttttt    1980
tttttttaagt agaaaaattg tttccaaagt gcatgtcaca tgccacaacc acggtcacac   2040
ctcactgtca tctgccagga cgtttgttga acaaaactga ccttgactac tcagtccagc   2100
gctcaggaat atcgtaacca gttttttcac ctccatgtca tccgagcaag gtggacatct   2160
tcacgaacag cgttttttaac aagatttcag cttggtagag ctgacaaagc agataaaatc   2220
tactccaaat tattttcaag agagtgtgac tcatcaggca gcccaaaagt ttattggact   2280
tggggtttct attcctttt atttgtttgc aatattttca gaagaaaggc attgcacaga   2340
gtgaacttaa tggacgaagc aacaaatatg tcaagaacag gacatagcac gaatctgtta   2400
ccagtaggag gaggatgagc cacagaaatt gcataatttt ctaatttcaa gtcttcctga   2460
tacatgactg aatagtgtgg ttcagtgagc tgcactgacc tctacatttt gtatgatatg   2520
taaaacagat ttttttgtaga gcttactttt attattaaat gtattgaggt attatattta   2580
aaaaaaacta tgttcagaac ttcatctgcc actggttatt ttttctaag gagtaacttg    2640
caagttttca gtacaaatct gtgctacact ggataaaaat ctaatttatg aattttactt   2700
gcaccttata gttcatagca attaactgat ttgtagtgat tcattgtttg tttttatatac  2760
caatgacttc catattttaa aagagaaaaa caactttatg ttgcaggaaa ccctttttgt    2820
aagtctttat tatttactt gcatttttgtt tcactcttc cagataagca gagttgctct    2880
tcaccagtgt ttttcttcat gtgcaaagtg actatttgtt ctataatact tttatgtgtg   2940
ttatatcaaa tgtgtcttaa gcttcatgca aactcagtca tcagttcgtg ttgtctgaag   3000
```

```
caagtgggag atatataaat acccagtagc taaaatggtc agtcttttt     3060
            agatgttttc
ctacttagta tctcctaata acgttttgct gtgtcactag atgttcattt   3120
            cacaagtgca
tgtcttcta  ataatccaca catttcatgc tctaataatc cacacattc    3180
            atgctcattt
ttattgtttt tacagccagt tatagtaaga aaaaggtttt tccccttgtg   3240
            ctgctttata
atttagcgtg tgtctgaacc ttatccatgt ttgctagatg aggtcttgtc   3300
            aaatatatca
ctaccattgt caccggtgaa aagaaacagg tagttaagtt agggttaaca   3360
            ttcatttcaa
ccacgaggtt gtatatcatg actagctttt actcttggtt tacagagaaa   3420
            agttaaacag
ccaactaggc agttttaag  aatattaaca atatattaac aaacaccaat   3480
            acaactaatc
ctatttggtt ttaatgattt caccatggga ttaagaacta tcaggaac     3540
            atccctgaga
aacggtttta agtgtagcaa ctactcttcc ttaatggaca gccacataac   3600
            gtgtaggaag
tcctttatca cttatcctcg atccataagc atatcttgca gagggaact    3660
            acttctttaa
acacatggag ggaaagaaga tgatgccact ggcaccagag ggttagtact   3720
            gtgatgcatc
ctaaaatatt tattatattg gtaaaaattc tggttaaata aaaaattaga   3780
            gatcactctt
ggctgatttc agcaccagga actgtattac agttttagag attaattcct   3840
            agtgtttacc
tgattatagc agttggcatc atggggcatt taattctgac tttatcccca   3900
            cgtcagcctt
aataaagtct tctttacctt ctctatgaag actttaaagc ccaaataatc   3960
            attttcaca
ttgatattca agaattgaga tagatagaag ccaaagtggg tatctgacaa   4020
            gtggaaaatc
aaacgtttaa gaagaattac aactctgaaa agcatttata tgtggaactt   4080
            ctcaaggagc
ctcctgggga ctggaaagta agtcatcagc caggcaaatg actcatgctg   4140
            aagagagtcc
ccatttcagt cccctgagat ctagctgatg cttagatcct ttgaaataaa   4200
            aattatgtct
ttataactct gatcttttac ataaagcaga agaggaatca actagttaat   4260
            tgcaaggttt
ctactctgtt tcctctgtaa agatcagatg gtaatctttc aaataagaaa   4320
            aaaataaaga
cgtatgtttg accaagtagt ttcacaagaa tatttgggaa cttgtttctt   4380
            ttaatttat
ttgtccctga gtgaagtcta gaaagaaagg taaagagtct agagtttatt   4440
            cctctttcca
aaacattctc attcctctcc tccctacact tagtatttcc cccacagagt   4500
            gcctagaatc
ttaataatga ataaaataaa aagcagcaat atgtcattaa caaatccaga   4560
            cctgaaaggg
taaagggttt ataactgcac taataaagag aggctctttt ttttcttcc    4620
            agtttgttgg
ttttttaatgg taccgtgttg taaagatacc cactaatgga caatcaaatt  4680
            gcagaaaagg
ctcaatatcc aagagacagg gactaatgca ctgtacaatc tgcttatcct   4740
            tgcccttctc
tcttgccaaa gtgtgcttca gaaatatata ctgctttaaa aaagaataaa   4800
            agaatatcct
tttacaagtg gctttacatt tcctaaaatg ccataagaaa atgcaatatc   4860
            tgggtactgt
atggggaaaa aaatgtccaa gtttgtgtaa aaccagtgca tttcagcttg   4920
            caagttactg
aacacaataa tgctgtttta attttgtttt atatcagtta aaattcacaa   4980
            taatgtagat
agaacaaatt acagacaagg aaagaaaaaa cttgaatgaa atggattta    5040
            cagaaagctt
tatgataatt tttgaatgca ttatttattt tttgtgccat gcatttttt    5100
            tctcaccaaa
tgaccttacc tgtaatacag tcttgttgt  ctgtttacaa ccatgtattt   5160
            attgcaatgt
acatactgta atgttaattg taaattatct gttcttatta aacatcatc    5220
            ccatgatggg
atggtgttga tatatttgga aactcttggt gagagaatga atggtgtgta   5280
            tacatactct
gtacattttt cttttctcct gtaatatagt cttgtcacct tagagcttgt   5340
            ttatggaaga
```

```
ttcaagaaaa ctataaaata cttaaagata tataaattta aaaaaacata gctgcaggtc    5400
tttggtccca gggctgtgcc ttaactttaa ccaatatttt cttctgtttt gctgcatttg    5460
aaaggtaaca gtggagctag ggctgggcat tttacatcca ggcttttaat tgattagaat    5520
tctgccaata ggtggatttt acaaaaccac agacaacctc tgaaagattc tgagaccctt    5580
ttgagacaga agctcttaag tacttcttgc cagggagcag cactgcatgt gtgatggttg    5640
tttgccatct gttgatcagg aactacttca gctacttgca tttgattatt tccttttttt    5700
ttttttttaa ctcggaaaca caactgggga aatatattct ttcccagtga ttataaacaa    5760 tcttttctt ttttttaagt cctttggct tctagagctc ataggaaaat ggacttgatt     5820
tgaaattgga gccagagttt actcgtgttg gttatctatt catcagcttc ctgacatgtt    5880
aagagaatac attaaagaga aaatactgtt ttttaatcct aaaattttc ttccactaag     5940 ataaaccaaa tgtccttaca tatatgtaaa cccatctatt taaacgcaaa ggtgggttga    6000
tgtcagttta catagcagaa agcattcact atcctctaag atttgtttct gcaaaacttt    6060
cattgcttta gaattttaaa atttcacctt gtacaatggc cagcccctaa agcaggaaac    6120
atttataatg gattatatgg aaacatcctc ccagtacttg cccagcccctt gaatcatgtg    6180 gcttttcagt gaaggaaag attcttttttc taggaaaaat gagcctattt tatttttattt    6240 tatttttattt tttgacacaa actgtagatt ttagcagccc tggcccaaag gaatttgatt    6300
acttttgttt taaacagtac aaagggggaca ctataattac aaaaacatcc ttaactgatt    6360
tgagttgttt ttatttcttt ggatatattt tcagagtggt aaattgtgtg tgagaattac    6420
aaatgattat tcttttagtg gtttcttagc ctctcttaca gcccacgggg atagtactgt    6480
acatcaatac cttcatatga aattttttata tgcaatgaaa ataaaagcat gggttgattc    6540
tgcctattta tgactcaatc ttttacaaat aaaagattat tcattttaaa ttatagttca    6600
atcagcatgt ctcttaggat actgaacgtg gttgaaatga aaggatagtg acatcataag    6660
ttagtactga tattcataac caaataaagc caacttgagt aattttgcta cattaaaaat    6720
taccaaaatt acttagatgg cctataagat taagcatggt gttttctaag caagctttga    6780
aaggggcctt ccatacttac ttaattgaat attctgggat attgaaaatt attcagatac    6840
ttgacaatta ttttttggtta cctactccgc aaactacaaa gtttttaagga ctcaacaata    6900 agttaatgag acacagtgtt tgctttcatg gagcttacag tctggagggg acaaaggctt    6960
aaacaatact catataatta tatatgtgat cagtacaatg aaggagctca gtgggtaaa     7020 taagcaggaa cctgaacttg atctgttccg gagggccaca gaaggcttcc ttgaggcctt    7080
gagaaagtga tttgcatctg agttctgaag gattgtaaga ggtaactagg gaaaaagttg    7140
acaggaagag gaaggggatc cagacaagaa acatttgcaa agatcttgag gcataaatga    7200
gcttgagaca tctggagaaa ctgaggaaaa gtgagagagt aggcagggcc tggagccgca    7260
gagccattgc taaccatcct gtgtgagata tcccccattc tgtagcttta ttctcataac    7320
cctgctcaat tttctttata acacttctca cagatttata tacgtgtttg ttttttgttat    7380 ctgtctctcc caccagacca cagctccatg agagcaaggt ctttgcttac caatatatca    7440
ctagcactta aaactatgcc tggtacacag taggttctta atatgtgttg aatatagcca    7500
tcaaattgat attggatata attcaatctg ataagatatt ttgagatatt aaagagtttt    7560
taacttgata ccataaaaaa aaaaaaaaa a                                    7591
```

<210> SEQ ID NO 18
<211> LENGTH: 518

-continued

```
<212> TYPE: PRT
<213> ORGANISM: Homo sapiens

<400> SEQUENCE: 18

Met Pro Glu Ala Asn Tyr Leu Leu Ser Val Ser Trp Gly Tyr Ile Lys
1               5                   10                  15

Phe Lys Arg Met Leu Asn Arg Glu Leu Thr His Leu Ser Glu Met Ser
                20                  25                  30

Arg Ser Gly Asn Gln Val Ser Glu Phe Ile Ser Asn Thr Phe Leu Asp
            35                  40                  45

Lys Gln His Glu Val Glu Ile Pro Ser Pro Thr Gln Lys Glu Lys Glu
        50                  55                  60

Lys Lys Lys Arg Pro Met Ser Gln Ile Ser Gly Val Lys Lys Leu Met
65                  70                  75                  80

His Ser Ser Ser Leu Thr Asn Ser Ser Ile Pro Arg Phe Gly Val Lys
                85                  90                  95

Thr Glu Gln Glu Asp Val Leu Ala Lys Glu Leu Glu Asp Val Asn Lys
                100                 105                 110

Trp Gly Leu His Val Phe Arg Ile Ala Glu Leu Ser Gly Asn Arg Pro
            115                 120                 125

Leu Thr Val Ile Met His Thr Ile Phe Gln Glu Arg Asp Leu Leu Lys
        130                 135                 140

Thr Phe Lys Ile Pro Val Asp Thr Leu Ile Thr Tyr Leu Met Thr Leu
145                 150                 155                 160

Glu Asp His Tyr His Ala Asp Val Ala Tyr His Asn Asn Ile His Ala
                165                 170                 175

Ala Asp Val Val Gln Ser Thr His Val Leu Leu Ser Thr Pro Ala Leu
            180                 185                 190

Glu Ala Val Phe Thr Asp Leu Glu Ile Leu Ala Ala Ile Phe Ala Ser
        195                 200                 205

Ala Ile His Asp Val Asp His Pro Gly Val Ser Asn Gln Phe Leu Ile
        210                 215                 220

Asn Thr Asn Ser Glu Leu Ala Leu Met Tyr Asn Asp Ser Ser Val Leu
225                 230                 235                 240

Glu Asn His His Leu Ala Val Gly Phe Lys Leu Leu Gln Glu Glu Asn
                245                 250                 255

Cys Asp Ile Phe Gln Asn Leu Thr Lys Lys Gln Arg Gln Ser Leu Arg
            260                 265                 270

Lys Met Val Ile Asp Ile Val Leu Ala Thr Asp Met Ser Lys His Met
        275                 280                 285

Asn Leu Leu Ala Asp Leu Lys Thr Met Val Glu Thr Lys Lys Val Thr
        290                 295                 300

Ser Ser Gly Val Leu Leu Leu Asp Asn Tyr Asp Arg Ile Gln Val
305                 310                 315                 320

Leu Gln Asn Met Val His Cys Ala Asp Leu Ser Asn Pro Thr Lys Pro
                325                 330                 335

Leu Gln Leu Tyr Arg Gln Trp Thr Asp Arg Ile Met Glu Glu Phe Phe
            340                 345                 350

Arg Gln Gly Asp Arg Glu Arg Glu Arg Gly Met Glu Ile Ser Pro Met
        355                 360                 365

Cys Asp Lys His Asn Ala Ser Val Glu Lys Ser Gln Val Gly Phe Ile
        370                 375                 380

Asp Tyr Ile Val His Pro Leu Trp Glu Thr Trp Ala Asp Leu Val His
385                 390                 395                 400
```

```
Pro Asp Ala Gln Asp Ile Leu Asp Thr Leu Glu Asp Asn Arg Glu Trp
                405                 410                 415
Tyr Gln Ser Thr Ile Pro Gln Ser Pro Ser Pro Ala Pro Asp Asp Pro
            420                 425                 430
Glu Glu Gly Arg Gln Gly Gln Thr Glu Lys Phe Gln Phe Glu Leu Thr
        435                 440                 445
Leu Glu Glu Asp Gly Glu Ser Asp Thr Glu Lys Asp Ser Gly Ser Gln
    450                 455                 460
Val Glu Glu Asp Thr Ser Cys Ser Asp Ser Lys Thr Leu Cys Thr Gln
465                 470                 475                 480
Asp Ser Glu Ser Thr Glu Ile Pro Leu Asp Gln Val Glu Glu Glu
                485                 490                 495
Ala Val Gly Glu Glu Glu Ser Gln Pro Glu Ala Cys Val Ile Asp
                500                 505                 510
Asp Arg Ser Pro Asp Thr
            515

<210> SEQ ID NO 19
<211> LENGTH: 8130
<212> TYPE: DNA
<213> ORGANISM: Homo sapiens

<400> SEQUENCE: 19
agattatagc ccagcgtacg agaagcacga gtcctatagt tggcgtaccc tgaggcctgc      60
cagttcctgc cttaatgcat atgtagtcgt aattgagttc tgacacggcc ttggatgttt     120
ctgtcctaaa tagctgacat tgcatcttca agactgtcat tccagttggc ttttgagtgg     180
atacgtgcag tgagatcatt gacactggaa acactagttc ccattttaat tacttaaaac     240
accacgatga aagaaatac ctgtgatttg ctttctcgga gcaaaagtgc ctctgaggaa      300
acactacatt ccagtaatga gaggaagac cctttccgcg gaatggaacc ctatcttgtc      360
cggagacttt catgtcgcaa tattcagctt ccccctctcg ccttcagaca gttggaacaa     420
gctgacttga aaagtgaatc agagaacatt caacgaccaa ccagcctccc cctgaagatt     480
ctgccgctga ttgctatcac ttctgcagaa tccagtggtt tgatgtgga caatggcaca      540 tctgcgggac ggagtccctt ggatcccatg accagcccag atccgggct aattctccaa      600 gcaaattttg tccacagtca acgacgggag tccttcctgt atcgatccga cagcgattat     660
gacctctctc caaagtctat gtcccggaac tcctccattg ccagtgatat acacggagat     720
gacttgattg tgactccatt tgctcaggtc ttggccagtc tgcgaactgt acgaaacaac     780
tttgctgcat taactaattt gcaagatcga gcacctagca aaagatcacc catgtgcaac     840
caaccatcca tcaacaaagc caccataaca gaggaggcct accagaaact ggccagcgag     900
accctggagg agctggactg gtgtctggac cagctagaga ccctacagac caggcactcc     960
gtcagtgaga tggcctccaa caagtttaaa aggatgctta tcgggagct cacccatctc    1020 tctgaaatga gtcggtctgg aaatcaagtg tcagagttta tcaaacac attcttagat      1080 aagcaacatg aagtggaaat tccttctcca actcagaagg aaaaggagaa aagaaaaga    1140 ccaatgtctc agatcagtgg agtcaagaaa ttgatgcaca gctctagtct gactaattca    1200
agtatcccaa ggtttggagt taaaactgaa caagaagatg tccttgccaa ggaactagaa    1260
gatgtgaaca atggggtct tcatgttttc agaatagcag agttgtctgg taaccggccc    1320
ttgactgtta tcatgcacac catttttcag gaacgggatt tattaaaaac atttaaaatt   1380
```

```
ccagtagata ctttaattac atatcttatg actctcgaag accattacca tgctgatgtg    1440
gcctatcaca acaatatcca tgctgcagat gttgtccagt ctactcatgt gctattatct    1500
acacctgctt tggaggctgt gtttacagat ttggagattc ttgcagcaat ttttgccagt    1560
gcaatacatg atgtagatca tcctggtgtg tccaatcaat ttctgatcaa tacaaactct    1620
gaacttgcct tgatgtacaa tgattcctca gtcttagaga accatcattt ggctgtgggc    1680
tttaaattgc ttcaggaaga aaactgtgac attttccaga atttgaccaa aaaacaaaga    1740
caatctttaa ggaaaatggt cattgacatc gtacttgcaa cagatatgtc aaaacacatg    1800
aatctactgg ctgatttgaa gactatggtt gaaactaaga aagtgacaag ctctggagtt    1860
cttcttcttg ataattattc cgataggatt caggttcttc agaatatggt gcactgtgca    1920
gatctgagca acccaacaaa gcctctccag ctgtaccgcc agtggacgga ccggataatg    1980
gaggagttct tccgccaagg agaccgagag agggaacgtg gcatggagat aagccccatg    2040
tgtgacaagc acaatgcttc cgtggaaaaa tcacaggtgg gcttcataga ctatattgtt    2100
catcccctct gggagacatg ggcagacctc gtccaccctg acgccaggaa tatttggac     2160 actttggagg acaatcgtga atggtaccag agcacaatcc ctcagagccc ctctcctgca    2220
cctgatgacc cagaggaggg ccggcagggt caaactgaga aattccagtt tgaactaact    2280
ttagaggaag atggtgagtc agacacggaa aaggacagtg gcagtcaagt ggaagaagac    2340
actagctgca gtgactccaa gactcttttgt actcaagact cagagtctac tgaaattccc    2400
cttgatgaac aggttgaaga ggaggcagta ggggaagaag aggaaagcca gcctgaagcc    2460
tgtgtcatag atgatcgttc tcctgacacg taacagtgca aaaactttca tgccttttt     2520 tttttttaagt agaaaaattg tttccaaagt gcatgtcaca tgccacaacc acggtcacac    2580
ctcactgtca tctgccagga cgtttgttga acaaaactga ccttgactac tcagtccagc    2640
gctcaggaat atcgtaacca gttttttcac ctccatgtca tccgagcaag gtggacatct    2700
tcacgaacag cgttttttaac aagatttcag cttggtagag ctgacaaagc agataaaatc    2760
tactccaaat tattttcaag agagtgtgac tcatcaggca gcccaaaagt ttattggact    2820
tggggtttct attccttttt atttgtttgc aatattttca gaagaaaggc attgcacaga    2880
gtgaacttaa tggacgaagc aacaaatatg tcaagaacag gacatagcac gaatctgtta    2940
ccagtaggag gaggatgagc cacagaaatt gcataatttt ctaatttcaa gtcttcctga    3000
tacatgactg aatagtgtgg ttcagtgagc tgcactgacc tctacatttt gtatgatatg    3060
taaaacagat ttttttgtaga gcttactttt attattaaat gtattgaggt attatattta    3120
aaaaaaacta tgttcagaac ttcatctgcc actggttatt ttttctaag gagtaacttg      3180 caagttttca gtacaaatct gtgctacact ggataaaaat ctaatttatg aattttactt    3240
gcaccttata gttcatagca attaactgat ttgtagtgat tcattgtttg ttttatatac    3300
caatgacttc catattttaa aagagaaaaa caacttttatg ttgcaggaaa ccctttttgt    3360
aagtctttat tatttacttt gcattttgtt tcactctttc cagataagca gagttgctct    3420
tcaccagtgt ttttcttcat gtgcaaagtg actatttgtt ctataatact tttatgtgtg    3480
ttatatcaaa tgtgtcttaa gcttcatgca aactcagtca tcagttcgtg ttgtctgaag    3540
caagtgggag atatataaat acccagtagc taaaatggtc agtctttttt agatgttttc    3600
ctacttagta tctcctaata acgttttgct gtgtcactag atgttcattt cacaagtgca    3660 tgtcttttcta ataatccaca catttcatgc tctaataatc cacacatttc atgctcattt    3720
ttattgtttt tacagccagt tatagtaaga aaaaggttttt tccccttgtg ctgctttata    3780
```

```
atttagcgtg tgtctgaacc ttatccatgt ttgctagatg aggtcttgtc aaatatatca    3840
ctaccattgt caccggtgaa agaaacagg tagttaagtt agggttaaca ttcatttcaa     3900
ccacgaggtt gtatatcatg actagctttt actcttggtt tacagagaaa agttaaacag    3960
ccaactaggc agttttaag aatattaaca atatattaac aaacaccaat acaactaatc     4020
ctatttggtt ttaatgattt caccatggga ttaagaacta tatcaggaac atccctgaga    4080
aacggtttta agtgtagcaa ctactcttcc ttaatggaca gccacataac gtgtaggaag    4140
tcctttatca cttatcctcg atccataagc atatcttgca gagggaact acttctttaa     4200 acacatggag ggaaagaaga tgatgccact ggcaccagag ggttagtact gtgatgcatc    4260
ctaaaatatt tattatattg gtaaaaattc tggttaaata aaaaattaga gatcactctt    4320
ggctgatttc agcaccagga actgtattac agttttagag attaattcct agtgtttacc    4380
tgattatagc agttggcatc atgggcatt taattctgac tttatcccca cgtcagcctt     4440
aataaagtct tctttacctt ctctatgaag actttaaagc ccaataatc attttttcaca    4500 ttgatattca agaattgaga tagatagaag ccaaagtggg tatctgacaa gtggaaaatc    4560
aaacgtttaa gaagaattac aactctgaaa agcatttata tgtggaactt ctcaaggagc    4620
ctcctgggga ctggaaagta agtcatcagc caggcaaatg actcatgctg aagagagtcc    4680
ccatttcagt cccctgagat ctagctgatg cttagatcct ttgaaataaa aattatgtct    4740
ttataactct gatcttttac ataaagcaga agaggaatca actagttaat tgcaaggttt    4800
ctactctgtt tcctctgtaa agatcagatg gtaatctttc aaataagaaa aaataaaga    4860 cgtatgtttg accaagtagt ttcacaagaa tatttgggaa cttgtttctt ttaatttat    4920 ttgtccctga gtgaagtcta gaaagaaagg taaagagtct agagtttatt cctcttttcca    4980 aaacattctc attcctctcc tccctacact tagtatttcc cccacagagt gcctagaatc    5040
ttaataatga ataaaataaa aagcagcaat atgtcattaa caaatccaga cctgaaaggg    5100
taaagggttt ataactgcac taataaagag aggctctttt ttttctttcc agtttgttgg    5160 ttttttaatgg taccgtgttg taaagatacc cactaatgga caatcaaatt gcagaaaagg    5220
ctcaatatcc aagagacagg gactaatgca ctgtacaatc tgcttatcct tgcccttctc    5280
tcttgccaaa gtgtgcttca gaaatatata ctgctttaaa aagaataaa agaatatcct    5340 tttacaagtg gctttacatt tcctaaaatg ccataagaaa atgcaatatc tgggtactgt    5400
atggggaaaa aaatgtccaa gtttgtgtaa aaccagtgca tttcagcttg caagttactg    5460
aacacaataa tgctgtttta attttgtttt atatcagtta aaattcacaa taatgtagat    5520
agaacaaatt acagacaagg aaagaaaaaa cttgaatgaa atggatttta cagaaagctt    5580
tatgataatt tttgaatgca ttattttattt tttgtgccat gcatttttt tctcaccaaa    5640 tgaccttacc tgtaatacag tcttgtttgt ctgtttacaa ccatgtattt attgcaatgt    5700
acatactgta atgttaattg taaattatct gttcttatta aaacatcatc ccatgatggg    5760
atggtgttga tatatttgga aactcttggt gagagaatga atggtgtgta tacatactct    5820
gtacattttt ctttttctcct gtaatatagt cttgtcacct tagagcttgt ttatggaaga    5880
ttcaagaaaa ctataaaata cttaaagata tataaattta aaaaaacata gctgcaggtc    5940
tttggtccca gggctgtgcc ttaactttaa ccaatatttt cttctgtttt gctgcatttg    6000
aaaggtaaca gtggagctag ggctgggcat tttacatcca ggcttttaat tgattagaat    6060
tctgccaata ggtggatttt acaaaaccac agacaacctc tgaaagattc tgagacccct    6120
```

|  |  |  |  |  |  |
|---|---|---|---|---|---|
| ttgagacaga | agctcttaag | tacttcttgc | cagggagcag | cactgcatgt | gtgatggttg | 6180 |
| tttgccatct | gttgatcagg | aactacttca | gctacttgca | tttgattatt | tccttttttt | 6240 |
| ttttttttaa | ctcggaaaca | caactgggga | aatatattct | ttcccagtga | ttataaacaa | 6300 |
| tcttttctt | ttttttaagt | ccttttggct | tctagagctc | ataggaaaat | ggacttgatt | 6360 |
| tgaaattgga | gccagagttt | actcgtgttg | gttatctatt | catcagcttc | ctgacatgtt | 6420 |
| aagagaatac | attaaagaga | aaatactgtt | ttttaatcct | aaaattttc | ttccactaag | 6480 |
| ataaaccaaa | tgtccttaca | tatatgtaaa | cccatctatt | taaacgcaaa | ggtgggttga | 6540 |
| tgtcagttta | catagcagaa | agcattcact | atcctctaag | atttgtttct | gcaaaacttt | 6600 |
| cattgcttta | gaattttaaa | atttcacctt | gtacaatggc | cagcccctaa | agcaggaaac | 6660 |
| atttataatg | gattatatgg | aaacatcctc | ccagtacttg | cccagccctt | gaatcatgtg | 6720 |
| gcttttcagt | gaaaggaaag | attcttttc | taggaaaaat | gagcctattt | tatttattt | 6780 |
| tattttattt | tttgacacaa | actgtagatt | ttagcagccc | tggcccaaag | gaatttgatt | 6840 |
| actttgtttt | taaacagtac | aaaggggaca | ctataattac | aaaaacatcc | ttaactgatt | 6900 |
| tgagttgttt | ttatttcttt | ggatatattt | tcagagtggt | aaattgtgtg | tgagaattac | 6960 |
| aaaatgattat | tcttttagtg | gtttcttagc | ctctcttaca | gcccacgggg | atagtactgt | 7020 |
| acatcaatac | cttcatatga | aattttttata | tgcaatgaaa | ataaaagcat | gggttgattc | 7080 |
| tgcctattta | tgactcaatc | ttttacaaat | aaaagattat | tcattttaaa | ttatagttca | 7140 |
| atcagcatgt | ctcttaggat | actgaacgtg | gttgaaatga | aggatagtg | acatcataag | 7200 |
| ttagtactga | tattcataac | caaataaagc | caacttgagt | aattttgcta | cattaaaaat | 7260 |
| taccaaaatt | acttagatgg | cctataagat | taagcatggt | gttttctaag | caagctttga | 7320 |
| aaggggcctt | ccatacttac | ttaattgaat | attctgggat | attgaaaatt | attcagatac | 7380 |
| ttgacaatta | tttttggtta | cctactccgc | aaactacaaa | gttttaagga | ctcaacaata | 7440 |
| agttaatgag | acacagtgtt | tgctttcatg | gagcttacag | tctggagggg | acaaaggctt | 7500 |
| aaacaatact | catataatta | tatatgtgat | cagtacaatg | aaggagctca | gtggggtaaa | 7560 |
| taagcaggaa | cctgaacttg | atctgttccg | gagggccaca | gaaggcttcc | ttgaggcctt | 7620 |
| gagaaagtga | tttgcatctg | agttctgaag | gattgtaaga | ggtaactagg | gaaaagttg | 7680 |
| acaggaagag | gaaggggatc | cagacaagaa | acatttgcaa | agatcttgag | gcataaatga | 7740 |
| gcttgagaca | tctggagaaa | ctgaggaaaa | gtgagagagt | aggcagggcc | tggagccgca | 7800 |
| gagccattgc | taaccatcct | gtgtgagata | tcccccattc | tgtagcttta | ttctcataac | 7860 |
| cctgctcaat | tttctttata | acacttctca | cagatttata | tacgtgtttg | ttttttgttat | 7920 |
| ctgtctctcc | caccagacca | cagctccatg | agagcaaggt | ctttgcttac | caatatatca | 7980 |
| ctagcactta | aaactatgcc | tggtacacag | taggttctta | atatgtgttg | aatatagcca | 8040 |
| tcaaattgat | attggatata | attcaatctg | ataagatatt | ttgagatatt | aaagagtttt | 8100 |
| taacttgata | ccataaaaaa | aaaaaaaaaa | | | | 8130 |

<210> SEQ ID NO 20
<211> LENGTH: 748
<212> TYPE: PRT
<213> ORGANISM: Homo sapiens

<400> SEQUENCE: 20

Met Lys Arg Asn Thr Cys Asp Leu Leu Ser Arg Ser Lys Ser Ala Ser
1               5                   10                  15

-continued

```
Glu Glu Thr Leu His Ser Ser Asn Glu Glu Asp Pro Phe Arg Gly
             20                  25                  30
Met Glu Pro Tyr Leu Val Arg Arg Leu Ser Cys Arg Asn Ile Gln Leu
         35                  40                  45
Pro Pro Leu Ala Phe Arg Gln Leu Glu Gln Ala Asp Leu Lys Ser Glu
     50                  55                  60
Ser Glu Asn Ile Gln Arg Pro Thr Ser Leu Pro Leu Lys Ile Leu Pro
 65                  70                  75                  80
Leu Ile Ala Ile Thr Ser Ala Glu Ser Ser Gly Phe Asp Val Asp Asn
                 85                  90                  95
Gly Thr Ser Ala Gly Arg Ser Pro Leu Asp Pro Met Thr Ser Pro Gly
                100                 105                 110
Ser Gly Leu Ile Leu Gln Ala Asn Phe Val His Ser Gln Arg Arg Glu
            115                 120                 125
Ser Phe Leu Tyr Arg Ser Asp Ser Asp Tyr Asp Leu Ser Pro Lys Ser
    130                 135                 140
Met Ser Arg Asn Ser Ser Ile Ala Ser Asp Ile His Gly Asp Asp Leu
145                 150                 155                 160
Ile Val Thr Pro Phe Ala Gln Val Leu Ala Ser Leu Arg Thr Val Arg
                165                 170                 175
Asn Asn Phe Ala Ala Leu Thr Asn Leu Gln Asp Arg Ala Pro Ser Lys
            180                 185                 190
Arg Ser Pro Met Cys Asn Gln Pro Ser Ile Asn Lys Ala Thr Ile Thr
        195                 200                 205
Glu Glu Ala Tyr Gln Lys Leu Ala Ser Glu Thr Leu Glu Glu Leu Asp
    210                 215                 220
Trp Cys Leu Asp Gln Leu Glu Thr Leu Gln Thr Arg His Ser Val Ser
225                 230                 235                 240
Glu Met Ala Ser Asn Lys Phe Lys Arg Met Leu Asn Arg Glu Leu Thr
                245                 250                 255
His Leu Ser Glu Met Ser Arg Ser Gly Asn Gln Val Ser Glu Phe Ile
            260                 265                 270
Ser Asn Thr Phe Leu Asp Lys Gln His Glu Val Glu Ile Pro Ser Pro
        275                 280                 285
Thr Gln Lys Glu Lys Glu Lys Lys Arg Pro Met Ser Gln Ile Ser
    290                 295                 300
Gly Val Lys Lys Leu Met His Ser Ser Ser Leu Thr Asn Ser Ser Ile
305                 310                 315                 320
Pro Arg Phe Gly Val Lys Thr Glu Gln Glu Asp Val Leu Ala Lys Glu
                325                 330                 335
Leu Glu Asp Val Asn Lys Trp Gly Leu His Val Phe Arg Ile Ala Glu
            340                 345                 350
Leu Ser Gly Asn Arg Pro Leu Thr Val Ile Met His Thr Ile Phe Gln
        355                 360                 365
Glu Arg Asp Leu Leu Lys Thr Phe Lys Ile Pro Val Asp Thr Leu Ile
    370                 375                 380
Thr Tyr Leu Met Thr Leu Glu Asp His Tyr His Ala Asp Val Ala Tyr
385                 390                 395                 400
His Asn Asn Ile His Ala Ala Asp Val Val Gln Ser Thr His Val Leu
                405                 410                 415
Leu Ser Thr Pro Ala Leu Glu Ala Val Phe Thr Asp Leu Glu Ile Leu
            420                 425                 430
Ala Ala Ile Phe Ala Ser Ala Ile His Asp Val Asp His Pro Gly Val
```

```
                435                 440                 445
Ser Asn Gln Phe Leu Ile Asn Thr Asn Ser Glu Leu Ala Leu Met Tyr
450                 455                 460

Asn Asp Ser Ser Val Leu Glu Asn His His Leu Ala Val Gly Phe Lys
465                 470                 475                 480

Leu Leu Gln Glu Glu Asn Cys Asp Ile Phe Gln Asn Leu Thr Lys Lys
                485                 490                 495

Gln Arg Gln Ser Leu Arg Lys Met Val Ile Asp Ile Val Leu Ala Thr
                500                 505                 510

Asp Met Ser Lys His Met Asn Leu Leu Ala Asp Leu Lys Thr Met Val
                515                 520                 525

Glu Thr Lys Lys Val Thr Ser Ser Gly Val Leu Leu Leu Asp Asn Tyr
530                 535                 540

Ser Asp Arg Ile Gln Val Leu Gln Asn Met Val His Cys Ala Asp Leu
545                 550                 555                 560

Ser Asn Pro Thr Lys Pro Leu Gln Leu Tyr Arg Gln Trp Thr Asp Arg
                565                 570                 575

Ile Met Glu Glu Phe Phe Arg Gln Gly Asp Arg Glu Arg Glu Arg Gly
                580                 585                 590

Met Glu Ile Ser Pro Met Cys Asp Lys His Asn Ala Ser Val Glu Lys
                595                 600                 605

Ser Gln Val Gly Phe Ile Asp Tyr Ile Val His Pro Leu Trp Glu Thr
610                 615                 620

Trp Ala Asp Leu Val His Pro Asp Ala Gln Asp Ile Leu Asp Thr Leu
625                 630                 635                 640

Glu Asp Asn Arg Glu Trp Tyr Gln Ser Thr Ile Pro Gln Ser Pro Ser
                645                 650                 655

Pro Ala Pro Asp Asp Pro Glu Glu Gly Arg Gln Gly Thr Glu Lys
                660                 665                 670

Phe Gln Phe Glu Leu Thr Leu Glu Glu Asp Gly Glu Ser Asp Thr Glu
                675                 680                 685

Lys Asp Ser Gly Ser Gln Val Glu Glu Asp Thr Ser Cys Ser Asp Ser
                690                 695                 700

Lys Thr Leu Cys Thr Gln Asp Ser Glu Ser Thr Glu Ile Pro Leu Asp
705                 710                 715                 720

Glu Gln Val Glu Glu Ala Val Gly Glu Glu Glu Ser Gln Pro
                725                 730                 735

Glu Ala Cys Val Ile Asp Asp Arg Ser Pro Asp Thr
                740                 745
```

<210> SEQ ID NO 21
<211> LENGTH: 20
<212> TYPE: DNA
<213> ORGANISM: Artificial Sequence
<220> FEATURE:
<223> OTHER INFORMATION: PDE4D7_forward primer

<400> SEQUENCE: 21
gaacattcaa cgaccaacca                                        20

<210> SEQ ID NO 22
<211> LENGTH: 20
<212> TYPE: DNA
<213> ORGANISM: Artificial Sequence
<220> FEATURE:
<223> OTHER INFORMATION: PDE4D7_reverse primer

<400> SEQUENCE: 22
tgccattgtc cacatcaaaa                                              20

<210> SEQ ID NO 23
<211> LENGTH: 27
<212> TYPE: DNA
<213> ORGANISM: Artificial Sequence
<220> FEATURE:
<223> OTHER INFORMATION: PDE4D7 probe

<400> SEQUENCE: 23
ctgccgctga ttgctatcac ttctgca                                      27

<210> SEQ ID NO 24
<211> LENGTH: 22
<212> TYPE: DNA
<213> ORGANISM: Artificial Sequence
<220> FEATURE:
<223> OTHER INFORMATION: PDE4D7 Forward Primer 2

<400> SEQUENCE: 24
cgctgattgc tatcacttct gc                                           22

<210> SEQ ID NO 25
<211> LENGTH: 24
<212> TYPE: DNA
<213> ORGANISM: Artificial Sequence
<220> FEATURE:
<223> OTHER INFORMATION: PDE4D7 Reverse primer

<400> SEQUENCE: 25
gtcgttgact gtggacaaaa tttg                                         24

<210> SEQ ID NO 26
<211> LENGTH: 34
<212> TYPE: DNA
<213> ORGANISM: Artificial Sequence
<220> FEATURE:
<223> OTHER INFORMATION: PDE4D7 Probe 2

<400> SEQUENCE: 26
ttcccttgga tcccatgacc agcccataag ggaa                              34

<210> SEQ ID NO 27
<211> LENGTH: 8130
<212> TYPE: DNA
<213> ORGANISM: Homo sapiens

<400> SEQUENCE: 27
agattatagc ccagcgtacg agaagcacga gtcctatagt tggcgtaccc tgaggcctgc   60
cagttcctgc cttaatgcat atgtagtcgt aattgagttc tgacacggcc ttggatgttt  120
ctgtcctaaa tagctgacat tgcatcttca agactgtcat tccagttggc ttttgagtgg  180
atacgtgcag tgagatcatt gacactggaa acactagttc ccattttaat tacttaaaac  240
accacgatga aagaaatac ctgtgatttg ctttctcgga gcaaaagtgc ctctgaggaa   300
acactacatt ccagtaatga agaggaagac cctttccgcg gaatggaacc ctatcttgtc   360
cggagacttt catgtcgcaa tattcagctt ccccctctcg ccttcagaca gttggaacaa   420
gctgacttga aaagtgaatc agagaacatt caacgaccaa ccagcctccc cctgaagatt   480
ctgccgctga ttgctatcac ttctgcagaa tccagtggtt ttgatgtgga caatggcaca   540
tctgcgggac ggagtcccct ggatcccatg accagcccag atccgggct aattctccaa   600

```
gcaaattttg tccacagtca acgacgggag tccttcctgt atcgatccga cagcgattat    660
gacctctctc caaagtctat gtcccggaac tcctccattg ccagtgatat acacggagat    720
gacttgattg tgactccatt tgctcaggtc ttggccagtc tgcgaactgt acgaaacaac    780
tttgctgcat taactaattt gcaagatcga gcacctagca aaagatcacc catgtgcaac    840
caaccatcca tcaacaaagc caccataaca gaggaggcct accagaaact ggccagcgag    900
accctggagg agctggactg tgtctggac cagctagaga ccctacagac caggcactcc    960
gtcagtgaga tggcctccaa caagtttaaa aggatgctta atcgggagct cacccatctc   1020
tctgaaatga gtcggtctgg aaatcaagtg tcagagttta tatcaaacac attcttagat   1080
aagcaacatg aagtggaaat tccttctcca actcagaagg aaaggagaa aagaaaaga   1140 ccaatgtctc agatcagtgg agtcaagaaa ttgatgcaca gctctagtct gactaattca   1200
agtatcccaa ggtttggagt taaaactgaa caagaagatg tccttgccaa ggaactagaa   1260
gatgtgaaca atgggtct tcatgttttc agaatagcag agttgtctgg taaccggccc   1320
ttgactgtta tcatgcacac cattttcag gaacgggatt tattaaaaac atttaaaatt   1380
ccagtagata ctttaattac atatcttatg actctcgaag accattacca tgctgatgtg   1440
gcctatcaca acaatatcca tgctgcagat gttgtccagt ctactcatgt gctattatct   1500
acacctgctt tggaggctgt gtttacagat ttggagattc ttgcagcaat ttttgccagt   1560
gcaatacatg atgtagatca tcctggtgtg tccaatcaat ttctgatcaa tacaaactct   1620
gaacttgcct tgatgtacaa tgattcctca gtcttagaga accatcattt ggctgtgggc   1680
tttaaattgc ttcaggaaga aaactgtgac attttccaga atttgaccaa aaacaaaga   1740 caatctttaa ggaaaatggt cattgacatc gtacttgcaa cagatatgtc aaaacacatg   1800
aatctactgg ctgatttgaa gactatggtt gaaactaaga aagtgacaag ctctggagtt   1860
cttcttcttg ataattattc cgataggatt caggttcttc agaatatggt gcactgtgca   1920
gatctgagca acccaacaaa gcctctccag ctgtaccgcc agtggacgga ccggataatg   1980
gaggagttct tccgccaagg agaccgagag agggaacgtg gcatggagat aagccccatg   2040
tgtgacaagc acaatgcttc cgtggaaaaa tcacaggtgg gcttcataga ctatattgtt   2100 catccctct gggagacatg gcagaccctc gtccaccctg acgcccagga tattttggac   2160
actttggagg acaatcgtga atggtaccag agcacaatcc ctcagagccc ctctcctgca   2220
cctgatgacc cagaggaggg ccggcagggt caaactgaga aattccagtt tgaactaact   2280
ttagaggaag atggtgagtc agacacggaa aaggacagtg gcagtcaagt ggaagaagac   2340
actagctgca gtgactccaa gactctttgt actcaagact cagagtctac tgaaattccc   2400
cttgatgaac aggttgaaga ggaggcagta ggggaagaag aggaaagcca gcctgaagcc   2460
tgtgtcatag atgatcgttc tcctgacacg taacagtgca aaaactttca tgccttttt   2520 tttttaagt agaaaattg tttccaaagt gcatgtcaca tgccacaacc acggtcacac   2580
ctcactgtca tctgccagga cgtttgttga acaaaactga ccttgactac tcagtccagc   2640
gctcaggaat atcgtaacca gttttttcac ctccatgtca tccgagcaag gtggacatct   2700
tcacgaacag cgttttaac aagatttcag cttggtagag ctgacaaagc agataaaatc   2760
tactccaaat tattttcaag agagtgtgac tcatcaggca gcccaaaagt ttattggact   2820 tgggtttct attccttttt atttgtttgc aatattttca gaagaaaggc attgcacaga   2880
gtgaacttaa tggacgaagc aacaaatatg tcaagaacag gacatagcac gaatctgtta   2940
```

```
ccagtaggag gaggatgagc cacagaaatt gcataatttt ctaatttcaa gtcttcctga    3000
tacatgactg aatagtgtgg ttcagtgagc tgcactgacc tctacatttt gtatgatatg    3060
taaaacagat ttttgtaga gcttactttt attattaaat gtattgaggt attatattta     3120
aaaaaaacta tgttcagaac ttcatctgcc actggttatt tttttctaag gagtaacttg    3180
caagttttca gtacaaatct gtgctacact ggataaaaat ctaatttatg aatttactt    3240 gcaccttata gttcatagca attaactgat ttgtagtgat tcattgtttg ttttatatac    3300
caatgacttc catattttaa aagagaaaaa caactttatg ttgcaggaaa ccctttttgt    3360
aagtctttat tatttacttt gcattttgtt tcactctttc cagataagca gagttgctct    3420
tcaccagtgt ttttcttcat gtgcaaagtg actatttgtt ctataatact tttatgtgtg    3480
ttatatcaaa tgtgtcttaa gcttcatgca aactcagtca tcagttcgtg ttgtctgaag    3540
caagtgggag atatataaat acccagtagc taaaatggtc agtcttttt agatgttttc     3600 ctacttagta tctcctaata acgttttgct gtgtcactag atgttcattt cacaagtgca    3660 tgtcttttcta ataatccaca catttcatgc tctaataatc cacacatttc atgctcattt   3720
ttattgtttt tacagccagt tatagtaaga aaaaggtttt tccccttgtg ctgctttata    3780
atttagcgtg tgtctgaacc ttatccatgt ttgctagatg aggtcttgtc aaatatatca    3840
ctaccattgt caccggtgaa aagaaacagg tagttaagtt agggttaaca ttcatttcaa    3900
ccacgaggtt gtatatcatg actagctttt actcttggtt tacagagaaa agttaaacag    3960
ccaactaggc agttttaag aatattaaca atatattaac aaacaccaat acaactaatc     4020
ctatttggtt ttaatgattt caccatggga ttaagaacta tatcaggaac atccctgaga    4080 aacggttta agtgtagcaa ctactcttcc ttaatggaca gccacataac gtgtaggaag     4140
tcctttatca cttatcctcg atccataagc atatcttgca gagggaact acttcttaaa     4200 acacatggag ggaaagaaga tgatgccact ggcaccagag ggttagtact gtgatgcatc    4260
ctaaaatatt tattatattg gtaaaaattc tggttaaata aaaaattaga gatcactctt    4320 ggctgattc agcaccagga actgtattac agttttagag attaattcct agtgtttacc     4380
tgattatagc agttggcatc atggggcatt taattctgac tttatcccca cgtcagcctt    4440
aataaagtct tctttacctt ctctatgaag actttaaagc ccaaataatc attttttcaca   4500 ttgatattca agaattgaga tagatagaag ccaaagtggg tatctgacaa gtggaaaatc    4560
aaacgtttaa gaagaattac aactctgaaa agcatttata tgtggaactt ctcaaggagc    4620
ctcctgggga ctggaaagta agtcatcagc caggcaaatg actcatgctg aagagagtcc    4680
ccatttcagt cccctgagat ctagctgatg cttagatcct ttgaaataaa aattatgtct    4740
ttataactct gatcttttac ataaagcaga agaggaatca actagttaat tgcaaggttt    4800
ctactctgtt tcctctgtaa agatcagatg gtaatctttc aaataagaaa aaaataaaga    4860
cgtatgtttg accaagtagt ttcacaagaa tatttgggaa cttgtttctt ttaattttat    4920
ttgtccctga gtgaagtcta gaaagaaagg taaagagtct agagtttatt cctctttcca    4980
aaacattctc attcctctcc tccctacact tagtatttcc cccacagagt gcctagaatc    5040
ttaataatga ataaaataaa aagcagcaat atgtcattaa caaatccaga cctgaaaggg    5100
taaagggttt ataactgcac taataaagag aggctctttt tttttcttcc agtttgttgg    5160
tttttaatgg taccgtgttg taaagatacc cactaatgga caatcaaatt gcagaaaagg    5220
ctcaatatcc aagagacagg gactaatgca ctgtacaatc tgcttatcct tgcccttctc    5280
tcttgccaaa gtgtgcttca gaaatatata ctgctttaaa aagaataaaa agaatatcct    5340
```

```
tttacaagtg gctttacatt tcctaaaatg ccataagaaa atgcaatatc tgggtactgt    5400
atggggaaaa aaatgtccaa gtttgtgtaa aaccagtgca tttcagcttg caagttactg    5460
aacacaataa tgctgtttta attttgtttt atatcagtta aaattcacaa taatgtagat    5520
agaacaaatt acagacaagg aaagaaaaaa cttgaatgaa atggatttta cagaaagctt    5580
tatgataatt tttgaatgca ttatttattt tttgtgccat gcattttttt tctcaccaaa    5640
tgaccttacc tgtaatacag tcttgtttgt ctgtttacaa ccatgtattt attgcaatgt    5700
acatactgta atgttaattg taaattatct gttcttatta aaacatcatc ccatgatggg    5760
atggtgttga tatatttgga aactcttggt gagagaatga atggtgtgta tacatactct    5820
gtacattttt cttttctcct gtaatatagt cttgtcacct tagagcttgt ttatggaaga    5880
ttcaagaaaa ctataaaata cttaaagata tataaattta aaaaaacata gctgcaggtc    5940
tttggtccca gggctgtgcc ttaactttaa ccaatatttt cttctgtttt gctgcatttg    6000
aaaggtaaca gtggagctag ggctgggcat tttacatcca ggcttttaat tgattagaat    6060
tctgccaata ggtggatttt acaaaaccac agacaacctc tgaaagattc tgagacccct    6120
ttgagacaga agctcttaag tacttcttgc cagggagcag cactgcatgt gtgatggttg    6180
tttgccatct gttgatcagg aactacttca gctacttgca tttgattatt ccttttttt     6240 ttttttttaa ctcggaaaca caactgggga aatatattct ttcccagtga ttataaacaa    6300 tcttttttctt ttttttaagt ccttttggct tctagagctc ataggaaaat ggacttgatt    6360
tgaaattgga gccagagttt actcgtgttg gttatctatt catcagcttc ctgcatgtt     6420 aagagaatac attaaagaga aaatactgtt ttttaatcct aaaattttc ttccactaag     6480 ataaaccaaa tgtccttaca tatatgtaaa cccatctatt taaacgcaaa ggtgggttga    6540
tgtcagttta catagcagaa agcattcact atcctctaag atttgtttct gcaaaacttt    6600
cattgcttta gaattttaaa atttcacctt gtacaatggc cagcccctaa agcaggaaac    6660
atttataatg gattatatgg aaacatcctc ccagtacttg cccagccctt gaatcatgtg    6720
gcttttcagt gaaaggaaag attcttttttc taggaaaaat gagcctattt tatttttattt    6780 tatttttattt tttgacacaa actgtagatt ttagcagccc tggcccaaag gaatttgatt    6840
acttttgttt taaacagtac aaaggggaca ctataattac aaaaacatcc ttaactgatt    6900
tgagttgttt ttatttcttt ggatatattt tcagagtggg aaattgtgtg tgagaattac    6960
aaatgattat tcttttagtg gtttcttagc ctctcttaca gcccacgggg atagtactgt    7020
acatcaatac cttcatatga aatttttata tgcaatgaaa ataaaagcat gggttgattc    7080
tgcctattta tgactcaatc ttttacaaat aaaagattat tcatttttaaa ttatagttca    7140 atcagcatgt ctcttaggat actgaacgtg gttgaaatga aaggatagtg acatcataag    7200
ttagtactga tattcataac caaataaagc caacttgagt aattttgcta cattaaaaat    7260
taccaaaatt acttagatgg cctataagat taagcatggt gttttctaag caagctttga    7320
aagggccctt ccatacttac ttaattgaat attctgggat attgaaaatt attcagatac    7380
ttgacaatta tttttggtta cctactccgc aaactacaaa gttttaagga ctcaacaata    7440
agttaatgag acacagtgtt tgctttcatg gagcttacag tctggagggg acaaaggctt    7500
aaacaatact catataatta tatatgtgat cagtacaatg aaggagctca gtggggtaaa    7560
taagcaggaa cctgaacttg atctgttccg gagggccaca gaaggcttcc ttgaggcctt    7620
gagaaagtga tttgcatctg agttctgaag gattgtaaga ggtaactagg gaaaaagttg    7680
```

-continued

```
acaggaagag gaaggggatc cagacaagaa acatttgcaa agatcttgag gcataaatga    7740
gcttgagaca tctggagaaa ctgaggaaaa gtgagagagt aggcagggcc tggagccgca    7800
gagccattgc taaccatcct gtgtgagata tcccccattc tgtagcttta ttctcataac    7860
cctgctcaat tttctttata acacttctca cagatttata tacgtgtttg tttttgttat    7920
ctgtctctcc caccagacca cagctccatg agagcaaggt ctttgcttac caatatatca    7980
ctagcactta aaactatgcc tggtacacag taggttctta atatgtgttg aatatagcca    8040
tcaaattgat attggatata attcaatctg ataagatatt ttgagatatt aaagagtttt    8100
taacttgata ccataaaaaa aaaaaaaaaa                                    8130
```

<210> SEQ ID NO 28
<211> LENGTH: 687
<212> TYPE: PRT
<213> ORGANISM: Homo sapiens

<400> SEQUENCE: 28

```
Met Ala Phe Val Trp Asp Pro Leu Gly Ala Thr Val Pro Gly Pro Ser
1               5                   10                  15

Thr Arg Ala Lys Ser Arg Leu Arg Phe Ser Lys Ser Tyr Ser Phe Asp
            20                  25                  30

Val Asp Asn Gly Thr Ser Ala Gly Arg Ser Pro Leu Asp Pro Met Thr
        35                  40                  45

Ser Pro Gly Ser Gly Leu Ile Leu Gln Ala Asn Phe Val His Ser Gln
    50                  55                  60

Arg Arg Glu Ser Phe Leu Tyr Arg Ser Asp Ser Asp Tyr Asp Leu Ser
65                  70                  75                  80

Pro Lys Ser Met Ser Arg Asn Ser Ser Ile Ala Ser Asp Ile His Gly
                85                  90                  95

Asp Asp Leu Ile Val Thr Pro Phe Ala Gln Val Leu Ala Ser Leu Arg
            100                 105                 110

Thr Val Arg Asn Asn Phe Ala Ala Leu Thr Asn Leu Gln Asp Arg Ala
        115                 120                 125

Pro Ser Lys Arg Ser Pro Met Cys Asn Gln Pro Ser Ile Asn Lys Ala
    130                 135                 140

Thr Ile Thr Glu Glu Ala Tyr Gln Lys Leu Ala Ser Glu Thr Leu Glu
145                 150                 155                 160

Glu Leu Asp Trp Cys Leu Asp Gln Leu Glu Thr Leu Gln Thr Arg His
                165                 170                 175

Ser Val Ser Glu Met Ala Ser Asn Lys Phe Lys Arg Met Leu Asn Arg
            180                 185                 190

Glu Leu Thr His Leu Ser Glu Met Ser Arg Ser Gly Asn Gln Val Ser
        195                 200                 205

Glu Phe Ile Ser Asn Thr Phe Leu Asp Lys Gln His Glu Val Glu Ile
    210                 215                 220

Pro Ser Pro Thr Gln Lys Glu Lys Glu Lys Lys Arg Pro Met Ser
225                 230                 235                 240

Gln Ile Ser Gly Val Lys Lys Leu Met His Ser Ser Leu Thr Asn
            245                 250                 255

Ser Ser Ile Pro Arg Phe Gly Val Lys Thr Glu Gln Glu Asp Val Leu
        260                 265                 270

Ala Lys Glu Leu Glu Asp Val Asn Lys Trp Gly Leu His Val Phe Arg
    275                 280                 285

Ile Ala Glu Leu Ser Gly Asn Arg Pro Leu Thr Val Ile Met His Thr
```

```
                290                 295                 300
Ile Phe Gln Glu Arg Asp Leu Leu Lys Thr Phe Lys Ile Pro Val Asp
305                 310                 315                 320

Thr Leu Ile Thr Tyr Leu Met Thr Leu Glu Asp His Tyr His Ala Asp
                325                 330                 335

Val Ala Tyr His Asn Asn Ile His Ala Asp Val Val Gln Ser Thr
                340                 345                 350

His Val Leu Leu Ser Thr Pro Ala Leu Glu Ala Val Phe Thr Asp Leu
                355                 360                 365

Glu Ile Leu Ala Ala Ile Phe Ala Ser Ala Ile His Asp Val Asp His
370                 375                 380

Pro Gly Val Ser Asn Gln Phe Leu Ile Asn Thr Asn Ser Glu Leu Ala
385                 390                 395                 400

Leu Met Tyr Asn Asp Ser Ser Val Leu Glu Asn His His Leu Ala Val
                405                 410                 415

Gly Phe Lys Leu Leu Gln Glu Glu Asn Cys Asp Ile Phe Gln Asn Leu
                420                 425                 430

Thr Lys Lys Gln Arg Gln Ser Leu Arg Lys Met Val Ile Asp Ile Val
                435                 440                 445

Leu Ala Thr Asp Met Ser Lys His Met Asn Leu Leu Ala Asp Leu Lys
450                 455                 460

Thr Met Val Glu Thr Lys Lys Val Thr Ser Ser Gly Val Leu Leu Leu
465                 470                 475                 480

Asp Asn Tyr Ser Asp Arg Ile Gln Val Leu Gln Asn Met Val His Cys
                485                 490                 495

Ala Asp Leu Ser Asn Pro Thr Lys Pro Leu Gln Leu Tyr Arg Gln Trp
                500                 505                 510

Thr Asp Arg Ile Met Glu Glu Phe Phe Arg Gln Gly Asp Arg Glu Arg
                515                 520                 525

Glu Arg Gly Met Glu Ile Ser Pro Met Cys Asp Lys His Asn Ala Ser
530                 535                 540

Val Glu Lys Ser Gln Val Gly Phe Ile Asp Tyr Ile Val His Pro Leu
545                 550                 555                 560

Trp Glu Thr Trp Ala Asp Leu Val His Pro Asp Ala Gln Asp Ile Leu
                565                 570                 575

Asp Thr Leu Glu Asp Asn Arg Glu Trp Tyr Gln Ser Thr Ile Pro Gln
                580                 585                 590

Ser Pro Ser Pro Ala Pro Asp Asp Pro Glu Glu Gly Arg Gln Gly Gln
                595                 600                 605

Thr Glu Lys Phe Gln Phe Glu Leu Thr Leu Glu Glu Asp Gly Glu Ser
610                 615                 620

Asp Thr Glu Lys Asp Ser Gly Ser Gln Val Glu Glu Asp Thr Ser Cys
625                 630                 635                 640

Ser Asp Ser Lys Thr Leu Cys Thr Gln Asp Ser Glu Ser Thr Glu Ile
                645                 650                 655

Pro Leu Asp Glu Gln Val Glu Glu Ala Val Gly Glu Glu Glu Glu
                660                 665                 670

Ser Gln Pro Glu Ala Cys Val Ile Asp Asp Arg Ser Pro Asp Thr
                675                 680                 685

<210> SEQ ID NO 29
<211> LENGTH: 8395
<212> TYPE: DNA
<213> ORGANISM: Homo sapiens
```

<400> SEQUENCE: 29

```
ttctcactgc cctgcggtgt tttgaactgc cttcttacag acgtcataca gcccttgagg      60
aatagtttct gcctggtgag attgaatgat agttctcatt cacaaaaccc tggattctaa     120
gcagggacac acagaaatta ctttcgcagg taaatcagcc cacccagcca agtgtggag      180
agatttgttc cttggctgac ttctttgctc cacggagagg agtgttttcc tgtgcttgcc    240
ctgaaatgga acttccttga cagctctccc gtgttacagt acctcccggt cattttcttt    300
ttctctctct ctacctgcgc tcttcgagtg tcagaaacct ttaaagctgt tactatggaa    360
ttgcaaaaaa gagatcaagt gactctttca ctatgctggt ttcccttgtg acccagatga    420
agaatcaatt cagaattcag ttcctcccctt ggcattgcaa gacacagaag aaactgtcac   480
ttcctaacag cctagtactg gagtaaaattc agtatgaagg aagaaagcgc tcctgcgtgt    540
tagaaccttg cccatgagct ggaccgagga caggagatgg actccaggaa aattggatt     600
cttcaagcag cctcccttgg aaatggaata tctttaaaat cttctttgca gaaagacagt    660
tagaatgtat taatcagaat agttgaagac ttattttcct ttttattttt tttcaaaatg    720
agcattatta tgaagccaag atcccgatct acaagttccc taaggactgc agaggcagtt    780
tgttttgatg tggacaatgg cacatctgcg ggacggagtc ccttggatcc catgaccagc    840
ccaggatccg ggctaattct ccaagcaaat tttgtccaca gtcaacgacg ggagtccttc     900
ctgtatcgat ccgacagcga ttatgacctc tctccaaagt ctatgtcccg gaactcctcc    960
attgccagtg atatacacgg agatgacttg attgtgactc catttgctca ggtcttggcc   1020
agtctgcgaa ctgtacgaaa caactttgct gcattaacta atttgcaaga tcgagcacct   1080
agcaaaagat cacccatgtg caaccaacca tccatcaaca aagccaccat aacagaggag   1140
gcctaccaga aactggccag cgagaccctg gaggagctgg actggtgtct ggaccagcta   1200
gagaccctac agaccaggca ctccgtcagt gagatggcct ccaacaagtt taaaaggatg   1260
cttaatcggg agctcaccca tctctctgaa atgagtcggt ctggaaatca agtgtcagag   1320
tttatatcaa acacattctt agataagcaa catgaagtgg aaattccttc tccaactcag   1380
aaggaaaagg agaaaaagaa aagaccaatg tctcagatca gtggagtcaa gaaattgatg   1440
cacagctcta gtctgactaa ttcaagtatc ccaaggtttg gagttaaaac tgaacaagaa   1500
gatgtccttg ccaaggaact agaagatgtg aacaaatggg gtcttcatgt tttcagaata   1560
gcagagttgt ctggtaaccg gcccttgact gttatcatgc acaccatttt tcaggaacgg   1620
gatttattaa aaacatttaa aattccagta gatactttaa ttacatatct tatgactctc   1680
gaagaccatt accatgctga tgtggcctat cacaacaata tccatgctgc agatgttgtc   1740
cagtctactc atgtgctatt atctacacct gctttggagg ctgtgtttac agatttggag   1800
attcttgcag caattttttgc cagtgcaata catgatgtag atcatcctgg tgtgtccaat   1860
caatttctga tcaatacaaa ctctgaactt gccttgatgt acaatgattc ctcagtctta   1920
gagaaccatc atttggctgt gggctttaaa ttgcttcagg aagaaaactg tgacattttc   1980
cagaatttga ccaaaaaaca aagacaatct ttaaggaaaa tggtcattga catcgtactt   2040
gcaacagata tgtcaaaaca catgaatcta ctggctgatt tgaagactat ggttgaaact   2100
aagaaagtga caagctctgg agttcttctt cttgataatt attccgatag gattcaggtt   2160
cttcagaata tggtgcactg tgcagatctg agcaacccaa caaagcctct ccagctgtac   2220
cgccagtgga cggaccggat aatggaggag ttcttccgcc aaggagaccg agagagggaa   2280
```

```
cgtggcatgg agataagccc catgtgtgac aagcacaatg cttccgtgga aaaatcacag    2340
gtgggcttca tagactatat tgttcatccc ctctgggaga catgggcaga cctcgtccac    2400
cctgacgccc aggatatttt ggacactttg gaggacaatc gtgaatggta ccagagcaca    2460
atccctcaga gcccctctcc tgcacctgat gacccagagg agggccggca gggtcaaact    2520
gagaaattcc agtttgaact aactttagag gaagatggtg agtcagacac ggaaaaggac    2580
agtggcagtc aagtggaaga agacactagc tgcagtgact ccaagactct ttgtactcaa    2640
gactcagagt ctactgaaat tccccttgat gaacaggttg aagaggaggc agtaggggaa    2700
gaagaggaaa gccagcctga agcctgtgtc atagatgatc gttctcctga cacgtaacag    2760
tgcaaaaact ttcatgcctt tttttttttt aagtagaaaa attgtttcca aagtgcatgt    2820
cacatgccac aaccacggtc acacctcact gtcatctgcc aggacgtttg ttgaacaaaa    2880
ctgaccttga ctactcagtc cagcgctcag gaatatcgta accagttttt tcacctccat    2940
gtcatccgag caaggtggac atcttcacga acagcgtttt taacaagatt tcagcttggt    3000
agagctgaca aagcagataa aatctactcc aaattatttt caagagagtg tgactcatca    3060
ggcagcccaa aagtttattg gacttggggt ttctattcct ttttatttgt ttgcaatatt    3120
ttcagaagaa aggcattgca cagagtgaac ttaatgacg aagcaacaaa tatgtcaaga    3180
acaggacata gcacgaatct gttaccagta ggaggaggat gagccacaga aattgcataa    3240
ttttctaatt tcaagtcttc ctgatacatg actgaatagt gtggttcagt gagctgcact    3300
gacctctaca ttttgtatga tatgtaaaac agattttttg tagagcttac ttttattatt    3360
aaatgtattg aggtattata tttaaaaaaa actatgttca gaacttcatc tgccactggt    3420 tattttttc taaggagtaa cttgcaagtt ttcagtacaa atctgtgcta cactggataa    3480
aaatctaatt tatgaatttt acttgcacct tatagttcat agcaattaac tgatttgtag    3540
tgattcattg tttgttttat ataccaatga cttccatatt ttaaaagaga aaaacaactt    3600
tatgttgcag gaaacccttt ttgtaagtct ttattattta ctttgcattt tgtttcactc    3660
tttccagata agcagagttg ctcttcacca gtgttttttct tcatgtgcaa agtgactatt    3720
tgttctataa tactttttatg tgtgttatat caaatgtgtc ttaagcttca tgcaaactca    3780
gtcatcagtt cgtgttgtct gaagcaagtg ggagatatat aaatacccag tagctaaaat    3840
ggtcagtctt ttttagatgt tttcctactt agtatctcct aataacgttt tgctgtgtca    3900
ctagatgttc atttcacaag tgcatgtctt tctaataatc cacacatttc atgctctaat    3960
aatccacaca tttcatgctc attttttattg ttttttacagc cagttatagt aagaaaaagg    4020
tttttcccct tgtgctgctt tataatttag cgtgtgtctg aaccttatcc atgtttgcta    4080
gatgaggtct tgtcaaatat atcactacca ttgtcaccgg tgaaaagaaa caggtagtta    4140
agttagggtt aacattcatt tcaaccacga ggttgtatat catgactagc ttttactctt    4200
ggtttacaga gaaagttaa acagccaact aggcagtttt taagaatatt aacaatatat    4260
taacaaacac caatacaact aatcctattt ggttttaatg atttcaccat gggattaaga    4320
actatatcag gaacatccct gagaaacggt tttaagtgta gcaactactc ttccttaatg    4380
gacagccaca taacgtgtag gaagtccttt atcacttatc ctcgatccat aagcatatct    4440
tgcagagggg aactacttct ttaaacacat ggagggaaag aagatgatgc cactggcacc    4500
agagggttag tactgtgatg catcctaaaa tatttattat attggtaaaa attctggtta    4560
aataaaaaat tagagatcac tcttggctga tttcagcacc aggaactgta ttacagtttt    4620
agagattaat tcctagtgtt tacctgatta tagcagttgg catcatgggg catttaattc    4680
```

-continued

```
tgactttatc cccacgtcag ccttaataaa gtcttcttta ccttctctat gaagacttta    4740
aagcccaaat aatcattttt cacattgata ttcaagaatt gagatagata gaagccaaag    4800
tgggtatctg acaagtggaa aatcaaacgt ttaagaagaa ttacaactct gaaaagcatt    4860
tatatgtgga acttctcaag gagcctcctg gggactggaa agtaagtcat cagccaggca    4920
aatgactcat gctgaagaga gtccccattt cagtcccctg agatctagct gatgcttaga    4980
tcctttgaaa taaaaattat gtcttttataa ctctgatctt ttacataaag cagaagagga    5040
atcaactagt taattgcaag gtttctactc tgtttcctct gtaaagatca gatggtaatc    5100
tttcaaataa gaaaaaaata aagacgtatg tttgaccaag tagtttcaca agaatatttg    5160
ggaacttgtt tcttttaatt ttatttgtcc ctgagtgaag tctagaaaga aaggtaaaga    5220
gtctagagtt tattcctctt tccaaaacat tctcattcct ctcctcccta cacttagtat    5280
ttcccccaca gagtgcctag aatcttaata atgaataaaa taaaaagcag caatatgtca    5340
ttaacaaatc cagacctgaa agggtaaagg gtttataact gcactaataa agagaggctc    5400 ttttttttc ttccagtttg ttggtttta atggtaccgt gttgtaaaga tacccactaa    5460
tggacaatca aattgcagaa aaggctcaat atccaagaga cagggactaa tgcactgtac    5520
aatctgctta tccttgccct tctctcttgc caaagtgtgc ttcagaaata tatactgctt    5580
taaaaaagaa taaagaata tccttttaca agtggcttta catttcctaa aatgccataa    5640
gaaaatgcaa tatctgggta ctgtatgggg aaaaaaatgt ccaagtttgt gtaaaaccag    5700
tgcatttcag cttgcaagtt actgaacaca ataatgctgt tttaattttg ttttatatca    5760
gttaaaattc acaataatgt agatagaaca aattacagac aaggaaagaa aaaacttgaa    5820
tgaaatggat tttacagaaa gctttatgat aattttgaa tgcattattt attttttgtg    5880
ccatgcattt ttttctcac caaatgacct tacctgtaat acagtcttgt ttgtctgttt    5940
acaaccatgt atttattgca atgtacatac tgtaatgtta attgtaaatt atctgttctt    6000
attaaaacat catcccatga tgggatggtg ttgatatatt tggaaactct tggtgagaga    6060
atgaatggtg tgtatacata ctctgtacat ttttcttttc tcctgtaata tagtcttgtc    6120
accttagagc ttgtttatgg aagattcaag aaaactataa aatacttaaa gatatataaa    6180
tttaaaaaaa catagctgca ggtctttggt cccagggctg tgccttaact ttaaccaata    6240
ttttcttctg ttttgctgca tttgaaaggt aacagtggag ctagggctgg gcattttaca    6300
tccaggcttt taattgatta gaattctgcc aataggtgga ttttacaaaa ccacagacaa    6360
cctctgaaag attctgagac ccttttgaga cagaagctct taagtacttc ttgccaggga    6420
gcagcactgc atgtgtgatg gttgtttgcc atctgttgat caggaactac ttcagctact    6480
tgcatttgat tatttccttt ttttttttt ttaactcgga aacacaactg gggaaatata    6540
ttctttccca gtgattataa acaatctttt tcttttttt aagtcctttt ggcttctaga    6600
gctcatagga aaatggactt gatttgaaat tggagccaga gttactcgt gttggttatc    6660 tattcatcag cttcctgaca tgttaagaga atacattaaa gagaaaatac tgtttttaa    6720 tcctaaaatt tttcttccac taagataaac caaatgtcct tacatatatg taaacccatc    6780
tatttaaacg caaaggtggg ttgatgtcag tttacatagc agaaagcatt cactatcctc    6840
taagatttgt ttctgcaaaa ctttcattgc tttagaattt taaaatttca ccttgtacaa    6900
tggccagccc ctaaagcagg aaacattat aatggattat atggaaacat cctcccagta    6960
cttgcccagc ccttgaatca tgtggctttt cagtgaaagg aaagattctt tttctaggaa    7020
```

```
aaatgagcct attttatttt attttatttt attttttgac acaaactgta gattttagca    7080
gccctggccc aaaggaattt gattactttt gttttaaaca gtacaagggg gacactataa    7140
ttacaaaaac atccttaact gatttgagtt gttttttattt ctttggatat attttcagag    7200
tggtaaattg tgtgtgagaa ttacaaatga ttattctttt agtggtttct tagcctctct    7260
tacagcccac ggggatagta ctgtacatca ataccttcat atgaaatttt tatatgcaat    7320
gaaaataaaa gcatggggtg attctgccta tttatgactc aatcttttac aaataaaaga    7380
ttattcattt taaattatag ttcaatcagc atgtctctta ggatactgaa cgtggttgaa    7440
atgaaaggat agtgacatca taagttagta ctgatattca taaccaaata aagccaactt    7500
gagtaatttt gctacattaa aaattaccaa aattacttag atggcctata agattaagca    7560
tggtgttttc taagcaagct ttgaaagggg ccttccatac ttacttaatt gaatattctg    7620
ggatattgaa aattattcag atacttgaca attattttg gttacctact ccgcaaacta    7680
caaagtttta aggactcaac aataagttaa tgagacacag tgtttgcttt catggagctt    7740
acagtctgga ggggacaaag gcttaaacaa tactcatata attatatatg tgatcagtac    7800
aatgaaggag ctcagtgggg taaataagca ggaacctgaa cttgatctgt tccggagggc    7860
cacagaaggc ttccttgagg ccttgagaaa gtgatttgca tctgagttct gaaggattgt    7920
aagaggtaac tagggaaaaa gttgacagga agaggaaggg gatccagaca agaaacattt    7980
gcaaagatct tgaggcataa atgagcttga acatctggaa gaaactgagg aaaagtgaga    8040
gagtaggcag ggcctggagc cgcagagcca ttgctaacca tcctgtgtga gatatccccc    8100
attctgtagc tttattctca taaccctgct caatttctt tataacactt ctcacagatt    8160
tatatacgtg tttgtttttg ttatctgtct ctcccaccag accacagctc catgagagca    8220
aggtctttgc ttaccaatat atcactagca cttaaaacta tgcctggtac acagtaggtt    8280
cttaatatgt gttgaatata gccatcaaat tgatattgga tataattcaa tctgataaga    8340
tattttgaga tattaaagag ttttaactt gataccataa aaaaaaaaaa aaaaa         8395
```

<210> SEQ ID NO 30
<211> LENGTH: 679
<212> TYPE: PRT
<213> ORGANISM: Homo sapiens

<400> SEQUENCE: 30

```
Met Ser Ile Ile Met Lys Pro Arg Ser Arg Ser Thr Ser Ser Leu Arg
1               5                   10                  15

Thr Ala Glu Ala Val Cys Phe Asp Val Asp Asn Gly Thr Ser Ala Gly
            20                  25                  30

Arg Ser Pro Leu Asp Pro Met Thr Ser Pro Gly Ser Gly Leu Ile Leu
        35                  40                  45

Gln Ala Asn Phe Val His Ser Gln Arg Arg Glu Ser Phe Leu Tyr Arg
    50                  55                  60

Ser Asp Ser Asp Tyr Asp Leu Ser Pro Lys Ser Met Ser Arg Asn Ser
65                  70                  75                  80

Ser Ile Ala Ser Asp Ile His Gly Asp Asp Leu Ile Val Thr Pro Phe
                85                  90                  95

Ala Gln Val Leu Ala Ser Leu Arg Thr Val Arg Asn Asn Phe Ala Ala
            100                 105                 110

Leu Thr Asn Leu Gln Asp Arg Ala Pro Ser Lys Arg Ser Pro Met Cys
        115                 120                 125

Asn Gln Pro Ser Ile Asn Lys Ala Thr Ile Thr Glu Glu Ala Tyr Gln
```

```
             130                 135                 140
Lys Leu Ala Ser Glu Thr Leu Glu Glu Leu Asp Trp Cys Leu Asp Gln
145                 150                 155                 160

Leu Glu Thr Leu Gln Thr Arg His Ser Val Ser Glu Met Ala Ser Asn
                165                 170                 175

Lys Phe Lys Arg Met Leu Asn Arg Glu Leu Thr His Leu Ser Glu Met
            180                 185                 190

Ser Arg Ser Gly Asn Gln Val Ser Glu Phe Ile Ser Asn Thr Phe Leu
        195                 200                 205

Asp Lys Gln His Glu Val Glu Ile Pro Ser Pro Thr Gln Lys Glu Lys
    210                 215                 220

Glu Lys Lys Lys Arg Pro Met Ser Gln Ile Ser Gly Val Lys Lys Leu
225                 230                 235                 240

Met His Ser Ser Ser Leu Thr Asn Ser Ser Ile Pro Arg Phe Gly Val
                245                 250                 255

Lys Thr Glu Gln Glu Asp Val Leu Ala Lys Glu Leu Glu Asp Val Asn
                260                 265                 270

Lys Trp Gly Leu His Val Phe Arg Ile Ala Glu Leu Ser Gly Asn Arg
            275                 280                 285

Pro Leu Thr Val Ile Met His Thr Ile Phe Gln Glu Arg Asp Leu Leu
        290                 295                 300

Lys Thr Phe Lys Ile Pro Val Asp Thr Leu Ile Thr Tyr Leu Met Thr
305                 310                 315                 320

Leu Glu Asp His Tyr His Ala Asp Val Ala Tyr His Asn Asn Ile His
                325                 330                 335

Ala Ala Asp Val Val Gln Ser Thr His Val Leu Leu Ser Thr Pro Ala
            340                 345                 350

Leu Glu Ala Val Phe Thr Asp Leu Glu Ile Leu Ala Ala Ile Phe Ala
        355                 360                 365

Ser Ala Ile His Asp Val Asp His Pro Gly Val Ser Asn Gln Phe Leu
    370                 375                 380

Ile Asn Thr Asn Ser Glu Leu Ala Leu Met Tyr Asn Asp Ser Ser Val
385                 390                 395                 400

Leu Glu Asn His His Leu Ala Val Gly Phe Lys Leu Leu Gln Glu Glu
                405                 410                 415

Asn Cys Asp Ile Phe Gln Asn Leu Thr Lys Lys Gln Arg Gln Ser Leu
            420                 425                 430

Arg Lys Met Val Ile Asp Ile Val Leu Ala Thr Asp Met Ser Lys His
        435                 440                 445

Met Asn Leu Leu Ala Asp Leu Lys Thr Met Val Glu Thr Lys Lys Val
    450                 455                 460

Thr Ser Ser Gly Val Leu Leu Leu Asp Asn Tyr Ser Asp Arg Ile Gln
465                 470                 475                 480

Val Leu Gln Asn Met Val His Cys Ala Asp Leu Ser Asn Pro Thr Lys
                485                 490                 495

Pro Leu Gln Leu Tyr Arg Gln Trp Thr Asp Arg Ile Met Glu Glu Phe
            500                 505                 510

Phe Arg Gln Gly Asp Arg Glu Arg Glu Arg Gly Met Glu Ile Ser Pro
        515                 520                 525

Met Cys Asp Lys His Asn Ala Ser Val Glu Lys Ser Gln Val Gly Phe
    530                 535                 540

Ile Asp Tyr Ile Val His Pro Leu Trp Glu Thr Trp Ala Asp Leu Val
545                 550                 555                 560
```

```
His Pro Asp Ala Gln Asp Ile Leu Asp Thr Leu Glu Asp Asn Arg Glu
                565                 570                 575

Trp Tyr Gln Ser Thr Ile Pro Gln Ser Pro Ser Ala Pro Asp Asp
            580                 585                 590

Pro Glu Glu Gly Arg Gln Gly Gln Thr Glu Lys Phe Gln Phe Glu Leu
        595                 600                 605

Thr Leu Glu Glu Asp Gly Glu Ser Asp Thr Glu Lys Asp Ser Gly Ser
        610                 615                 620

Gln Val Glu Glu Asp Thr Ser Cys Ser Asp Ser Lys Thr Leu Cys Thr
625                 630                 635                 640

Gln Asp Ser Glu Ser Thr Glu Ile Pro Leu Asp Glu Gln Val Glu Glu
                645                 650                 655

Glu Ala Val Gly Glu Glu Glu Ser Gln Pro Glu Ala Cys Val Ile
            660                 665                 670

Asp Asp Arg Ser Pro Asp Thr
        675

<210> SEQ ID NO 31
<211> LENGTH: 26
<212> TYPE: DNA
<213> ORGANISM: Artificial Sequence
<220> FEATURE:
<223> OTHER INFORMATION: PDE4D9_forward primer

<400> SEQUENCE: 31
atgagcatta ttatgaagcc aagatc                                    26

<210> SEQ ID NO 32
<211> LENGTH: 22
<212> TYPE: DNA
<213> ORGANISM: Artificial Sequence
<220> FEATURE:
<223> OTHER INFORMATION: PDE4D9_reverse primer

<400> SEQUENCE: 32
gtgccattgt ccacatcaaa ac                                        22

<210> SEQ ID NO 33
<211> LENGTH: 27
<212> TYPE: DNA
<213> ORGANISM: Artificial Sequence
<220> FEATURE:
<223> OTHER INFORMATION: PDE4D9 probe

<400> SEQUENCE: 33
ctacaagttc cctaaggact gcagagg                                   27

<210> SEQ ID NO 34
<211> LENGTH: 1435
<212> TYPE: DNA
<213> ORGANISM: Homo sapiens

<400> SEQUENCE: 34
ggcggggcct gcttctcctc agcttcaggc ggctgcgacg agccctcagg cgaacctctc    60
ggctttcccg cgcggcgccg cctcttgctg cgcctccgcc tcctcctctg ctccgccacc   120
ggcttcctcc tcctgagcag tcagcccgcg cgccggccgg ctccgttatg cgacccgca   180 gccctggcgt cgtgattagt gatgatgaac caggttatga ccttgattta ttttgcatac   240
ctaatcatta tgctgaggat ttggaaaggg tgtttattcc tcatggacta attatggaca   300
```

-continued

```
ggactgaacg tcttgctcga gatgtgatga aggagatggg aggccatcac attgtagccc    360
tctgtgtgct caaggggggc tataaattct ttgctgacct gctggattac atcaaagcac    420
tgaatagaaa tagtgataga tccattccta tgactgtaga ttttatcaga ctgaagagct    480
attgtaatga ccagtcaaca ggggacataa aagtaattgg tggagatgat ctctcaactt    540
taactggaaa gaatgtcttg attgtggaag atataattga cactggcaaa acaatgcaga    600
ctttgctttc cttggtcagg cagtataatc caaagatggt caaggtcgca agcttgctgg    660
tgaaaaggac cccacgaagt gttggatata agccagactt tgttggattt gaaattccag    720
acaagtttgt tgtaggatat gcccttgact ataatgaata cttcagggat ttgaatcatg    780
tttgtgtcat tagtgaaact ggaaaagcaa aatacaaagc ctaagatgag agttcaagtt    840
gagtttggaa acatctggag tcctattgac atcgccagta aaattatcaa tgttctagtt    900
ctgtggccat ctgcttagta gagcttttg catgtatctt ctaagaattt tatctgtttt     960
gtactttaga aatgtcagtt gctgcattcc taaactgttt atttgcacta tgagcctata   1020
gactatcagt tcccttggg cggattgttg tttaacttgt aaatgaaaaa attctcttaa    1080
accacagcac tattgagtga acattgaac tcatatctgt aagaaataaa gagaagatat    1140
attagttttt taattggtat tttaatttt atatatgcag gaaagaatag aagtgattga    1200
atattgttaa ttataccacc gtgtgttaga aaagtaagaa gcagtcaatt ttcacatcaa   1260
agacagcatc taagaagttt tgttctgtcc tggaattatt ttagtagtgt ttcagtaatg   1320
ttgactgtat tttccaactt gttcaaatta ttaccagtga atctttgtca gcagttccct   1380
tttaaatgca aatcaataaa ttcccaaaaa tttaaaaaaa aaaaaaaaaa aaaaa         1435
```

<210> SEQ ID NO 35
<211> LENGTH: 218
<212> TYPE: PRT
<213> ORGANISM: Homo sapiens

<400> SEQUENCE: 35

Met Ala Thr Arg Ser Pro Gly Val Val Ile Ser Asp Asp Glu Pro Gly
1               5                   10                  15

Tyr Asp Leu Asp Leu Phe Cys Ile Pro Asn His Tyr Ala Glu Asp Leu
            20                  25                  30

Glu Arg Val Phe Ile Pro His Gly Leu Ile Met Asp Arg Thr Glu Arg
        35                  40                  45

Leu Ala Arg Asp Val Met Lys Glu Met Gly Gly His His Ile Val Ala
    50                  55                  60

Leu Cys Val Leu Lys Gly Gly Tyr Lys Phe Phe Ala Asp Leu Leu Asp
65                  70                  75                  80

Tyr Ile Lys Ala Leu Asn Arg Asn Ser Asp Arg Ser Ile Pro Met Thr
                85                  90                  95

Val Asp Phe Ile Arg Leu Lys Ser Tyr Cys Asn Asp Gln Ser Thr Gly
            100                 105                 110

Asp Ile Lys Val Ile Gly Gly Asp Asp Leu Ser Thr Leu Thr Gly Lys
        115                 120                 125

Asn Val Leu Ile Val Glu Asp Ile Ile Asp Thr Gly Lys Thr Met Gln
    130                 135                 140

Thr Leu Leu Ser Leu Val Arg Gln Tyr Asn Pro Lys Met Val Lys Val
145                 150                 155                 160

Ala Ser Leu Leu Val Lys Arg Thr Pro Arg Ser Val Gly Tyr Lys Pro
                165                 170                 175

Asp Phe Val Gly Phe Glu Ile Pro Asp Lys Phe Val Gly Tyr Ala
            180                 185                 190

Leu Asp Tyr Asn Glu Tyr Phe Arg Asp Leu Asn His Val Cys Val Ile
        195                 200                 205

Ser Glu Thr Gly Lys Ala Lys Tyr Lys Ala
    210                 215

<210> SEQ ID NO 36
<211> LENGTH: 24
<212> TYPE: DNA
<213> ORGANISM: Artificial Sequence
<220> FEATURE:
<223> OTHER INFORMATION: HPRT1_forward primer

<400> SEQUENCE: 36
gaggatttgg aaagggtgtt tatt                                              24

<210> SEQ ID NO 37
<211> LENGTH: 21
<212> TYPE: DNA
<213> ORGANISM: Artificial Sequence
<220> FEATURE:
<223> OTHER INFORMATION: HPRT1_reverse primer

<400> SEQUENCE: 37
acagagggct acaatgtgat g                                                 21

<210> SEQ ID NO 38
<211> LENGTH: 26
<212> TYPE: DNA
<213> ORGANISM: Artificial Sequence
<220> FEATURE:
<223> OTHER INFORMATION: HPRT1 probe

<400> SEQUENCE: 38
acgtcttgct cgagatgtga tgaagg                                            26

<210> SEQ ID NO 39
<211> LENGTH: 1771
<212> TYPE: DNA
<213> ORGANISM: Homo sapiens

<400> SEQUENCE: 39
ggcggccagg ccgggcgcgg agtgggcgcg cggggccgga ggaggggcca gcgaccgcgg        60
caccgcctgt gcccgcccgc ccctccgcag ccgctactta agaggctcca gcgccggccc      120
cgccctagtg cgttacttac ctcgactctt agcttgtcgg ggacggtaac cgggacccgg      180
tgtctgctcc tgtcgccttc gcctcctaat ccctagccac tatgcgtgag tgcatctcca      240
tccacgttgg ccaggctggt gtccagattg gcaatgcctg ctgggagctc tactgcctgg      300
aacacggcat ccagcccgat ggccagatgc aagtgacaa gaccattggg ggaggagatg       360
actccttcaa caccttcttc agtgagacgg gcgctggcaa gcacgtgccc cgggctgtgt      420 tgtagactt ggaacccaca gtcattgatg aagttcgcac tggcacctac cgccagctct       480
tccaccctga gcagctcatc acaggcaagg aagatgctgc caataactat gcccgagggc      540
actacaccat tggcaaggag atcattgacc ttgtgttgga ccgaattcgc aagctggctg      600
accagtgcac cggtcttcag ggcttcttgg ttttccacag cttttggtggg ggaactggtt     660 ctgggttcac ctccctgctc atggaacgtc tctcagttga ttatggcaag aagtccaagc      720
tggagttctc catttaccca gcaccccagg tttccacagc tgtagttgag ccctacaact      780

```
ccatcctcac cacccacacc accctggagc actctgattg tgccttcatg gtagacaatg    840
aggccatcta tgacatctgt cgtagaaacc tcgatatcga gcgcccaacc tacactaacc    900
ttaaccgcct tattagccag attgtgtcct ccatcactgc ttccctgaga tttgatggag    960
ccctgaatgt tgacctgaca gaattccaga ccaacctggt gccctacccc cgcatcccact  1020
tccctctggc cacatatgcc cctgtcatct ctgctgagaa agcctaccat gaacagcttt   1080
ctgtagcaga gatcaccaat gcttgctttg agccagccaa ccagatggtg aaatgtgacc   1140
ctcgccatgg taaatacatg gcttgctgcc tgttgtaccg tggtgacgtg gttcccaaag   1200
atgtcaatgc tgccattgcc accatcaaaa ccaagcgcag catccagttt gtggattggt   1260
gccccactgg cttcaaggtt ggcatcaact accagcctcc cactgtggtg cctggtggag   1320
acctggccaa ggtacagaga gctgtgtgca tgctgagcaa caccacagcc attgctgagg   1380
cctgggctcg cctggaccac aagtttgacc tgatgtatgc caagcgtgcc tttgttcact   1440
ggtacgtggg tgaggggatg gaggaaggcg agttttcaga ggcccgtgaa gatatggctg   1500
cccttgagaa ggattatgag gaggttggtg tggattctgt tgaaggagag ggtgaggaag   1560
aaggagagga atactaatta tccattcctt ttggccctgc agcatgtcat gctcccagaa   1620
tttcagcttc agcttaactg acagacgtta aagctttctg gttagattgt tttcacttgg   1680
tgatcatgtc ttttccatgt gtacctgtaa tattttttcca tcatatctca aagtaaagtc   1740
attaacatca aaaaaaaaaa aaaaaaaaaa a                                   1771
```

<210> SEQ ID NO 40
<211> LENGTH: 451
<212> TYPE: PRT
<213> ORGANISM: Homo sapiens

<400> SEQUENCE: 40

```
Met Arg Glu Cys Ile Ser Ile His Val Gly Gln Ala Gly Val Gln Ile
1               5                   10                  15

Gly Asn Ala Cys Trp Glu Leu Tyr Cys Leu Glu His Gly Ile Gln Pro
            20                  25                  30

Asp Gly Gln Met Pro Ser Asp Lys Thr Ile Gly Gly Gly Asp Asp Ser
        35                  40                  45

Phe Asn Thr Phe Phe Ser Glu Thr Gly Ala Gly Lys His Val Pro Arg
    50                  55                  60

Ala Val Phe Val Asp Leu Glu Pro Thr Val Ile Asp Glu Val Arg Thr
65                  70                  75                  80

Gly Thr Tyr Arg Gln Leu Phe His Pro Glu Gln Leu Ile Thr Gly Lys
                85                  90                  95

Glu Asp Ala Ala Asn Asn Tyr Ala Arg Gly His Tyr Thr Ile Gly Lys
            100                 105                 110

Glu Ile Ile Asp Leu Val Leu Asp Arg Ile Arg Lys Leu Ala Asp Gln
        115                 120                 125

Cys Thr Gly Leu Gln Gly Phe Leu Val Phe His Ser Phe Gly Gly Gly
    130                 135                 140

Thr Gly Ser Gly Phe Thr Ser Leu Leu Met Glu Arg Leu Ser Val Asp
145                 150                 155                 160

Tyr Gly Lys Lys Ser Lys Leu Glu Phe Ser Ile Tyr Pro Ala Pro Gln
                165                 170                 175

Val Ser Thr Ala Val Val Glu Pro Tyr Asn Ser Ile Leu Thr Thr His
            180                 185                 190

Thr Thr Leu Glu His Ser Asp Cys Ala Phe Met Val Asp Asn Glu Ala
```

```
          195                 200                 205
Ile Tyr Asp Ile Cys Arg Arg Asn Leu Asp Ile Glu Arg Pro Thr Tyr
    210                 215                 220

Thr Asn Leu Asn Arg Leu Ile Ser Gln Ile Val Ser Ser Ile Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Pro Leu Ala Thr Tyr
            260                 265                 270

Ala Pro Val Ile Ser Ala Glu Lys Ala Tyr His Glu Gln Leu Ser Val
        275                 280                 285

Ala Glu Ile Thr Asn Ala Cys Phe Glu Pro Ala Asn Gln Met Val Lys
    290                 295                 300

Cys Asp Pro Arg His Gly Lys Tyr Met Ala Cys Cys Leu Leu Tyr Arg
305                 310                 315                 320

Gly Asp Val Val Pro Lys Asp Val Asn Ala Ala Ile Ala Thr Ile Lys
                325                 330                 335

Thr Lys Arg Ser Ile Gln Phe Val Asp Trp Cys Pro Thr Gly Phe Lys
            340                 345                 350

Val Gly Ile Asn Tyr Gln Pro Pro Thr Val Val Pro Gly Gly Asp Leu
        355                 360                 365

Ala Lys Val Gln Arg Ala Val Cys Met Leu Ser Asn Thr Thr Ala Ile
370                 375                 380

Ala Glu Ala Trp Ala Arg Leu Asp His Lys Phe Asp Leu Met Tyr Ala
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Met Ala Ala Leu Glu Lys Asp Tyr
            420                 425                 430

Glu Glu Val Gly Val Asp Ser Val Glu Gly Glu Gly Glu Glu Gly
        435                 440                 445

Glu Glu Tyr
    450

<210> SEQ ID NO 41
<211> LENGTH: 22
<212> TYPE: DNA
<213> ORGANISM: Artificial Sequence
<220> FEATURE:
<223> OTHER INFORMATION: TUBA1B_forward primer

<400> SEQUENCE: 41
tgactccttc aacaccttct tc                                           22

<210> SEQ ID NO 42
<211> LENGTH: 18
<212> TYPE: DNA
<213> ORGANISM: Artificial Sequence
<220> FEATURE:
<223> OTHER INFORMATION: TUBA1B_reverse primer

<400> SEQUENCE: 42
tgccagtgcg aacttcat                                                18

<210> SEQ ID NO 43
<211> LENGTH: 24
<212> TYPE: DNA
<213> ORGANISM: Artificial Sequence
```

<220> FEATURE:
<223> OTHER INFORMATION: TUBA1B probe

<400> SEQUENCE: 43
ccgggctgtg tttgtagact tgga     24

<210> SEQ ID NO 44
<211> LENGTH: 5416
<212> TYPE: DNA
<213> ORGANISM: Homo sapiens

<400> SEQUENCE: 44

| | | | | | |
|---|---|---|---|---|---|
| agtgggccgc | catgttgtcg | gagtgaaagg | taaggggag | cgagagcgcc | agagagagaa | 60 |
| gatcgggggg | ctgaaatcca | tcttcatcct | accgctccgc | ccgtgttggt | ggaatgagcg | 120 |
| ttgcatgtgt | cttgaagaga | aaagcagtgc | tttggcagga | ctctttcagc | ccccacctga | 180 |
| aacatcaccc | tcaagaacca | gctaatccca | acatgcctgt | tgttttgaca | tctggaacag | 240 |
| ggtcgcaagc | gcagccacaa | ccagctgcaa | atcaggctct | tgcagctggg | actcactcca | 300 |
| gccctgtccc | aggatctata | ggagttgcag | gccgttccca | ggacgacgct | atggtggact | 360 |
| acttctttca | gaggcagcat | ggtgagcagc | ttggggagg | aggaagtgga | ggaggcggct | 420 |
| ataataatag | caaacatcga | tggcctactg | gggataacat | tcatgcagaa | catcaggtgc | 480 |
| gttccatgga | tgaactgaat | catgattttc | aagcacttgc | tctggaggga | agagcgatgg | 540 |
| gagagcagct | cttgccaggt | aaaaagtttt | gggaaacaga | tgaatccagc | aaagatggac | 600 |
| caaaaggaat | attcctgggt | gatcaatggc | gagacagtgc | ctggggaaca | tcagatcatt | 660 |
| cagtttccca | gccaatcatg | gtgcagagaa | gacctggtca | gagtttccat | gtgaacagtg | 720 |
| aggtcaattc | tgtactgtcc | ccacgatcgg | agagtggggg | actaggcgtt | agcatggtgg | 780 |
| agtatgtgtt | gagctcatcc | ccgggcgatt | cctgtctaag | aaaaggagga | tttggcccaa | 840 |
| gggatgcaga | cagtgatgaa | aacgacaaag | gtgaaaagaa | gaacaagggt | acgtttgatg | 900 |
| gagataagct | aggagatttg | aaggaggagg | gtgatgtgat | ggacaagacc | aatggtttac | 960 |
| cagtgcagaa | tgggattgat | gcagacgtca | aagattttag | ccgtaccccct | ggtaattgcc | 1020 |
| agaactctgc | taatgaagtg | gatcttctgg | gtccaaacca | gaatggttct | gagggcttag | 1080 |
| cccagctgac | cagcaccaat | ggtgccaagc | ctgtggagga | tttctccaac | atggagtccc | 1140 |
| agagtgtccc | cttggacccc | atggaacatg | tgggcatgga | gcctcttcag | tttgattatt | 1200 |
| caggcacgca | ggtacctgtg | gactcagcag | cagcaactgt | gggactttttt | gactacaatt | 1260 |
| ctcaacaaca | gctgttccaa | agacctaatg | cgcttgctgt | ccagcagttg | acagctgctc | 1320 |
| agcagcagca | gtatgcactg | gcagctgctc | atcagccgca | catcggttta | gctcccgctg | 1380 |
| cgtttgtccc | caatccatac | atcatcagcg | ctgctccccc | agggacggac | ccctacacag | 1440 |
| ctggattggc | tgcagcagcg | acactaggcc | cagctgtggt | ccctcaccag | tattatggag | 1500 |
| ttactccctg | gggagtctac | cctgccagtc | ttttccagca | gcaagctgcc | gctgccgctg | 1560 |
| cagcaactaa | ttcagctaat | caacagacca | ccccacaggc | tcagcaagga | cagcagcagg | 1620 |
| ttctccgtgg | aggagccagc | caacgtcctt | tgaccccaaa | ccagaaccag | cagggacagc | 1680 |
| aaacggatcc | ccttgtggca | gctgcagcag | tgaattctgc | ccttgcattt | ggacaaggtc | 1740 |
| tggcagcagg | catgccaggt | tatccggtgt | tggctcctgc | tgcttactat | gaccaaactg | 1800 |
| gtgcccttgt | agtgaatgca | ggcgcgagaa | atggtcttgg | agctcctgtt | cgacttgtag | 1860 |
| ctcctgcccc | agtcatcatt | agttcctcag | ctgcacaagc | agctgttgca | gcagccgcag | 1920 |

```
cttcagcaaa tggagcagct ggtggtcttg ctggaacaac aaatggacca tttcgccctt      1980
taggaacaca gcagcctcag ccccagcccc agcagcagcc caataacaac ctggcatcca      2040
gttctttcta cggcaacaac tctctgaaca gcaattcaca gagcagctcc ctcttctccc      2100
agggctctgc ccagcctgcc aacacatcct tgggattcgg aagtagcagt tctctcggcg      2160
ccaccctggg atccgccctt ggagggtttg aacagcagt tgcaaactcc aacactggca       2220
gtggctcccg ccgtgactcc ctgactggca gcagtgacct ttataagagg acatcgagca      2280
gcttgacccc cattggacac agttttata cggccttag cttttcctcc tctcctggac         2340
ccgtgggcat gcctctccct agtcagggac caggacattc acagacacca cctccttccc      2400
tctcttcaca tggatcctct tcaagcttaa acctgggagg actcacgaat ggcagtggaa      2460
gatacatctc tgctgctcca ggcgctgaag ccaagtaccg cagtgcaagc agcgcctcca      2520
gcctcttcag cccgagcagc actctttct cttcctctcg tttgcgatat ggaatgtctg        2580
atgtcatgcc ttctggcagg agcaggcttt tggaagattt tcgaaacaac cggtaccccca     2640 atttacaact gcgggagatt gctggacata taatggaatt ttcccaagac cagcatgggt      2700
ccagattcat tcagctgaaa ctggagcgtg ccacaccagc tgagcgccag cttgtcttca      2760
atgaaatcct ccaggctgcc taccaactca tggtggatgt gtttggtaat tacgtcattc      2820
agaagttctt tgaatttggc agtcttgaac agaagctggc tttggcagaa cggattcgag      2880
gccacgtcct gtcattggca ctacagatgt atggctgccg tgttatccag aaagctcttg      2940
agtttattcc ttcagaccag caggtaatta atgagatggt tcgggaacta gatggccatg      3000
tcttgaagtg tgtgaaagat cagaatggca atcacgtggt tcagaaatgc attgaatgtg      3060
tacagcccca gtctttgcaa tttatcatcg atgcgtttaa gggacaggta tttgccttat      3120
ccacacatcc ttatgctgc cgagtgattc agagaatcct ggagcactgt ctccctgacc        3180
agacactccc tattttagag gagcttcacc agcacacaga gcagcttgta caggatcaat      3240
atggaaatta tgtaatccaa catgtactgg agcacggtcg tcctgaggat aaaagcaaaa      3300
ttgtagcaga aatccgaggc aatgtacttg tattgagtca gcacaaattt gcaagcaatg      3360
ttgtggagaa gtgtgttact cacgcctcac gtacggagcg cgctgtgctc atcgatgagg      3420
tgtgcaccat gaacgacggt ccccacagtg ccttatacac catgatgaag gaccagtatg      3480
ccaactacgt ggtccagaag atgattacg tggcggagcc aggccagcgg aagatcgtca       3540
tgcataagat ccggccccac atcgcaactc ttcgtaagta cacctatggc aagcacattc      3600
tggccaagct ggagaagtac tacatgaaga acggtgttga cttagggccc atctgtggcc      3660
cccctaatgg tatcatctga ggcagtgtca cccgctgttc cctcattccc gctgacctca      3720
ctggcccact ggcaaatcca accagcaacc agaaatgttc tagtgtagag tctgagacgg      3780
gcaagtggtt gctccaggat tactccctcc tccaaaaaag gaatcaaatc cacgagtgga      3840
aaagcctttg taaatttaat tttattacac ataacatgta ctatttttt taattgacta       3900 attgccctgc tgttttactg gtgtatagga tacttgtaca taggtaacca atgtacatgg      3960
gaggccacat attttgttca ctgttgtatc tatatttcac atgtggaaac tttcagggtg      4020
gttggtttaa caaaaaaaaa aagctttaaa aaaaaagaa aaaaggaaa aggttttag         4080 ctcatttgcc tggccggcaa gttttgcaaa tagctcttcc ccacctcctc attttagtaa      4140
aaaacaaaca aaaacaaaaa aacctgagaa gtttgaattg tagttaaatg accccaaact      4200
ggcatttaac actgttata aaaatatat atatatat atatatat aatgaaaaag             4260 gtttcagagt tgctaaagct tcagtttgtg acattaagtt tatgaaattc taaaaaatgc      4320
```

```
cttttttgga gactatatta tgctgaagaa ggctgttcgt gaggaggaga tgcgagcacc    4380
cagaacgtct tttgaggctg ggcgggtgtg attgtttact gcctactgga ttttttttcta  4440 ttaacattga aaggtaaaat ctgattattt agcatgagaa aaaaaaatcc aactctgctt   4500
ttggtcttgc ttctataaat atatagtgta tacttggtgt agactttgca tatatacaaa   4560
tttgtagtat tttcttgttt tgatgtctaa tctgtatcta taatgtaccc tagtagtcga   4620
acatactttt gattgtacaa ttgtacattt gtatacctgt aatgtaaatg tggagaagtt   4680
tgaatcaaca taaacacgtt ttttggtaag aaaagagaat tagccagccc tgtgcattca   4740
gtgtatattc tcaccttta tggtcgtagc atatagtgtt gtatattgta aattgtaatt    4800
tcaaccagaa gtaattttt ttcttttgaa ggaataaatg ttctttatac agcctagtta    4860
atgtttaaaa agaaaaaaat agcttggttt tatttgtcat ctagtctcaa gtatagcgag   4920
attctttcta aatgttattc aagattgagt tctcactagt gttttttaa tcctaaaaaa    4980 gtaatgtttt gattttgtga cagtcaaaag gacgtgcaaa agtctagcct tgcccgagct   5040
ttccttacaa tcagagcccc tctcaccttg taaagtgtga atcgcccttc ccttttgtac   5100
agaagatgaa ctgtattttg cattttgtct acttgtaagt gaatgtaaca tactgtcaat   5160
tttccttgtt tgaatataga attgtaacac tacacggtgt acatttccag agccttgtgt   5220
atatttccaa tgaacttttt tgcaagcaca cttgtaacca tatgtgtata attaacaaac   5280
ctgtgtatgc ttatgcctgg gcaactatt  tttgtaactc ttgtgtagat tgtctctaaa   5340
caatgtgtga tctttatttt gaaaaataca gaactttgga atctgaaaaa aaaaaaaaa    5400 aaaaaaaaaa aaaaaa                                                    5416

<210> SEQ ID NO 45
<211> LENGTH: 5410
<212> TYPE: DNA
<213> ORGANISM: Homo sapiens

<400> SEQUENCE: 45
agtgggccgc catgttgtcg gagtgaaagg taaggggag cgagagcgcc agagagagaa      60
gatcgggggg ctgaaatcca tcttcatcct accgctccgc ccgtgttggt ggaatgagcg    120
ttgcatgtgt cttgaagaga aaagcagtgc tttggcagga ctctttcagc ccccacctga   180
aacatcaccc tcaagaacca gctaatccca acatgcctgt tgttttgaca tctggaacag   240
ggtcgcaagc gcagccacaa ccagctgcaa atcaggctct tgcagctggg actcactcca   300
gccctgtccc aggatctata ggagttgcag gccgttccca ggacgacgct atggtggact   360
acttctttca gaggcagcat ggtgagcagc ttggggagg aggaagtgga ggaggcggct    420
ataataatag caaacatcga tggcctactg gggataacat tcatgcagaa catcaggtgc   480
gttccatgga tgaactgaat catgattttc aagcacttgc tctggaggga agagcgatgg   540
gagagcagct cttgccaggt aaaaagtttt gggaaacaga tgaatccagc aaagatggac   600
caaaaggaat attcctgggt gatcaatggc gagacagtgc ctggggaaca tcagatcatt   660
cagtttccca gccaatcatg gtgcagagaa gacctggtca gagtttccat gtgaacagtg   720
aggtcaattc tgtactgtcc ccacgatcgg agagtggggg actaggcgtt agcatggtgg   780
agtatgtgtt gagctcatcc ccgggcgatt cctgtctaag aaaaggagga tttggcccaa   840
gggatgcaga cagtgatgaa aacgacaaag gtgaaaagaa gaacaagggt acgtttgatg   900
gagataagct aggagatttg aaggaggagg gtgatgtgat ggacaagacc aatggtttac   960
```

```
cagtgcagaa tgggattgat gcagacgtca aagattttag ccgtacccct ggtaattgcc   1020
agaactctgc taatgaagtg gatcttctgg gtccaaacca gaatggttct gagggcttag   1080
cccagctgac cagcaccaat ggtgccaagc ctgtggagga tttctccaac atggagtccc   1140
agagtgtccc cttggacccc atggaacatg tgggcatgga gcctcttcag tttgattatt   1200
caggcacgca ggtacctgtg gactcagcag cagcaactgt gggactttt gactacaatt    1260 ctcaacaaca gctgttccaa agacctaatg cgcttgctgt ccagcagttg acagctgctc   1320
agcagcagca gtatgcactg gcagctgctc atcagccgca catcggttta gctcccgctg   1380
cgtttgtccc caatccatac atcatcagcg ctgctccccc agggacggac ccctacacag   1440
ctggattggc tgcagcagcg acactaggcc cagctgtggt ccctcaccag tattatggag   1500
ttactccctg gggagtctac cctgccagtc ttttccagca gcaagctgcc gctgccgctg   1560
cagcaactaa ttcagctaat caacagacca ccccacaggc tcagcaagga cagcagcagg   1620
ttctccgtgg aggagccagc caacgtcctt gacccaaa ccagaaccag cagggacagc     1680
aaacggatcc ccttgtggca gctgcagcag tgaattctgc ccttgcattt ggacaaggtc   1740
tggcagcagg catgccaggt tatccggtgt tggctcctgc tgcttactat gaccaaactg   1800
gtgcccttgt agtgaatgca ggcgcgagaa atggtcttgg agctcctgtt cgacttgtag   1860
ctcctgcccc agtcatcatt agttcctcag ctgcacaagc agctgttgca gcagccgcag   1920
cttcagcaaa tggagcagct ggtggtcttg ctggaacaac aaatggacca tttcgcccctt  1980 taggaacaca gcagcctcag ccccagcccc agcagcagcc caataacaac ctggcatcca   2040
gttctttcta cggcaacaac tctctgaaca gcaattcaca gagcagctcc ctcttctccc   2100
agggctctgc ccagcctgcc aacacatcct tgggattcgg aagtagcagt tctctcggcg   2160
ccaccctggg atccgccctt ggagggtttg aacagcagt gcaaactcc aacactggca    2220 gtggctcccg ccgtgactcc ctgactggca gcagtgacct ttataagagg acatcgagca   2280
gcttgacccc cattggacac agtttttata acggccttag cttttcctcc tctcctggac   2340
ccgtgggcat gcctctccct agtcagggac caggacattc acagacacca cctccttccc   2400
tctcttcaca tggatcctct tcaagcttaa acctgggagg actcacgaat ggcagtggaa   2460
gatacatctc tgctgctcca ggcgctgaag ccaagtaccg cagtgcaagc agcgcctcca   2520
gcctcttcag cccgagcagc actctttct cttcctctcg tttgcgatat ggaatgtctg    2580
atgtcatgcc ttctggcagg agcaggcttt tggaagattt tcgaaacaac cggtacccca   2640
atttacaact gcgggagatt gctggacata taatggaatt ttcccaagac cagcatgggt   2700
ccagattcat tcagctgaaa ctggagcgtg ccacaccagc tgagcgccag cttgtcttca   2760
atgaaatcct ccaggctgcc taccaactca tggtggatgt gtttggtaat tacgtcattc   2820
agaagttctt tgaatttggc agtcttgaac agaagctggc tttggcagaa cggattcgag   2880
gccacgtcct gtcattggca ctacagatgt atggctgccg tgttatccag aaagctcttg   2940
agtttattcc ttcagaccag cagaatgaga tggttcggga actagatggc catgtcttga   3000
agtgtgtgaa agatcagaat ggcaatcacg tggttcagaa atgcattgaa tgtgtacagc   3060
cccagtcttt gcaatttatc atcgatgcgt ttaaggaca ggtatttgcc ttatccacac    3120
atccttatgg ctgccgagtg attcagagaa tcctggagca ctgtctccct gaccagacac   3180
tccctatttt agaggagctt caccagcaca cagagcagct tgtacaggat caatatggaa   3240
attatgtaat ccaacatgta ctggagcacg gtcgtcctga ggataaaagc aaaattgtag   3300
cagaaatccg aggcaatgta cttgtattga gtcagcacaa atttgcaagc aatgttgtgg   3360
```

```
agaagtgtgt tactcacgcc tcacgtacgg agcgcgctgt gctcatcgat gaggtgtgca    3420
ccatgaacga cggtccccac agtgccttat acaccatgat gaaggaccag tatgccaact    3480
acgtggtcca gaagatgatt gacgtggcgg agccaggcca gcggaagatc gtcatgcata    3540
agatccggcc ccacatcgca actcttcgta agtacaccta tggcaagcac attctggcca    3600
agctggagaa gtactacatg aagaacggtg ttgacttagg gcccatctgt ggcccccta     3660
atggtatcat ctgaggcagt gtcacccgct gttccctcat tcccgctgac ctcactggcc    3720
cactggcaaa tccaaccagc aaccagaaat gttctagtgt agagtctgag acgggcaagt    3780
ggttgctcca ggattactcc ctcctccaaa aaaggaatca aatccacgag tggaaaagcc    3840
tttgtaaatt taattttatt acacataaca tgtactattt tttttaattg actaattgcc    3900
ctgctgtttt actggtgtat aggatacttg tacataggta accaatgtac atgggaggcc    3960
acatattttg ttcactgttg tatctatatt tcacatgtgg aaactttcag ggtggttggt    4020
ttaacaaaaa aaaaagctt taaaaaaaaa agaaaaaaag gaaaaggttt ttagctcatt     4080
tgcctggccg gcaagttttg caaatagctc ttccccacct cctcatttta gtaaaaaaca    4140
aacaaaaaca aaaaaacctg agaagtttga attgtagtta aatgacccca aactggcatt    4200
taacactgtt tataaaaaat atatatatat atatatatat atataatgaa aaaggtttca    4260
gagttgctaa agcttcagtt tgtgacatta agtttatgaa attctaaaaa atgccttttt    4320
tggagactat attatgctga agaaggctgt tcgtgaggag gagatgcgag cacccagaac    4380
gtcttttgag gctgggcggg tgtgattgtt tactgcctac tggattttt tctattaaca     4440
ttgaaaggta aaatctgatt atttagcatg agaaaaaaaa atccaactct gcttttggtc    4500
ttgcttctat aaatatatag tgtatacttg gtgtagactt tgcatatata caaatttgta    4560
gtattttctt gttttgatgt ctaatctgta tctataatgt accctagtag tcgaacatac    4620
ttttgattgt acaattgtac atttgtatac ctgtaatgta aatgtggaga agtttgaatc    4680
aacataaaca cgttttttgg taagaaaaga gaattagcca gccctgtgca ttcagtgtat    4740
attctcacct tttatggtcg tagcatatag tgttgtatat tgtaaattgt aatttcaacc    4800
agaagtaaat ttttttcttt tgaaggaata atgttctttt atacagccta gttaatgttt    4860
aaaaagaaaa aaatagcttg gttttatttg tcatctagtc tcaagtatag cgagattctt    4920
tctaaatgtt attcaagatt gagttctcac tagtgttttt ttaatcctaa aaagtaatg    4980
ttttgattt gtgacagtca aaaggacgtg caaaagtcta gccttgcccg agctttcctt    5040
acaatcagag cccctctcac cttgtaaagt gtgaatcgcc cttccctttt gtacagaaga    5100
tgaactgtat tttgcatttt gtctacttgt aagtgaatgt aacatactgt caattttcct    5160
tgtttgaata tagaattgta acactacacg gtgtacattt ccagagcctt gtgtatattt    5220
ccaatgaact tttttgcaag cacacttgta accatatgtg tataattaac aaacctgtgt    5280
atgcttatgc ctgggcaact attttttgta actcttgtgt agattgtctc taaacaatgt    5340
gtgatctta ttttgaaaaa tacagaactt tggaatctga aaaaaaaaa aaaaaaaaa      5400
aaaaaaaaa                                                            5410
```

<210> SEQ ID NO 46
<211> LENGTH: 1188
<212> TYPE: PRT
<213> ORGANISM: Homo sapiens

<400> SEQUENCE: 46

```
Met Ser Val Ala Cys Val Leu Lys Arg Lys Ala Val Leu Trp Gln Asp
 1               5                  10                  15
Ser Phe Ser Pro His Leu Lys His His Pro Gln Glu Pro Ala Asn Pro
             20                  25                  30
Asn Met Pro Val Val Leu Thr Ser Gly Thr Gly Ser Gln Ala Gln Pro
             35                  40                  45
Gln Pro Ala Ala Asn Gln Ala Leu Ala Ala Gly Thr His Ser Ser Pro
 50                  55                  60
Val Pro Gly Ser Ile Gly Val Ala Gly Arg Ser Gln Asp Asp Ala Met
 65                  70                  75                  80
Val Asp Tyr Phe Phe Gln Arg Gln His Gly Glu Gln Leu Gly Gly Gly
             85                  90                  95
Gly Ser Gly Gly Gly Gly Tyr Asn Asn Ser Lys His Arg Trp Pro Thr
             100                 105                 110
Gly Asp Asn Ile His Ala Glu His Gln Val Arg Ser Met Asp Glu Leu
             115                 120                 125
Asn His Asp Phe Gln Ala Leu Ala Leu Glu Gly Arg Ala Met Gly Glu
             130                 135                 140
Gln Leu Leu Pro Gly Lys Lys Phe Trp Glu Thr Asp Glu Ser Ser Lys
145                 150                 155                 160
Asp Gly Pro Lys Gly Ile Phe Leu Gly Asp Gln Trp Arg Asp Ser Ala
             165                 170                 175
Trp Gly Thr Ser Asp His Ser Val Ser Gln Pro Ile Met Val Gln Arg
             180                 185                 190
Arg Pro Gly Gln Ser Phe His Val Asn Ser Glu Val Asn Ser Val Leu
             195                 200                 205
Ser Pro Arg Ser Glu Ser Gly Gly Leu Gly Val Ser Met Val Glu Tyr
210                 215                 220
Val Leu Ser Ser Ser Pro Gly Asp Ser Cys Leu Arg Lys Gly Gly Phe
225                 230                 235                 240
Gly Pro Arg Asp Ala Asp Ser Asp Glu Asn Asp Lys Gly Glu Lys Lys
             245                 250                 255
Asn Lys Gly Thr Phe Asp Gly Asp Lys Leu Gly Asp Leu Lys Glu Glu
             260                 265                 270
Gly Asp Val Met Asp Lys Thr Asn Gly Leu Pro Val Gln Asn Gly Ile
             275                 280                 285
Asp Ala Asp Val Lys Asp Phe Ser Arg Thr Pro Gly Asn Cys Gln Asn
             290                 295                 300
Ser Ala Asn Glu Val Asp Leu Leu Gly Pro Asn Gln Asn Gly Ser Glu
305                 310                 315                 320
Gly Leu Ala Gln Leu Thr Ser Thr Asn Gly Ala Lys Pro Val Glu Asp
             325                 330                 335
Phe Ser Asn Met Glu Ser Gln Ser Val Pro Leu Asp Pro Met Glu His
             340                 345                 350
Val Gly Met Glu Pro Leu Gln Phe Asp Tyr Ser Gly Thr Gln Val Pro
             355                 360                 365
Val Asp Ser Ala Ala Ala Thr Val Gly Leu Phe Asp Tyr Asn Ser Gln
             370                 375                 380
Gln Gln Leu Phe Gln Arg Pro Asn Ala Leu Ala Val Gln Gln Leu Thr
385                 390                 395                 400
Ala Ala Gln Gln Gln Gln Tyr Ala Leu Ala Ala Ala His Gln Pro His
             405                 410                 415
Ile Gly Leu Ala Pro Ala Ala Phe Val Pro Asn Pro Tyr Ile Ile Ser
```

```
                420            425            430
Ala Ala Pro Pro Gly Thr Asp Pro Tyr Thr Ala Gly Leu Ala Ala Ala
            435                440                445

Ala Thr Leu Gly Pro Ala Val Val Pro His Gln Tyr Gly Val Thr
        450                455                460

Pro Trp Gly Val Tyr Pro Ala Ser Leu Phe Gln Gln Gln Ala Ala Ala
465                470                475                480

Ala Ala Ala Ala Thr Asn Ser Ala Asn Gln Gln Thr Thr Pro Gln Ala
            485                490                495

Gln Gln Gly Gln Gln Gln Val Leu Arg Gly Ala Ser Gln Arg Pro
                500                505            510

Leu Thr Pro Asn Gln Asn Gln Gln Gly Gln Gln Thr Asp Pro Leu Val
        515                520                525

Ala Ala Ala Ala Val Asn Ser Ala Leu Ala Phe Gly Gln Gly Leu Ala
            530                535                540

Ala Gly Met Pro Gly Tyr Pro Val Leu Ala Pro Ala Ala Tyr Tyr Asp
545                550                555                560

Gln Thr Gly Ala Leu Val Val Asn Ala Gly Ala Arg Asn Gly Leu Gly
                565                570                575

Ala Pro Val Arg Leu Val Ala Pro Ala Pro Val Ile Ile Ser Ser Ser
                580                585                590

Ala Ala Gln Ala Ala Val Ala Ala Ala Ala Ser Ala Asn Gly Ala
            595                600                605

Ala Gly Gly Leu Ala Gly Thr Thr Asn Gly Pro Phe Arg Pro Leu Gly
        610                615                620

Thr Gln Gln Pro Gln Pro Gln Pro Gln Gln Pro Asn Asn Asn Leu
625                630                635                640

Ala Ser Ser Ser Phe Tyr Gly Asn Asn Ser Leu Asn Ser Asn Ser Gln
                645                650                655

Ser Ser Ser Leu Phe Ser Gln Gly Ser Ala Gln Pro Ala Asn Thr Ser
            660                665                670

Leu Gly Phe Gly Ser Ser Ser Leu Gly Ala Thr Leu Gly Ser Ala
        675                680                685

Leu Gly Gly Phe Gly Thr Ala Val Ala Asn Ser Asn Thr Gly Ser Gly
        690                695                700

Ser Arg Arg Asp Ser Leu Thr Gly Ser Ser Asp Leu Tyr Lys Arg Thr
705                710                715                720

Ser Ser Ser Leu Thr Pro Ile Gly His Ser Phe Tyr Asn Gly Leu Ser
                725                730                735

Phe Ser Ser Ser Pro Gly Pro Val Gly Met Pro Leu Pro Ser Gln Gly
            740                745                750

Pro Gly His Ser Gln Thr Pro Pro Ser Leu Ser Ser His Gly Ser
        755                760                765

Ser Ser Ser Leu Asn Leu Gly Gly Leu Thr Asn Gly Ser Gly Arg Tyr
770                775                780

Ile Ser Ala Ala Pro Gly Ala Glu Ala Lys Tyr Arg Ser Ala Ser Ser
785                790                795                800

Ala Ser Ser Leu Phe Ser Pro Ser Ser Thr Leu Phe Ser Ser Arg
            805                810                815

Leu Arg Tyr Gly Met Ser Asp Val Met Pro Ser Gly Arg Ser Arg Leu
                820                825                830

Leu Glu Asp Phe Arg Asn Asn Arg Tyr Pro Asn Leu Gln Leu Arg Glu
            835                840                845
```

Ile Ala Gly His Ile Met Glu Phe Ser Gln Asp Gln His Gly Ser Arg
850                 855                 860

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
            885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
        915                 920                 925

Ala Leu Gln Met Tyr Gly Cys Arg Val Ile Gln Lys Ala Leu Glu Phe
    930                 935                 940

Ile Pro Ser Asp Gln Gln Val Ile Asn Glu Met Val Arg Glu Leu Asp
945                 950                 955                 960

Gly His Val Leu Lys Cys Val Lys Asp Gln Asn Gly Asn His Val Val
            965                 970                 975

Gln Lys Cys Ile Glu Cys Val Gln Pro Gln Ser Leu Gln Phe Ile Ile
            980                 985                 990

Asp Ala Phe Lys Gly Gln Val Phe Ala Leu Ser Thr His Pro Tyr Gly
            995                 1000                1005

Cys Arg Val Ile Gln Arg Ile Leu Glu His Cys Leu Pro Asp Gln
    1010                1015                1020

Thr Leu Pro Ile Leu Glu Glu Leu His Gln His Thr Glu Gln Leu
    1025                1030                1035

Val Gln Asp Gln Tyr Gly Asn Tyr Val Ile Gln His Val Leu Glu
    1040                1045                1050

His Gly Arg Pro Glu Asp Lys Ser Lys Ile Val Ala Glu Ile Arg
    1055                1060                1065

Gly Asn Val Leu Val Leu Ser Gln His Lys Phe Ala Ser Asn Val
    1070                1075                1080

Val Glu Lys Cys Val Thr His Ala Ser Arg Thr Glu Arg Ala Val
    1085                1090                1095

Leu Ile Asp Glu Val Cys Thr Met Asn Asp Gly Pro His Ser Ala
    1100                1105                1110

Leu Tyr Thr Met Met Lys Asp Gln Tyr Ala Asn Tyr Val Val Gln
    1115                1120                1125

Lys Met Ile Asp Val Ala Glu Pro Gly Gln Arg Lys Ile Val Met
    1130                1135                1140

His Lys Ile Arg Pro His Ile Ala Thr Leu Arg Lys Tyr Thr Tyr
    1145                1150                1155

Gly Lys His Ile Leu Ala Lys Leu Glu Lys Tyr Tyr Met Lys Asn
    1160                1165                1170

Gly Val Asp Leu Gly Pro Ile Cys Gly Pro Pro Asn Gly Ile Ile
    1175                1180                1185

<210> SEQ ID NO 47
<211> LENGTH: 1186
<212> TYPE: PRT
<213> ORGANISM: Homo sapiens

<400> SEQUENCE: 47

Met Ser Val Ala Cys Val Leu Lys Arg Lys Ala Val Leu Trp Gln Asp
1               5                   10                  15

Ser Phe Ser Pro His Leu Lys His His Pro Gln Glu Pro Ala Asn Pro

```
            20                  25                  30
Asn Met Pro Val Val Leu Thr Ser Gly Thr Gly Ser Gln Ala Gln Pro
            35                  40                  45

Gln Pro Ala Ala Asn Gln Ala Leu Ala Ala Gly Thr His Ser Ser Pro
50                  55                  60

Val Pro Gly Ser Ile Gly Val Ala Gly Arg Ser Gln Asp Asp Ala Met
65                  70                  75                  80

Val Asp Tyr Phe Phe Gln Arg Gln His Gly Glu Gln Leu Gly Gly Gly
                85                  90                  95

Gly Ser Gly Gly Gly Gly Tyr Asn Asn Ser Lys His Arg Trp Pro Thr
            100                 105                 110

Gly Asp Asn Ile His Ala Glu His Gln Val Arg Ser Met Asp Glu Leu
            115                 120                 125

Asn His Asp Phe Gln Ala Leu Ala Leu Glu Gly Arg Ala Met Gly Glu
            130                 135                 140

Gln Leu Leu Pro Gly Lys Lys Phe Trp Glu Thr Asp Glu Ser Ser Lys
145                 150                 155                 160

Asp Gly Pro Lys Gly Ile Phe Leu Gly Asp Gln Trp Arg Asp Ser Ala
                165                 170                 175

Trp Gly Thr Ser Asp His Ser Val Ser Gln Pro Ile Met Val Gln Arg
            180                 185                 190

Arg Pro Gly Gln Ser Phe His Val Asn Ser Glu Val Asn Ser Val Leu
            195                 200                 205

Ser Pro Arg Ser Glu Ser Gly Gly Leu Gly Val Ser Met Val Glu Tyr
            210                 215                 220

Val Leu Ser Ser Ser Pro Gly Asp Ser Cys Leu Arg Lys Gly Gly Phe
225                 230                 235                 240

Gly Pro Arg Asp Ala Asp Ser Asp Glu Asn Asp Lys Gly Glu Lys Lys
                245                 250                 255

Asn Lys Gly Thr Phe Asp Gly Asp Lys Leu Gly Asp Leu Lys Glu Glu
            260                 265                 270

Gly Asp Val Met Asp Lys Thr Asn Gly Leu Pro Val Gln Asn Gly Ile
            275                 280                 285

Asp Ala Asp Val Lys Asp Phe Ser Arg Thr Pro Gly Asn Cys Gln Asn
            290                 295                 300

Ser Ala Asn Glu Val Asp Leu Leu Gly Pro Asn Gln Asn Gly Ser Glu
305                 310                 315                 320

Gly Leu Ala Gln Leu Thr Ser Thr Asn Gly Ala Lys Pro Val Glu Asp
                325                 330                 335

Phe Ser Asn Met Glu Ser Gln Ser Val Pro Leu Asp Pro Met Glu His
            340                 345                 350

Val Gly Met Glu Pro Leu Gln Phe Asp Tyr Ser Gly Thr Gln Val Pro
            355                 360                 365

Val Asp Ser Ala Ala Thr Val Gly Leu Phe Asp Tyr Asn Ser Gln
            370                 375                 380

Gln Gln Leu Phe Gln Arg Pro Asn Ala Leu Ala Val Gln Gln Leu Thr
385                 390                 395                 400

Ala Ala Gln Gln Gln Tyr Ala Leu Ala Ala His Gln Pro His
                405                 410                 415

Ile Gly Leu Ala Pro Ala Ala Phe Val Pro Asn Pro Tyr Ile Ile Ser
            420                 425                 430

Ala Ala Pro Pro Gly Thr Asp Pro Tyr Thr Ala Gly Leu Ala Ala Ala
            435                 440                 445
```

```
Ala Thr Leu Gly Pro Ala Val Pro His Gln Tyr Tyr Gly Val Thr
    450                 455                 460

Pro Trp Gly Val Tyr Pro Ala Ser Leu Phe Gln Gln Gln Ala Ala
465                 470                 475                 480

Ala Ala Ala Ala Thr Asn Ser Ala Asn Gln Gln Thr Thr Pro Gln Ala
                485                 490                 495

Gln Gln Gly Gln Gln Val Leu Arg Gly Gly Ala Ser Gln Arg Pro
            500                 505                 510

Leu Thr Pro Asn Gln Asn Gln Gln Gly Gln Gln Thr Asp Pro Leu Val
            515                 520                 525

Ala Ala Ala Ala Val Asn Ser Ala Leu Ala Phe Gly Gln Gly Leu Ala
        530                 535                 540

Ala Gly Met Pro Gly Tyr Pro Val Leu Ala Pro Ala Ala Tyr Tyr Asp
545                 550                 555                 560

Gln Thr Gly Ala Leu Val Val Asn Ala Gly Ala Arg Asn Gly Leu Gly
                565                 570                 575

Ala Pro Val Arg Leu Val Ala Pro Ala Pro Val Ile Ile Ser Ser Ser
                580                 585                 590

Ala Ala Gln Ala Ala Val Ala Ala Ala Ala Ser Ala Asn Gly Ala
        595                 600                 605

Ala Gly Gly Leu Ala Gly Thr Thr Asn Gly Pro Phe Arg Pro Leu Gly
    610                 615                 620

Thr Gln Gln Pro Gln Pro Gln Pro Gln Gln Gln Pro Asn Asn Asn Leu
625                 630                 635                 640

Ala Ser Ser Ser Phe Tyr Gly Asn Asn Ser Leu Asn Ser Asn Ser Gln
                645                 650                 655

Ser Ser Ser Leu Phe Ser Gln Gly Ser Ala Gln Pro Ala Asn Thr Ser
            660                 665                 670

Leu Gly Phe Gly Ser Ser Ser Leu Gly Ala Thr Leu Gly Ser Ala
            675                 680                 685

Leu Gly Gly Phe Gly Thr Ala Val Ala Asn Ser Asn Thr Gly Ser Gly
    690                 695                 700

Ser Arg Arg Asp Ser Leu Thr Gly Ser Ser Asp Leu Tyr Lys Arg Thr
705                 710                 715                 720

Ser Ser Ser Leu Thr Pro Ile Gly His Ser Phe Tyr Asn Gly Leu Ser
                725                 730                 735

Phe Ser Ser Ser Pro Gly Pro Val Gly Met Pro Leu Pro Ser Gln Gly
                740                 745                 750

Pro Gly His Ser Gln Thr Pro Pro Pro Ser Leu Ser Ser His Gly Ser
            755                 760                 765

Ser Ser Ser Leu Asn Leu Gly Gly Leu Thr Asn Gly Ser Gly Arg Tyr
    770                 775                 780

Ile Ser Ala Ala Pro Gly Ala Glu Ala Lys Tyr Arg Ser Ala Ser Ser
785                 790                 795                 800

Ala Ser Ser Leu Phe Ser Pro Ser Ser Thr Leu Phe Ser Ser Ser Arg
                805                 810                 815

Leu Arg Tyr Gly Met Ser Asp Val Met Pro Ser Gly Arg Ser Arg Leu
            820                 825                 830

Leu Glu Asp Phe Arg Asn Asn Arg Tyr Pro Asn Leu Gln Leu Arg Glu
        835                 840                 845

Ile Ala Gly His Ile Met Glu Phe Ser Gln Asp Gln His Gly Ser Arg
    850                 855                 860
```

Phe Ile Gln Leu Lys Leu Glu Arg Ala Thr Pro Ala Glu Arg Gln Leu
865                 870                 875                 880

Val Phe Asn Glu Ile Leu Gln Ala Ala Tyr Gln Leu Met Val Asp Val
            885                 890                 895

Phe Gly Asn Tyr Val Ile Gln Lys Phe Phe Glu Phe Gly Ser Leu Glu
            900                 905                 910

Gln Lys Leu Ala Leu Ala Glu Arg Ile Arg Gly His Val Leu Ser Leu
            915                 920                 925

Ala Leu Gln Met Tyr Gly Cys Arg Val Ile Gln Lys Ala Leu Glu Phe
        930                 935                 940

Ile Pro Ser Asp Gln Gln Asn Glu Met Val Arg Glu Leu Asp Gly His
945                 950                 955                 960

Val Leu Lys Cys Val Lys Asp Gln Asn Gly Asn His Val Val Gln Lys
            965                 970                 975

Cys Ile Glu Cys Val Gln Pro Gln Ser Leu Gln Phe Ile Ile Asp Ala
            980                 985                 990

Phe Lys Gly Gln Val Phe Ala Leu Ser Thr His Pro Tyr Gly Cys Arg
            995                 1000                1005

Val Ile Gln Arg Ile Leu Glu His Cys Leu Pro Asp Gln Thr Leu
    1010                1015                1020

Pro Ile Leu Glu Glu Leu His Gln His Thr Glu Gln Leu Val Gln
    1025                1030                1035

Asp Gln Tyr Gly Asn Tyr Val Ile Gln His Val Leu Glu His Gly
    1040                1045                1050

Arg Pro Glu Asp Lys Ser Lys Ile Val Ala Glu Ile Arg Gly Asn
    1055                1060                1065

Val Leu Val Leu Ser Gln His Lys Phe Ala Ser Asn Val Val Glu
    1070                1075                1080

Lys Cys Val Thr His Ala Ser Arg Thr Glu Arg Ala Val Leu Ile
    1085                1090                1095

Asp Glu Val Cys Thr Met Asn Asp Gly Pro His Ser Ala Leu Tyr
    1100                1105                1110

Thr Met Met Lys Asp Gln Tyr Ala Asn Tyr Val Val Gln Lys Met
    1115                1120                1125

Ile Asp Val Ala Glu Pro Gly Gln Arg Lys Ile Val Met His Lys
    1130                1135                1140

Ile Arg Pro His Ile Ala Thr Leu Arg Lys Tyr Thr Tyr Gly Lys
    1145                1150                1155

His Ile Leu Ala Lys Leu Glu Lys Tyr Tyr Met Lys Asn Gly Val
    1160                1165                1170

Asp Leu Gly Pro Ile Cys Gly Pro Pro Asn Gly Ile Ile
    1175                1180                1185

<210> SEQ ID NO 48
<211> LENGTH: 22
<212> TYPE: DNA
<213> ORGANISM: Artificial Sequence
<220> FEATURE:
<223> OTHER INFORMATION: PUM1_forward primer

<400> SEQUENCE: 48
gccagcttgt cttcaatgaa at                                             22

<210> SEQ ID NO 49
<211> LENGTH: 21
<212> TYPE: DNA

```
<213> ORGANISM: Artificial Sequence
<220> FEATURE:
<223> OTHER INFORMATION: PUM1_reverse primer

<400> SEQUENCE: 49
caaagccagc ttctgttcaa g                                          21

<210> SEQ ID NO 50
<211> LENGTH: 24
<212> TYPE: DNA
<213> ORGANISM: Artificial Sequence
<220> FEATURE:
<223> OTHER INFORMATION: PUM1 probe

<400> SEQUENCE: 50
atccaccatg agttggtagg cagc                                       24

<210> SEQ ID NO 51
<211> LENGTH: 1921
<212> TYPE: DNA
<213> ORGANISM: Homo sapiens

<400> SEQUENCE: 51
ggcggaagtg acattatcaa cgcgcgccag gggttcagtg aggtcgggca ggttcgctgt    60
ggcgggcgcc tgggccgccg gctgtttaac ttcgcttccg ctggcccata gtgatctttg   120
cagtgaccca gcatcactgt ttcttggcgt gtgaagataa cccaaggaat tgaggaagtt   180
gctgagaaga gtgtgctgga gatgctctag gaaaaaattg aatagtgaga cgagttccag   240
cgcaagggtt tctggtttgc caagaagaaa gtgaacatca tggatcagaa caacagcctg   300
ccaccttacg ctcagggctt ggcctcccct cagggtgcca tgactcccgg aatccctatc   360
tttagtccaa tgatgcctta tggcactgga ctgaccccac agcctattca gaacaccaat   420
agtctgtcta ttttggaaga gcaacaaagg cagcagcagc aacaacaaca gcagcagcag   480
cagcagcagc agcaacagca acagcagcag cagcagcagc agcagcagca gcagcagcag   540
cagcagcagc agcagcagca acaggcagtg gcagctgcag ccgttcagca gtcaacgtcc   600
cagcaggcaa cacagggaac ctcaggccag gcaccacagc tcttccactc acagactctc   660
acaactgcac ccttgccggg caccactcca ctgtatccct cccccatgac tcccatgacc   720
cccatcactc ctgccacgcc agcttcggag agttctggga ttgtaccgca gctgcaaaat   780
attgtatcca cagtgaatct tggttgtaaa cttgacctaa agaccattgc acttcgtgcc   840
cgaaacgccg aatataatcc caagcggttt gctgcggtaa tcatgaggat aagagagcca   900
cgaaccacgg cactgatttt cagttctggg aaaatggtgt gcacaggagc caagagtgaa   960
gaacagtcca gactggcagc aagaaaaatat gctagagttg tacagaagtt gggttttcca  1020
gctaagttct tggacttcaa gattcagaat atggtgggga gctgtgatgt gaagtttcct  1080
ataaggttag aaggccttgt gctcacccac caacaattta gtagttatga gccagagtta  1140
tttcctggtt taatctacag aatgatcaaa cccagaattg ttctccttat ttttgtttct  1200
ggaaaagttg tattaacagg tgctaaagtc agagcagaaa tttatgaagc atttgaaaac  1260
atctacccta ttctaaaggg attcaggaag acgacgtaat ggctctcatg tacccttgcc  1320
tcccccaccc ccttcttttt tttttttaa acaaatcagt ttgttttggt acctttaaat  1380
ggtggtgttg tgagaagatg gatgttgagt tgcagggtgt ggcaccaggt gatgcccttc  1440
tgtaagtgcc caccgcggga tgccgggaag gggcattatt tgtgcactga gaacaccgcg  1500
cagcgtgact gtgagttgct cataccgtgc tgctatctgg gcagcgctgc ccatttattt  1560
```

```
atatgtagat tttaaacact gctgttgaca agttggtttg agggagaaaa ctttaagtgt    1620
taaagccacc tctataattg attggacttt ttaattttaa tgttttccc catgaaccac    1680 agttttata  tttctaccag aaaagtaaaa atcttttta  aaagtgttgt ttttctaatt    1740
tataactcct aggggttatt tctgtgccag acacattcca cctctccagt attgcaggac    1800
agaatatatg tgttaatgaa atgaatggc  tgtacatatt tttttctttc ttcagagtac    1860
tctgtacaat aaatgcagtt tataaaagtg ttagattgtt gttaaaaaaa aaaaaaaaaa    1920
a                                                                   1921
```

<210> SEQ ID NO 52
<211> LENGTH: 339
<212> TYPE: PRT
<213> ORGANISM: Homo sapiens

<400> SEQUENCE: 52

```
Met Asp Gln Asn Asn Ser Leu Pro Pro Tyr Ala Gln Gly Leu Ala Ser
1               5                   10                  15

Pro Gln Gly Ala Met Thr Pro Gly Ile Pro Ile Phe Ser Pro Met Met
            20                  25                  30

Pro Tyr Gly Thr Gly Leu Thr Pro Gln Pro Ile Gln Asn Thr Asn Ser
        35                  40                  45

Leu Ser Ile Leu Glu Glu Gln Gln Arg Gln Gln Gln Gln Gln Gln Gln
    50                  55                  60

Gln Gln Gln Gln Gln Gln Gln Gln Gln Gln Gln Gln Gln Gln Gln Gln
65                  70                  75                  80

Gln Gln Gln Gln Gln Gln Gln Gln Gln Gln Gln Gln Gln Gln Gln Ala
                85                  90                  95

Val Ala Ala Ala Val Gln Gln Ser Thr Ser Gln Gln Ala Thr Gln
            100                 105                 110

Gly Thr Ser Gly Gln Ala Pro Gln Leu Phe His Ser Gln Thr Leu Thr
        115                 120                 125

Thr Ala Pro Leu Pro Gly Thr Thr Pro Leu Tyr Pro Ser Pro Met Thr
    130                 135                 140

Pro Met Thr Pro Ile Thr Pro Ala Thr Pro Ala Ser Glu Ser Ser Gly
145                 150                 155                 160

Ile Val Pro Gln Leu Gln Asn Ile Val Ser Thr Val Asn Leu Gly Cys
                165                 170                 175

Lys Leu Asp Leu Lys Thr Ile Ala Leu Arg Ala Arg Asn Ala Glu Tyr
            180                 185                 190

Asn Pro Lys Arg Phe Ala Ala Val Ile Met Arg Ile Arg Glu Pro Arg
        195                 200                 205

Thr Thr Ala Leu Ile Phe Ser Ser Gly Lys Met Val Cys Thr Gly Ala
    210                 215                 220

Lys Ser Glu Glu Gln Ser Arg Leu Ala Ala Arg Lys Tyr Ala Arg Val
225                 230                 235                 240

Val Gln Lys Leu Gly Phe Pro Ala Lys Phe Leu Asp Phe Lys Ile Gln
                245                 250                 255

Asn Met Val Gly Ser Cys Asp Val Lys Phe Pro Ile Arg Leu Glu Gly
            260                 265                 270

Leu Val Leu Thr His Gln Gln Phe Ser Ser Tyr Glu Pro Glu Leu Phe
        275                 280                 285

Pro Gly Leu Ile Tyr Arg Met Ile Lys Pro Arg Ile Val Leu Leu Ile
    290                 295                 300
```

```
Phe Val Ser Gly Lys Val Val Leu Thr Gly Ala Lys Val Arg Ala Glu
305                 310                 315                 320

Ile Tyr Glu Ala Phe Glu Asn Ile Tyr Pro Ile Leu Lys Gly Phe Arg
                325                 330                 335

Lys Thr Thr

<210> SEQ ID NO 53
<211> LENGTH: 23
<212> TYPE: DNA
<213> ORGANISM: Artificial Sequence
<220> FEATURE:
<223> OTHER INFORMATION: TBP_forward primer

<400> SEQUENCE: 53
gccaagaaga aagtgaacat cat                                         23

<210> SEQ ID NO 54
<211> LENGTH: 20
<212> TYPE: DNA
<213> ORGANISM: Artificial Sequence
<220> FEATURE:
<223> OTHER INFORMATION: TBP_reverse primer

<400> SEQUENCE: 54
atagggattc cgggagtcat                                             20

<210> SEQ ID NO 55
<211> LENGTH: 24
<212> TYPE: DNA
<213> ORGANISM: Artificial Sequence
<220> FEATURE:
<223> OTHER INFORMATION: TBP probe

<400> SEQUENCE: 55
tcagaacaac agcctgccac ctta                                        24

<210> SEQ ID NO 56
<211> LENGTH: 1852
<212> TYPE: DNA
<213> ORGANISM: Homo sapiens

<400> SEQUENCE: 56
accgccgaga ccgcgtccgc cccgcgagca cagagcctcg cctttgccga tccgccgccc    60
gtccacaccc gccgccagct caccatggat gatgatatcg ccgcgctcgt cgtcgacaac   120
ggctccggca tgtgcaaggc cggcttcgcg ggcgacgatg ccccccgggc cgtcttcccc   180
tccatcgtgg ggcgcccag gcaccagggc gtgatggtgg gcatgggtca gaaggattcc   240
tatgtgggcg acgaggccca gagcaagaga ggcatcctca ccctgaagta ccccatcgag   300
cacggcatcg tcaccaactg ggacgacatg gagaaaatct ggcaccacac cttctacaat   360
gagctgcgtg tggctcccga ggagcacccc gtgctgctga ccgaggcccc cctgaacccc   420
aaggccaacc gcgagaagat gacccagatc atgtttgaga ccttcaacac cccagccatg   480
tacgttgcta tccaggctgt gctatccctg tacgcctctg gccgtaccac tggcatcgtg   540
atggactccg gtgacggggt cacccacact gtgcccatct acgagggta tgccctcccc   600 catgccatcc tgcgtctgga cctggctggc cgggacctga ctgactacct catgaagatc   660
ctcaccgagc gcggctacag cttcaccacc acggccgagc gggaaatcgt gcgtgacatt   720
aaggagaagc tgtgctacgt cgccctggac ttcgagcaag agatggccac ggctgcttcc   780
```

-continued

```
agctcctccc tggagaagag ctacgagctg cctgacggcc aggtcatcac cattggcaat      840
gagcggttcc gctgccctga ggcactcttc cagccttcct tcctgggcat ggagtcctgt      900
ggcatccacg aaactacctt caactccatc atgaagtgtg acgtggacat ccgcaaagac      960
ctgtacgcca acacagtgct gtctggcggc accaccatgt accctggcat tgccgacagg     1020
atgcagaagg agatcactgc cctggcaccc agcacaatga agatcaagat cattgctcct     1080
cctgagcgca agtactccgt gtggatcggc ggctccatcc tggcctcgct gtccaccttc     1140
cagcagatgt ggatcagcaa gcaggagtat gacgagtccg gcccctccat cgtccaccgc     1200
aaatgcttct aggcggacta tgacttagtt gcgttacacc ctttcttgac aaaacctaac     1260
ttgcgcagaa acaagatga gattggcatg gctttatttg tttttttttgt tttgttttgg     1320 ttttttttt tttttggct tgactcagga tttaaaaact ggaacggtga aggtgacagc     1380
agtcggttgg agcgagcatc ccccaaagtt cacaatgtgg ccgaggactt tgattgcaca     1440
ttgttgtttt tttaatagtc attccaaata tgagatgcgt tgttacagga agtcccttgc     1500
catcctaaaa gccaccccac ttctctctaa ggagaatggc ccagtcctct cccaagtcca     1560
cacaggggag gtgatagcat tgctttcgtg taaattatgt aatgcaaaat ttttttaatc     1620
ttcgccttaa tactttttta ttttgtttta ttttgaatga tgagccttcg tgccccccct     1680 tcccccttt ttgtccccca acttgagatg tatgaaggct tttggtctcc ctgggagtgg     1740
gtggaggcag ccagggctta cctgtacact gacttgagac cagttgaata aaagtgcaca     1800
ccttaaaaat gaaaaaaaaa aaaaaaaaa aaaaaaaaa aaaaaaaaaa aa              1852
```

<210> SEQ ID NO 57
<211> LENGTH: 375
<212> TYPE: PRT
<213> ORGANISM: Homo sapiens

<400> SEQUENCE: 57

Met Asp Asp Asp Ile Ala Ala Leu Val Val Asp Asn Gly Ser Gly Met
1               5                   10                  15

Cys Lys Ala Gly Phe Ala Gly Asp Asp Ala Pro Arg Ala Val Phe Pro
            20                  25                  30

Ser Ile Val Gly Arg Pro Arg His Gln Gly Val Met Val Gly Met Gly
        35                  40                  45

Gln Lys Asp Ser Tyr Val Gly Asp Glu Ala Gln Ser Lys Arg Gly Ile
    50                  55                  60

Leu Thr Leu Lys Tyr Pro Ile Glu His Gly Ile Val Thr Asn Trp Asp
65                  70                  75                  80

Asp Met Glu Lys Ile Trp His His Thr Phe Tyr Asn Glu Leu Arg Val
                85                  90                  95

Ala Pro Glu Glu His Pro Val Leu Leu Thr Glu Ala Pro Leu Asn Pro
            100                 105                 110

Lys Ala Asn Arg Glu Lys Met Thr Gln Ile Met Phe Glu Thr Phe Asn
        115                 120                 125

Thr Pro Ala Met Tyr Val Ala Ile Gln Ala Val Leu Ser Leu Tyr Ala
    130                 135                 140

Ser Gly Arg Thr Thr Gly Ile Val Met Asp Ser Gly Asp Gly Val Thr
145                 150                 155                 160

His Thr Val Pro Ile Tyr Glu Gly Tyr Ala Leu Pro His Ala Ile Leu
                165                 170                 175

Arg Leu Asp Leu Ala Gly Arg Asp Leu Thr Asp Tyr Leu Met Lys Ile
            180                 185                 190

-continued

Leu Thr Glu Arg Gly Tyr Ser Phe Thr Thr Ala Glu Arg Glu Ile
            195                 200                 205

Val Arg Asp Ile Lys Glu Lys Leu Cys Tyr Val Ala Leu Asp Phe Glu
210                 215                 220

Gln Glu Met Ala Thr Ala Ala Ser Ser Ser Leu Glu Lys Ser Tyr
225                 230                 235                 240

Glu Leu Pro Asp Gly Gln Val Ile Thr Ile Gly Asn Glu Arg Phe Arg
            245                 250                 255

Cys Pro Glu Ala Leu Phe Gln Pro Ser Phe Leu Gly Met Glu Ser Cys
            260                 265                 270

Gly Ile His Glu Thr Thr Phe Asn Ser Ile Met Lys Cys Asp Val Asp
            275                 280                 285

Ile Arg Lys Asp Leu Tyr Ala Asn Thr Val Leu Ser Gly Gly Thr Thr
290                 295                 300

Met Tyr Pro Gly Ile Ala Asp Arg Met Gln Lys Glu Ile Thr Ala Leu
305                 310                 315                 320

Ala Pro Ser Thr Met Lys Ile Lys Ile Ile Ala Pro Pro Glu Arg Lys
            325                 330                 335

Tyr Ser Val Trp Ile Gly Gly Ser Ile Leu Ala Ser Leu Ser Thr Phe
            340                 345                 350

Gln Gln Met Trp Ile Ser Lys Gln Glu Tyr Asp Glu Ser Gly Pro Ser
            355                 360                 365

Ile Val His Arg Lys Cys Phe
            370                 375

<210> SEQ ID NO 58
<211> LENGTH: 18
<212> TYPE: DNA
<213> ORGANISM: Artificial Sequence
<220> FEATURE:
<223> OTHER INFORMATION: ACTB_forward primer

<400> SEQUENCE: 58
ccaaccgcga gaagatga                                                  18

<210> SEQ ID NO 59
<211> LENGTH: 20
<212> TYPE: DNA
<213> ORGANISM: Artificial Sequence
<220> FEATURE:
<223> OTHER INFORMATION: ACTB_reverse primer

<400> SEQUENCE: 59
ccagaggcgt acagggatag                                                20

<210> SEQ ID NO 60
<211> LENGTH: 23
<212> TYPE: DNA
<213> ORGANISM: Artificial Sequence
<220> FEATURE:
<223> OTHER INFORMATION: ACTB probe

<400> SEQUENCE: 60
ccatgtacgt tgctatccag gct                                            23

<210> SEQ ID NO 61
<211> LENGTH: 1229
<212> TYPE: DNA
<213> ORGANISM: Homo sapiens

<400> SEQUENCE: 61

```
gtctgacggg cgatggcgca gccaatagac aggagcgcta tccgcggttt ctgattggct    60
actttgttcg cattataaaa ggcacgcgcg ggcgcgaggc ccttctctcg ccaggcgtcc   120
tcgtggaagt gacatcgtct ttaaaccctg cgtggcaatc cctgacgcac cgccgtgatg   180
cccagggaag acagggcgac ctggaagtcc aactacttcc ttaagatcat ccaactattg   240
gatgattatc cgaaatgttt cattgtggga gcagacaatg tgggctccaa gcagatgcag   300
cagatccgca tgtcccttcg cgggaaggct gtggtgctga tgggcaagaa caccatgatg   360
cgcaaggcca tccgagggca cctggaaaac aacccagctc tggagaaact gctgcctcat   420
atccggggga atgtgggctt tgtgttcacc aaggaggacc tcactgagat cagggacatg   480
ttgctggcca ataaggtgcc agctgctgcc cgtgctggtg ccattgcccc atgtgaagtc   540
actgtgccag cccagaacac tggtctcggg cccgagaaga cctccttttt ccaggcttta   600
ggtatcacca ctaaaatctc caggggcacc attgaaatcc tgagtgatgt gcagctgatc   660
aagactggag acaaagtggg agccagcgaa gccacgctgc tgaacatgct caacatctcc   720
cccttctcct ttgggctggt catccagcag gtgttcgaca atggcagcat ctacaaccct   780
gaagtgcttg atatcacaga ggaaactctg cattctcgct tcctggaggg tgtccgcaat   840
gttgccagtg tctgtctgca gattggctac ccaactgttg catcagtacc ccattctatc   900
atcaacgggt acaaacgagt cctggccttg tctgtggaga cggattacac cttcccactt   960
gctgaaaagg tcaaggcctt cttggctgat ccatctgcct tgtggctgc tgcccctgtg  1020
gctgctgcca ccacagctgc tcctgctgct gctgcagccc cagctaaggt tgaagccaag  1080
gaagagtcgg aggagtcgga cgaggatatg ggatttggtc tctttgacta atcaccaaaa  1140
agcaaccaac ttagccagtt ttatttgcaa aacaaggaaa taaaggctta cttctttaaa  1200
aagtaaaaaa aaaaaaaaaa aaaaaaaaa                                    1229
```

<210> SEQ ID NO 62
<211> LENGTH: 317
<212> TYPE: PRT
<213> ORGANISM: Homo sapiens

<400> SEQUENCE: 62

```
Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
                20                  25                  30

Asp Asn Val Gly Ser Lys Gln Met Gln Gln Ile Arg Met Ser Leu Arg
            35                  40                  45

Gly Lys Ala Val Val Leu Met Gly Lys Asn Thr Met Met Arg Lys Ala
        50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
                100                 105                 110

Ala Gly Ala Ile Ala Pro Cys Glu Val Thr Val Pro Ala Gln Asn Thr
            115                 120                 125

Gly Leu Gly Pro Glu Lys Thr Ser Phe Phe Gln Ala Leu Gly Ile Thr
        130                 135                 140
```

-continued

```
Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205

Glu Thr Leu His Ser Arg Phe Leu Gly Val Arg Asn Val Ala Ser
    210                 215                 220

Val Cys Leu Gln Ile Gly Tyr Pro Thr Val Ala Ser Val Pro His Ser
225                 230                 235                 240

Ile Ile Asn Gly Tyr Lys Arg Val Leu Ala Leu Ser Val Glu Thr Asp
                245                 250                 255

Tyr Thr Phe Pro Leu Ala Glu Lys Val Lys Ala Phe Leu Ala Asp Pro
                260                 265                 270

Ser Ala Phe Val Ala Ala Pro Val Ala Ala Thr Thr Ala Ala
            275                 280                 285

Pro Ala Ala Ala Ala Pro Ala Lys Val Glu Ala Lys Glu Glu Ser
290                 295                 300

Glu Glu Ser Asp Glu Asp Met Gly Phe Gly Leu Phe Asp
305                 310                 315
```

<210> SEQ ID NO 63
<211> LENGTH: 317
<212> TYPE: PRT
<213> ORGANISM: Homo sapiens
<400> SEQUENCE: 63

```
Met Pro Arg Glu Asp Arg Ala Thr Trp Lys Ser Asn Tyr Phe Leu Lys
1               5                   10                  15

Ile Ile Gln Leu Leu Asp Asp Tyr Pro Lys Cys Phe Ile Val Gly Ala
            20                  25                  30

Asp Asn Val Gly Ser Lys Gln Met Gln Gln Ile Arg Met Ser Leu Arg
        35                  40                  45

Gly Lys Ala Val Val Leu Met Gly Lys Asn Thr Met Met Arg Lys Ala
    50                  55                  60

Ile Arg Gly His Leu Glu Asn Asn Pro Ala Leu Glu Lys Leu Leu Pro
65                  70                  75                  80

His Ile Arg Gly Asn Val Gly Phe Val Phe Thr Lys Glu Asp Leu Thr
                85                  90                  95

Glu Ile Arg Asp Met Leu Leu Ala Asn Lys Val Pro Ala Ala Ala Arg
            100                 105                 110

Ala Gly Ala Ile Ala Pro Cys Glu Val Thr Val Pro Ala Gln Asn Thr
        115                 120                 125

Gly Leu Gly Pro Glu Lys Thr Ser Phe Phe Gln Ala Leu Gly Ile Thr
    130                 135                 140

Thr Lys Ile Ser Arg Gly Thr Ile Glu Ile Leu Ser Asp Val Gln Leu
145                 150                 155                 160

Ile Lys Thr Gly Asp Lys Val Gly Ala Ser Glu Ala Thr Leu Leu Asn
                165                 170                 175

Met Leu Asn Ile Ser Pro Phe Ser Phe Gly Leu Val Ile Gln Gln Val
            180                 185                 190

Phe Asp Asn Gly Ser Ile Tyr Asn Pro Glu Val Leu Asp Ile Thr Glu
        195                 200                 205
```

```
Glu Thr Leu His Ser Arg Phe Leu Glu Gly Val Arg Asn Val Ala Ser
    210                 215                 220
Val Cys Leu Gln Ile Gly Tyr Pro Thr Val Ala Ser Val Pro His Ser
225                 230                 235                 240
Ile Ile Asn Gly Tyr Lys Arg Val Leu Ala Leu Ser Val Glu Thr Asp
                245                 250                 255
Tyr Thr Phe Pro Leu Ala Glu Lys Val Lys Ala Phe Leu Ala Asp Pro
            260                 265                 270
Ser Ala Phe Val Ala Ala Pro Val Ala Ala Thr Thr Ala Ala
        275                 280                 285
Pro Ala Ala Ala Ala Pro Ala Lys Val Glu Ala Lys Glu Glu Ser
    290                 295                 300
Glu Glu Ser Asp Glu Asp Met Gly Phe Gly Leu Phe Asp
305                 310                 315
```

<210> SEQ ID NO 64
<211> LENGTH: 18
<212> TYPE: DNA
<213> ORGANISM: Artificial Sequence
<220> FEATURE:
<223> OTHER INFORMATION: RPLP0_forward primer

<400> SEQUENCE: 64
taaaccctgc gtggcaat                                                 18

<210> SEQ ID NO 65
<211> LENGTH: 27
<212> TYPE: DNA
<213> ORGANISM: Artificial Sequence
<220> FEATURE:
<223> OTHER INFORMATION: RPLP0_reverse primer

<400> SEQUENCE: 65
acatttcgga taatcatcca atagttg                                       27

<210> SEQ ID NO 66
<211> LENGTH: 24
<212> TYPE: DNA
<213> ORGANISM: Artificial Sequence
<220> FEATURE:
<223> OTHER INFORMATION: RPLP0 probe

<400> SEQUENCE: 66
aagtagttgg acttccaggt cgcc                                          24

<210> SEQ ID NO 67
<211> LENGTH: 2458
<212> TYPE: DNA
<213> ORGANISM: Homo sapiens

<400> SEQUENCE: 67
cagaagaagg cagcgcccaa ggcgcatgcg cagcggtcac tcccgctgta tattaaggcg    60
ccggcgatcg cggcctgagg ctgctcccgg acaagggcaa cgagcgtttc gtttggactt   120
ctcgacttga gtgcccgcct ccttcgccgc cgcctctgca gtcctcagcg cagttatgcc   180
cagttcttcc cgctgtgggg acacgaccac ggaggaatcc ttgcttcagg gactcgggac   240
cctgctggac cccttcctcg ggtttagggg atgtggggac caggagaaag tcaggatccc   300
taagagtctt ccctgcctgg atggatgagt ggcttcttct ccacctagat ctttccaca    360 ggagccagca tacttcctga acatggagag tgttgttcgc cgctgcccat tcttatcccg   420

```
agtcccccag gcctttctgc agaaagcagg caaatctctg ttgttctatg cccaaaactg      480
ccccaagatg atggaagttg gggccaagcc agccctcgg gcattgtcca ctgcagcagt       540
acactaccaa cagatcaaag aaaccctcc ggccagtgag aaagacaaaa ctgctaaggc       600
caaggtccaa cagactcctg atggatccca gcagagtcca gatggcacac agcttccgtc     660
tggacacccc ttgcctgcca caagccaggg cactgcaagc aaatgccctt tcctggcagc     720
acagatgaat cagagaggca gcagtgtctt ctgcaaagcc agtcttgagc ttcaggagga    780
tgtgcaggaa atgaatgccg tgaggaaaga ggttgctgaa acctcagcag gccccagtgt   840
ggttagtgtg aaaaccgatg gaggggatcc cagtggactg ctgaagaact tccaggacat   900
catgcaaaag caaagaccag aaagagtgtc tcatcttctt caagataact tgccaaaatc   960
tgtttccact tttcagtatg atcgtttctt tgagaaaaaa attgatgaga aaagaatga    1020 ccacacctat cgagttttta aaactgtgaa ccggcgagca cacatcttcc ccatggcaga   1080
tgactattca gactccctca tcaccaaaaa gcagtgtca gtctggtgca gtaatgacta   1140
cctaggaatg agtcgccacc cacgggtgtg tggggcagtt atggacactt tgaaacaaca   1200
tggtgctggg gcaggtggta ctagaaatat ttctggaact agtaaattcc atgtggactt   1260
agagcgggag ctggcagacc tccatgggaa agatgccgca ctcttgtttt cctcgtgctt   1320
tgtggccaat gactcaaccc tcttcaccct ggctaagatg atgccaggct gtgagattta   1380
ctctgattct gggaaccatg cctccatgat ccaagggatt cgaaacagcc gagtgccaaa   1440
gtacatcttc cgccacaatg atgtcagcca cctcagagaa ctgctgcaaa gatctgaccc   1500
ctcagtcccc aagattgtgg catttgaaac tgtccattca atggatgggg cggtgtgccc   1560
actggaagag ctgtgtgatg tggcccatga gtttggagca atcaccttcg tggatgaggt   1620
ccacgcagtg gggctttatg gggctcgagg cggagggatt ggggatcggg atggagtcat   1680
gccaaaaatg gacatcattt ctggaacact tggcaaagcc tttggttgtg ttggagggta   1740
catcgccagc acgagttctc tgattgacac cgtacggtcc tatgctgctg gcttcatctt   1800
caccacctct ctgccaccca tgctgctggc tggagccctg gagtctgtgc ggatcctgaa   1860
gagcgctgag ggacgggtgc ttcgccgcca gcaccagcgc aacgtcaaac tcatgagaca   1920
gatgctaatg gatgccggcc tccctgttgt ccactgcccc agccacatca tccctgtgcg   1980
ggttgcagat gctgctaaaa acacagaagt ctgtgatgaa ctaatgagca gacataacat   2040
ctacgtgcaa gcaatcaatt accctacggt gccccgggga gaagagctcc tacggattgc   2100
ccccacccct caccacacac cccagatgat gaactacttc cttgagaatc tgctagtcac   2160
atggaagcaa gtggggctgg aactgaagcc tcattcctca gctgagtgca acttctgcag   2220
gaggccactg catttgaag tgatgagtga aagagaaag tcctatttct caggcttgag    2280
caagttggta tctgctcagg cctgagcatg acctcaatta tttcacttaa ccccaggcca   2340
ttatcatatc cagatggtct tcagagttgt ctttatatgt gaattaagtt atattaaatt   2400
ttaatctata gtaaaaacat agtcctggaa ataaattctt gcttaaatgg tgaaaaaaa   2458
```

<210> SEQ ID NO 68
<211> LENGTH: 2281
<212> TYPE: DNA
<213> ORGANISM: Homo sapiens

<400> SEQUENCE: 68

```
cagaagaagg cagcgcccaa ggcgcatgcg cagcggtcac tcccgctgta tattaaggcg       60
```

```
ccggcgatcg cggcctgagg ctgctcccgg acaagggcaa cgagcgtttc gtttggactt      120
ctcgacttga gtcccgcct ccttcgccgc cgcctctgca gtcctcagcg cagtctttcc       180
acaggagcca gcatacttcc tgaacatgga gagtgttgtt cgccgctgcc cattcttatc     240
ccgagtcccc caggcctttc tgcagaaagc aggcaaatct ctgttgttct atgcccaaaa      300
ctgccccaag atgatggaag ttggggccaa gccagcccct cgggcattgt ccactgcagc     360
agtacactac caacagatca agaaaccccc tccggccagt gagaaagaca aaactgctaa     420
ggccaaggtc caacagactc ctgatggatc ccagcagagt ccagatggca cacagcttcc     480
gtctggacac cccttgcctg ccacaagcca gggcactgca agcaaatgcc ctttcctggc     540
agcacagatg aatcagagag gcagcagtgt cttctgcaaa gccagtcttg agcttcagga    600
ggatgtgcag gaaatgaatg ccgtgaggaa agaggttgct gaaacctcag caggccccag     660
tgtggttagt gtgaaaaccg atggagggga tcccagtgga ctgctgaaga acttccagga   720
catcatgcaa aagcaaagac cagaaagagt gtctcatctt cttcaagata acttgccaaa    780
atctgtttcc acttttcagt atgatcgttt ctttgagaaa aaaattgatg agaaaaagaa     840
tgaccacacc tatcgagttt ttaaaactgt gaaccggcga gcacacatct cccccatggc     900
agatgactat tcagactccc tcatcaccaa aaagcaagtg tcagtctggt gcagtaatga     960
ctacctagga atgagtcgcc acccacgggt gtgtgggca gttatggaca ctttgaaaca   1020
acatggtgct ggggcaggtg gtactagaaa tatttctgga actagtaaat tccatgtgga    1080
cttagagcgg gagctggcag acctccatgg gaaagatgcc gcactcttgt tttcctcgtg   1140 cttttgtggcc aatgactcaa ccctcttcac cctggctaag atgatgccag ctgtgagat    1200 ttactctgat tctgggaacc atgcctccat gatccaaggg attcgaaaca gccgagtgcc    1260
aaagtacatc ttccgccaca tgatgtcag ccacctcaga gaactgctgc aaagatctga   1320 ccctcagtc cccaagattg tggcattttga aactgtccat tcaatggatg gggcggtgtg    1380
cccactggaa gagctgtgtg atgtggccca tgagtttgga gcaatcacct tcgtggatga    1440
ggtccacgca gtggggcttt atggggctcg aggcggaggg attggggatc gggatggagt    1500
catgccaaaa atggacatca tttctggaac acttggcaaa gcctttggtt gtgttggagg   1560
gtacatcgcc agcacgagtt ctctgattga caccgtacgg tcctatgctg ctggcttcat    1620
cttcaccacc tctctgccac ccatgctgct ggctggagcc ctggagtctg tgcggatcct    1680
gaagagcgct gagggacggg tgcttcgccg ccagcaccag cgcaacgtca aactcatgag    1740
acagatgcta atggatgccg gcctccctgt tgtccactgc cccagccaca tcatccctgt   1800
gcgggttgca gatgctgcta aaacacaga agtctgtgat gaactaatga gcagacataa    1860
catctacgtg caagcaatca attacccta ggtgccccgg ggagaagagc tcctacggat    1920
tgcccccacc cctcaccaca caccccagat gatgaactac ttccttgaga atctgctagt    1980
cacatggaag caagtgggc tggaactgaa gcctcattcc tcagctgagt gcaacttctg   2040
caggaggcca ctgcatttga agtgatgag tgaaagagag aagtcctatt tctcaggctt     2100
gagcaagttg gtatctgctc aggcctgagc atgacctcaa ttatttcact taaccccagg     2160
ccattatcat atccagatgg tcttcagagt tgtctttata tgtgaattaa gttatattaa    2220
attttaatct atagtaaaaa catagtcctg gaaataaatt cttgcttaaa tggtgaaaaa    2280
a                                                                    2281
```

<210> SEQ ID NO 69
<211> LENGTH: 640

<212> TYPE: PRT
<213> ORGANISM: Homo sapiens

<400> SEQUENCE: 69

```
Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
        35                  40                  45

Ser Thr Ala Ala Val His Tyr Gln Gln Ile Lys Glu Thr Pro Pro Ala
    50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
                85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
        115                 120                 125

Glu Leu Gln Glu Asp Val Gln Glu Met Asn Ala Val Arg Lys Glu Val
    130                 135                 140

Ala Glu Thr Ser Ala Gly Pro Ser Val Val Ser Val Lys Thr Asp Gly
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
            180                 185                 190

Ser Val Ser Thr Phe Gln Tyr Asp Arg Phe Phe Glu Lys Lys Ile Asp
        195                 200                 205

Glu Lys Lys Asn Asp His Thr Tyr Arg Val Phe Lys Thr Val Asn Arg
    210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255

Ser Arg His Pro Arg Val Cys Gly Ala Val Met Asp Thr Leu Lys Gln
            260                 265                 270

His Gly Ala Gly Ala Gly Gly Thr Arg Asn Ile Ser Gly Thr Ser Lys
        275                 280                 285

Phe His Val Asp Leu Glu Arg Glu Leu Ala Asp Leu His Gly Lys Asp
    290                 295                 300

Ala Ala Leu Leu Phe Ser Ser Cys Phe Val Ala Asn Asp Ser Thr Leu
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
            340                 345                 350

Lys Tyr Ile Phe Arg His Asn Asp Val Ser His Leu Arg Glu Leu Leu
        355                 360                 365

Gln Arg Ser Asp Pro Ser Val Pro Lys Ile Val Ala Phe Glu Thr Val
    370                 375                 380

His Ser Met Asp Gly Ala Val Cys Pro Leu Glu Glu Leu Cys Asp Val
385                 390                 395                 400
```

```
Ala His Glu Phe Gly Ala Ile Thr Phe Val Asp Val His Ala Val
            405                 410                 415

Gly Leu Tyr Gly Ala Arg Gly Gly Ile Gly Asp Arg Asp Gly Val
            420                 425                 430

Met Pro Lys Met Asp Ile Ile Ser Gly Thr Leu Gly Lys Ala Phe Gly
            435                 440                 445

Cys Val Gly Gly Tyr Ile Ala Ser Thr Ser Leu Ile Asp Thr Val
450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
            485                 490                 495

Gly Arg Val Leu Arg Arg Gln His Gln Arg Asn Val Lys Leu Met Arg
            500                 505                 510

Gln Met Leu Met Asp Ala Gly Leu Pro Val Val His Cys Pro Ser His
            515                 520                 525

Ile Ile Pro Val Arg Val Ala Asp Ala Ala Lys Asn Thr Glu Val Cys
            530                 535                 540

Asp Glu Leu Met Ser Arg His Asn Ile Tyr Val Gln Ala Ile Asn Tyr
545                 550                 555                 560

Pro Thr Val Pro Arg Gly Glu Glu Leu Leu Arg Ile Ala Pro Thr Pro
                    565                 570                 575

His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
            595                 600                 605

Cys Asn Phe Cys Arg Arg Pro Leu His Phe Glu Val Met Ser Glu Arg
            610                 615                 620

Glu Lys Ser Tyr Phe Ser Gly Leu Ser Lys Leu Val Ser Ala Gln Ala
625                 630                 635                 640

<210> SEQ ID NO 70
<211> LENGTH: 640
<212> TYPE: PRT
<213> ORGANISM: Homo sapiens

<400> SEQUENCE: 70

Met Glu Ser Val Val Arg Arg Cys Pro Phe Leu Ser Arg Val Pro Gln
1               5                   10                  15

Ala Phe Leu Gln Lys Ala Gly Lys Ser Leu Leu Phe Tyr Ala Gln Asn
            20                  25                  30

Cys Pro Lys Met Met Glu Val Gly Ala Lys Pro Ala Pro Arg Ala Leu
            35                  40                  45

Ser Thr Ala Ala Val His Tyr Gln Gln Ile Lys Glu Thr Pro Pro Ala
50                  55                  60

Ser Glu Lys Asp Lys Thr Ala Lys Ala Lys Val Gln Gln Thr Pro Asp
65                  70                  75                  80

Gly Ser Gln Gln Ser Pro Asp Gly Thr Gln Leu Pro Ser Gly His Pro
            85                  90                  95

Leu Pro Ala Thr Ser Gln Gly Thr Ala Ser Lys Cys Pro Phe Leu Ala
            100                 105                 110

Ala Gln Met Asn Gln Arg Gly Ser Ser Val Phe Cys Lys Ala Ser Leu
            115                 120                 125

Glu Leu Gln Glu Asp Val Gln Glu Met Asn Ala Val Arg Lys Glu Val
```

```
               130                 135                 140
Ala Glu Thr Ser Ala Gly Pro Ser Val Ser Val Lys Thr Asp Gly
145                 150                 155                 160

Gly Asp Pro Ser Gly Leu Leu Lys Asn Phe Gln Asp Ile Met Gln Lys
                165                 170                 175

Gln Arg Pro Glu Arg Val Ser His Leu Leu Gln Asp Asn Leu Pro Lys
                180                 185                 190

Ser Val Ser Thr Phe Gln Tyr Asp Arg Phe Glu Lys Lys Ile Asp
                195                 200                 205

Glu Lys Lys Asn Asp His Thr Tyr Arg Val Phe Lys Thr Val Asn Arg
210                 215                 220

Arg Ala His Ile Phe Pro Met Ala Asp Asp Tyr Ser Asp Ser Leu Ile
225                 230                 235                 240

Thr Lys Lys Gln Val Ser Val Trp Cys Ser Asn Asp Tyr Leu Gly Met
                245                 250                 255

Ser Arg His Pro Arg Val Cys Gly Ala Val Met Asp Thr Leu Lys Gln
                260                 265                 270

His Gly Ala Gly Ala Gly Gly Thr Arg Asn Ile Ser Gly Thr Ser Lys
                275                 280                 285

Phe His Val Asp Leu Glu Arg Glu Leu Ala Asp Leu His Gly Lys Asp
                290                 295                 300

Ala Ala Leu Leu Phe Ser Ser Cys Phe Val Ala Asn Asp Ser Thr Leu
305                 310                 315                 320

Phe Thr Leu Ala Lys Met Met Pro Gly Cys Glu Ile Tyr Ser Asp Ser
                325                 330                 335

Gly Asn His Ala Ser Met Ile Gln Gly Ile Arg Asn Ser Arg Val Pro
                340                 345                 350

Lys Tyr Ile Phe Arg His Asn Asp Val Ser His Leu Arg Glu Leu Leu
                355                 360                 365

Gln Arg Ser Asp Pro Ser Val Pro Lys Ile Val Ala Phe Glu Thr Val
                370                 375                 380

His Ser Met Asp Gly Ala Val Cys Pro Leu Glu Glu Leu Cys Asp Val
385                 390                 395                 400

Ala His Glu Phe Gly Ala Ile Thr Phe Val Asp Glu Val His Ala Val
                405                 410                 415

Gly Leu Tyr Gly Ala Arg Gly Gly Gly Ile Gly Asp Arg Asp Gly Val
                420                 425                 430

Met Pro Lys Met Asp Ile Ile Ser Gly Thr Leu Gly Lys Ala Phe Gly
                435                 440                 445

Cys Val Gly Gly Tyr Ile Ala Ser Thr Ser Ser Leu Ile Asp Thr Val
                450                 455                 460

Arg Ser Tyr Ala Ala Gly Phe Ile Phe Thr Thr Ser Leu Pro Pro Met
465                 470                 475                 480

Leu Leu Ala Gly Ala Leu Glu Ser Val Arg Ile Leu Lys Ser Ala Glu
                485                 490                 495

Gly Arg Val Leu Arg Arg Gln His Gln Arg Asn Val Lys Leu Met Arg
                500                 505                 510

Gln Met Leu Met Asp Ala Gly Leu Pro Val Val His Cys Pro Ser His
                515                 520                 525

Ile Ile Pro Val Arg Val Ala Asp Ala Lys Asn Thr Glu Val Cys
                530                 535                 540

Asp Glu Leu Met Ser Arg His Asn Ile Tyr Val Gln Ala Ile Asn Tyr
545                 550                 555                 560
```

```
Pro Thr Val Pro Arg Gly Glu Glu Leu Leu Arg Ile Ala Pro Thr Pro
                565                 570                 575

His His Thr Pro Gln Met Met Asn Tyr Phe Leu Glu Asn Leu Leu Val
            580                 585                 590

Thr Trp Lys Gln Val Gly Leu Glu Leu Lys Pro His Ser Ser Ala Glu
        595                 600                 605

Cys Asn Phe Cys Arg Arg Pro Leu His Phe Glu Val Met Ser Glu Arg
    610                 615                 620

Glu Lys Ser Tyr Phe Ser Gly Leu Ser Lys Leu Val Ser Ala Gln Ala
625                 630                 635                 640

<210> SEQ ID NO 71
<211> LENGTH: 17
<212> TYPE: DNA
<213> ORGANISM: Artificial Sequence
<220> FEATURE:
<223> OTHER INFORMATION: ALAS-1_forward primer

<400> SEQUENCE: 71
agccacatca tccctgt                                              17

<210> SEQ ID NO 72
<211> LENGTH: 22
<212> TYPE: DNA
<213> ORGANISM: Artificial Sequence
<220> FEATURE:
<223> OTHER INFORMATION: ALAS-1_reverse primer

<400> SEQUENCE: 72
cgtagatgtt atgtctgctc at                                        22

<210> SEQ ID NO 73
<211> LENGTH: 22
<212> TYPE: DNA
<213> ORGANISM: Artificial Sequence
<220> FEATURE:
<223> OTHER INFORMATION: ALAS-1 probe

<400> SEQUENCE: 73
tttagcagca tctgcaaccc gc                                        22
```